US011439811B2

(12) United States Patent
de Miguel, Sr. et al.

(10) Patent No.: US 11,439,811 B2
(45) Date of Patent: Sep. 13, 2022

(54) ADVANCED ELECTRODE ARRAY INSERTION WITH CONDITIONING

(71) Applicants: Ángel Ramos de Miguel, Sr., Las Palmas (ES); Ángel Manuel Ramos Macías, Las Palmas (ES); D. Juan Carlos Falcon Gonzalez, Las Palmas (ES); Riaan Rottier, Macquarie University (ES); Christopher Bennett, Macquarie Park (AU)

(72) Inventors: Ángel Ramos de Miguel, Sr., Las Palmas (ES); Ángel Manuel Ramos Macías, Las Palmas (ES); D. Juan Carlos Falcon Gonzalez, Las Palmas (ES); Riaan Rottier, Macquarie University (ES); Christopher Bennett, Macquarie Park (AU)

(73) Assignee: Cochlear Limited, Macquarie University (AU)

( * ) Notice: Subject to any disclaimer, the term of this patent is extended or adjusted under 35 U.S.C. 154(b) by 647 days.

(21) Appl. No.: 15/707,197

(22) Filed: Sep. 18, 2017

(65) Prior Publication Data

US 2018/0140829 A1  May 24, 2018

Related U.S. Application Data

(63) Continuation-in-part of application No. PCT/ES2017/000049, filed on Apr. 19, 2017.

(30) Foreign Application Priority Data

Apr. 21, 2016 (ES) ............................... ES201600344

(51) Int. Cl.
*A61N 1/00* (2006.01)
*A61N 1/05* (2006.01)
(Continued)

(52) U.S. Cl.
CPC ............. *A61N 1/0541* (2013.01); *A61N 1/08* (2013.01); *A61N 1/36038* (2017.08);
(Continued)

(58) Field of Classification Search
CPC .................. H04R 25/70; A61N 1/0541; A61N 1/36038; A61N 1/08; G16H 20/30; G16H 40/63; G16H 50/20
See application file for complete search history.

(56) References Cited

U.S. PATENT DOCUMENTS

| 4,532,930 A | 8/1985 | Crosby et al. |
| 5,626,629 A | 5/1997 | Faltys et al. |

(Continued)

FOREIGN PATENT DOCUMENTS

| WO | 02082982 A1 | 10/2002 | |
| WO | 2009026625 A1 | 3/2009 | |
| WO | WO-2015139715 A1 * | 9/2015 | ........... A61B 5/4851 |

OTHER PUBLICATIONS

International Search Report and Written Opinion for PCT/ES2017/000049, dated Aug. 4, 2017.
(Continued)

*Primary Examiner* — Rex R Holmes
*Assistant Examiner* — Sana Sahand
(74) *Attorney, Agent, or Firm* — Pilloff Passino & Cosenza LLP; Martin J. Cosenza

(57) ABSTRACT

A method, including obtaining information indicative of a phenomenon sensed at a read electrode of a cochlear implant electrode array relative to a reference and/or at a read electrode remote from the electrode array relative to a reference, where one of the electrodes of the cochlear implant electrode array was energized executing a first analysis of the information to identify one or more first meanings from among a first group of meanings of the
(Continued)

sensed phenomenon, conditioning the obtained information based on the identified one or more first meanings, and executing a second analysis of the conditioned information to identify one or more second meanings from among a second group of meanings of the sensed phenomenon.

20 Claims, 88 Drawing Sheets

(51) Int. Cl.
| | |
|---|---|
| *A61N 1/36* | (2006.01) |
| *A61N 1/372* | (2006.01) |
| *A61N 1/08* | (2006.01) |
| *G16H 40/63* | (2018.01) |
| *G16H 50/20* | (2018.01) |
| *G16H 20/30* | (2018.01) |

(52) U.S. Cl.
CPC ......... *A61N 1/37252* (2013.01); *G16H 20/30* (2018.01); *G16H 40/63* (2018.01); *G16H 50/20* (2018.01)

(56) References Cited

U.S. PATENT DOCUMENTS

| | | | |
|---|---|---|---|
| 5,674,264 | A | 10/1997 | Carter et al. |
| 6,751,505 | B1 | 6/2004 | Van Den Honert et al. |
| 7,206,640 | B1 | 4/2007 | Overstreet |
| 7,684,856 | B2 | 3/2010 | Virtanen et al. |
| 8,014,853 | B2 | 9/2011 | Kraus et al. |
| 8,073,354 | B2* | 12/2011 | Yamada ................ G03G 21/02 399/79 |
| 8,532,781 | B1 | 9/2013 | Vanpoucke |
| 9,173,585 | B2 | 11/2015 | Tsampazis et al. |
| 9,320,887 | B2 | 4/2016 | Kals |
| 2005/0101878 | A1 | 5/2005 | Daly et al. |
| 2010/0114288 | A1* | 5/2010 | Haller ................ A61B 17/3468 607/137 |
| 2010/0268302 | A1* | 10/2010 | Botros ............... A61N 1/36038 607/57 |
| 2011/0087085 | A1 | 4/2011 | Tsampazis et al. |
| 2012/0191161 | A1* | 7/2012 | van Dijk ............. A61N 1/0541 607/57 |
| 2012/0316454 | A1 | 12/2012 | Carter |
| 2014/0363036 | A1* | 12/2014 | Hillbratt ................ H04R 25/45 381/318 |
| 2015/0112408 | A1 | 4/2015 | Kals |
| 2015/0314122 | A1* | 11/2015 | Kabot ..................... A61N 1/08 607/137 |
| 2016/0059014 | A1 | 3/2016 | Johnston et al. |
| 2016/0059015 | A1 | 3/2016 | Risi et al. |
| 2017/0340883 | A1* | 11/2017 | Johnston ............... A61B 5/7282 |

OTHER PUBLICATIONS

Wilko Grolman et al., "Spread of Excitation Measurements for the Detection of Electrode Array Foldovers: A Prospective Study Comparing 3-Dimensional Rotational X-ray and Intraoperative Spread of Excitation Measurements," Otology & Neurotology, Jan. 1, 2009, pp. 27-33, vol. 30.

Octavio Garaycochea et al., "Intra-operative radiological diagnosis of a tip roll-over electrode array displacement using fluoroscopy, when electrophysiological testing is normal: the importance of both techniques in cochlear implant surgery," Brazilian Journal of Otorhinolaryngology, Jun. 2017.

Luke Campbell et al., "Intraoperative Real-time Cochlear Response Telemetry Predicts Hearing Preservation in Cochlear Implantation," Otology & Neurotology, Apr. 2016.

Filiep J. Vanpoucke et al., "Identification of the Impedance Model of an Implanted Cochlear Prosthesis From Intracochlear Potential Measurements," IEEE Transactions on Biomedical Engineering, Dec. 2004, pp. 2174-2183, vol. 51, No. 12.

S. Abdul et al., "The use of electrical impedance spectroscopy in the detection of cervical intraepithelial neoplasia," Int J Gynecol Cancer, Sep. 2006, pp. 1823-1832, vol. 16.

Chin-Tuan Tan et al., "Real-time measurement of electrode impedance during intracochlear electrode insertion," Laryngoscope, Apr. 2013, vol. 123, No. 4.

Phillip Tran, "Investigation of cochlear implant stimulation using a finite element model," Mar. 2015, University of Sydney PhD thesis.

Justin C Williams et al., "Complex impedance spectroscopy for monitoring tissue responses to inserted neural implants," Journal of Neural Engineering, Nov. 27, 2007, pp. 410-423, vol. 4.

Marcus Yip et al., "Energy-efficient waveform for electrical stimulation of the cochlear nerve," Scientific Reports, Oct. 19, 2017, vol. 7.

Jason Pile et al., "Characterization of Friction and Speed Effects and Methods for Detection of Cochlear Implant Electrode Tip Foldover," 2013 IEEE International Conference on Robotics and Automation (ICRA), May 2013, pp. 4409-4414.

Alan G. Micco et al., "Electrical Resistivity Measurements in the Mammalian Cochlea After Neural Degeneration," Laryngoscope, Aug. 2006, pp. 1334-141, vol. 116.

\* cited by examiner

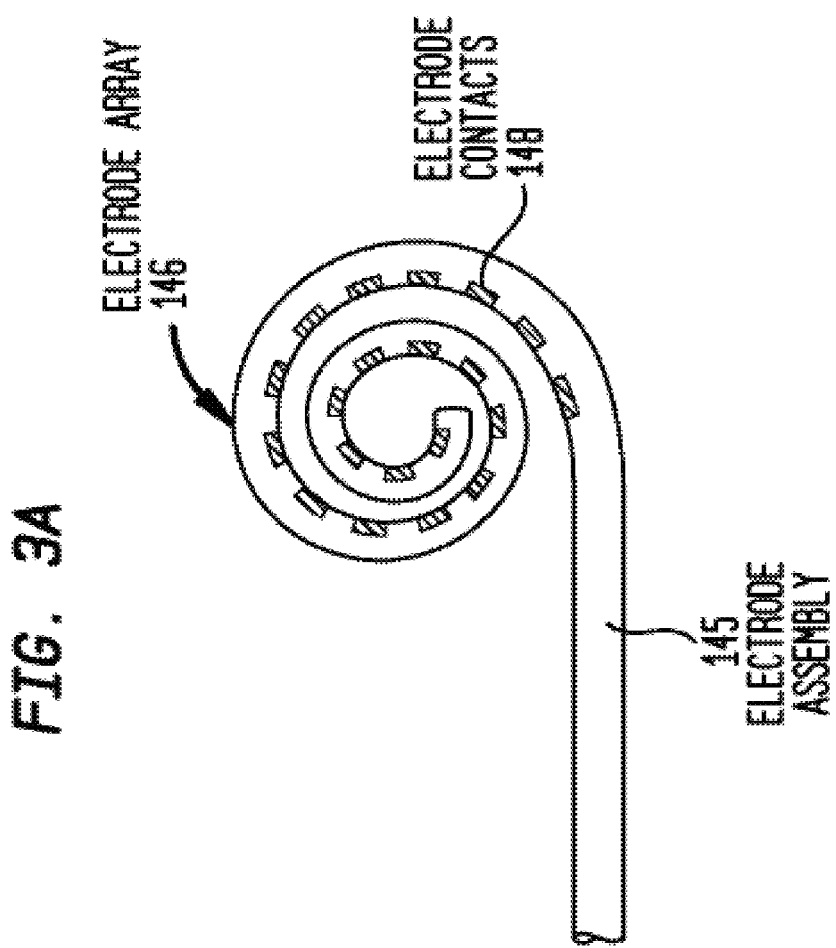

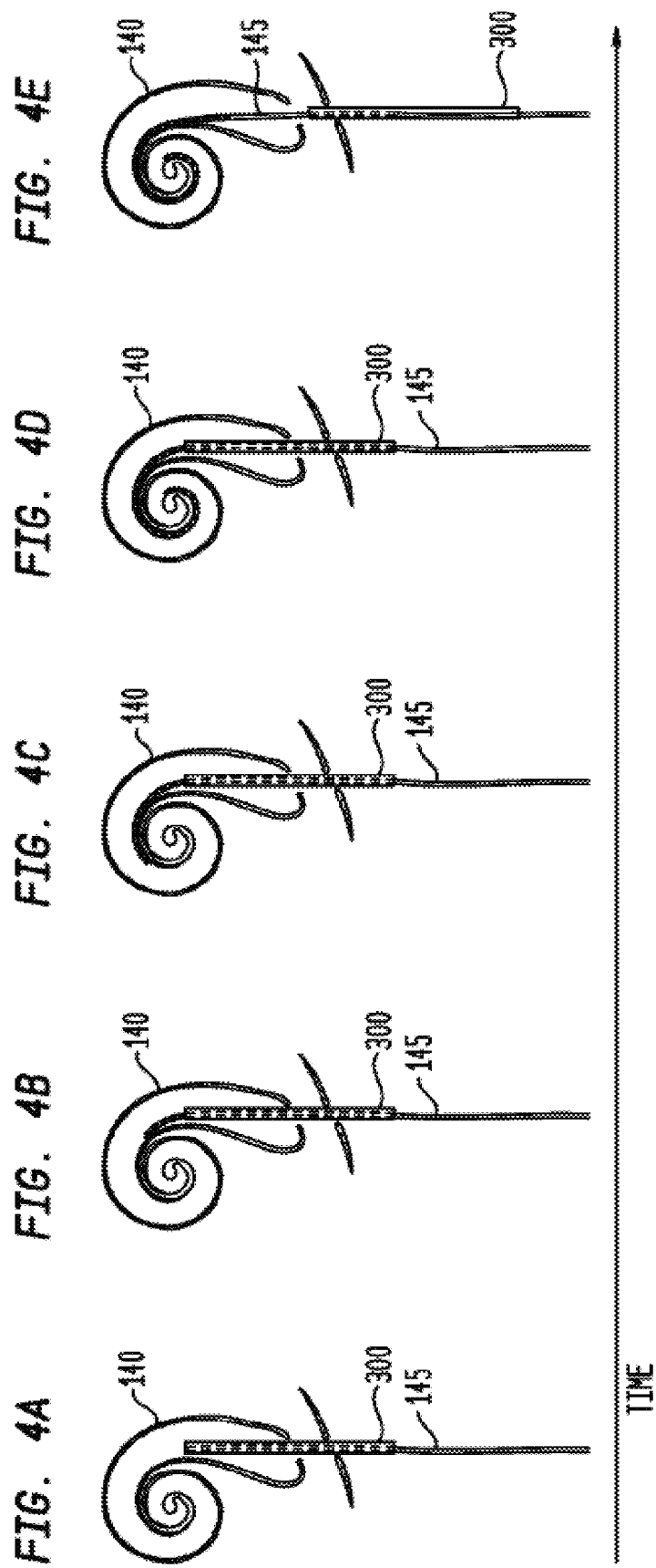

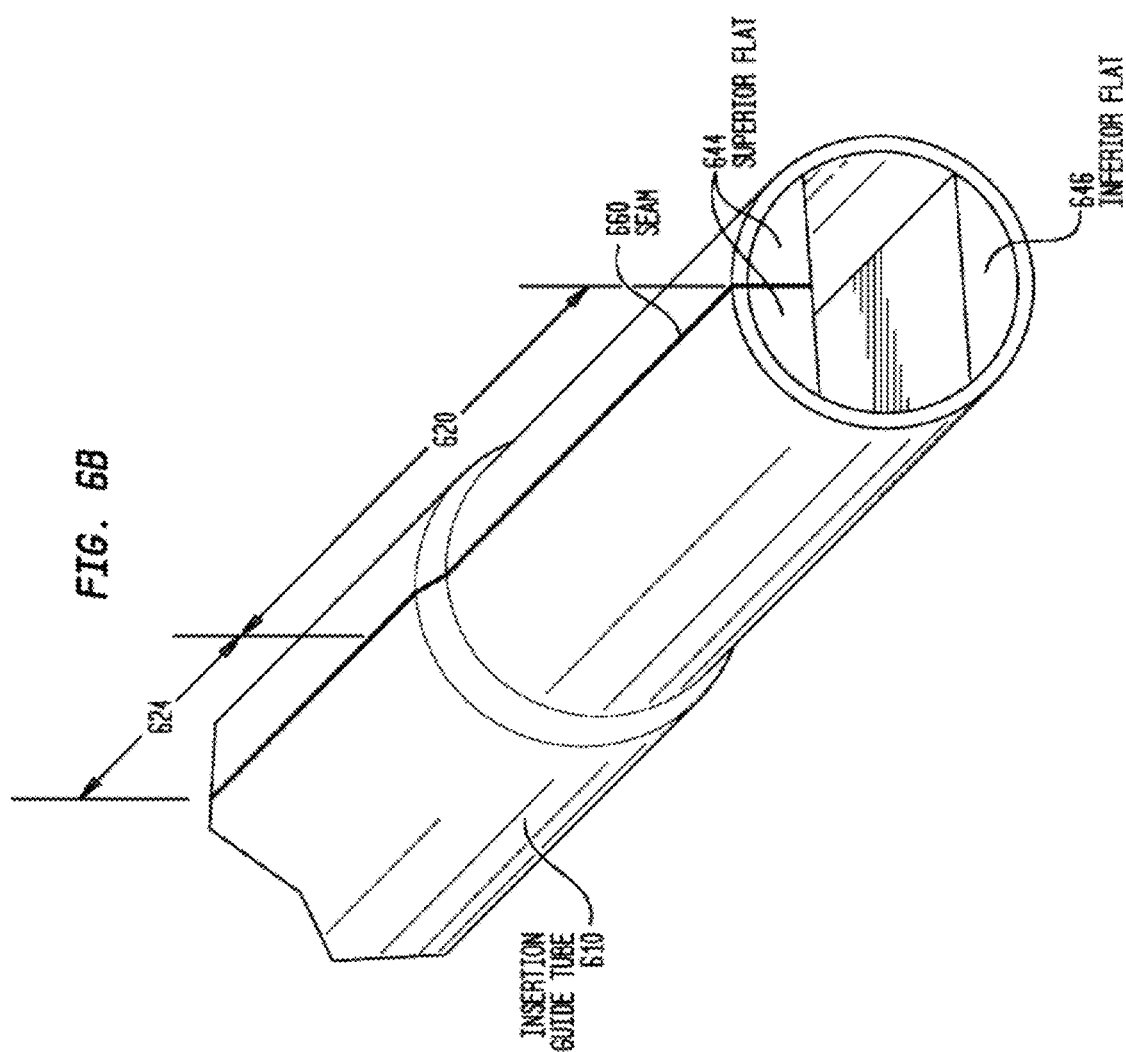

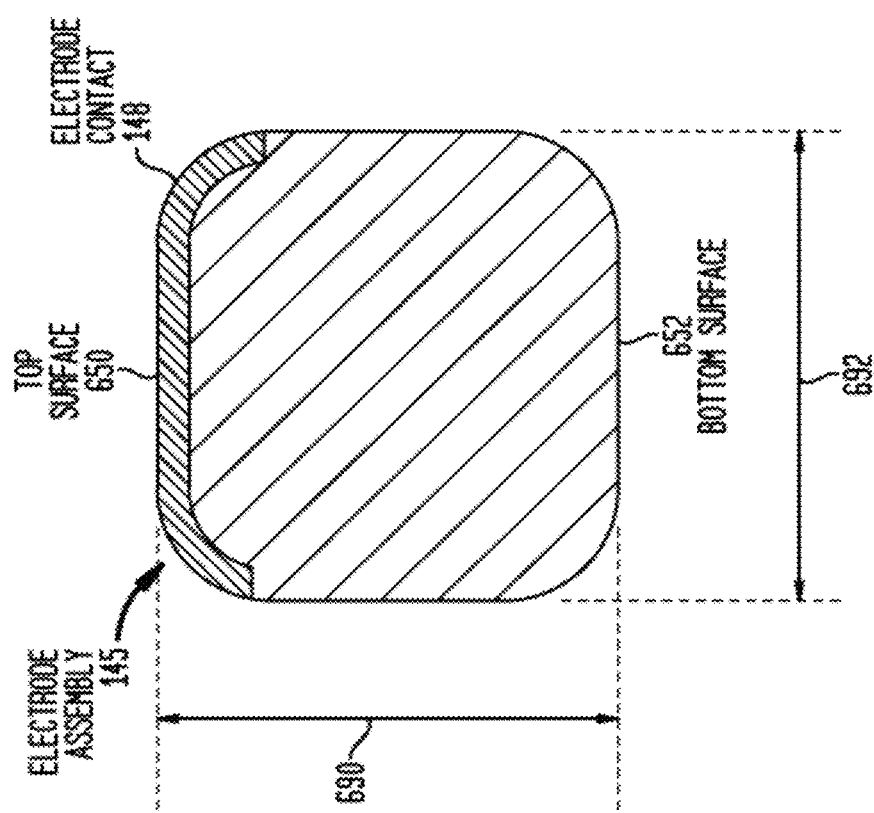

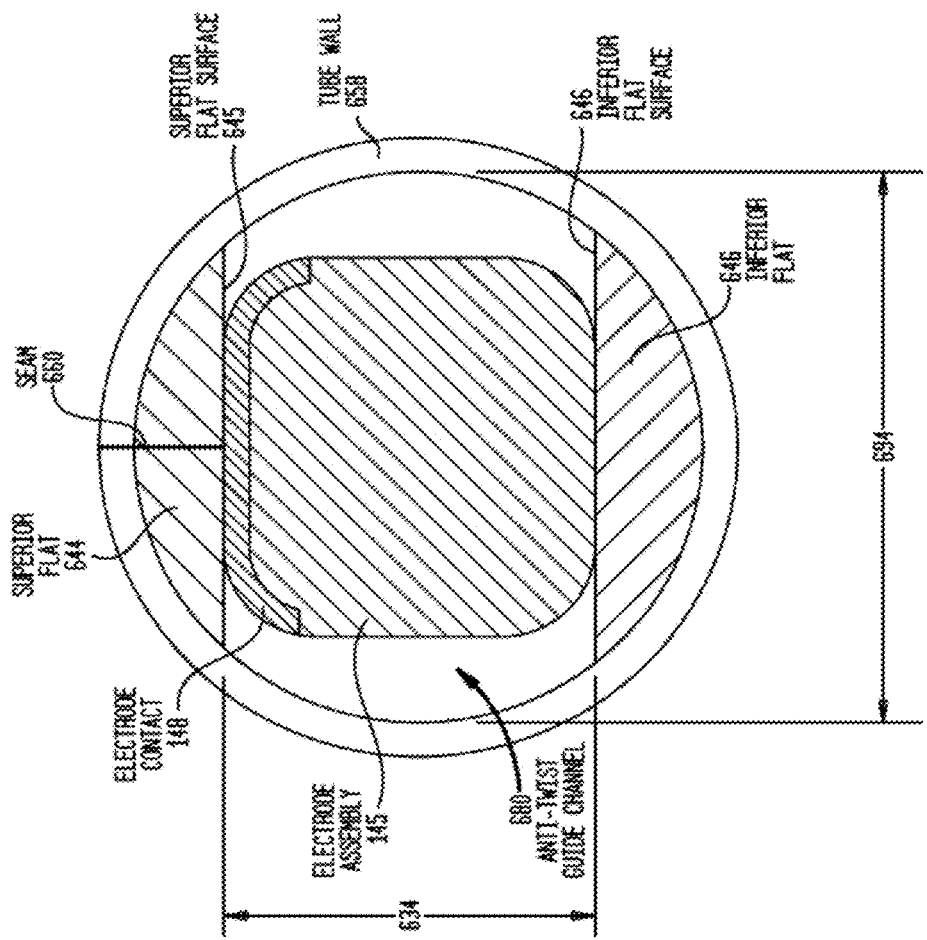

*FIG. 10*

| 0.04 | 0.05 | 0.001 | 2 |
|---|---|---|---|
| -0.001 | 0.001 | 15 | 0.001 |
| 0.1 | 2 | -0.001 | 0.051 |
| 2 | 0.09 | 0.002 | 0.04 |

FIG. 14

| 0.0095 | 0.011 | 0.01 | 14 |
|---|---|---|---|
| 0.05 | 0.11 | 2 | 0.01 |
| 0.1 | 2 | 0.1 | 0.009 |
| 2 | 0.09 | 0.05 | 0.011 |

FIG. 29
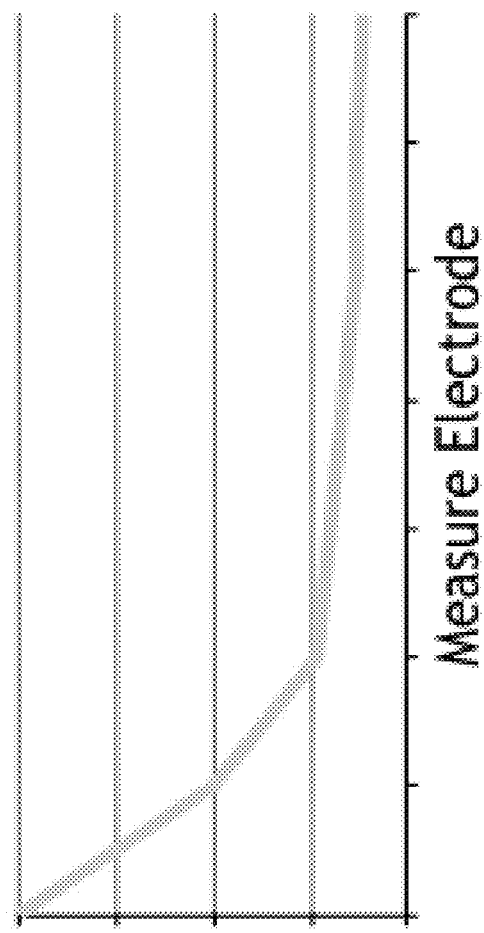
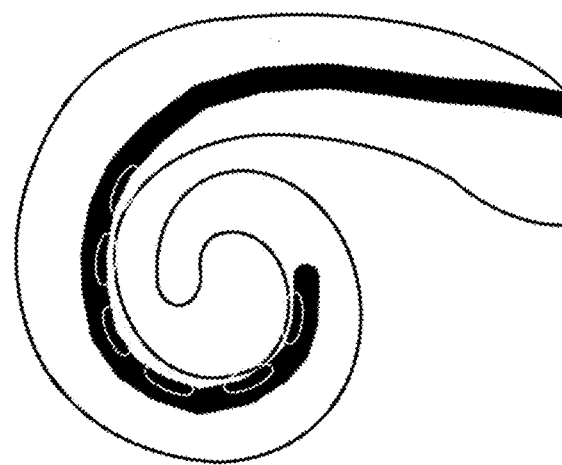

FIG. 30
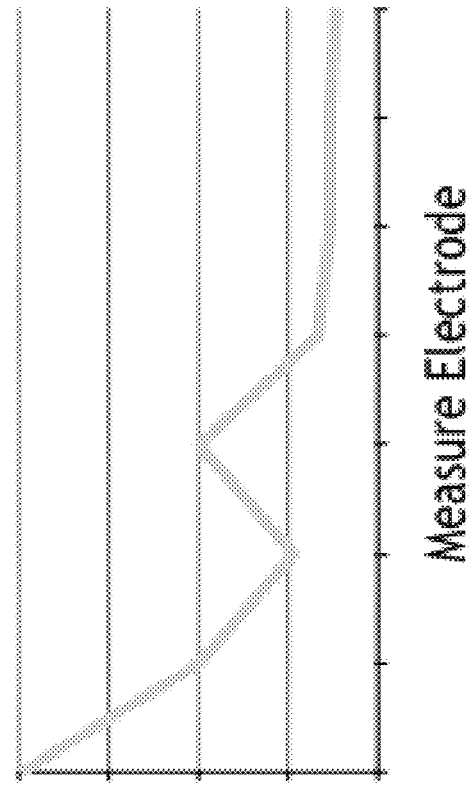
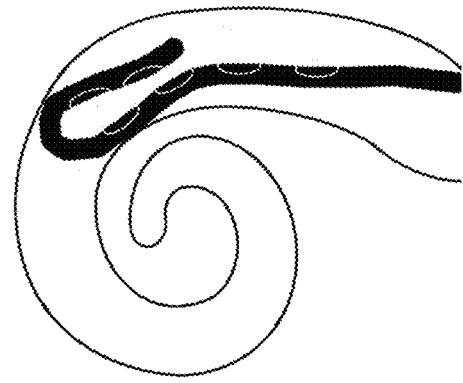

ADVANCED ELECTRODE ARRAY INSERTION WITH CONDITIONING

The present application is a Continuation-in-Part of PCT/ES2017/000049, filed Apr. 19, 2017, which claims priority benefit of Spain Application No. P201600344, filed Apr. 21, 2016. The entire contents of these applications are incorporated herein by reference in their entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is a method, comprising obtaining information indicative of a phenomenon sensed at a read electrode of a cochlear implant electrode array relative to a reference and/or at a read electrode remote from the electrode array relative to a reference where one of the electrodes of the cochlear implant electrode array was energized, executing a first analysis of the information to identify one or more first meanings from among a first group of meanings of the sensed phenomenon, conditioning the obtained information based on the identified one or more first meanings, and executing a second analysis of the conditioned information to identify one or more second meanings from among a second group of meanings of the sensed phenomenon.

In another exemplary embodiment, there is a method, comprising, commencing insertion of a cochlear electrode array into a cochlea of a person, energizing at least one stimulation electrode of the electrode array that is located inside the cochlea and/or an electrode remote from the electrode array; reading a read electrode, relative to a reference, that received an electrical signal from the energized stimulation electrode, and determining, based on the reading, that a physical characteristic associated with the electrode array that is strictly local to the electrode array existed and/or exists In another embodiment, there is a method, comprising (i) obtaining information indicative of a phenomenon sensed at a read electrode of a cochlear implant electrode array, relative to a reference; and (ii) using that information to determine whether or not a deleterious cochlear electrode array position exists inside the cochlea of a recipient, wherein the actions used to make the determination correspond to a statistical based accuracy rating of at least 90 out of 100 vis-à-vis determinations that a deleterious cochlear electrode array position exists.

In another embodiment, there is a system, comprising a control unit configured to receive telemetry from an implantable system of a cochlear implant electrode array and determine a feature related to a global position of the electrode array relative to an interior of the cochlea of the recipient, wherein the telemetry includes data based on electrical phenomenon associated with the electrode array, the control unit is further configured to automatically analyze the data to determine whether or not portions of the data are acceptable for use in determining the feature, and the control unit is configured to automatically modify the data to at least one of eliminate or replace the portions of the data that are deemed not acceptable for use in determining the feature, and use the modified data to determine the feature related to the global position of the electrode.

BRIEF DESCRIPTION OF THE DRAWINGS

Embodiments are described below with reference to the attached drawings, in which:

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIGS. 6A and 6B are views of an embodiment of the insertion guide tube;

FIGS. 6C and 6D are views of an exemplary electrode array and such located in the insertion guide tube;

FIGS. 8-16 present some exemplary graphics associated with some exemplary insertion regimes;

FIGS. 28-30 present some exemplary graphics associated with some exemplary insertion regimes;

DETAILED DESCRIPTION

Figure 1:
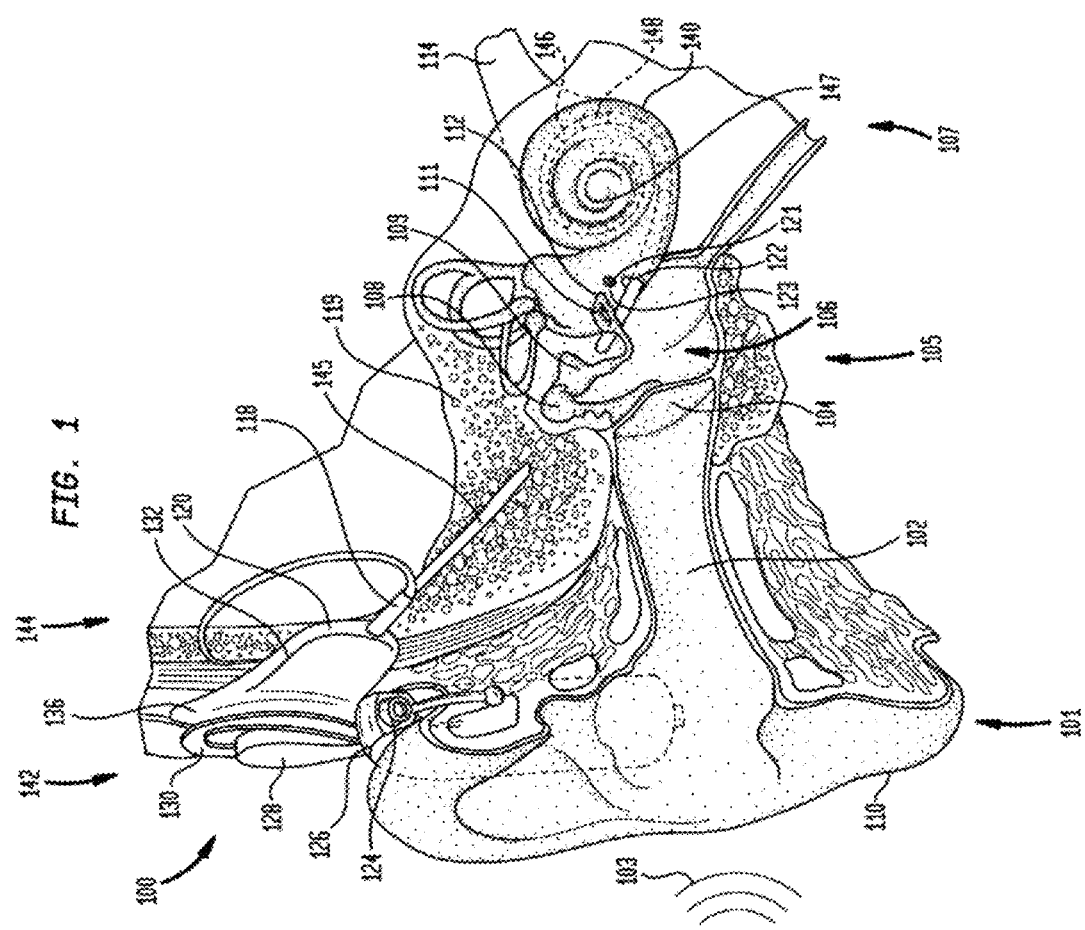
FIG. 1 is a perspective view of an exemplary hearing prosthesis in which at least some of the teachings detailed herein are applicable.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Electrode assembly 145 may be inserted into cochlea 140 with the use of an insertion guide. It is noted that while the embodiments detailed herein are described in terms of utilizing an insertion guide or other type of tool to guide the array into the cochlea, in some alternate insertion embodiments, a tool is not utilized. Instead, the surgeon utilizes his or her fingertips or the like to insert the electrode array into the cochlea. That said, in some embodiments, alternate types of tools can be utilized other than and/or in addition to insertion guides. By way of example only and not by way of limitation, surgical tweezers like can be utilized. Any device, system, and/or method of inserting the electrode array into the cochlea can be utilized according to at least some exemplary embodiments.

An atraumatic electrode array insertion process and obtaining the correct final position of the electrodes has utilitarian value with respect to obtaining utilitarian electrode array insertion outcomes. In addition to trauma resulting from the electrode impacting sensitive cochlea structure during insertion of the electrode array, an anomalous final position of one or more electrodes can impact the ultimate performance of the electrode array. Such anomalous final positions can be, by way of example only and not by way of example, the electrode array dislocating from the scala tympani to the scala vestibuli. Another anomalous position can be, for example, a scenario where the electrode is inserted to an inappropriate depth. This can cause a frequency gap and/or can cause some part of a pre-curved array to "bow" away from the modiolus, resulting in greater current spread (sometimes excessive current spread), relative to that which would be the case without the bowing, etc. Also, the electrode tip could get stuck during the insertion process, causing the electrode fold over itself, which could cause excessive spread (or at least more current spread relative to that been the case without the fold over), and/or can require some electrodes to be disabled.

The teachings detailed herein are directed towards identifying at least one of the aforementioned electrode array insertion scenarios. Some embodiments can include utilizing verifying electrode position via medical imaging (e.g., CT scan, X-ray, etc.), which require the patient to be exposed to radiation during the process of obtaining medical images, as well as the need for medical equipment in the operating room to provide and otherwise obtain the imaging, as well as a subsequent analysis by an expert to assess the correct insertion of the electrode holder. Some embodiments of the teachings detailed herein utilize such, while other embodiments specifically do not utilize such, but instead utilize other methods to evaluate or otherwise obtain information indicative of a given electrode array insertion scenario. Some embodiments include the action of measuring neuronal activation after stimulation. This exemplary embodiment can require subjective expert analysis and/or can also be dependent on having a good/acceptable neural response. However, in some instances, such is not always obtainable. Again, as with the aforementioned imaging, some embodiments herein utilize such while other embodiments specifically do not utilize such methods. In at least some exemplary embodiments, methods of determining an insertion scenario can utilize voltage measurements in the cochlea. In an exemplary embodiment of such embodiments, the interpretation of the obtained voltage measurements still requires subjective analysis by an expert. In addition, these measurements can be rendered more difficult to interpret than otherwise might be the case by the presence of so-called air bubbles, open electrodes, shorted electrodes, and/or electrode extrusion. Some embodiments of the teachings detailed herein utilize the aforementioned voltage measurements coupled with expert analysis, while in other embodiments some of the teachings detailed herein specifically avoid utilization of expert analysis to obtain or otherwise analyze and electrode array insertion scenario.

Some embodiments include obtaining voltage measurements from inside and/or outside the cochlea and analyzing them in, by way of example only and not by way of limitation, an automated manner, by comparing the voltage measurements to statistical data. Such can enable the removal or otherwise the elimination of the use of expert analysis to evaluate a given electrode array fold over based on one of the obtained voltage measurements. Some such embodiments enable the interpretation of the voltage measurements in a manner that is robust to the variations in the cochlea environment that may lead to incorrect results, including so-called false positives. Robust results can have utilitarian value in at least some exemplary scenarios because some of the anomalous positions only occur very rarely (e.g., 1 in 70, 1 in 100, 1 in 150, etc.). Accordingly, even a relatively small occurrence of false positive identification of an anomalous position could far exceed the natural occurrence of the anomaly and thereby render the elimination of the expert analysis lacking utilitarian value.

Figure 2A:
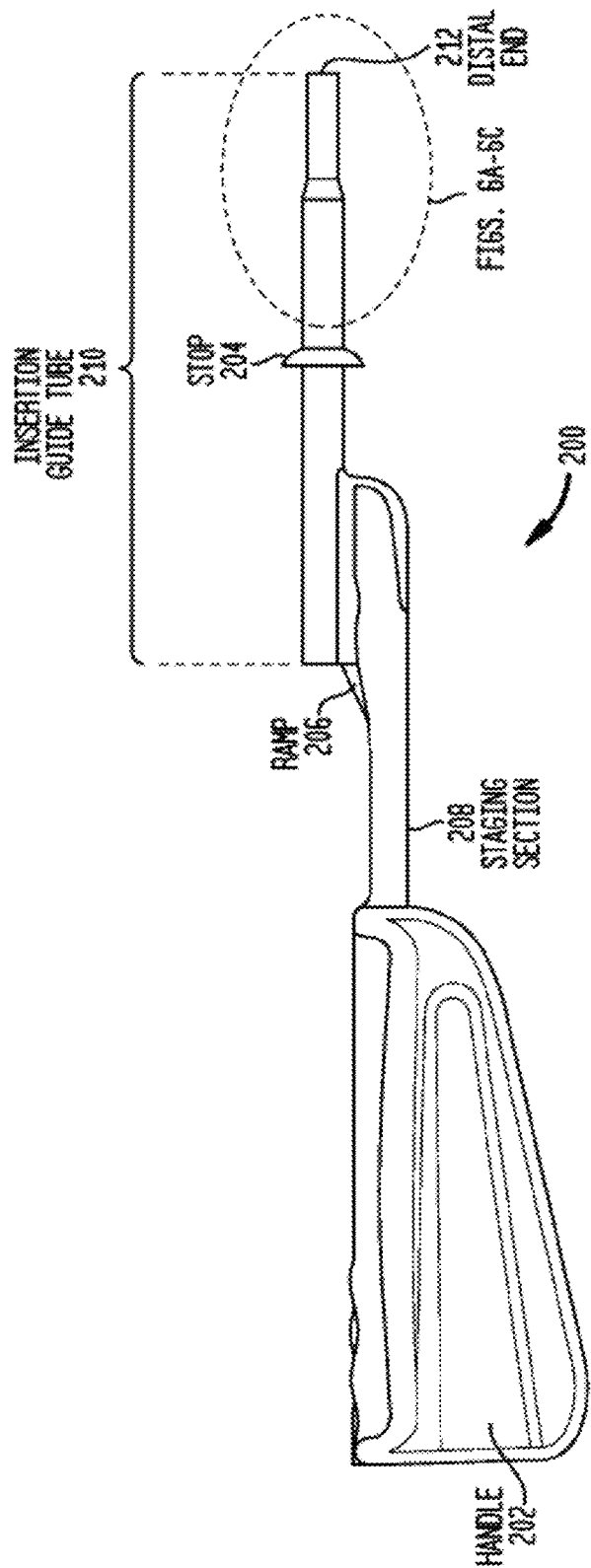
FIGS. 2A and 2B are side views of an embodiment of an insertion guide for implanting a cochlear implant electrode assembly such as the electrode assembly illustrated in FIG. 1.

FIG. 2A presents a side view of an embodiment of an insertion guide for implanting an elongate electrode assembly generally represented by electrode assembly 145 into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 2B:
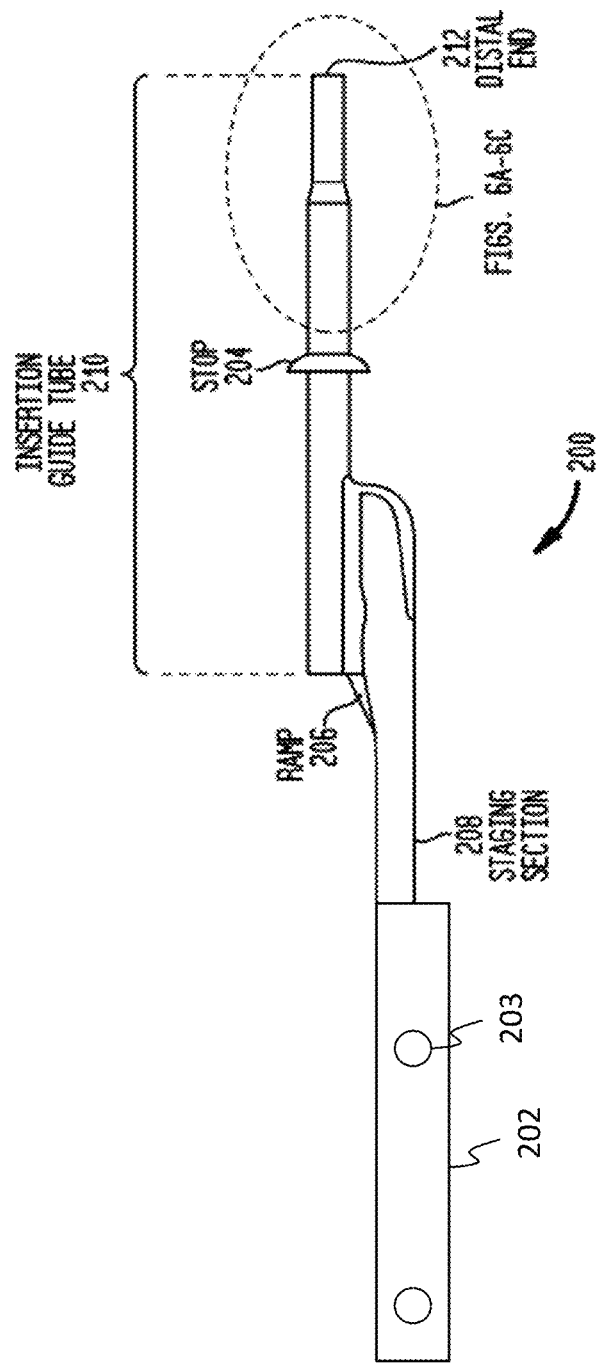

FIG. 2B depicts an alternate embodiment of the insertion guide 200, that includes a handle 202 that is ergonomically designed to be held by a surgeon. This in lieu of the robotic arm adapter 202.

Figure 3B:
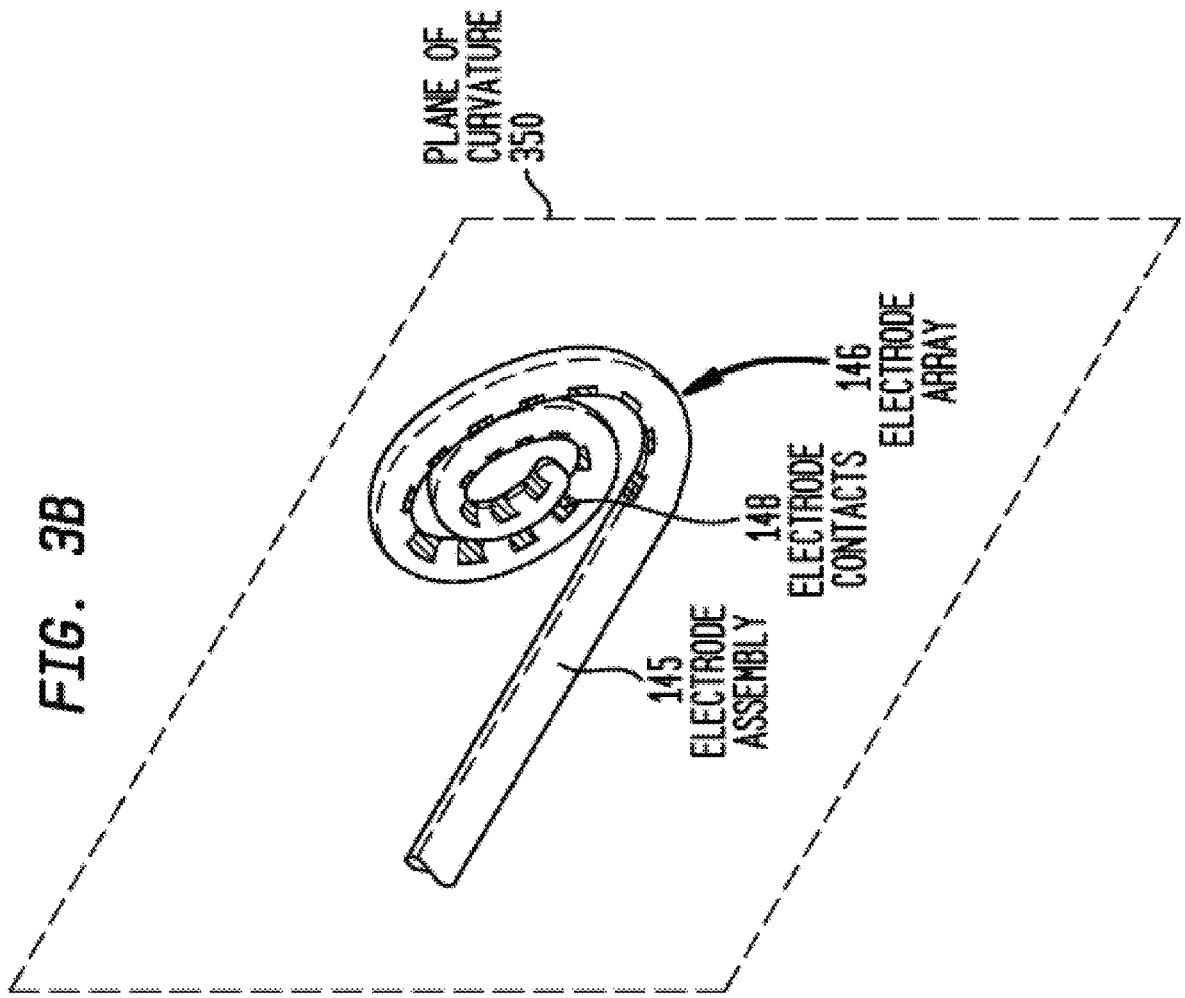

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube, etc., but instead remains straight.

FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 500 retains electrode assembly 145 in a substantially straight configuration, thereby preventing the assembly from taking on the configuration shown in FIG. 3B.

The inability of electrode assembly 145 to curve to accommodate the bias force induces stress in the assembly. Pre-curved electrode assembly 145 will tend to twist while exiting insertion guide tube 510 to reduce this stress. With the distal end of the electrode assembly is curved to abut the lumen wall, the assembly twists proximally.

Figure 5A:
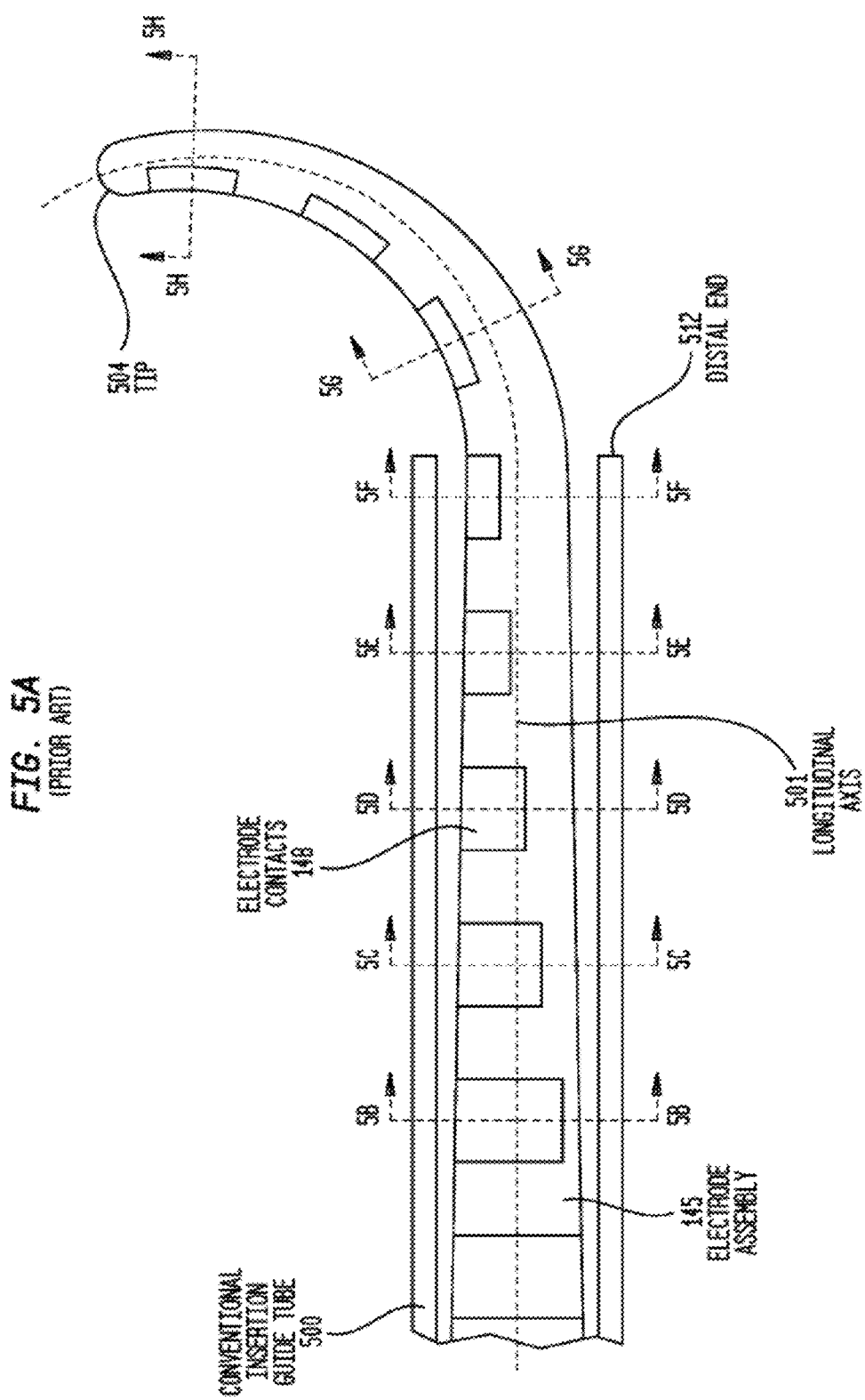
FIG. 5A is a side view of a perimodiolar electrode assembly partially extended out of a conventional insertion guide tube showing how the assembly may twist while in the guide tube.
Figure 5E:
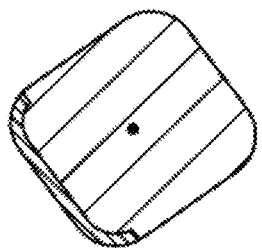
FIGS. 5B-5I are cross-sectional views of the electrode assembly illustrated in FIG. 5A.
Figure 5D:
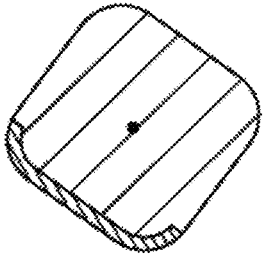
Figure 5C:
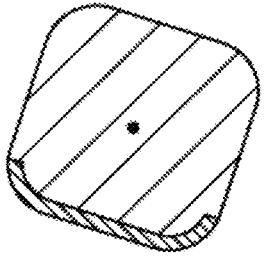
Figure 5B:
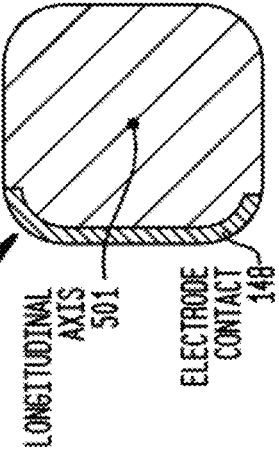

This is illustrated in FIGS. 5A-5I. FIG. 5A is a side view of perimodiolar electrode assembly 145 partially extended out of a conventional insertion guide tube 500, showing how the assembly may twist while in the guide tube. FIGS. 5B-5F are cross-sectional views taken through respective sections 5B-5B, 5C-5C, 5D-5D, 5E-5E, and 5F-5F of electrode assembly 145 in FIG. 5A.

As shown in FIGS. 5A-5F, the portion of electrode assembly 145 in insertion guide tube 510 is twisted about its longitudinal axis, resulting in electrode contacts 148 in the twisted region to have a different radial position relative to insertion guide tube 510. As shown in FIGS. 5A and 5G-I, as electrode assembly 145 exists in insertion guide tube 500, the assembly is free to curve in accordance with its bias force. However, the orientation of electrode contacts in the deployed region of the assembly is adversely affected by the twisted region of the assembly remaining in guide tube 510.

Accordingly, some embodiments detailed herein and/or variations thereof are directed towards an insertion guide having an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This generally ensures that when the electrode assembly is deployed from the distal end of the insertion guide tube, the electrode assembly and insertion guide tube have a known relative orientation.

Figure 6A:
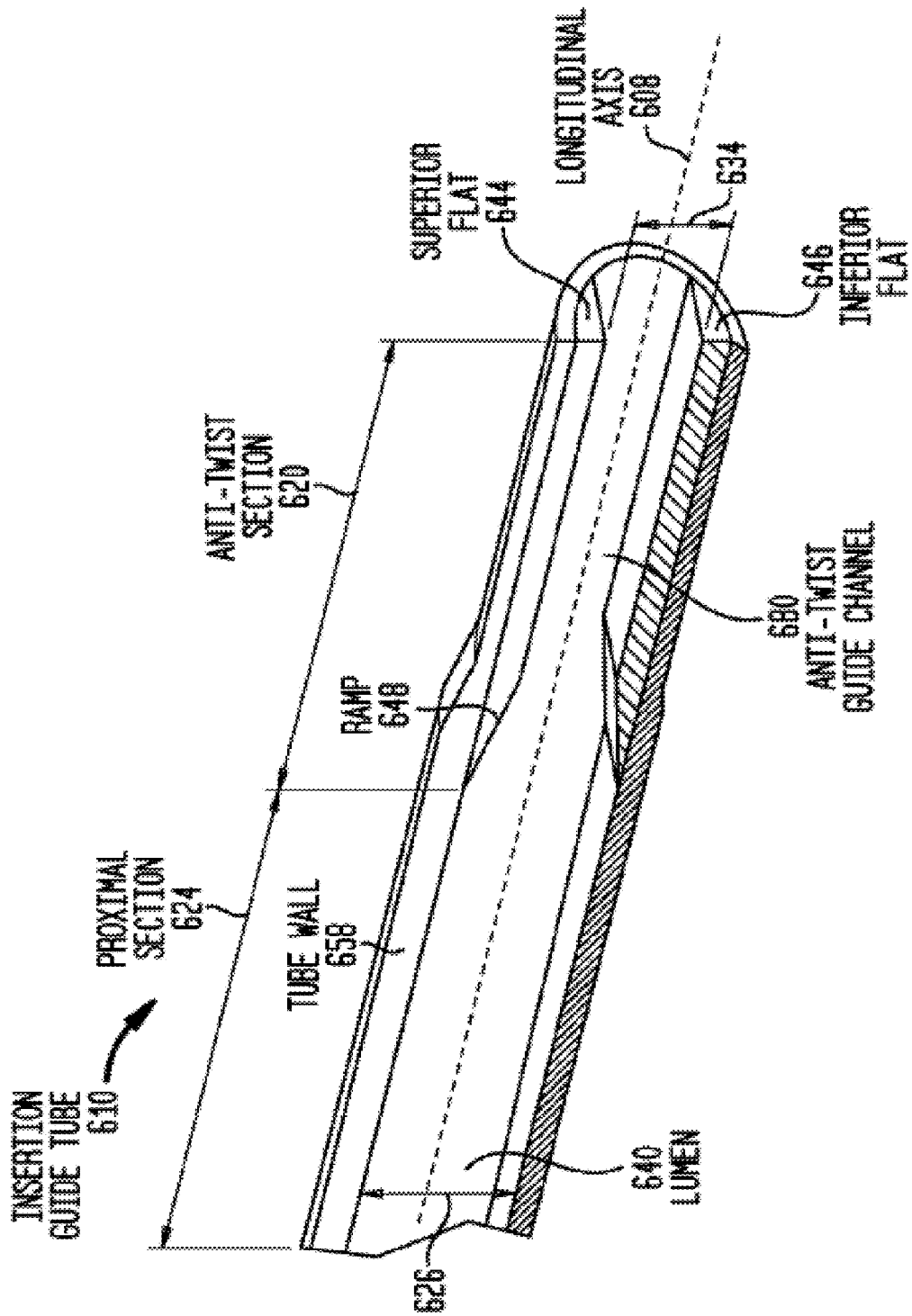

FIGS. 6A-6D are different views of but some exemplary embodiments of insertion guide tube 210, referred to herein at insertion guide tube 610. For ease of description, features of the guide tube will be described with reference to the orientation of the guide tube illustrated in the figures. FIG. 6A is a partial cross-sectional view of an embodiment of insertion guide tube 210, referred to herein as insertion guide tube 610. As can be seen, insertion guide tube 610 includes an anti-twist section 620 formed at the distal end of the guide tube. Anti-twist section 320 is contiguous with the remaining part of guide tube 610. Guide tube 610 has a lumen 640 which, in proximal section 624 has a vertical dimension 626, and an distal anti-twist section 620 has a smaller vertical dimension 634 described below. The vertical dimension of lumen 640 decreases from dimension 626 to dimension 634 due to a ramp 648 at the proximal end of anti-twist section 642.

Anti-twist section 620 causes a twisted electrode assembly traveling through guide tube 610 to return to its untwisted state, and retains the electrode assembly in a straight configuration such that the orientation of the electrode assembly relative to the insertion guide tube 610 does not change.

As shown in FIG. 6C, electrode assembly 145 has a rectangular cross-sectional shape, with the surface formed in part by the surface of the electrode contact, referred to herein as top surface 650, and the opposing surface, referred to herein as bottom surface 652, are substantially planar. These substantially planar surfaces are utilized in embodiments of the insertion guide tube described herein.

Tube wall 658 in anti-twist section 620 has surfaces 644 and 646 which extend radially inward to form an anti-twist guide channel 680. Specifically, a superior flat 644 provides a substantially planar lumen surface along the length of section 620. As shown best in FIGS. 6A, 6B, and 6D, superior flat 644 has a surface that is substantially planar and which therefore conforms with the substantially planar top surface 650 of electrode assembly 145. Similarly, inferior flat 646 has a surface that is substantially planar which conforms with the substantially planar bottom surface 652 of electrode assembly 145. As shown in FIG. 6D, when a distal region of electrode assembly 145 is located in anti-twist section 620, the surfaces of superior flat 644 and inferior flat 646 are in physical contact with top surface 650 and bottom surface 652, respectively, of the electrode assembly. This prevents the electrode assembly from curving, as described above.

In an exemplary embodiment, during insertion and/or after full insertion of the electrode array into the cochlea, stimulation of at least 1 electrode pair of the cochlear implant is executed and measurement/s are obtained that are related to the electric field in the cochlea resulting from the aforementioned stimulation. These measurements can be obtained by any utilitarian manner that can provide data to enable the teachings detailed herein. The stimulation intensity can be manually or automatically adjusted to obtain a good resolution signal. One method for performing the adjustment quickly and automatically is to measure the potential of the electrodes closest to the stimulating pair and adjusting the signal intensity and gain to ensure that this signal is using the full dynamic range. Another method is to measure the electrodes furthest from the stimulating pair with the narrowest separation and adjusting the signal intensity and gain to ensure sufficient level above the noise floor. In some exemplary embodiments, the stimulation intensity is set at two current levels. In some other embodiments, the stimulation intensity is set at other current level values. In an exemplary embodiment, a stimulation intensity is utilized that is the same throughout all the measurements. Still, in at least some exemplary embodiments, the teachings detailed herein can be executed along with a method action of calibrating the stimulation intensity with respect to executing the teachings detailed herein with respect to a given recipient. In some embodiments, there is thus a control unit configured to calibrate a stimulation intensity of the implantable system and cause the implantable system to stimulate tissue based on the calibration intensity so as to generate electrical current to create the electrical phenomenon. In some embodiments, the control unit is configured to execute the calibration procedure automatically.

In some exemplary embodiments, the electrode potential decays with distance in the case of fixed reference electrodes (although, in some embodiments, not with respect to depth sounding/modiolous wall distance, as well as impedance spectroscopy—more on this below), and, in some exemplary electrode array insertion scenarios, this decay pattern (or continuity pattern in some other embodiments—a continuity pattern can have a decay and then an increase, depending on what read electrodes are being used relative to the stimulating electrodes—herein, decay refers to the general phenomenon that voltage should decrease the further one is away from the stimulating electrodes) is interrupted by the presence of open electrodes, electrodes not in contact with tissue and/or shunted electrodes. In some instances, the potentials of the read electrodes change smoothly (e.g., depth sounding and/or impedance spectroscopy), this smooth change pattern is interrupted by the presence of open electrodes, electrodes not in contact with tissue and/or shunted electrodes. Some things look like discontinuity in a smooth change scenario. For example, a change in direction could indicate fold over, a step change can indicate scala dislocation. In some embodiments, the potentials change smoothly and the attributes of the change/features of the change can have utility with respect to identifying the given insertion scenario. The teachings detailed herein can be implemented to avoid confusing discontinuities/changes that can be utilitarian with respect to determining a deleterious array insertion scenario with those caused by open/short/shunt/bubbles, etc. Other scenarios that can interrupt the decay pattern and/or continuity pattern exist. There is utilitarian value in identifying the occurrence of the phenomenon that interrupts the continuity pattern, or at least identifying that a phenomenon exists that interrupts the decay/continuity pattern (i.e., in some embodiments, it is not necessary to identify specific phenomenon that interrupts the decay/continuity pattern, but only to identify that a phenomenon has occurred which will interrupt the decay pattern). This is because, in some embodiments of the teachings detailed herein, the decay pattern is utilized to determine whether or not one or more anomalous events have occurred (sometimes referred to herein deleterious events), such as by way of example only and not by way of limitation, fold over (including tip fold over), bowing of the electrode array, and dislocation (e.g., the puncturing of a wall of the cochlea, such that one or more electrodes of the electrode array have been driven outside the cochlea duct during the insertion process). According to some embodiments, there are devices, systems, and/or methods of combining several algorithmic components such that the end result is the provision of a robust determination of anomalous electrode position.

In an exemplary embodiment, there exists a method, as well as a device and/or system, for the detection of electrodes that should not be used in determining whether or not an anomalous condition exists. Additional details of this will be described below. For the moment however, it is noted that in at least some embodiments, these electrodes may not be used because, by way of example only and not by way of limitation, of an issue with the electrode, current source or sensing circuit and/or because of the presence of an air bubble proximate the electrode and/or because the electrode is outside cochlea. In an exemplary embodiment, method actions include the marking or removal of such electrodes so that subsequent actions can avoid erroneous results/results that might skew the data to result in a false positive resulting from reliance on data obtained from these electrodes. In at least some exemplary embodiments, the measurement results can be conditioned, as will be described in greater detail below. Briefly, however, the conditioning which can address variance due to noise, manufacturing, contaminants, insertion artefacts etc., can be executed to include one or more of the following: reduce the noise of these measurements, improve the detection of defective electrodes and scaling and normalised measurements at the interval [0,1] prior to the process stage.

Figure 7:
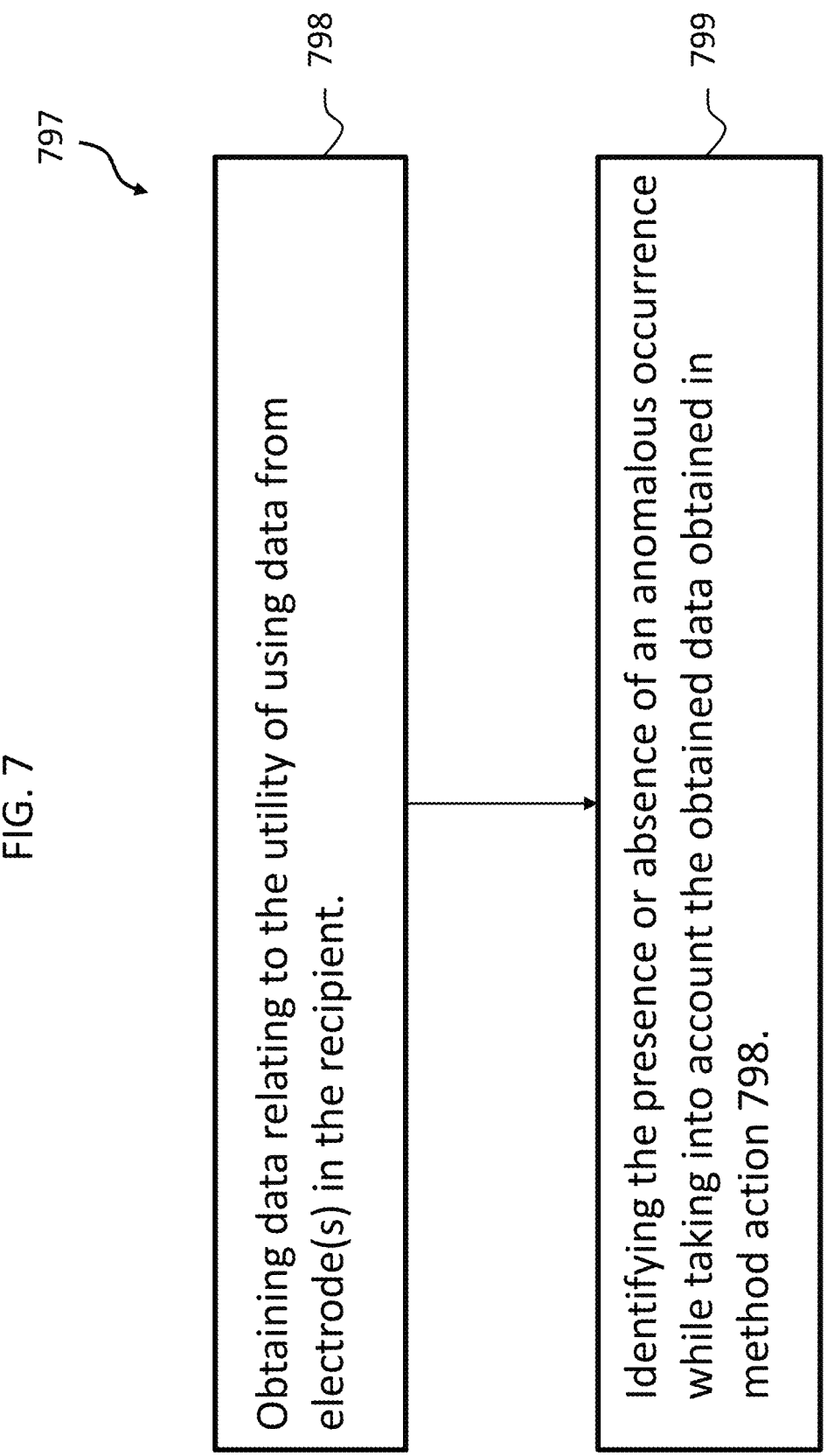
FIG. 7 is an exemplary flowchart for an exemplary method.

To put the aforementioned method action into context, FIG. 7 provides an exemplary algorithm for a method, method 797, that includes method action 798, which includes obtaining data relating to the utility of using data from one or more electrodes in the recipient. Such method actions can correspond to any method action that can result in the identification of one or more of the phenomenon detailed above and/or as will be detailed below. Method 797 further includes method action 799, which includes identifying the presence or absence of an anomalous occurrence while taking into account the obtained data obtained in method action 799. In this regard, method action 799 can include, following the preliminary action of method action 798, one or more of actions that result in one or more of the following determinations:

The determination of electrodes that are not in the cochlea and/or the depth of insertion;

The determination of electrodes that are folded over (excluding those outside the cochlea);

The determination of electrodes that are bowing away from the modiolus (excluding those outside the cochlea or faulty);

The determination of electrodes that are in the scala tympani (excluding those outside the cochlea);

The determination of scala dislocation (where the array rides up and punctures the basilar membrane and extends into the scala vestibule).

In at least some exemplary embodiments, the combination of various of the above elements can allow for the elimination of common sources of error in the algorithms aimed at identifying one or more of the aforementioned individual issues that can occur vis-à-vis the anomalous insertion. The individual determination algorithms can also be applied in different orders to eliminate bias. By way of example only and not by way of limitation, in an exemplary embodiment, if a fold over is present, this may affect the reliability of the algorithm to detect scala dislocation or detecting electrodes bowing away from the modiolus. In some embodiments, when the teachings detailed herein are used, at least in combination with a measurement technique that includes incremental updates, the determination of how many electrodes are inside the cochlea and, in some instances, along with one or more of the other determinations detailed herein, such can have utilitarian value with respect to reducing and/or eliminating false positives relative to that which would be the case in the absence of such. In at least some exemplary embodiments, the exact combinations are dependent on the individual algorithms. In at least some exemplary embodiments, there can be utilitarian value with respect to implementing the teachings detailed herein utilizing a hierarchical determination. Also, some exemplary embodiments include the combination of one or more algorithms, where the combination is not executed in a strictly ordered fashion, but instead, in an exemplary embodiment, the algorithm could be combined in parallel and recurrent fashions.

That is, method 797, as noted above, includes method action 799, which includes identifying the presence or absence of an anomalous occurrence while taking into account the obtained data obtained in method action 798. In an exemplary embodiment, taking into account the obtained data obtained in method action 798 includes conditioning the overall data. In this regard, in an exemplary embodiment, there includes a method action corresponding to conditioning the data, as distinct or otherwise distinguished from a method action of normalizing the data (more on this below). In an exemplary embodiment, the data is conditioned prior to actions of processing, which actions of processing are utilized to identify the presence or absence of an occurrence of an anomalous condition.

Some embodiments included executing one or more of several possible optional conditioning actions by observing that the recorded data has some common aspects the removal of which and/or the modification of which will result in improved reliability of detection and/or the reduced likelihood of a false positive.

Some such data that has utilitarian value vis-à-vis removal/modification thereof will now be described, along with some exemplary embodiments of identifying such.

Embodiments can include several alternative methods for determining electrode faults and/or determining specific anomalous positions. In at least some exemplary embodiments, some of the methods detailed herein are based on the representation of the measurements on n electrodes as an nxn matrix, where the data in each row correspond to the n observation made while stimulating on a given electrode pair. However, in some alternate embodiments, the representation could be changed, providing that such can enable the teachings detailed herein.

With reference back to FIG. 7, again, there is utilitarian value with respect to obtaining data relating to the utility of using data from the electrodes in a recipient. In general, the teachings detailed herein are directed to obtaining data in some form or another from one or more electrodes that are implanted in a recipient. (It is noted that the phrase "implanted in a recipient" as used herein includes both properly implanted electrodes as well as improperly implanted electrodes (e.g., electrodes that have been driven through the basilar membrane from the scala tympani to the scala vestibuli, such as through dislocation) as well as electrodes that have not reached their ultimate implantation location, but are, for all intents and purposes, are implanted in the recipient (e.g., the most proximal electrode on the electrode array where only the three or four most distal electrodes have been inserted into the cochlea at a given temporal location.) This data can be a result of the action of energizing an electrode of an electrode array that is inside the cochlea, energizing an electrode of the electrode array that is outside the cochlea, energizing an electrode of the cochlear implant that is not part of the array, etc. This can be a result of the action of using electrode/s of the electrode array that is partially or fully inside the cochlea as a read electrode/s (sometimes also referred to as observation electrode/s—any electrode/s from which data is obtained that can enable the teachings herein can be a read electrode/ observation electrode, relative to a reference), using an electrode of the electrode array that is outside the cochlea as a read electrode, utilizing an extra cochlear electrode as the read electrode, etc. Note also that in at least some exemplary embodiments, there are teachings directed herein to obtaining data from one or more electrodes that are not part of the device that is implanted, or otherwise not part of the device that will be implanted (e.g., the cochlear implant), but is/are part of a device that is utilized during the insertion process, providing that such can result in obtaining data relating to the utility of utilizing data from one or more electrodes in the recipient. Not only can this be the case for a read electrode/s (or a plurality of such), such can also be the case with respect to the energized electrode. That is, in an exemplary embodiment, the source of the electrical field that is sensed inside the cochlea can be generated or otherwise originated at a location outside the cochlea, and the generator of the current can be a device that is not part of the cochlear implant, but is a separate device that is utilized during insertion. Additional details of such will be provided below.

It is briefly noted that reference will often be made to electrodes in the singular, such as the stimulation electrode or the read electrode. It is to be understood that any such disclosure is also made with the understanding that any read electrode requires a reference, and thus typically another electrode, and any energizing electrode needs a corresponding electrode to serve as the sink, and visa/versa.

Still with reference to FIG. 7, and in particular, method action 799, the action of identifying the presence or absence of anomalous occurrence can be executed by analyzing a data matrix, which is briefly referred to above, in some of the more specific details of which will be provided below. This fact is briefly mentioned here because the following will reference in some instances, the matrix. For ease of understanding of the teachings detailed herein, the more specific features of the matrix are presented below, and thus the matrix will be referred to in the general sense in the near-term.

Figure 8:
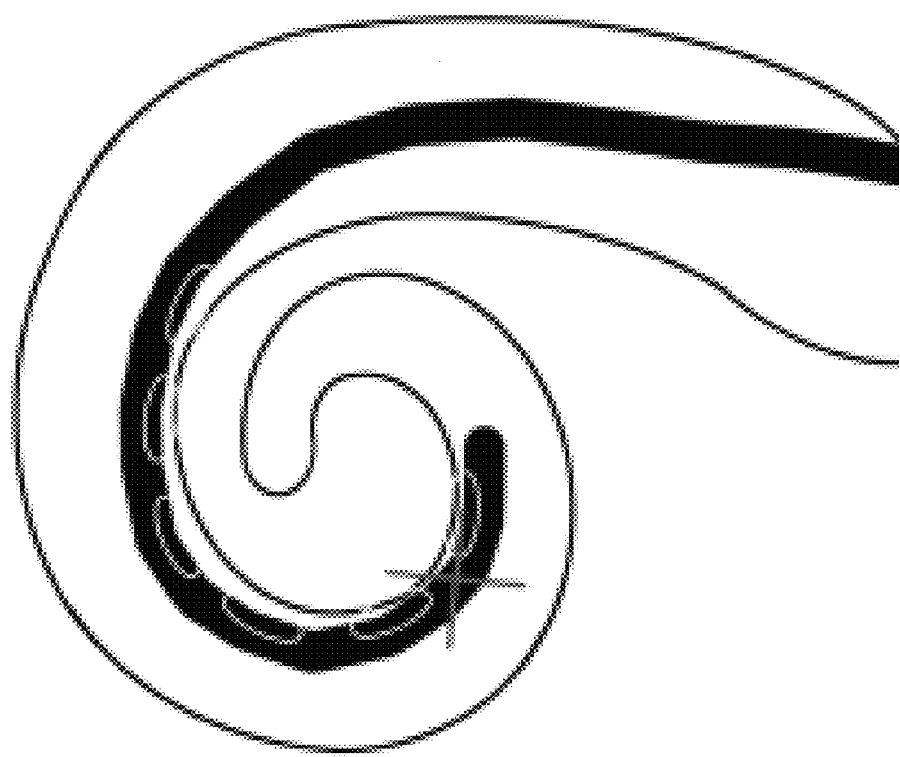
Figure 9:
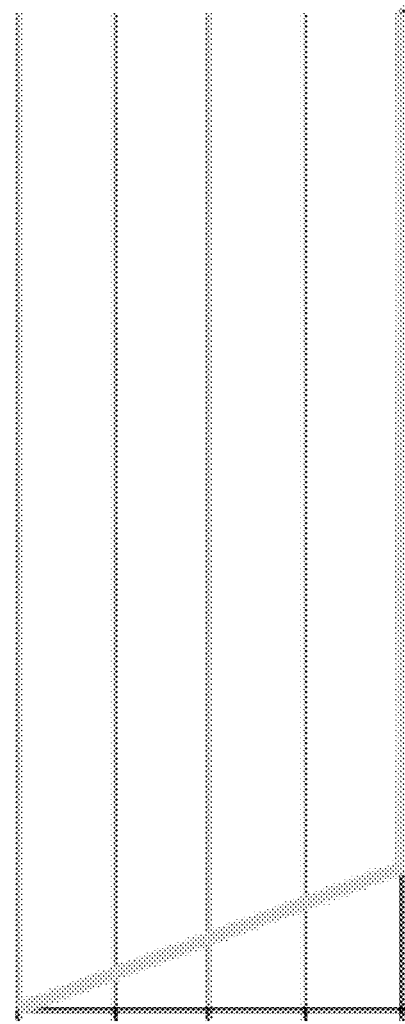

Some exemplary embodiments of method action 798 include determining electrode faults by, for example, in addition to the usage of separate 2-point impedance measurements to detect open circuits and/or short circuits, and/or making determinations directly from the rows of the matrix (final, after full insertion, and/or during "construction" of the matrix, as the rows are established, for example) by observing that when an electrode is in an open circuit state, it is disconnected from the current source, so the electrode will not be able to emit the impulse, as the connection has been interrupted. Some exemplary embodiments can utilize this fact to make the potential received in other electrodes null (0 and also negative values due to ADC) when the affected electrode emits the impulse, and maximum when measured on the electrode. FIG. 8 presents an exemplary conceptual example of an electrode experiencing a short, and FIG. 9 presents an exemplary voltage measurement resulting therefrom. FIG. 10 presents a simplified matrix that could result where the third electrode of a 4 electrode array (or where only 4 electrodes of a 22 electrode array have been measured) is experiencing an open circuit condition. An Open-Circuit electrode can have a maximum potential value of itself and close to ±zero (positive and negative values) on the other electrodes (possibly due to errors in the AD converter). As can be seen, the data in FIG. 10 shows an expected decay/continuity with respect to electrodes 1, 2, and 4 (each row represents the numeric electrode, with the diagonal showing the energization of that electrode). As can be seen, the blocks associated with electrode 3 have a difference of about an order of magnitude relative to the data associated with the other electrodes.

Figure 11:
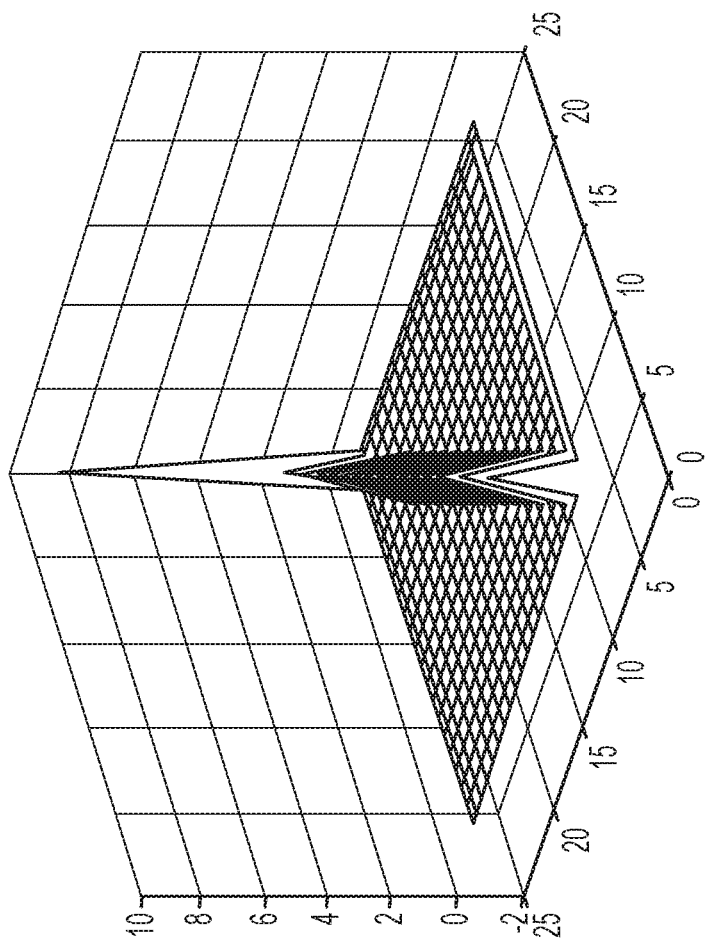

FIG. 11 presents a three-dimensional plot of data points associated with measurements from an electrode array. Electrode 22 is shown with an open circuit fault. One identifier of an open circuit, or otherwise an indication thereof, is an abnormally high value for the faulty electrode on the main diagonal i==j. Another identifier of an open circuit, or otherwise an indication thereof, is the presence of zero, or near zero, values for the faulty electrode off the main diagonal [i,22], and [22,j] (i=j–[1,22]). Accordingly, in an exemplary embodiment, a plot is presented to a surgeon or the like or other healthcare professional according to that seen in FIG. 11, or even the data seen in FIG. 10, the surgeon can determine that an open circuit is likely to exist. Note also that some embodiments include an automatic determination of such utilizing a computer or the like based on an analysis of the data.

In an exemplary embodiment, executing a direct detection can save measurement time and/or can provide improved protection against a single corrupt data point/bad data point. By direct detection, it is meant that the data directly from a matrix is used. An exemplary matrix with data representing an open circuit fault is shown in FIG. 10. The rows/columns associated with the faulty electrode are highlighted.

An exemplary embodiment of method action 798 includes determining whether an electrode is outside the cochlea or not in contact with tissue. In some exemplary embodiments, such can be determined via the usage of separate 2 point measurements which correlates a high impedance to a lack of tissue contact. Alternatively and/or in addition to this, in an exemplary embodiment, a determination can be made directly from the rows of the matrix by observing that the potential on the electrode not in contact with tissue will often or at least sometimes in a statistically significant manner present a maximum value at the stimulating electrode with a rapid drop and a low relatively constant value on all other electrode. In at least some exemplary embodiments, this value is higher than that which is observed in the open circuit scenario.

Figure 12:
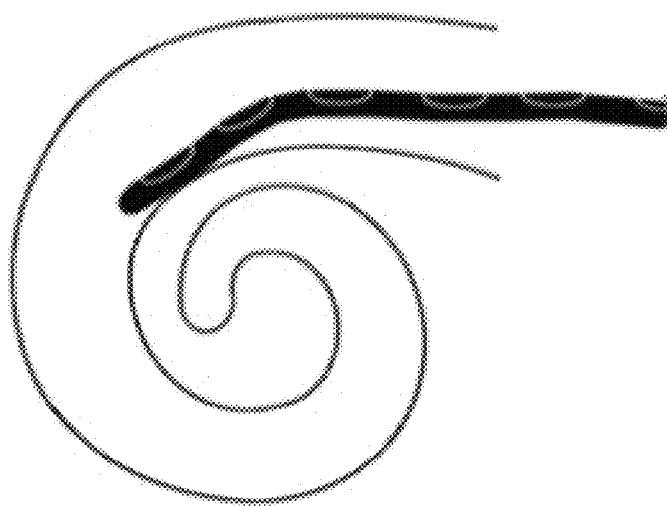
Figure 13:
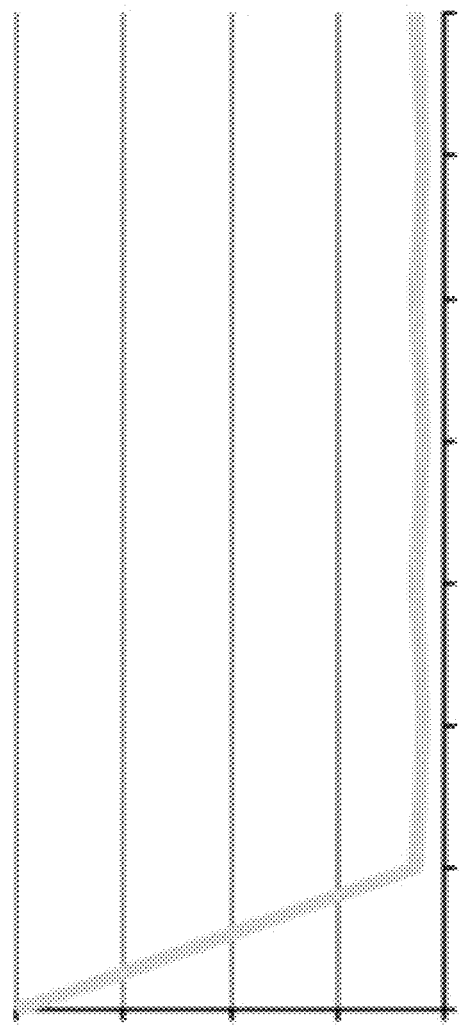

FIG. 12 presents an exemplary conceptual example of an electrode experiencing a non-insertion event, and FIG. 13 presents an exemplary voltage measurement resulting therefrom. FIG. 14 presents a simplified matrix that could result where the fourth electrode of a 4 electrode array (or where only four electrodes of a 22 electrode array have been measured) is experiencing a non-insertion/not yet inserted condition.

A no insert electrode can have a maximum potential value of itself and low values on the other electrodes (as distinguished from zero values, such as those of the open circuit). As can be seen, the data in FIG. 14 shows an expected decay/continuity with respect to electrodes 1, 2, and 3, and the blocks associated with electrode 4 have a difference at least about an order of magnitude relative to the data associated with the other electrodes.

Figure 15:
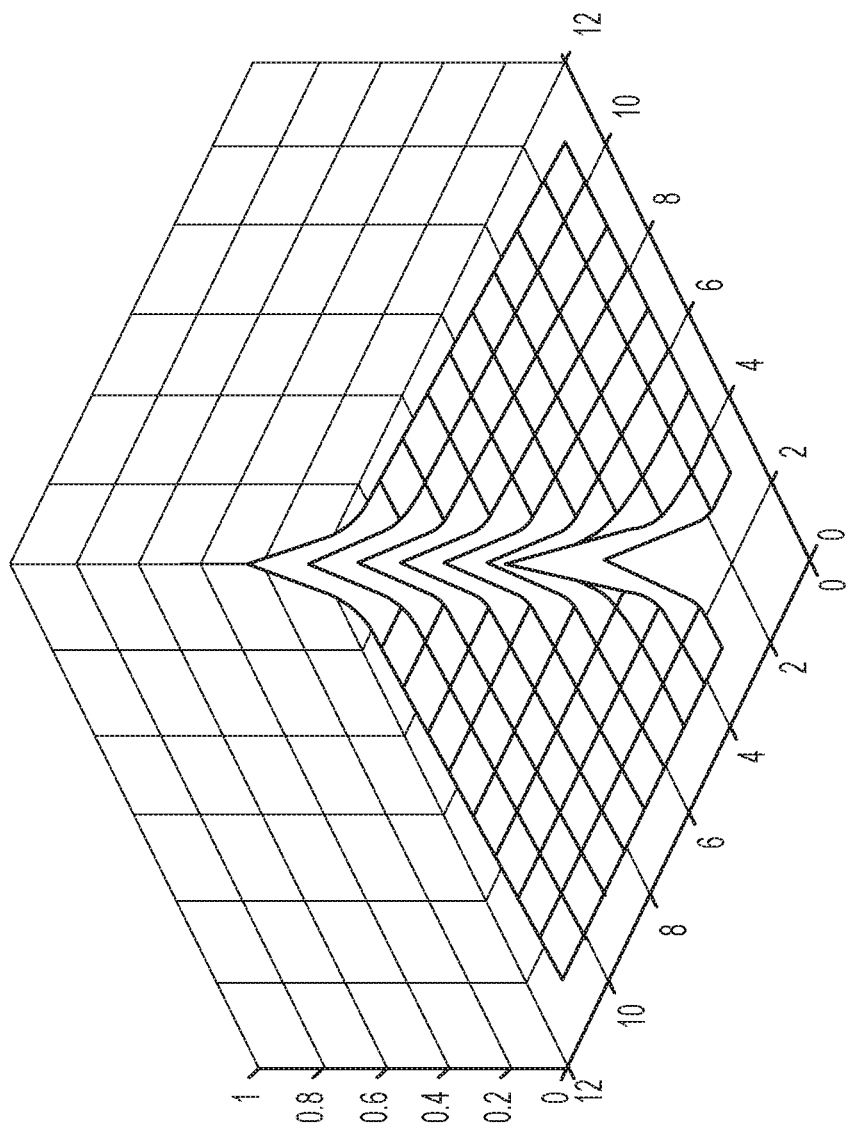

FIG. 15 presents a three-dimensional plot of data points associated with a matrix of no-insert electrodes, or otherwise an indication thereof can be seen via the presence of the main diagonal i==j, the presence of a high value on the specific electrode, and the presence of low values on [i,1], and [1,j] (i=j–[1,22]). Accordingly, in an exemplary embodiment, a plot is presented to a surgeon or the like or other healthcare professional according to that seen in FIG. 15, or even the data seen in FIG. 14, the surgeon can determine that a no insert condition is likely to exist. Note also that some embodiments include an automatic determination of such utilizing a computer or the like based on an analysis of the data.

In an exemplary embodiment, executing direct detection can save measurement time and/or can provide improved protection against a single corrupt data point, relative to that which would be the case without such direct detection. This method is also applicable for the identification of electrodes affected by air bubbles. (More on this below.)

Figure 36:
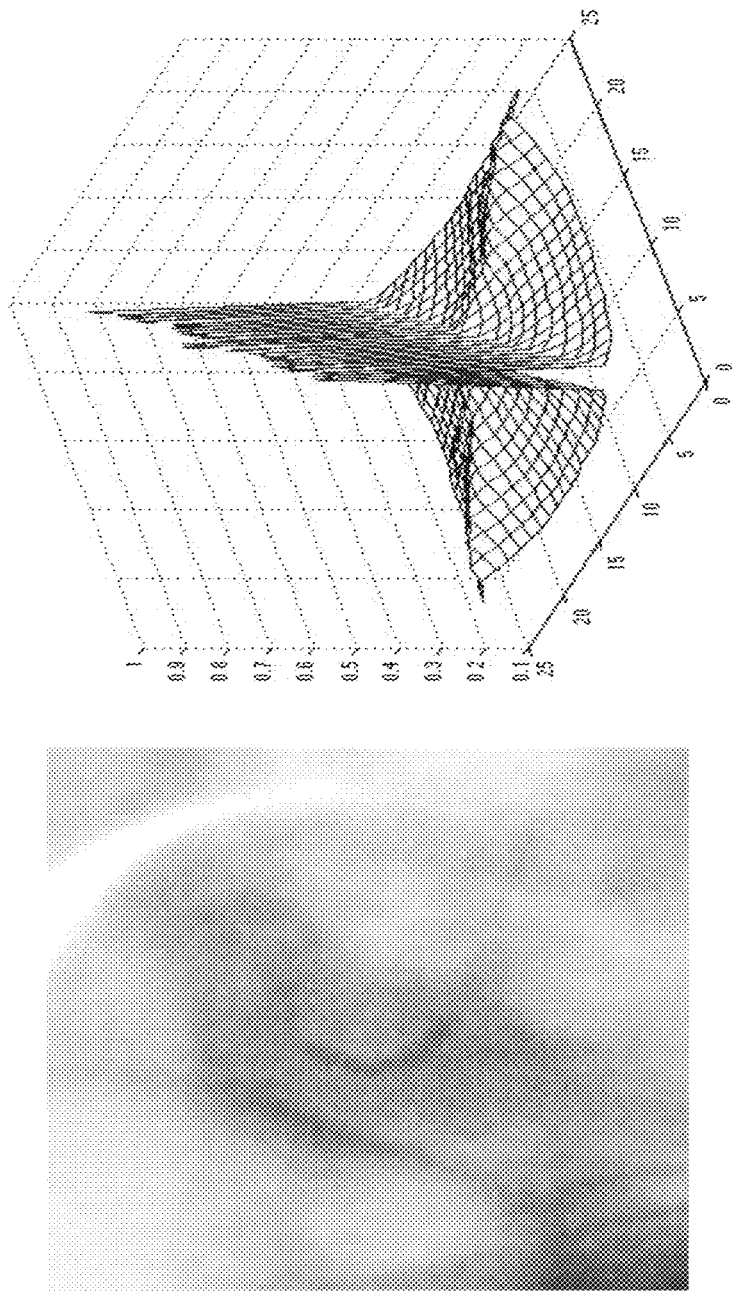

For the determination of array fold over, there can be utilitarian value with respect to representing such as a cross-diagonal ridge if the measured values are visualized in three-dimensional space with the Z-axis representing the size of the observation, as seen in FIG. 36. It is noted that teachings herein can be executed without utilizing such three-dimensional spaces as well.

Points that might constitute such a ridge in some exemplary embodiments, but not in others, can be obtained by identifying all off-diagonal values deviating from a monotonic change or exceeding a threshold. In some embodiments, this could be determined by taking the difference between all successive points along vectors parallel to the diagonal and comparing these to a pre-determined value. In some other embodiments, this could be done by taking the first derivative along the electrode rows moving away from the stimulating electrode identifying all points where the derivative changes sign. In yet another instance these points could have been identified by the preceding conditioning step, which could be executed using filtering, such as an edge filter, which can give output points that can be used to determine a deviation from the monotonic change.

In some embodiments, the confidence that a fold over is present increases as more points are identified. It is further observed that the confidence that a fold over is present increases further if the points can be shown to lie in the axis orthogonal to the diagonal. In one embodiment this can be identified by fitting a polynomial to the identified points and determining whether the slope lies orthogonal to the diagonal. In another embodiment this can be identified by segmenting the observation matrix orthogonally to the diagonal and observing the number of successive points identified in each segment. In yet another embodiment the matrix could be cross correlated with a set of ridge masking function and the correlation thresholded. It is further observed that the intersection of the ridge and the diagonal is the pivoting electrode (the electrode where the electrode array bends). This point could be identified in any of the above-mentioned ways.

Also, in some embodiments, it is the case that one or more of the techniques detailed herein are not compatible with incremental measurement methods, while others are. With respect to the former, such is dependent on many measurements which may be slow to obtain. For use with incremental measurement methods, there can be the alternative method of utilizing stimulation of at least one electrode pair and observation on at least two electrode pairs. This embodiment is based on the observation that for wide stimulation modes a monotonic change in voltage is expected as the observation electrode moves away from the stimulation electrodes and that a non-monotonic change (once confounding factors are controlled for) represents a fold over. In one embodiment the change could be detected by taking a derivative of the voltages and determining if the direction of the slope changes by detecting a change in the sign of the derivative. In another embodiment the change could be detected by comparing each measurement to a more apical measurement and detecting when the size of the measurement increases.

To make the determination more robust in the presence of movement—assuming the measurements are being conducted as the array is inserted—the measurements could use filtering techniques such as or similar to Kalman filters.

To increase the robustness of this method, it is observed that the comparing the depth of the dip (the lowest point if there has been a change in sign) with the average slope on the most basal electrodes provides some robustness against variations in cochlea anatomy. Comparing this relationship to a threshold provides robustness against misinterpreting a noisy signal. These two techniques taken together gives more robust detection.

An Alternative embodiment uses a narrow stimulation mode. In this instance it is observed that the direction of current flow will change if the electrodes involved in the narrow stimulation mode changes order. This change in direction of the current will lead to a change in voltage that can be detected by observing the voltage close to the stimulation pair. In one instance this can be done by stimulating on the most apical electrode pair and measuring the voltage from the neighboring electrode pair. If the sign of the voltage changes this indicates a possible fold over. As for the wide mode the same filtering can be used to increase the robustness of the determination in the presence of movement of the array.

As noted above, the teachings detailed herein can be utilized to determine scenario of electrode bowing away from the modiolus. In an exemplary embodiment, a slope of the voltage decay/continuity is related to the conductive properties of the elements in proximity of the stimulating and observation electrodes, and this principle can be utilized to determine the occurrence of such. In an exemplary embodiment, a distance indication can be achieved by taking the derivative of the voltage decay/continuity, the rate of voltage decay/continuity is somewhat related to the distance between the electrode/s generating the voltage and the bony cochlear wall. This is due to the effective reactance changes as the amount of electric field passing through a more conductive region is reduced. Alternatively, and/or in addition to this, the distance can be determined utilizing the measured voltages as parameters to a model that includes the electrode distance. For example this model can be an algorithmic model that predicts the effect of the distance between the electrode and the cochlea wall on all the voltages measured with a given measurement paradigm. The model can also be constrained by knowledge about the electrode array design. For example the change in distance cannot exceed the distance between two neighbouring electrodes, while in other embodiments it can. In another example this model can consist of pre-generated templates from a finite element model, each template has a different predicted set of voltage measurements and the set of measurements that most closely match the measured voltages can be selected and thus the distances determined from the best template.

In some scenarios, the degree of correlation with distance of these approaches changes over time as scar tissue is formed. Some exemplary embodiments compensate for this by using more than one of these techniques to provide additional robustness, at least if these measures are conducted some time after surgery, such as 2 days, 1 week, 2, 3, 4, 5, 6, 7, 8, 9, 10, 11, 12 weeks, 4, 5, 6, 7, 8, 9, 10, 11 or 12 months or more after surgery.

Additionally for the determination of electrodes that are "bowing" away from the modiolus, in some embodiments, the presence and state of cell matter surrounding an electrode can be detected through Electrical Impedance Spectroscopy (EIS), while other embodiments do not utilize such. Still, with respect to embodiments that utilize such, in a scenario where a cochlear implant electrode is surrounded by cell matter, it is likely to have a very different EIS signature to an electrode surrounded by perilymph (which is purely resistive). In some scenarios, this can be translated to distance by conducting impedance spectroscopy measurements using pairs of electrodes close together and using the ratio of impedances in different spectral bands to determine how close the electrode is to tissue. At least some embodiments rely upon the fact that degree of correlation with distance of these approaches changes over time as scar tissue is formed, and provide compensation for such by using more than one of these techniques to provide additional robustness if these measures are conducted some time after surgery. It is also noted that in at least some exemplary embodiments, any device, system, or method of determining distance of an electrode of the electrode array from the modiolus wall, such as via the utilization of depth sounding, can be utilized in some embodiments.

Figure 16:
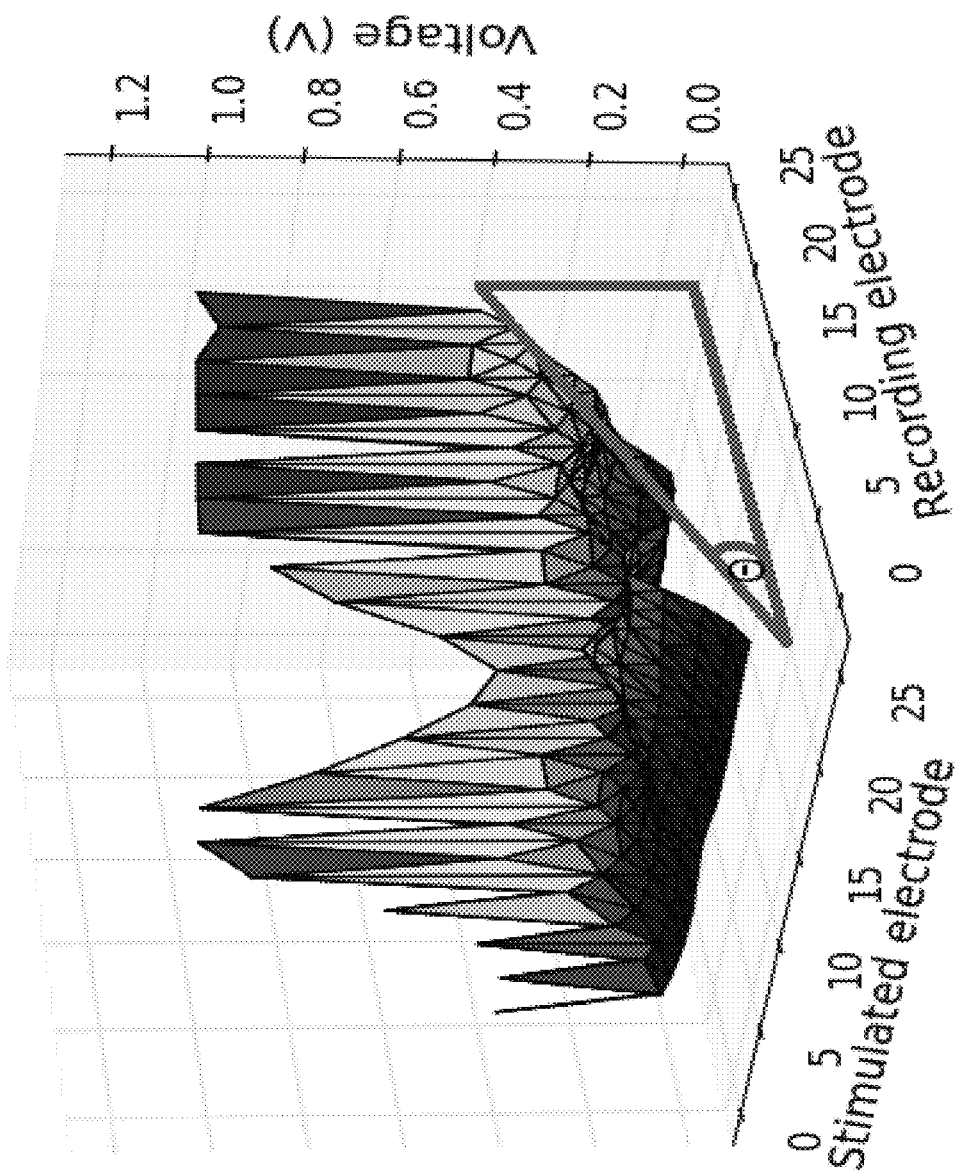

Another exemplary aspect of an occurrence that can result in data in the data matrix resulting in a false positive when analyzed and/or obscuring the occurrence of an anomalous electrode position can correspond to the feature of detrending. There tends to be a baseline trend in the measurements reflecting a measurement offset and the narrowing of the cochlear duct. This is seen by way of example only and not by way of limitation in FIG. 16, which provides an example of the baseline trend associated with the narrowing of the cochlea.

In an exemplary embodiment, this trend can be removed by subtracting the offset and rotating the matrix to minimize the error in relation to a flat plane. Alternatively, a similarity transformation can be used to normalize the matrix by observing that the degree of similarity in the voltages recorded by electrode i and j when all other electrodes are stimulating is closely related to the electrical distance between those. This measure is independent of the unknown peaks that can affect a distance matrix and is symmetric $D(i,j)=\mathrm{norm}(Z(idx,i)-Z(idx,j))/\mathrm{sqrt}(\mathrm{length}(idx))$.

Another exemplary aspect of an occurrence that can result in data in the data matrix resulting in a false positive when analyzed and/or obscuring the occurrence of an anomalous electrode position can correspond to the tendency of there to be variations, some relatively small, in the measurements reflecting manufacturing variation of the electrode surfaces and/or local anatomical variation(s) in the area of the array. For detection of trends in the array position, there is utilitarian value in removing these variations (again, in a conditioning action). However, for detection of a more localized global change (e.g., bowing of the array) it is utilitarian to maintain these variations. In instances where the removal is utilitarian, such can be achieved by one or more filtering elements of the electrical potential measurements where any of the implementations of these filters could be, median filter; mean filter; adaptive filter; directional filtering; edge enhancement filter (e.g., differentiation based filters like Sobel filters or Canny edge detector).

In addition, or as an alternative to using a filter, and/or in addition to, or as an alternative of removing a data point entirely, an individual point in the matrix can be replaced by an inferred point when the individual point may have been affected by measurement error or noise. For example, in at least some exemplary embodiments, the diagonal values in the matrix where at least one of the stimulating and recording electrodes are shared can have an open circuit, thus these measurements can be replaced by linear interpolation of the neighboring elements. In some embodiments, there are techniques related to maintaining a value over time such that when there is a measurement error one can replace the bad value/erroneous value with the one measured in the previous epoc. Accordingly, the teachings detailed herein are directed towards storing some or all data that is collected during the various data collection actions/read/measurement actions, and retrieving such data and utilizing such as a replacement or otherwise a stand-in for data that is bad. Such an exemplary embodiment can entail replacing a data point on the matrix with the stored data previously obtained.

Another aspect that can be relied upon when developing conditioning regimes and/or other data processing regimes having utilitarian value is that that there tends to be variation in the range between the minimum and maximum levels recorded in individual cochlea, due to the differences in cochlea size, electrode array configuration and biochemical differences. Some embodiments include avoiding these variations by utilizing subsequent algorithms such that the values can be adjusted within a set range, thus accounting for these variations, and thus the regimes take into account such variation.

Figure 17:
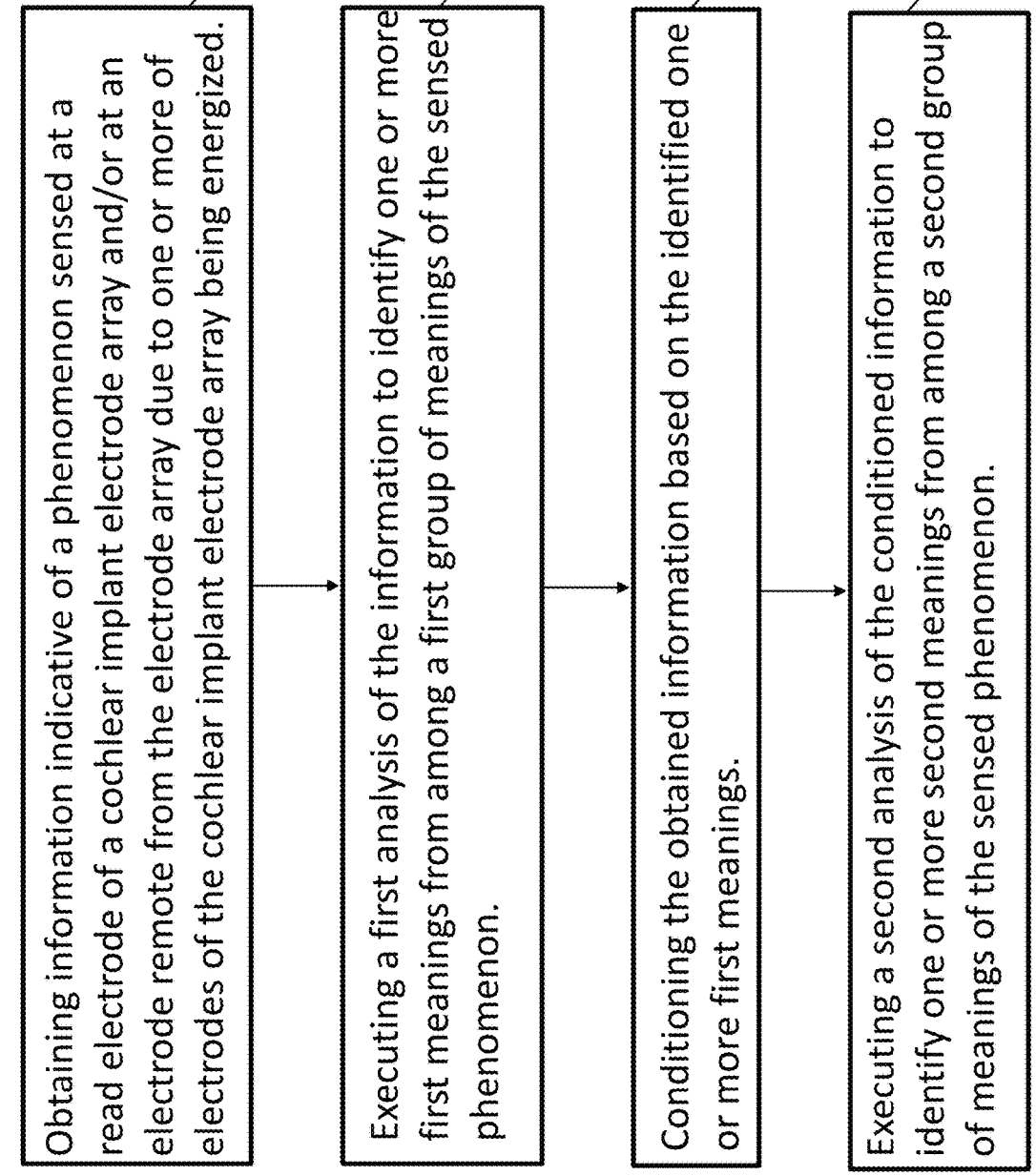
FIGS. 17-27 present some exemplary flowcharts for some exemplary methods.

FIG. 17 presents an exemplary algorithm for an exemplary method, method 1700, which includes method action 1710, which includes obtaining information indicative of a phenomenon sensed at a read electrode of a cochlear implant electrode array (again, relative to a reference) and/or at an electrode remote from the electrode array due to one or more electrodes of the cochlear implant electrode array being energized. With respect to the former, this can correspond to obtaining information indicative of a phenomenon sensed at electrode 2 due to electrode 1 being energized and/or due to a remote electrode being energized, as long as an electrode of the electrode array is utilized as the read electrode, relative to a reference, this feature is met. With respect to the latter, this can correspond to obtaining information indicative of a phenomenon at a remote electrode, such as, for example, an extra cochlea electrode (ECE) (such as the plate/can or so-called hardball electrode) or an electrode that is utilized as part of the method, such as an electrode that is part of or otherwise supported by an electrode array insertion tool (more on this below). As long as the phenomenon is a result of energizement of one or more of the electrodes of the electrode array, this feature is met.

Method 1700 further includes method action 1720, which includes executing a first analysis of the information obtained in method action 1710 to identify one or more first meanings from among a first group of meanings of the sensed phenomenon. In an exemplary embodiment, the first group of meanings includes or otherwise is a result of at least one of an open circuit, a short circuit, a shunt circuit, a bubble proximate the electrode array, an electrode not in the cochlea, an electrode conditioning phenomenon (as opposed to the conditioning process detailed herein), or a detrending phenomenon.

Briefly, it is noted that method action 1720 does not require that the specific type of phenomenon has occurred. Instead, it is sufficient to identify that a phenomenon based on one or more of the aforementioned examples has occurred. Indeed, in an exemplary embodiment, the shunt circuit could potentially yield similar results to the presence of a bubble, and/or the presence of a bubble could yield similar results to an open circuit. Still, in some embodiments, the identification of one or more first meanings can correspond to identifying the actual underlying phenomenon. Still further, the action of identifying the one or more first meanings can include identifying the specific phenomenon, such as a short circuit, as well as identifying another phenomenon in more general terms/only that the phenomenon exists.

The open circuit and the electrode not in the cochlea and the detrending phenomenon have been described above. With respect to the short circuit, this can correspond to a value at the read electrode or whatever electrode is being utilized that is abnormally high relative to that which would otherwise be the case. By way of example only and not by way of limitation, if the voltage reading on an electrode is the same as or relatively close to the voltage reading at another electrode, such can be indicative of a short between the two electrodes. Still further by way of example only and not by way of limitation, if the voltage reading on electrode three is the same as or relatively close to the voltage applied to electrode two or otherwise the voltage read at electrode two, such can be indicative of a short between those two electrodes. Any device, system, and/or method that will enable a determination that there exists a short circuit can be utilized in at least some exemplary embodiments. Note also that this is the case with respect to determining that there exists an open circuit and/or an electrode not in the cochlea and/or the detrending phenomenon. Indeed, in an exemplary embodiment, this is the case with respect to any of the features detailed herein associated with the first meanings.

With respect to a shunt circuit, in an exemplary embodiment, perilymph or another conductive fluid or semi conductive fluid or the like can creep into the electrode array or otherwise establish a conductive bridge between one electrode and another electrode. The phenomenon will not be the same as a short electrode, at least in some embodiments, but will still potentially skew the data of the matrix that is utilized to ultimately identify the anomalous electrode position. In an exemplary embodiment, the data set can be analyzed. In an exemplary embodiment, the voltage readings will be higher than that which would be the case with respect to an open circuit, but lower than that which would be the case with respect to a short circuit, at least in some embodiments. For example, a shunt can be indicated, at least in a matrix measurement, by a secondary peak, which can look similar to that which would exist for a fold over, but unlike a fold over this would only be present in a single row. In an exemplary embodiment, empirical data is obtained to develop a statistically significant database, and comparisons of the data obtained from method action 1710 to this statistically significant database can be executed to identify the occurrence of the shunt circuit, or at least that there exists one or more first meanings.

With respect to a bubble proximate the electrode array, in an exemplary embodiment, an air bubble can be present proximate a read electrode and/or a stimulating electrode, which bubble can skew or otherwise create data that is less than utilitarian with respect to the matrix. In at least some exemplary embodiments, such bubbles can dissipate with time, especially if the electrode array is further inserted into the cochlea, or otherwise can move to other electrodes. Some additional ramifications of this will be described in greater detail below, along with treating the data accordingly.

With respect to an electrode conditioning phenomenon (as distinguished from data conditioning), in at least some exemplary embodiments, one or more electrodes of the electrode array will experience a phenomenon akin to a corrosion scenario when the electrode is exposed to body fluids. A chemical reaction takes place on the surface of the electrode. Over time, this can change the ultimate result of the data that is obtained for use in determining whether or not an anomalous electrode position has occurred. By way of example only and not by way of limitation, in an exemplary embodiment, the data resulting from utilizing electrode 2 as a read electrode just after electrode 2 is inserted into the cochlea could be different than that which would result from utilizing electrode 2 is a read electrode after electrodes 3, 4, 5, 6, 7, 8, 9, 10, 11, 12, 13, 14, 15, 16, 17, and 18, for example, are also inserted into the cochlea (i.e., electrode 2 is subjected to more time being exposed to the perilymph/body fluids relative to its first use as a read electrode) owing to the effects of the electrode conditioning. Alternatively, and/or in addition to this, conditioning can occur as a result of the electrode being utilized as a stimulating electrode and/or because it is subject to electrical current. Regardless of how the electrode conditioning occurs, in an exemplary embodiment, method action 1720 includes executing a first analysis to identify one or more first meanings that can be a result of electrode conditioning.

Method 1700 further includes method action 1730, which includes conditioning the obtained information based on the identified one or more first meanings. Some details of the action of conditioning will be described in greater detail below. Briefly, however, in an exemplary embodiment, such as with respect to the data set of FIG. 10, interpolation can be executed to replace the 3,3 location with a value of 2 (as that is what should be the case with respect to the other electrodes), and to replace the 3,1 location with a value of 0.065 (halfway between 0.09 and 0.04), replace the 3,2 location with a value of 0.1 (as that is what read electrode 2 reads when electrode 1 is energized, and that is about what read electrode 1 reads when electrode 2 is energized), and the 3,4 location with a value of 0.1 (for the same reasons relating to the replacement of the 3,2 location). Still further, the 1,3 location (that reads −0.001) can be replaced with a value of 0.0.75, as that is halfway between 0.1 and 0.04, the 2,3 location can be replaced with a value of 0.1, as that is the value of the 1,2 location, or can be replaced with a value that is interpolated between 2 and 0.05, or a combination thereof, and the 4,3 location can be replaced with 0.09, as that is the value of the 2,1 location, or can be replaced with a value that is halfway between 2 and 0.051, or combination thereof.

Alternatively, and/or in addition to this, method action 1730 can include establishing a matrix that ignores or otherwise discounts the 1,3, 2,3, 3,3, 3,4, 3,1, 3,2, and 3,4 locations, or otherwise flags those data points as being data that should be ignored in the ultimate evaluation. Indeed, the action of conditioning the obtained information can simply correspond to flagging the information as being problematic or otherwise is being information that should be discounted in some manner.

Speaking of the ultimate evaluation, method 1700 includes method action 1740, which includes executing a second analysis of the conditioned information to identify one or more second meanings from among the second group of meanings of the sensed phenomenon. Some additional details of such will be described in greater detail below. Briefly however, in an exemplary embodiment, such corresponds to analyzing a conditioned data matrix and comparing the data to statistically significant results in deducing that an anomalous electrode position exists. More details of this will be described below. However, it is briefly noted that in some exemplary embodiments, method action 1740 is not executed until after the prior methods of method 1700 are executed multiple times. In this regard, it is to be understood that in at least some exemplary embodiments, method actions 1710, 1720, 1730 are executed a plurality of times, such as for example only and not by way of limitations, a number of times corresponding to the number of electrode arrays that have been inserted into the cochlea by the time that method action 1740 is executed.

In an exemplary embodiment, method action 1710 is executed each time an electrode of the electrode array is inserted into the cochlea. It is noted that in an exemplary embodiment, the measurements are repeated continuously and the post processing determines when another electrode has been inserted/correlates the data temporally and/or positionally (where position is relative to location on the array). Further, By way of example only and not by way of limitation, in an exemplary embodiment, method action 1710 and, in some embodiments, method action 1720 and/or method action 1730 is executed after electrode 1 (the most distal electrode of the electrode array) is inserted into the cochlea, and then method action 1710 is again executed after electrode 2 (the second most distal electrode of the electrode array) is inserted into the cochlea, and so on until all 22 electrodes are inserted into the cochlea. That said, in an exemplary embodiment, method action 1710 is executed each time only after a plurality of electrodes are inserted into the cochlea relative to that which was previously inserted into the cochlea where method action 1710 was executed last time. For example, method action 1710 is executed after the first three electrodes are inserted into the cochlea, and then after the next three electrodes are inserted into the cochlea and so on. Also, in an exemplary embodiment, method action 1710 is executed after the first three electrodes are inserted into the cochlea, and then each time after an electrode is inserted into the cochlea. Any regime that links the electrodes inserted into the cochlea to the method actions detailed herein can be utilized in at least some exemplary embodiments.

In an exemplary embodiment of method 1700, the one or more second meanings relates to a feature that impacts the condition of electricity globally relative to the electrode array. By way of example only and not by way of limitation, such can correspond to that which results from fold over, electrode array bowing and/or in electrode array located outside the cochlea or otherwise dislocated with the specific duct of the cochlea. By way of example only and not by way of limitation, these are phenomena that cannot be detected if the location of the source and/or the sink utilized to execute method 1710 were not known. In this regard, in an exemplary embodiment, such is the case because the data associated there with his relative to the position of other electrodes. This can be distinguished from, for example, the phenomenon which corresponds to the aforementioned first meanings, where the location of at least one of the source or the sink need not be known for the phenomenon to be identified, or at least to determine that something indicative of such phenomenon exists. In this regard, in an exemplary embodiment, the one or more first meanings relates to a feature that is identifiable irrespective of which of a plurality of potential intracochlear sources of current corresponding to respective electrodes of the cochlear array supplies current to the read electrode. Again, this can be distinguished from, for example, the aforementioned phenomenon associated with the anomalous positioning of the electrode array at least in some exemplary embodiments, and thus in some exemplary embodiments, the one or more second meanings relates to a feature that is identifiable only if a specific electrode is known of a plurality of potential intracochlear sources of current corresponding to respective electrodes of the cochlear array supplies current to the read electrode.

In some embodiments, the one or more first meanings corresponds to an electrical phenomenon that at least one of will not change (e.g., open or short circuit) or will change with time without further movement of the electrode array in the cochlea (e.g., shunt circuit, bubble, electrode conditioning), all other things being equal. Conversely, the one or more second meanings can, in some embodiments, correspond to electrical phenomenon that will only change with further movement of the electrode array in the cochlea, all other things being equal (fold over, bowing, dislocation).

Accordingly, in an exemplary embodiment, the first group of meanings includes at least one of an open circuit, a short circuit, shunt circuit, a bubble proximate the electrode array, an electrode not in the cochlea, an electrode conditioning phenomenon, or a detrending phenomenon, and the second group of meanings includes at least one of fold over, tip puncture, bowing, or electrode array misplacement.

It is noted that any disclosure herein of fold over corresponds to a disclosure of tip fold over as well as fold over of the main body of the electrode. In this regard, tip fold over is a specific type of fold over that occurs rather wise is generally limited to the tip of the electrode array. Some additional features of this scenario are described below with respect to the fact that in some exemplary scenarios, tip fold over may not necessarily result in a scenario where the electrode array is repositioned, whereas fold over at another location of the electrode array may result in such. It is noted that any disclosure herein of tip fold over also corresponds to a disclosure of the main body fold over and vice versa.

By electrode array misplacement, it is meant that the electrode array is located in a cavity in the body not intended. In this regard, by way of example only and not by way of limitation, in at least some exemplary embodiments, the electrode array is intended to be placed into the scala timpani. If the electrode array instead winds up in the scala vestibuli, such would result in electrode array misplacement. Still further, if the electrode array instead winds up in the scala media, such would result in electrode array misplacement. Also, it is noted that in an exemplary embodiment, during insertion, the tip of the electrode array could potentially pierce the inner boundary of the scala timpani, such that when the electrode array is fully inserted, or even partially inserted, the distal portions of the electrode array are no longer in the scala timpani, but instead in, for example, the scala vestibuli and/or the scala media. Such corresponds to a dislocation phenomenon. Accordingly, in an exemplary embodiment, with respect to method 1700, the first group of meanings includes least one of an open circuit, a short circuit, a shunt circuit, a bubble proximate the electrode array, an electrode not in the cochlea, an electrode conditioning phenomenon or a detrending phenomenon, and the second group of meanings includes electrode array dislocation.

Some exemplary scenarios of method action 1710 are executed as a result of data obtained during the actual electrode array insertion process, that is, while the electrode array is being inserted into the cochlea. Thus, in an exemplary embodiment, the phenomenon sensed at the read was sensed while the electrode array was being inserted into the cochlea. Conversely, some exemplary scenarios of method action 1710 are executed after the electrode array has been fully inserted into the cochlea (whether or not that full insertion has properly placed the cochlea—by full insertion, it is meant that the surgeon believes that he or she can no longer further insert the electrode array into the cochlea or otherwise should not further insert the electrode array into the cochlea because doing so would reduce the effectiveness of the cochlear implant these of the channel alignment with the tonotopical features of the cochlea). It is also noted that at least some exemplary embodiments of the execution of method action 1710 can be executed prior to the action of inserting the electrode array into the cochlea. By way of example only and not by way of limitation, in at least some exemplary embodiments, an open and/or short circuit determination can be made prior to removing the electrode array from shipping packages. In an exemplary embodiment, this data is provided to a control unit that assists or otherwise controls or otherwise execute one or more or all of the method actions detailed herein, as will be described in greater detail below.

With reference to method 1700, it is noted that in at least some exemplary embodiments, the phenomenon associated with method action 1710 corresponds to an interruption of the continuous pattern of a column or row of the matrix or of the data points in general. For example, if the most distal electrode of the electrode array fully inserted into the cochlea is stimulated with reference to an extra-cochlear electrode, the voltage readings at the other electrodes with reference to an extra-cochlear electrode should decay with distance from the most distal electrode, until, at least, approaching another stimulating electrode (hence why sometimes continuity is referred to.) If one or more of the electrodes indicates a voltage reading that is not decaying or otherwise decays in a manner that is different than the general trend, this can be indicative of one or more of the meanings of method action 1720. In this regard, in an exemplary embodiment, the first analysis can entail determining whether or not there exists an abnormality in a continuous pattern of the obtained information, such as an abnormality in the voltages read at the read electrodes. In an exemplary embodiment, the column and/or row and/or the entire matrix can be compared against a statistically significant and/or a theoretical template (it is noted that any disclosure herein of a statistically significant data set also corresponds to an embodiment that utilizes a theoretical data set and vice versa). If the data is similar to the statistically significant and/or theoretical template, a determination can be made that the information is not indicative of one or more of the first meanings. That said, in an exemplary embodiment, the statistically significant and/or theoretical template can be based on one that which corresponds to the existence of the one or more meetings. Thus, if the data is similar to the statistically significant and/or theoretical template, a determination can be made that the information is indicative of one or more the first meanings.

Briefly, in an exemplary embodiment of the interruption of a continuous pattern, an open circuit for example would interrupt the continuous pattern. Alternatively, and/or in addition to this, electrodes that are not in contact with tissue and/or electrodes that are not in the cochlea can also interrupt the continuous pattern. Accordingly, a continuous pattern with an interruption can be utilized in a first analysis of the information to identify one or more the first meanings.

It is noted that some utilitarian features of the teachings detailed herein can result in relatively fast identification of the one or more second meanings. In this regard, in an exemplary embodiment, an identification can be made in a relatively short timeframe that a fold over and/or a bowing and/or a dislocation has occurred, tip puncture, etc., while the recipient is still in surgery, and, in some embodiments, while the surgeon is still holding the electrode array during insertion process. In some embodiments, the second group of meanings is identified at least one of before or no later than X minutes after full insertion of the electrode array into the cochlea, where X is 0.1, 0.2, 0.3, 0.4, 0.5, 0.6, 0.7, 0.8, 0.9, 1.0, 1.25, 1.5, 1.75, 2, 3, 4, 5, 6, 7, 8, 9, 10, 11, 12, 13, 14, 15, 16, 17, 18, 19, or 20. Additional features as well as some of the exemplary utilitarian value of this embodiment will be described in greater detail below.

Figure 31:
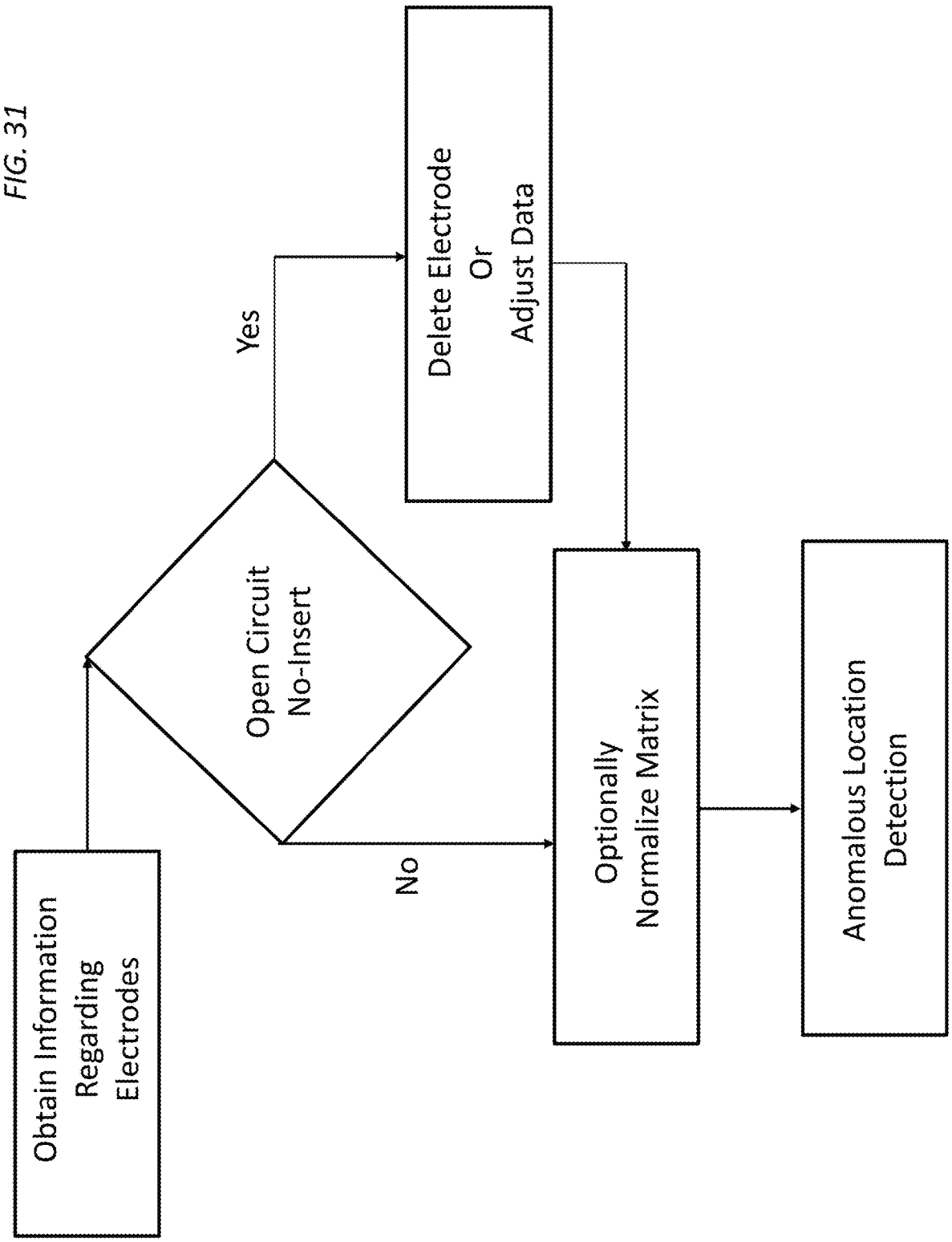
FIGS. 31-33 present some exemplary flowcharts for some exemplary methods.

Briefly jumping ahead, FIG. 31 provides another exemplary flowchart according to an exemplary method, the parallels to this and method 1700 can be seen, while tailored to the specific phenomenon associated with an open circuit and a no insert electrode. Some additional details of this are described below. Briefly, FIG. 31 is a subroutine to be executed in the automatic methods detailed herein, just as method 1700 can be executed in the automatic methods detailed herein.

Figure 18:
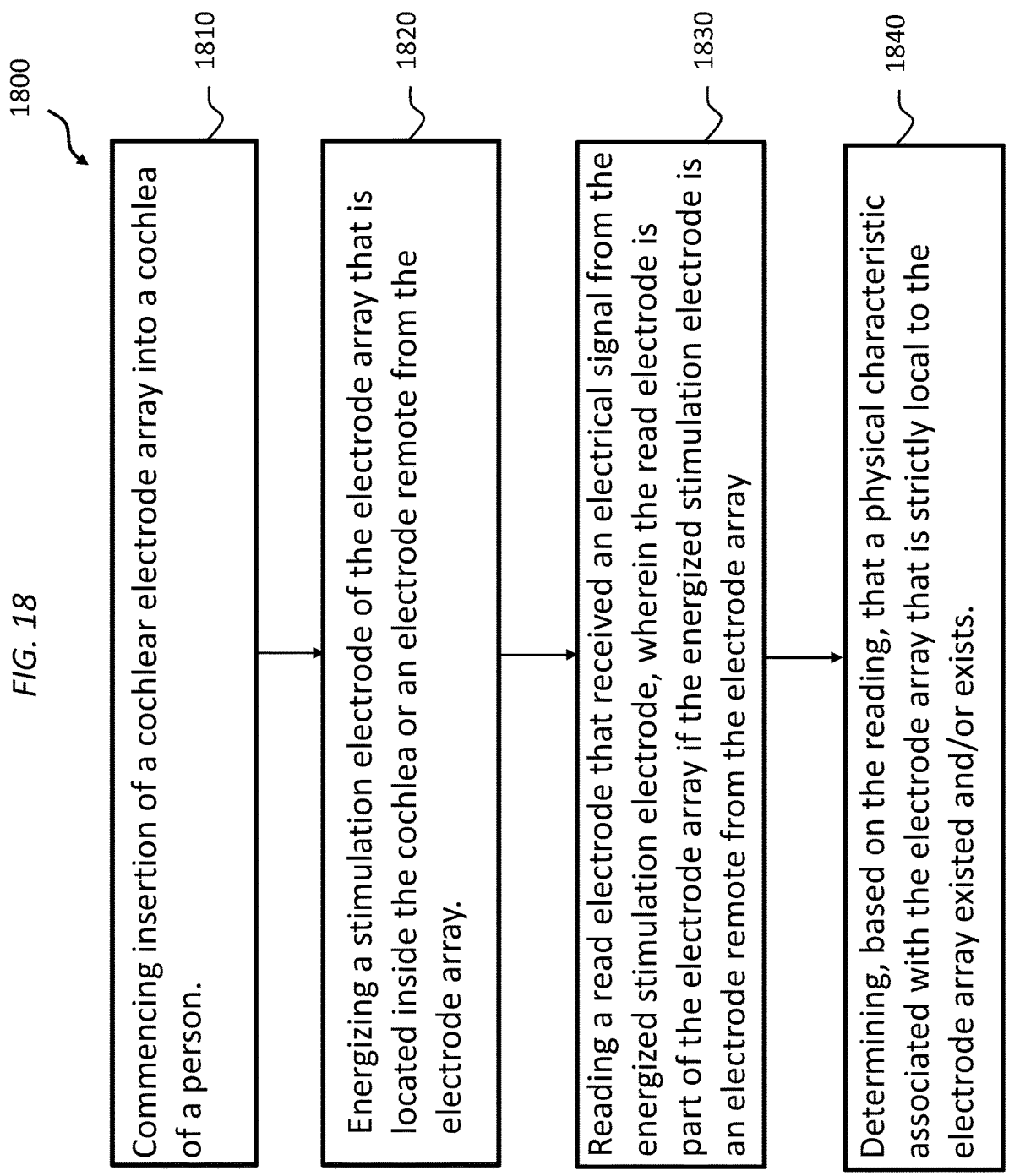

FIG. 18 presents an exemplary flowchart for an exemplary method, method 1800, which includes method action 1810, which includes commencing insertion of a cochlear electrode array into a cochlea of a person. In an exemplary embodiment, this can be done by hand while in other exemplary embodiments, this can be done by tool, such as a robotic insertion tool some of the details of which will be described in greater detail below. Method 1800 further includes method action 1820, which includes energizing a stimulation electrode of the electrode array that is located inside the cochlea or an electrode remote from the electrode array. By way of example only and not by way of limitation, in an exemplary embodiment, the cochlear implant assembly that includes the receiver stimulator in the electrode array assembly can be activated so as to provide an electrical signal to one or more of the electrodes of the electrode array. In an exemplary embodiment, this can be executed by providing an inductance signal to the receiver of the receiver stimulator, which inductance signal was received activates the electrode array. Any device, system, and/or method that can enable the energization of a stimulation electrode can be utilized in at least some exemplary embodiments. Alternatively, and/or in addition to this, in an exemplary embodiment, the so-called hardball or ECE can be used. Alternatively, and/or in addition to this, a separate electrode that is separate from the implant can be used, such as an electrode that is mounted on an insertion tool, the details of which will be described in greater detail below.

Method action 1830 of method 1800 includes the action of reading a read electrode that received an electrical signal from the energized stimulation electrode. In at least some exemplary embodiments, this can correspond to utilizing one or more of the electrodes of the electrode array as a read electrode. Alternatively, and/or in addition to this, in an exemplary embodiment, the so-called hardball or ECE can be used. Alternatively, and/or in addition to this, a separate read electrode that is separate from the implant can be used, such as an electrode that is mounted on an insertion tool, the details of which will be described in greater detail below. While method action 1830 requires that the read electrode be part of the electrode array of the energized stimulation electrode is an electrode remote from the electrode array, this does not mean that if the energized stimulation electrode of method action 1820 was an electrode of the electrode array, the read electrode of method action 1830 must be an electrode that is separate from the electrode array. In this regard, method actions 1820 and 1830 can both be executed utilizing electrodes of the electrode array.

Method 1800 further includes method action 1840, which includes determining, based on the reading, that a physical characteristic associated with the electrode array that is strictly local to the electrode array existed and/or exists. By "strictly local" to the electrode array, it is meant that the phenomenon exists regardless of where one of the source or sink electrode would be located. For example, an open circuit, a short circuit, or a shunt circuit can be determined utilizing any of the sources or sinks, providing at least that the location of one is known. Still further by example, the presence of a bubble can be determined, or at least the effects associated there with, providing that one of the locations of the source or sink is known. This is also the case with electrode conditioning, detrending, and outside electrode. Conversely, fold over determination for example, requires the location of both the source in the sink to be known.

In at least some exemplary embodiments of method 1800, the physical characteristic is a temporally static characteristic related to a physical condition of the electrode array. That is, a condition that does not change with time.

Conversely, in an exemplary embodiment, the physical characteristic is a temporally dynamic characteristic related to the physical condition of the electrode array. By way of example only and not by way of limitation, in an exemplary embodiment, the electrode conditioning is a physical characteristic that will change with time. Also by way of example, the shunt condition is a condition that will change with time. Conversely to these physical characteristics that are temporally dynamic, in some embodiments, the physical characteristic is a temporally dynamic characteristic that is related to the location of the electrode array. By way of example only and not by way of limitation, the presence of a bubble, electrode non-insertion, and the detrending characteristics are all characteristics that will vary based on the location of the electrode array.

In an exemplary embodiment of method 1800, there exists the action of reading other read electrodes that received the electrical signal from the energized stimulation electrode. In an exemplary embodiment, this can be executed in the same manner as method action 1830, at least with respect to embodiments where the read electrode is a read electrode of the electrode array. Still further, in an exemplary embodiment of method 1800, there is the additional action of identifying a continuous electrical phenomenon associated with the electrodes that were read. By way of example only and not by way of limitation, in a scenario where the energized electrode was the most apical electrode/the most distal electrode, a pattern should be seen where the voltage read at each of the electrodes decreases with respect to distance from that apical electrode. In an exemplary embodiment of method 1800, the action of determining of method action 1840 is based on a determination that the reading of method action 1830 is an abnormal reading relative to the identified decaying/continuity electrical phenomenon.

That said, in some exemplary embodiments, it is not necessary to obtain information from other read electrodes. In this regard, as noted above, in some exemplary embodiments, the obtained readings can be compared to statistically significant data and/or theoretical data, and a determination can be made based on the comparison. Accordingly, in an exemplary embodiment of method 1800, there is the additional action of obtaining information relating to an electrical phenomenon continuity pattern of the electrode array (e.g., such as obtaining a statistically significant and/or theoretical based template), wherein the action of determining is based on a determination that the reading is an abnormal reading relative to the obtained electrical phenomenon continuity pattern.

Figure 19:
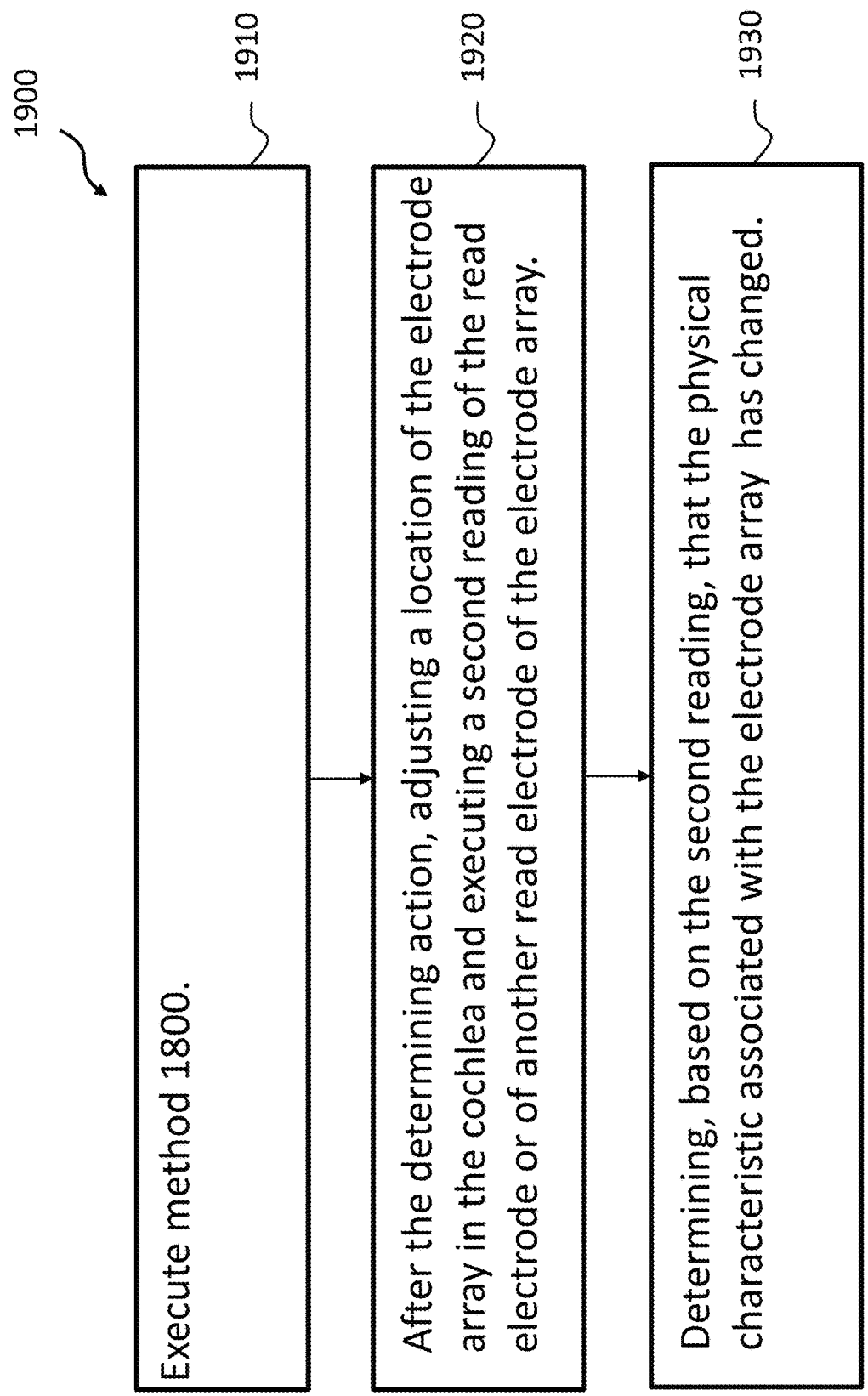

As noted above, embodiments of the teachings detailed herein can be utilized to condition the data that is ultimately used to make a determination of an anomalous electrode insertion. While some embodiments of this conditioning results in the permanent discounting of data from one or more of the read electrodes and/or data associated with one or more stimulating electrodes, in some other embodiments, the conditioning results in only temporarily discounting of the data. For example, in a scenario where, for example, data is obtained where a short circuit exists and/or a bubble is proximate an electrode, which results in the data being skewed, embodiments include obtaining further data at a later temporal period, such as when the electrode array is moved further into the cochlea, where the phenomenon that caused the data to be skewed is no longer present. This new data is utilized in the matrix and the old data can be eliminated. Accordingly, in an exemplary embodiment, as seen in FIG. 19, there is method 1900. Method 1900 includes executing method action 1910, which includes executing method 1800. Method 1900 also includes method action 1920 which includes, after the determining action of method action 1840, adjusting a location of the electrode array in the cochlea and executing a second reading of the read electrode or of another read electrode of the electrode array. By way of example only and not by way of limitation, in an exemplary embodiment, the action of adjusting the location of the electrode array in the cochlea can push the electrode array further into the cochlea. Again, in an exemplary embodiment, method 1800 can be executed with the electrode array only partially inserted into the cochlea.

Method 1900 further includes method action 1920, which includes determining, based on the reading, that the physical characteristic associated with the electrode array determined in method action 1840 has changed. Such can have utilitarian value with respect to determining that the phenomenon that skewed or otherwise interfered with the data that would ultimately be utilized to determine the anomalous electrode position is now producing a different result (if it is still present, that is).

Figure 20:
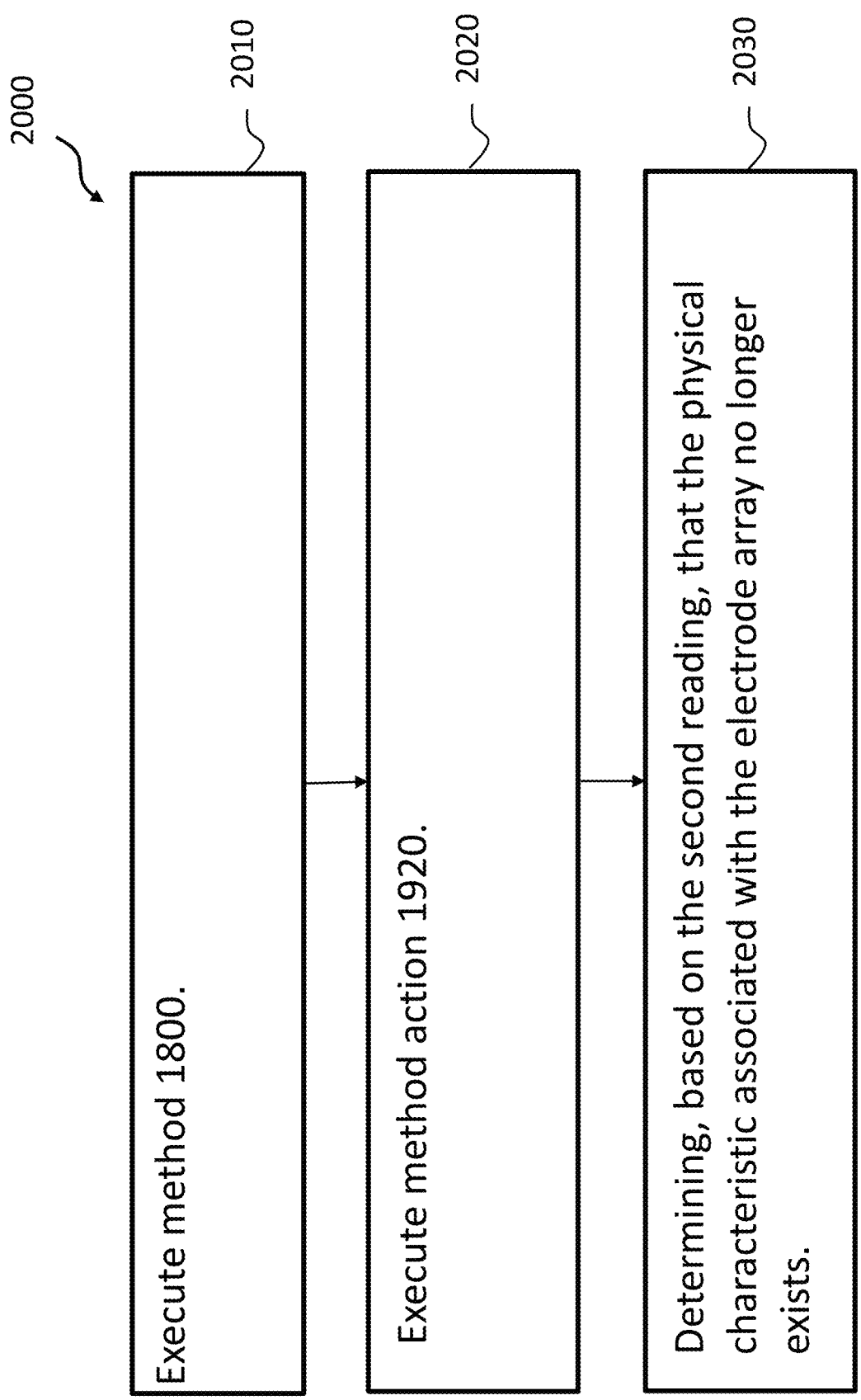

FIG. 20 presents an exemplary flowchart for an exemplary method, method 2000 which includes method action 2010, which includes executing method 1800, and method action 2020, which includes executing method action 1920. Method 2000 also includes method action 2030, which includes determining, based on the second reading, that the physical characteristic associated with the electrode array no longer exists. Such can have utilitarian value with respect to determining that the phenomenon that skewed or otherwise interfered with the data that would ultimately be utilized to determine the anomalous electrode position is no longer present, and thus the specific data can be so utilized or otherwise can be utilized in its raw form (albeit for potential normalization).

Figure 21:
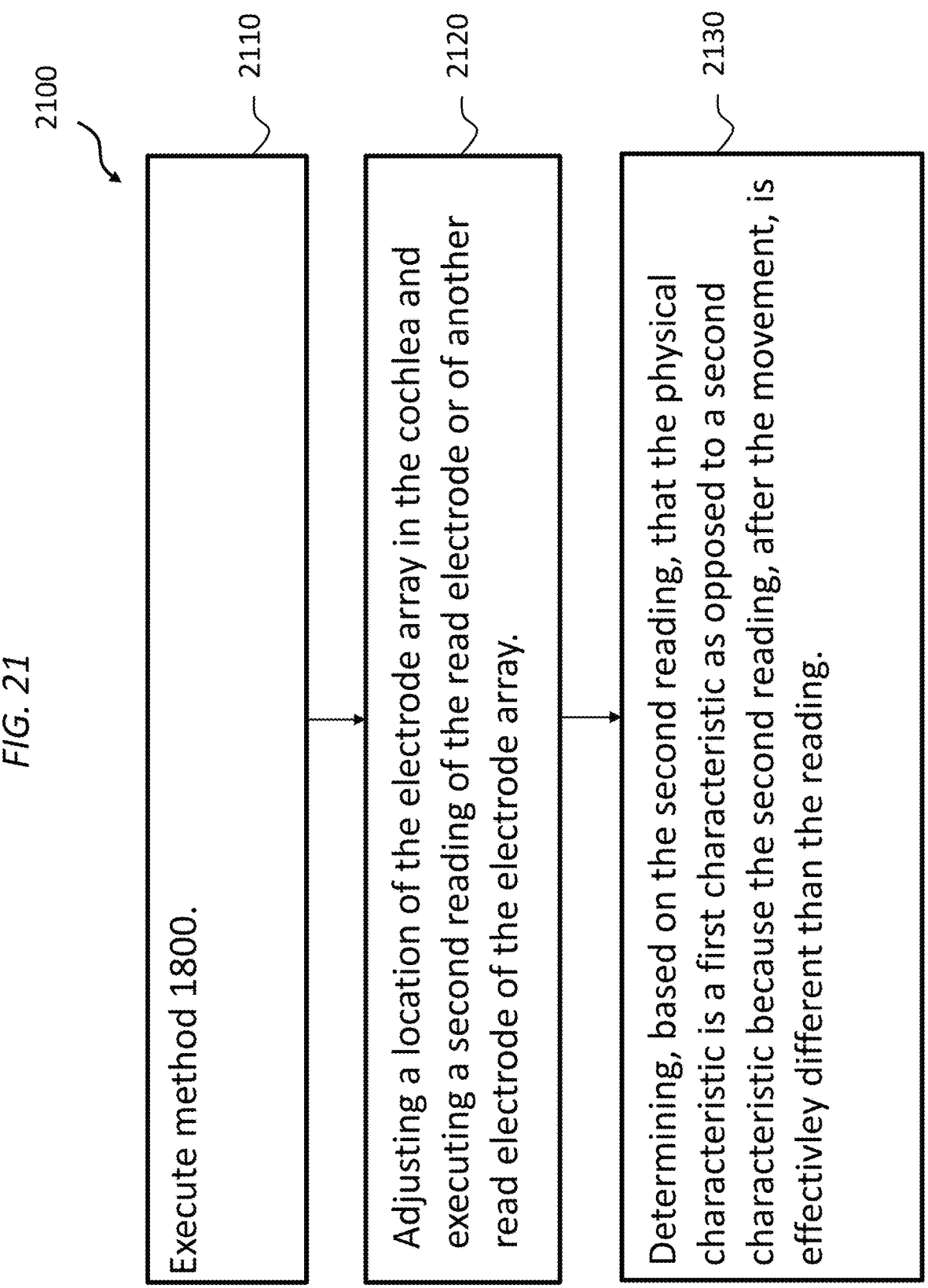

FIG. 21 presents an exemplary flowchart for an exemplary method, method 2100, which includes method action 2110, which includes executing method 1800. Method 2100 also includes method action 2120, which includes the action of adjusting a location of the electrode array, whether such is repositioning the electrode array or simply further inserting the electrode array, and executing a second reading of the read electrode or of another read electrode of the electrode array. Method 2100 also includes method action 2130, which includes determining, based on the second reading, that the physical characteristic is a first characteristic as opposed to a second characteristic because the second reading, after the movement, is effectively different than the reading of method 1800. By way of example only and not by way of limitation, in an exemplary embodiment, the first characteristic can correspond to the existence of a shunt circuit, a bubble, a detrending feature and/or electrode conditioning, and the second characteristic can correspond to an open circuit or a short circuit.

Figure 22:
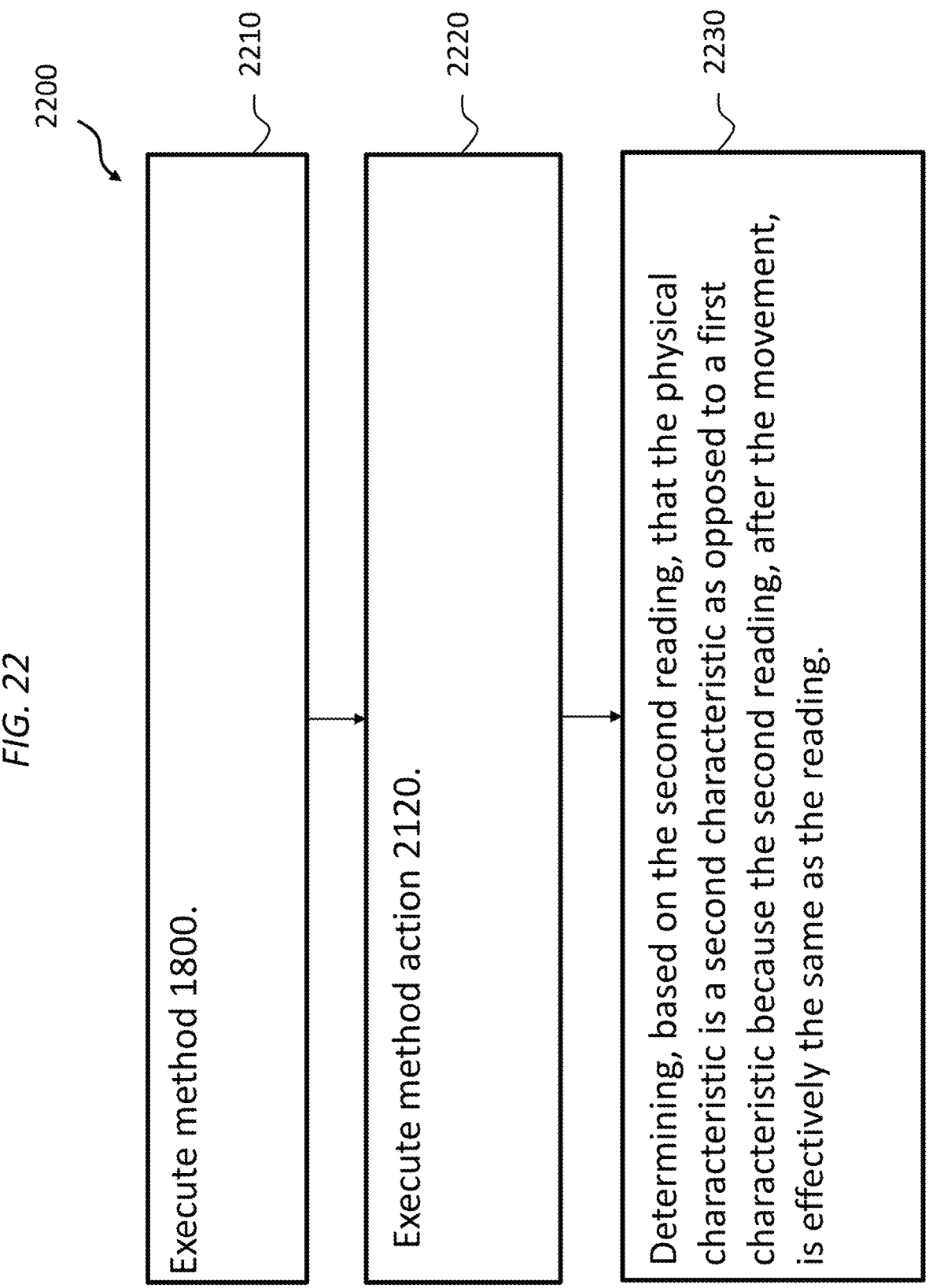

FIG. 22 presents an exemplary flowchart for an exemplary method, method 2200, which includes method action 2210, which includes executing method 1800, and method action 2220, which includes executing method action 2120. Method 2200 also includes method action 2230, which includes determining, based on the second reading, that the physical characteristic is a second characteristic as opposed to a first characteristic because the second reading, after the movement, is effectively the same as the reading.

It is noted that in at least some exemplary embodiments, method 1800 and/or the methods associated therewith detailed above is/are executed prior to the execution of any method actions that would lead to a determination that an anomalous electrode location exists. In an exemplary embodiment, method 1800 and the methods associated therewith are executed a plurality of times prior to the execution of any method actions that would lead to a determination that an anomalous location exists. By way of example only and not by way of limitation, method 1800 can be executed each time an electrode is inserted to the cochlea, where after a certain number of electrodes are inserted into the cochlea (e.g., 2, 3, 4, 5, 6 electrodes, or more, etc.). Still, it is noted that a continuous measurement regime can also be used. Also, there could be switching to other measurements based on what is observed. For example, one can establish a single row of matrix to detect when another electrode is inserted, once a full measurement on all of the electrodes in the cochlea is executed, and then one can return to a given row and evaluate that row. That said, in an exemplary embodiment, method 1800 (or method 1700, for that matter), is executed only after the electrode array has been fully inserted into the cochlea. Any regime that links the number of electrodes inserted into the cochlea to method 1800 and the methods associated there with can be utilized in at least some exemplary embodiments.

Figure 23:
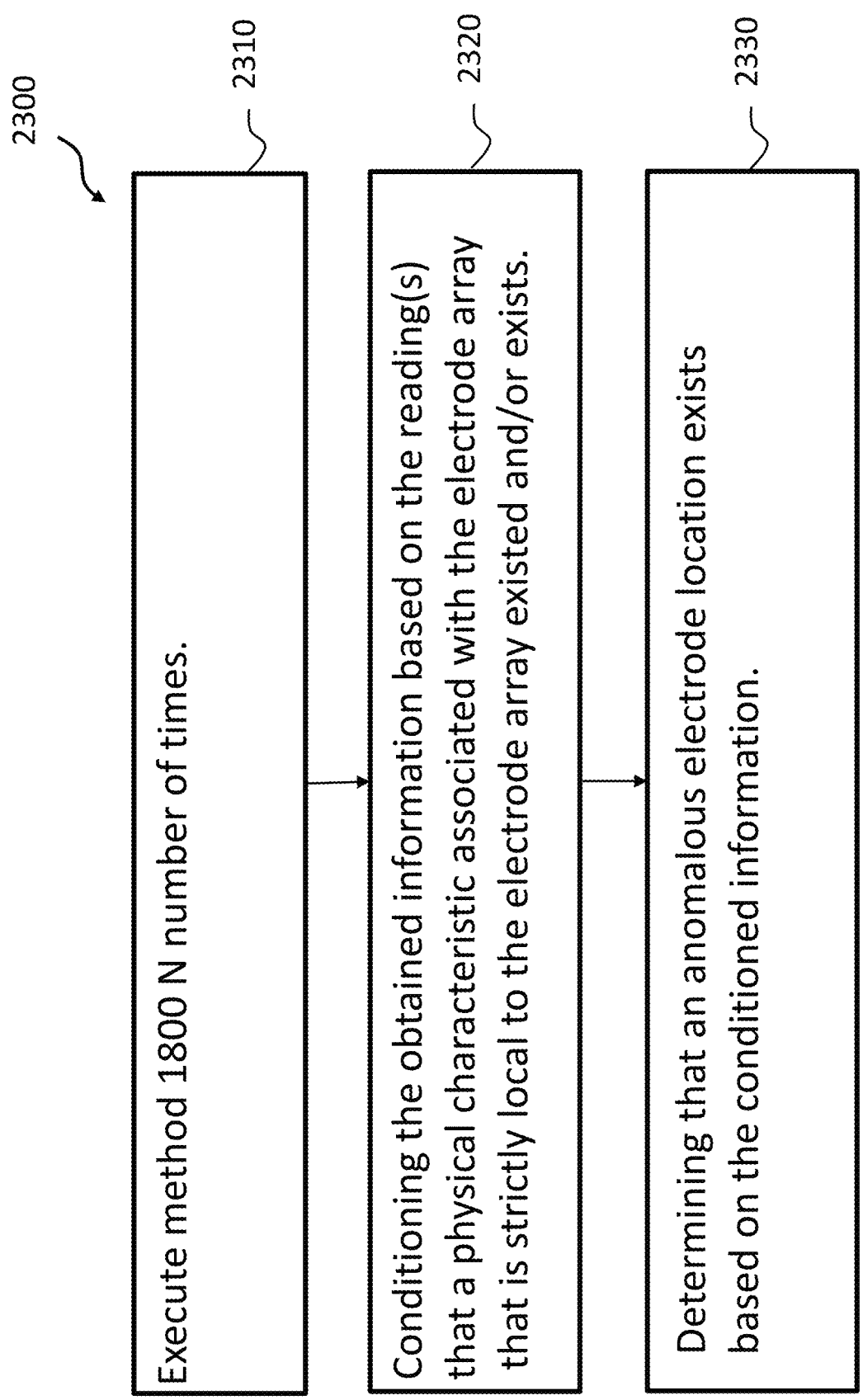

FIG. 23 presents an exemplary flowchart for an exemplary method, method 2300, which includes method action 2310, which includes executing method 1800 N number of times, where N can be 1, 2, 3, 4, 5, 6, 7, 8, 9, 10, 11, 12, 13, 14, 15, 16, 17, 18, 19, 20, 21, 22, or more. In an exemplary embodiment, method 1800 is executed in a manner that is related to the number of electrodes that have been inserted into the cochlea, such as after all of the electrodes have been inserted into the cochlea, including only after all of the electrodes have been inserted into the cochlea. Method action 2320 includes conditioning the obtained information based on the reading(s) of method action 2310 that a physical characteristic associated with the electrode array that is strictly local to the electrode array existed and/or exists. It is noted that while the embodiments of FIG. 23 depict method 2320 being executed only after method 2310 is executed the number of times represented by N, in an alternate embodiment, a method exists where method action 2310 is executed M number of times, followed by the execution of method action 2320, and then followed by the execution of method action 2310 P number of times, followed by the execution of method action 2320, and then followed by the execution of method action 2310 Q number of times, followed by the execution of method action 2320, and then followed by the execution of method action 2310 R number of times, followed by the execution of method action 2320, and then followed by the execution of method action 2310 S number of times, followed by the execution of method action 2320, and then followed by the execution of method action 2310 T number of times, followed by the execution of method action 2320, and then followed by the execution of method action 2310 U number of times, followed by the execution of method action 2320, and then followed by the execution of method action 2310 V number of times, followed by the execution of method action 2320, and then followed by the execution of method action 2310 W number of times, followed by the execution of method action 2320, and then followed by the execution of method action 2310 L number of times, followed by the execution of method action 2320, and then followed by the execution of method action 2310 J number of times, followed by the execution of method action 2320, and so on, where M, P, Q, R, S, T, U and V and W and L and J can be any number of 0, 1, 2, 3, 4, 5, 6, 7, 8, 9, 10, 11, 12, 13, 14, 15, 16, 17, 18, 19, 20, 21, or 22 in some embodiments, and M and P and Q and R and S and T and U and V and W and L and J need not equal each other. Further, the above can be extrapolated out for any number of executions of method action 2310 followed by the execution of method action 2320. Thus, it can be seen that an action of conditioning can be executed prior to the execution of all of the method actions corresponding to method 2310.

Figure 24:
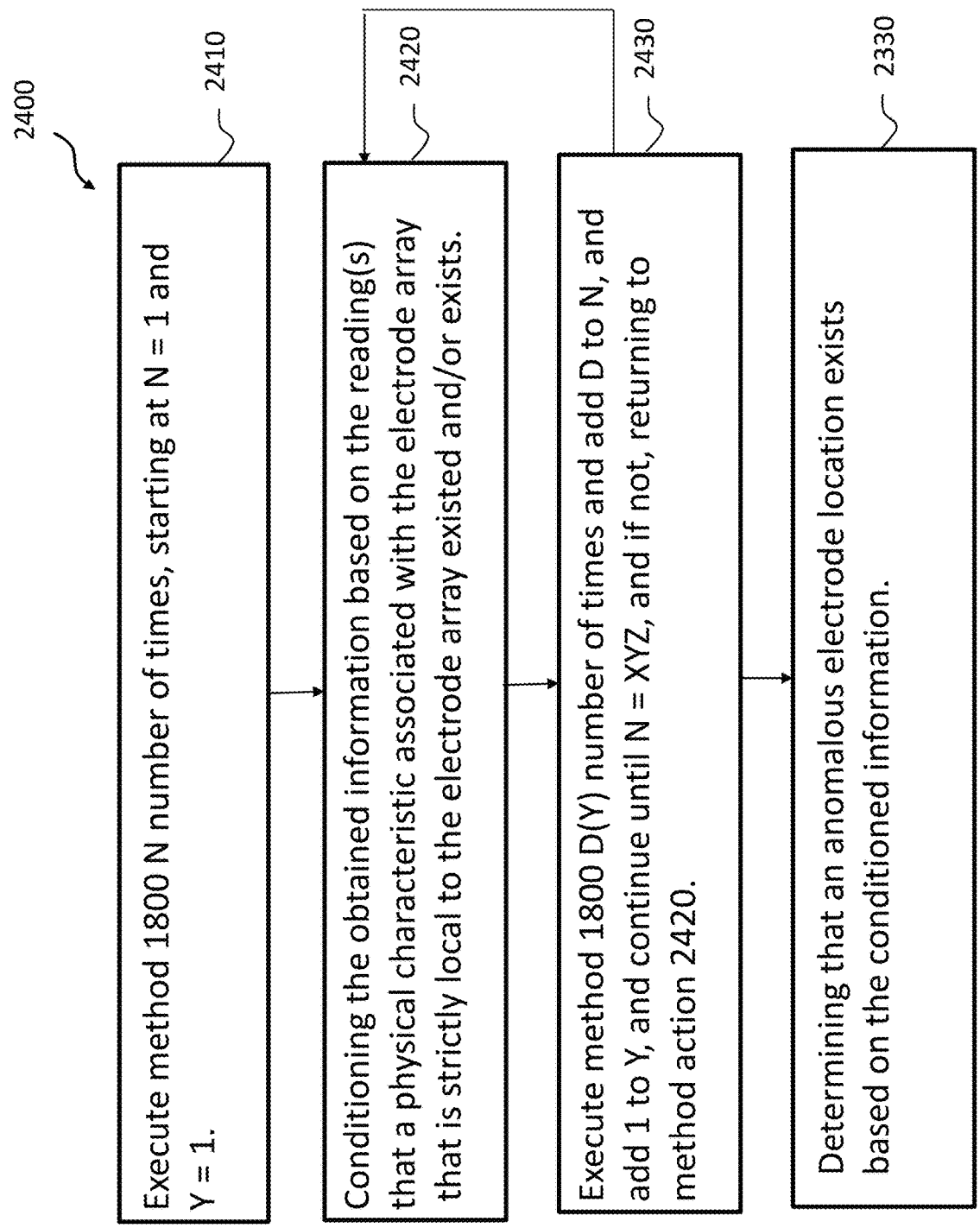

FIG. 24 presents an exemplary flowchart for an exemplary method, method 2400, which includes method action 2410, which includes executing method 1800 N number of times, starting at N=1 and Y=1. It is noted that while the embodiment of FIG. 24 keys off of method 1800, in an exemplary embodiment, not all of the method actions of method 1800 are executed at method action 2410 in some alternate embodiments. In this regard, any one or more or all of the method actions of method 1800 are executed at method action 2410. Method 2400 also includes method action 2420, which includes conditioning the obtained information based on the readings that a physical characteristic associated with the electrode array that is strictly local to the electrode array existed and/or exists. Method 2400 also includes method action 2430, which includes the action of executing method 1800 D(Y) number of times, and adding D to N, and adding 1 to Y, and continuing until N=XYZ, and if not, returning to method action 2420. In this regard, in an exemplary embodiment, D(Y) can be any integer (and for the purposes of this application, zero is to be considered an integer, recognizing a school of thought that zero is not an integer) between 0 and 22, 0 and 30, 0 and 40, 0 and 50, 0 and 100 or 0 and 1000 (inclusive), and Y can be any integer between 0 and 22, 0 and 30, 0 and 40, 0 and 50, 0 and 100 or 0 and 1000 (inclusive), and N can be any integer between 1 and 22, 1 and 30, 1 and 40, 1 and 50, 1 and 100 or 1 and 1000 (inclusive). For example, for D(1), D could be 3, and for D(2) (Y=2) D could be 4, etc. This goes on until N=ZYZ, which is a predetermined value corresponding to any of the aforementioned integers. In an example where N=22, such as for a 22 channel cochlear electrode array, the loop of method 2400 would be executed until N equals 22 (i.e., all the electrodes are in the cochlea). That said, even for a 22 channel electrode array, N could equal 30 or 40 or more, depending on how many times one seeks to execute method 1800 for a given insertion depth. Indeed, in an exemplary embodiment, after all the electrodes are inserted, method 1800 can be executed 4 or 5 times, just to "wait out" any physical phenomenon that will temporally change, such as air bubbles or shunt or electrode conditioning, and once a stable set of values has been obtained, that will be the data set used.

As with method action 2410, not all of the method actions of method 1800 are executed at method action 2430 in some alternate embodiments. In this regard, any one or more or all of the method actions of method 1800 are executed at method action 2430.

Figure 25:
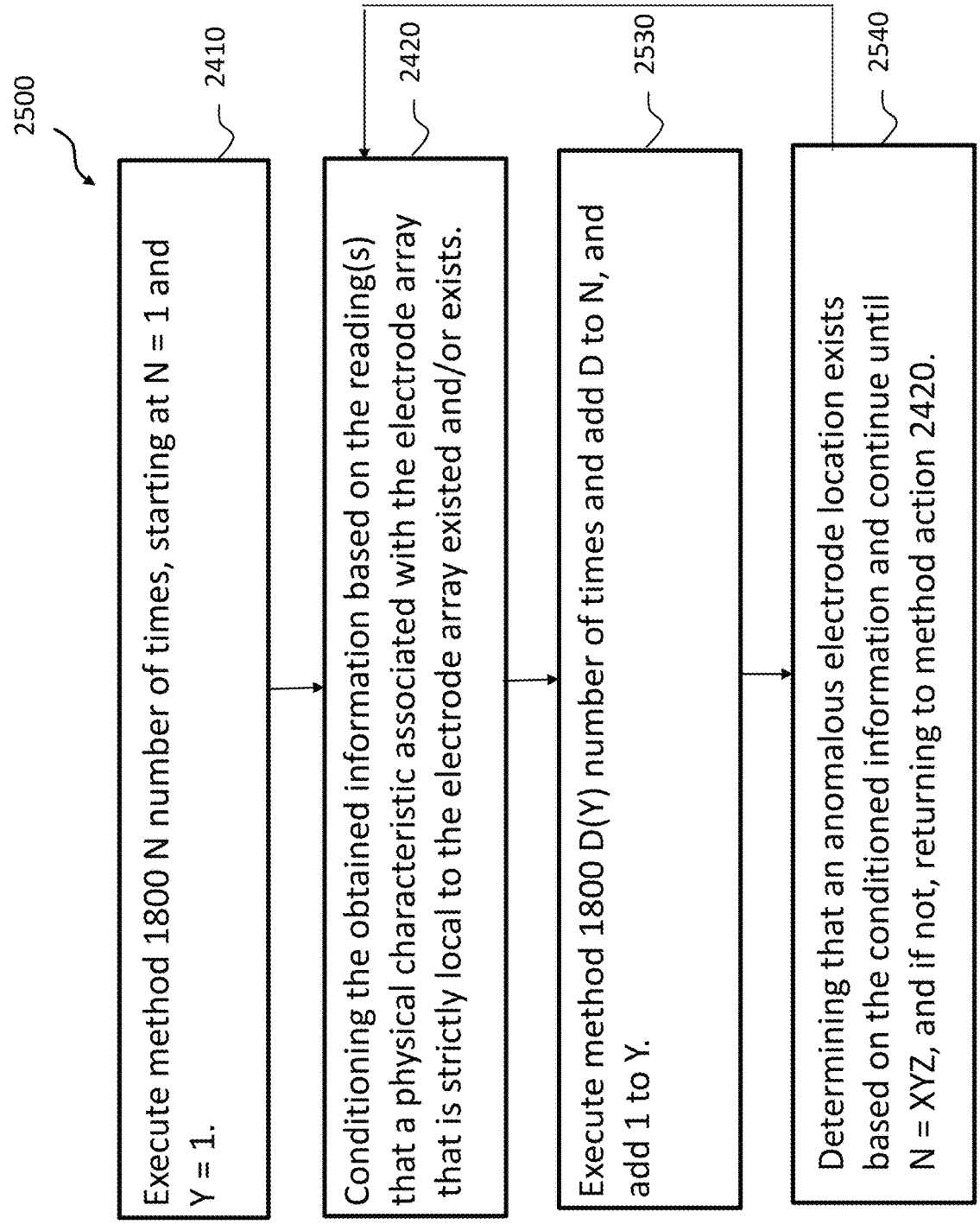

FIG. 25 represents an exemplary flowchart for an exemplary method, method 2500, which method actions are indicated as being similar to the method 2400 detailed above, except as indicated. Here, method action 2530 was executed in a manner analogous to method action 2430, except that after this method action is executed, the method proceeds to method action 2540, which entails executing method 2330, with the caveat that this is done until N=ZYZ, and if not, the method returns to method action 2420.

It is noted that in an exemplary embodiment of methods 2400 and/or 2500, any disclosure with respect to one or more of the method actions associated with method 1800 can correspond also to a disclosure of executing one or more of the method actions of method 1900, method 2000, method 2100 and/or method 2200.

Figure 26:
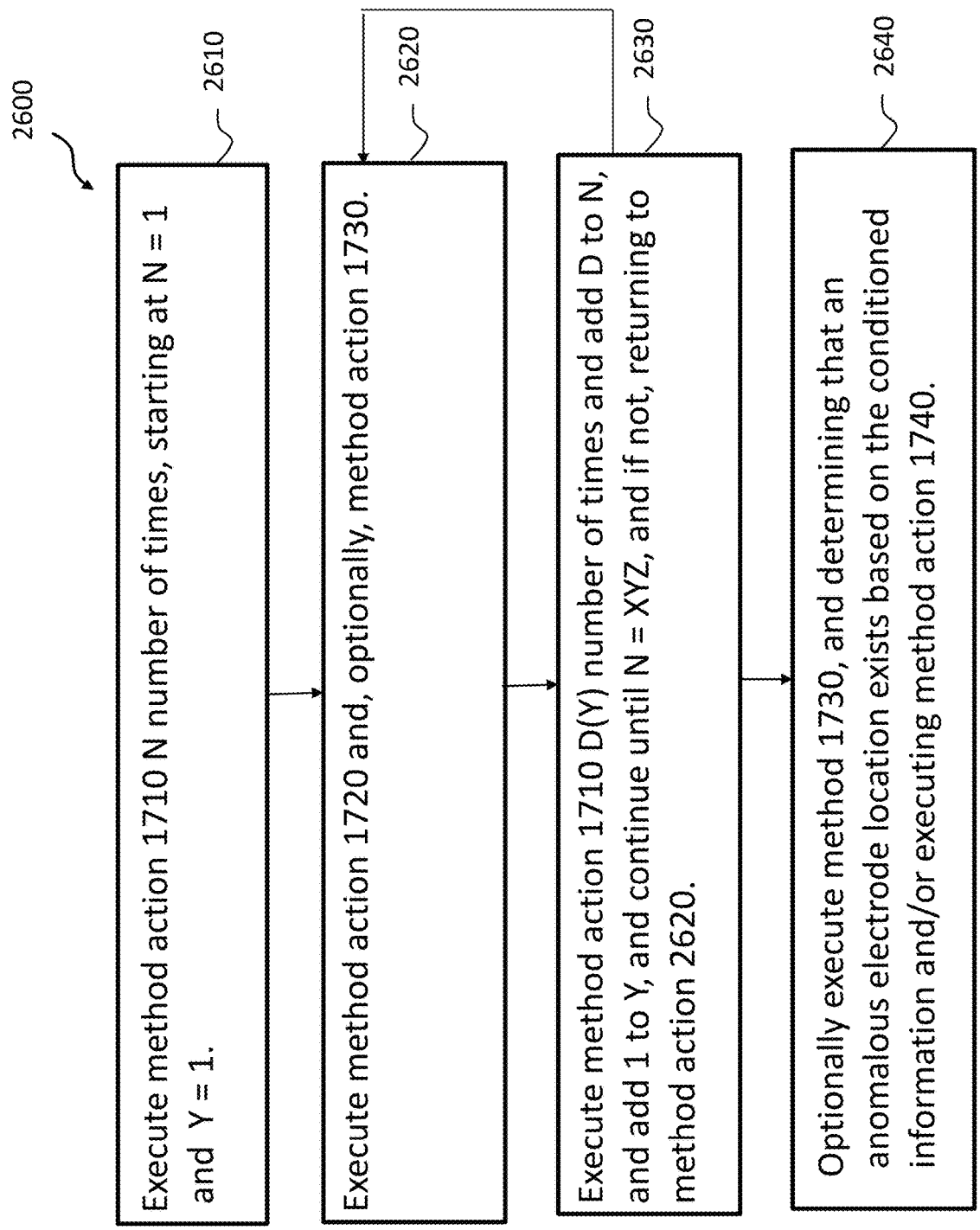

FIG. 26 presents an exemplary flowchart for an exemplary method, method 2600, which includes method action 2610, which includes executing method action 1710 N number of times, starting at N=1 and Y=1. Method 2600 also includes method action 2620, which includes executing method action 1720 and, optionally, method action 1730. Method 2600 also includes method action 2630, which includes, executing method action 1710 D(Y) number of times and add D to N, and add 1 to Y, and continue until N=XYZ, and if not, returning to method action 2420. Method 2600 also includes method action 2640, which includes optionally executing method action 1730, such as if this was not executed in method action 2620 (but it can be re-executed as well), and determining that an anomalous electrode location exists based on the conditioned information and/or executing method action 1740.

To reiterate, some of the method actions detailed herein can be executed during insertion of the electrode array, and can be executed continuously or otherwise in a stepwise fashion for incremental insertions the electrode array, and in other embodiments, the method actions detailed herein can be executed after the electrode array is fully inserted into the recipient. It is also noted that these actions can be executed both during the insertion process and after the insertion process is completed. In some embodiments, the teachings detailed herein can provide an indication to the surgeon or the like of an anomalous electrode location prior to full insertion of the electrode array. In an exemplary embodiment, can be the case with respect to providing an indication upon the insertion of but not more than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 electrodes of the electrode array.

In view of the above, it can be seen that the various method actions detailed herein are executed one or more times prior to developing or finalizing the ultimate matrix that is utilized to determine whether or not there exists an anomalous electrode location. In some exemplary embodiments, such can enable redundancy in the methods detailed herein. In an exemplary embodiment, it can be seen that in some instances, there are physical phenomena that exist during some temporal periods and/or locations of the electrode array, such as insertion depth, and do not exist during some other temporal periods and/or locations of the electrode array. By repeating some of the method actions detailed herein, and obtaining multiple data points for the same electrodes/same locations along the array, redundancy can be provided. This is because two or three or more data sets can be developed for the same location along the electrode array and/or for the same location of the electrode array in the cochlea, and data sets that are erroneous can be discounted or otherwise replaced with data sets that are not erroneous. In an exemplary embodiment, if a data set indicates an anomalous voltage reading, and any subsequent data set does not include that anomalous voltage reading, the subsequent data set can be utilized. Corollary to this is that if the prior data set contained readings that were not in error, but the later data set did contain such readings, the prior data set can be utilized. Note also that in an exemplary embodiment, the redundancy can be applied to replace only some rows and/or some columns and/or only some data points of the ultimate matrix that is utilized to identify the anomalous electrode location, such those detailed herein, for example (dislocation, fold over, etc.).

In some exemplary embodiments, redundancy can be achieved via testing for an open circuit in two ways. First, if the given electrode is energized, the readings from the other electrodes can be utilized to analyze or otherwise determine whether that energized electrode is in an open circuit. Second, if a given electrode is utilized as a read electrode, and there are no readings of that electrode, such can also be utilized to determine that such is an open circuit. Still further, as noted above, in some exemplary embodiments, air bubbles or the like can interfere with readings. By utilizing other electrodes, redundancy features can be implemented to avoid the deleterious effects of the air bubble. Still further, because the teachings detailed herein can be executed in a temporally progressing manner, the air bubble may be moved or otherwise dissipate, thus providing additional redundancy to the system. The devices, systems, and our methods detailed herein can be directed toward such or otherwise configured to embrace or otherwise take advantage of such redundancy. Also, reverse redundancy can be used. For example, one can detect a short, then the short resolves itself, and short re-appears. Based on this, one can (the system/computer can) remove a given electrode from further measurements because identified intermittent issue that could confuse the data or otherwise unexpectedly result in erroneous data.

To be clear, in an exemplary embodiment, the teachings detailed herein can provide redundancy with respect to measuring and/or testing for the same condition two or more different ways.

Moreover, the redundancy can enable multiple embodiments.

That said, in some exemplary embodiments, readings for other portions of the matrix can be utilized to fill-in or otherwise replace erroneous readings. By way of example only and not by way of limitation, in an exemplary embodiment, such as where 19 of 22 electrodes are inserted into the cochlea, and the first electrode, the most distal electrode, is stimulated, and a reading at electrode 18 is clearly anomalous, the reading from electrode 17 can be utilized for the reading at electrode 18. Also, one could avoid stimulating electrode 18 and instead could do more frequent stimulation or reading on electrode 17, or any other utilitarian electrode, to replace what would otherwise be the stimulation or reading on that electrode.

In some exemplary embodiments, there are methods according to the teachings detailed herein which implement only selective conditioning of the data. In an exemplary embodiment, as demonstrated above, there is utilitarian value with respect to conditioning the data prior to normalizing and/or prior to utilizing the data to determine the existence of an anomalous electrode location. That said, in another exemplary embodiment, there is utilitarian value with respect to specifically not conditioning the data prior to normalizing and/or prior to utilizing the data to determine the existence of an anomalous electrode location. That is, non-conditioned data is utilized to determine the existence of an anomalous electrode location. (It is noted that all disclosures herein with respect to the determination of the existence of an anomalous electrode location also corresponds to a disclosure of determining that an anomalous electrode location does not exist.) That said, in another exemplary embodiment, there is utilitarian value with respect to utilizing data that is conditioned in a different manner from other data that is utilized to determine the existence of an anomalous electrode location. That is, differently conditioned data is utilized to determine the existence of one or more types of anomalous electrode locations as opposed to conditioned data that is used to determine the existence of one or more other types of anomalous electrode locations. For example, for the anomalous electrode location relating to fold over, conditioned data that has been conditioned to account for detrending is utilized, whereas for the anomalous electrode location relating to electrode bowing, the data is conditioned, but not conditioned to account for the detrending phenomenon. That is, in an exemplary embodiment, two separate data sets are utilized to determine the existence of these two separate anomalous electrode location scenarios.

Further, while some embodiments include executing a normalization process on the conditioned data, some embodiments specifically exclude executing a normalization process on the conditioned data. Thus, in some exemplary embodiments, two separate data sets are utilized to determine the existence of separate anomalous electrode location scenarios. For example, normalization is executed with respect to determining the presence or absence of fold over, but not to determine the presence or absence of buckling, but one may do so for bucking in some embodiments. In some embodiments, there will instead be no detrending for buckling.

It is noted that while the embodiments herein often present normalizing as a later action/an action executed just before performing method action 1740, or even an action that is part of method action 1740, in other embodiments, the normalizing can be executed before the conditioning action, such as immediately after obtaining measurements from the read electrodes.

In view of the above, with respect to method 1700, in an exemplary embodiment, there is the additional action of executing a second conditioning action on the obtained information based on the identified one or more first meanings. There is also the additional action of executing a third analysis of the second conditioned information to identify one or more third meanings from among a second group of meanings of the sensed phenomenon.

Accordingly, in an exemplary embodiment, the methods detailed herein can include the action of selectively conditioning the data/conditioning the data in different manners based on the type of electrode location anomaly that is sought to be identified (which includes seeking to identify the absence of such).

Figure 27:
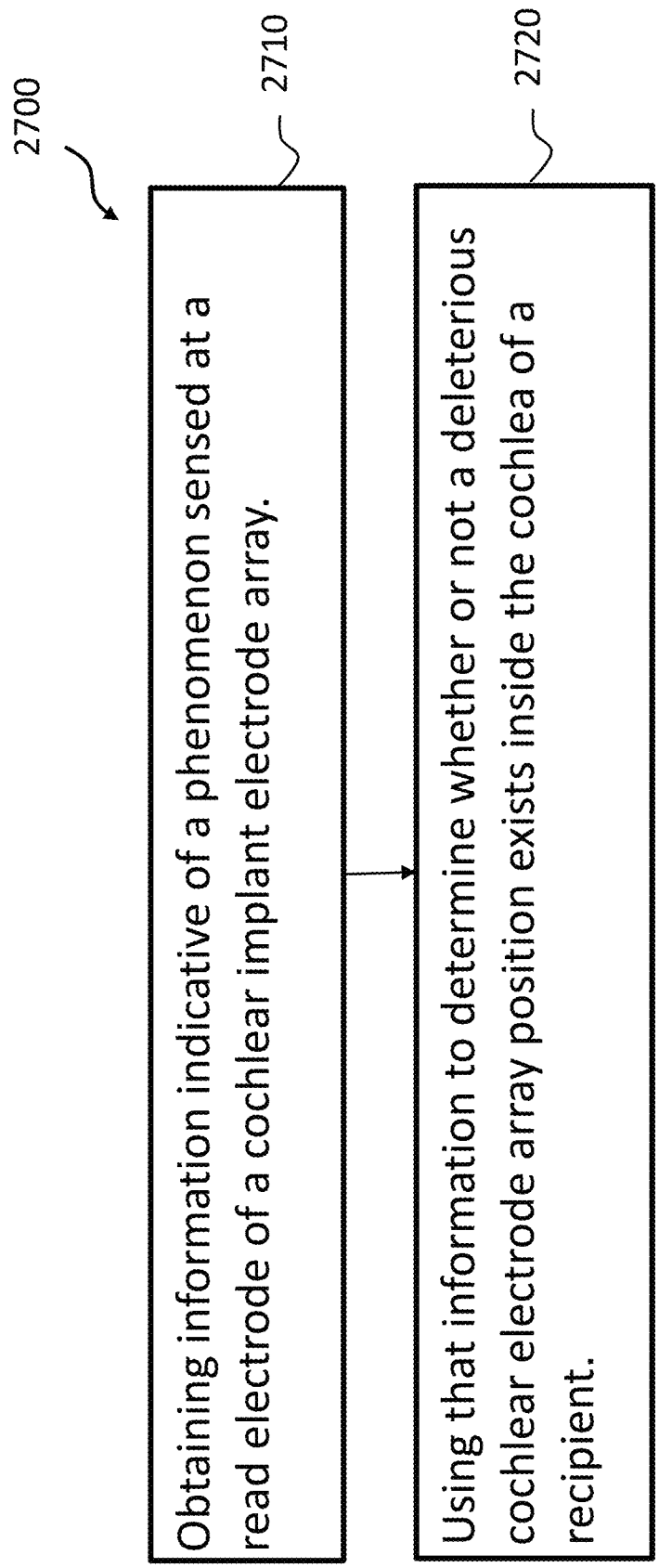

FIG. 27 presents an exemplary flowchart for another exemplary method, method 2700. Method 2700 includes method action 2710, which includes obtaining information indicative of a phenomenon sensed at a read electrode of a cochlear implant electrode array. Method 2700 also includes method action 2720, which includes using that information to determine whether or not a deleterious cochlear electrode array position exists inside the cochlea of a recipient. Such action can be executed according to any of the teachings detailed herein and/or variations thereof. In an exemplary embodiment of method 2700, the actions used to make the determination correspond to a statistically based accuracy rating of at least GG out of 100 vis-à-vis a determination that a deleterious position exists (not just whether or not it exists, but of the times that such deleterious position is indicated, it is accurate) where GG is 80, 81, 82, 83, 84, 85, 86, 87, 88, 89, 90, 91, 92, 93, 94, 95, 96, 97, 98, 99, 99.9, 99.99, 99.999, 99.9999, 99.999999 or 100. (In some embodiments, GG is any value between 97 and 100, inclusive, in 0.0000001 increments.) In this regard, in an exemplary embodiment, method action 2720, when executed utilizing certain actions, results in a correct determination of whether or not the deleterious cochlear electrode array position exists, vis-à-vis a determination that a deleterious position exists (not just whether or not it exists, but of the times that such deleterious position is indicated, it is accurate) for example, 90 times out of 100 times, 95 times out of 100 times, all other things being equal. That is, the teachings detailed herein enable method action 2720 to be executed with a high confidence level relative to other actions utilized to make such a determination according to method action 2720. In an exemplary embodiment, this can be because the data is conditioned according to the teachings detailed herein prior to making the determination.

It is noted that in an exemplary embodiment, the actions used to make the determination that a deleterious position exists (not just whether or not it exists, but of the times that such deleterious position is indicated, it is accurate) executed in method 2720 correspond to a statistically based accuracy rating of at least GG out of 99, 98, 97, 96, 95, 94, 93, 92, 91, 90, 89, 88, 87, 86, 85, 84, 83, 82, 81, or 80, where, of course, GG is never greater than one of those numbers.

In an exemplary embodiment, method action 2720 results in a determination that a deleterious position exists. In an exemplary embodiment, the likelihood that the determination is wrong upon such determination is less than HH out of 100, where HH is 20, 19, 18, 17, 16, 15, 14, 13, 12, 11, 10, 9, 8, 7, 6, 5, 4, 3, 2, 1, 0.5, 0.1, 0.05, 0.01, 0.001, 0.0001, 0.00001 or 0. (In some embodiments, HH is any value between 3 and 0, inclusive, in 0.0000001 increments.) In this regard, as noted above, there is negative utilitarian value with respect to receiving false positives with respect to determining whether or not, for example, one of the anomalous electrode positions has occurred or otherwise exists. In at least some exemplary prior art methods that attempt to determine whether or not an anomalous electrode position exists, the number of false positives can be high. Indeed, to the extent that many of the prior art methods have deficiencies, it is that they provide an indication that an anomalous electrode position exists when none exists. By implementing at least some of the teachings detailed herein, in an exemplary embodiment, the aforementioned reliability can be obtained. In an exemplary embodiment, method action 2720 results in a determination the likelihood of which such is wrong is less than HH out of 125, 150, 175, 200, 225, 250, 300, 350, 400, 450, 500, 550, 600, 650, 700, 750, 800, 850, 900, 950, or 1000. In an exemplary embodiment, the determination is a determination that a fold over exists, and thus, the likelihood that the determination is wrong can be less than, for example, 2 out of 100, 2 out of 175, etc., in accordance with the above teachings. In an exemplary embodiment, the determination is a determination that a fold over does not exist, and thus the likelihood that the determination is wrong can be less than, for example, 1 out of 500.

In an exemplary embodiment, the determination is a determination that a dislocation has occurred, and thus the likelihood that the determination is wrong can be less than, for example, 5 out of 150, 2 out of 100, etc. In an exemplary embodiment, the determination is a determination that bowing has occurred, or any other occurrence of any other phenomenon. With respect to fold over, In view of the above, in an exemplary embodiment there is the method 2700, further comprising, starting with N=2, an action "iii" which includes obtaining Nth information indicative of an Nth phenomenon sensed at an Nth read electrode of an Nth cochlear implant electrode array. This exemplary method further includes an action "iv," which includes using that Nth information to determine whether or not a deleterious cochlear electrode array position exists inside the cochlea of an Nth recipient. This method includes repeating actions "iii" and "iv" a number of times, such as until method 2700 is executed 100 times. When described in terms of an algorithm, the method includes adding 1 to N, and repeating actions "iii" and "iv" until N=100. It is noted however that any such claim to such action is only for the purposes of accounting. It is not necessary to actually add a number to N. In any event, in an exemplary embodiment of this example, of the N determinations, where N=100, at least GG of the determinations were accurate.

It is noted that the use of "first, second, third, etc." herein is used in terms of providing a proper noun for a given feature or action. Thus, with respect to the above, when N equals 100, the $100^{th}$ electrode can be any electrode one and electrode array having 22 electrodes.

Corollary to the above, in an exemplary embodiment, there is the method 2700, further comprising, starting with N=2, an action "iii" which includes obtaining Nth information indicative of an Nth phenomenon sensed at an Nth read electrode of an Nth cochlear implant electrode array. The method further includes an action "iv," which includes utilizing that Nth information to determine whether or not a deleterious cochlear electrode array position exists inside the cochlea of an Nth recipient. Consistent with the algorithm approach detailed above, the method also includes adding 1 to N, and repeating actions "iii" and "iv" until at least N=100, wherein of the determinations that a deleterious position existed, no more than 5% were false positives.

In accordance with the teachings detailed above, in an exemplary embodiment, method action 2720 includes first conditioning the information and then analyzing the conditioned information to make the determination. In an exemplary embodiment of such, method 2700 further comprises, after the conditioning action of the information in prior to the analyzing of the information, normalizing the conditioned information and then analyzing the normalized conditioned information to make the determination. That said, as noted above, some embodiments purposely avoid normalization of the data. Accordingly, in an exemplary embodiment, there is the action of reanalyzing the information without normalizing or analyzing the information before the normalizing to make a second determination as to whether or not another type of deleterious cochlear electrode array position exists inside the cochlea of the recipient, this "another type" being different than that which was the subject of method action 2720. By way of example only and not by way of limitation, in an exemplary embodiment, the first type can be fold over, and the second type can be a bowing deleterious position. Note also that in an exemplary embodiment, the action associated with first conditioning the obtained information can correspond to first conditioning the obtained information in a first manner and then performing the analysis for the occurrence of bowing, and then further conditioning the obtained information in a second manner (e.g., including accounting for detrending, as opposed to the first manner which did not so account for such), and then normalizing and then performing a second analysis for the occurrence of fold over. Note that in the aforementioned exemplary embodiment, instead of further conditioning, the data can be completely reconditioned.

An exemplary embodiment of method 2700 further includes, after method action 2710, the action of determining whether or not to execute a conditioning action on the obtained information and/or what type of conditioning action is to be executed on the obtained information. Further, in this exemplary embodiment, after the action of determining whether or not to execute the conditioning action and/or after determining the type of conditioning action, normalizing the information and analyzing the normalized information to make the determination.

In an exemplary embodiment of method 2700, after action 2710, there is an action of executing a first type of conditioning on the information. After executing the first type of conditioning, method action 2720 is executed based on the conditioned information conditioned according to the execution of the first type. In an exemplary embodiment, there is also the action of executing a second type of conditioning different from the first type of conditioning; and the method includes analyzing the conditioned information conditioned according to the execution of the second type to determine whether or not a second type of deleterious cochlear electrode array position exists inside the cochlea different from that determined in method action 2720. In an exemplary embodiment, the first type can include accounting for detrending, and the second type can include not accounting for detrending, or vice versa.

Still further, in an exemplary embodiment, there can be the action of executing a normalizing action when the information is conditioned according to the second type prior to analyzing such. Alternatively, and/or in addition to this, there can be the action of not executing a normalizing action one the information conditioned according to the first type prior to analyzing such.

In at least some exemplary embodiments, the result of the action of determining whether or not to execute the conditioning action is a determination not to execute the conditioning action, and the action of normalizing the information can correspond to normalizing the non-conditioned information. That said, in at least some exemplary embodiments, the results of the action of determining what type of conditioning action is a determination to execute a type of conditioning action that is conducive to determining whether or not fold over has occurred, and the action of normalizing the information corresponds to normalizing the conditioned information conditioned according to the type of conditioning that is conducive to determining whether or not fold over has occurred.

Conversely, the result of the action of determining what type of conditioning action is a determination to execute a type of conditioning action that is conducive to determining whether or not dislocation has occurred and method 2700 also includes determining not to normalize the information conditioned in accordance with the type of conditioning action that is conducive to determining whether or not dislocation has occurred.

In some embodiments, such as where the electrode array has pierced the basilar membrane, the impedance jumps across the membrane, or otherwise that there is an upward change or a discontinuity across the membrane, or, a statistically unusual degree of change between measurements crossing the membrane, and the measurements from the read electrodes can be utilized to identify the scenario. In at least some exemplary embodiments, the read electrodes reveal a discontinuity in the measurements. In at least some exemplary embodiments, a given type of discontinuity can be correlated to a dislocation. Some discontinuities will be different than others, and in some exemplary embodiments, at least based on statistical and/or empirical data, a given discontinuity scenario can be correlated to the statistical samples and such can be utilized to determine the presence or absence of dislocation/to distinguish a dislocation scenario from other readings indicative of other phenomena.

In view of the above, it is to be understood that the devices, systems, and/or methods detailed herein can have utilitarian value with respect to helping to satisfy an expectation during the surgery that implants a cochlear implant of correct insertion of electrode array, at least after the surgical procedure. Indeed, in an exemplary embodiment, the teachings detailed herein can have utilitarian value with respect to improving the general placement of the cochlear implant electrode array vis-à-vis placement of the electrodes in a localized manner in the scala tympani, such that the spiral ganglion cells are directly stimulated and the current dispersion is reduced relative to that which would be the case without the teachings detailed herein. Such can have utilitarian value with respect to reducing the amount of current consumption and improving the resolution of the stimulation vis-à-vis the achieved location of the electrode array relative to that which would be the case in the absence of the teachings detailed herein. Such improvement can correspond to an improvement of GG out of 100 relative to that which be the case in the absence of utilizing the teachings detailed herein.

At least some teachings detailed herein can prevent or otherwise limit the likelihood of an inadequate insertion trajectory to the basal turn of the cochlea during the cochleostomy, and thus reduce the likelihood that there can exist damage the basilar membrane, osseous spiral lamina and lateral cochlear walls and/or the likelihood that the electrode array could be displaced from the scala tympani to the scala vestibuli across the basilar membrane or osseous spiral lamina. At least some embodiments of the teachings detailed herein utilize techniques to determine the position of the electrode array within the cochlea utilizing radiology imaging methods, like fluoroscopy, phase-contrast radiography, rotational tomography (RT), combination of conventional radiographs and computed tomographic (CT) images, fusion of preoperative and postoperative CT imaging and micro-CT scanning. That said, some exemplary methods and techniques going to the teachings detailed herein explicitly do not utilize such radiological imaging methods/none at all, at least within 30, 45, 60, 75, 90, or 120 minutes after the electrode array is fully inserted into the cochlea. Accordingly, some exemplary embodiments include executing one or more all of the method actions detailed herein without executing such radiological methods within the aforementioned time periods. That said, one might exclude radiological methods if a normal result is obtained/the data indicates no anomalous electrode positioning, while using such methods if an abnormal result is obtained so as to confirm the results.

Such exclusion can include conventional cochlear view (X-ray) or high resolution CT (HRCT) are also commonly used for vestibular electrode insertion, scalar dislocations or tip folding evaluation. Such exclusion can also include cone beam computed tomography (CBCT).

Again, some exemplary methods detailed herein are executed without the consultation or the evaluation of an expert to verify the correct position of the electrodes. In an exemplary embodiment, the evaluation is executed in an automated and/or semi-automated manner. The end result can be provided to the surgeon or other healthcare professional based entirely on computer analysis/automated analysis. The end result of the analysis can be provided in a detailed manner and/or or can be a binary good/bad indication. This result can also be presented continuously as the array is inserted using, visual, auditory or haptic feedback or a combination of these.

Some embodiments can utilize Spread of Excitation (SOE) to determine whether or not tip fold over has occurred, and which can provide surgeons an intraoperatory tool that let them detect positioning problems. However, some embodiments explicitly exclude the utilization of such, while in other embodiments may utilize such but exclude the utilization of such to base the final diagnosis thereupon, whereas in some embodiments, methods 1700 to 2700 are so utilized to base the final diagnosis thereupon. One can also use conditioning alongside a neural response, rate of decay, and also when measuring stimulation artifacts. Some embodiments can utilize neural responses in combination with the methods disclosed above to provide further robustness or confirmation of the electrode position and add information about the electrode position in relation to the surviving neural body position.

In view of the above, an exemplary embodiment includes an automated system that makes use of the implant electronics to give feedback of the electrode array position before the patient leaves the operation theatre. In addition, if a wrong insertion exists, utilizing the teachings detailed herein, at least in some embodiments, such wrong insertion can be detected and corrected, avoiding unnecessary surgical re-intervention and radiation.

Some embodiments base the detection process on potential decay in a medium:

$$V = k \cdot \frac{Q}{r} \qquad \text{Eq. 1}$$

where V is the electrical potential, k is the Coulomb's constant (Nm$^2$/C$^2$), Q is the charge C and is the distance to the charge. It can be deduced that the lower the distance the higher the voltage received and vice versa.

An exemplary embodiment of the procedure is as follows. First, an electrode is stimulated in accordance with any of the teachings detailed above and/or any other manner that will enable the teachings detailed herein, and the received electric potential along the electrode array is recorded. In an exemplary embodiment, the neighbor electrode is then selected and the next data set is saved, repeating until the whole electrode array has been stimulated. Moving away from the stimulating electrode, the potential should decay in accordance with Eq. 1. In a perfect insertion, or at least a normal insertion, a maximum value will be seen on the stimulating electrode and a minimum value on the farthest one. In Fold over case, the global maximum will be the stimulating electrode but another local maximum will rise up, indicating the fold over.

Utilizing the teachings herein, such can provide utilitarian value of avoiding exposure of the recipient to radiation and the saving of surgical time because a separate imaging process is not needed.

Teachings detailed herein can enable the presence of tip fold over without radiation, along with the accuracies/reliabilities detailed above at least in some embodiments, in the surgical theatre (as opposed to the radiological theater) and such can be executed in some instances automatically. The success rate will be evaluated with the implemented automatic system, intraoperatively.

For the detection (which can correspond to, for example, method action 1710 above), some embodiments of the system are based on the measurement of the electric potential generated by the activation of an electrode. The goal of at least some exemplary embodiments is to provide to the surgeon a tool to validate the correct insertion of the electrode array in a few seconds, if not a few minutes, if not the times detailed above, after full insertion (again, less than 0.25, 0.5, 0.75, 1, 1.25, 1.5, 1.75, 2, 2.5, 3, 3.5, 4, 5, 6, 7, 8, 9, 10, 11, 12, 13, 14, or 15 minutes from the time of full insertion (the 22 second electrode or the last electrode of the array being inserted into the cochlea). Consistent with the teachings detailed herein, the system is designed, in some embodiments to detect the presence of tip fold over, as well as short-circuited and/or not inserted electrodes.

The applied signal to the electrodes can be a biphasic square signal, which amplitude level is settled to 200 current levels, corresponding to 648 μAmps. The gain factor is fixed at 0.2 units. The potential measurements can be done in the moment corresponding to the end of the first trailing edge.

The data can be recorded in a k×k matrix. The rows define the target electrode, where the measurement is made at, and the columns refer to the active electrode, where the stimulus is produced. In some embodiments, the electrode arrays utilized are the CI532 and CI512 from Cochlear Ltd.™, and thus the total among of electrodes is k=22. It is to be understood that in some alternate embodiments, the teachings detailed herein can be modified so as to account for electrode arrays having less than 22 electrodes or more than 22 electrodes, such as, for example, electrode arrays that have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, 250, 300, 350 or 400 or more electrodes or any value or range of values inclusively therebetween in 1 increments (77, 222, 12 to 399, etc.). Still, with respect to a 22 electrode array, in total 484 measurements are recorded in at least some exemplary embodiments to generate the full matrix data.

$$M_V = \begin{bmatrix} V_{1,1} & V_{1,2} & \cdots & V_{1,s} \\ V_{2,1} & V_{2,2} & \cdots & \cdots \\ \cdots & \cdots & \cdots & \cdots \\ V_{m,1} & \cdots & \cdots & V_{m,s} \end{bmatrix} \forall\, m, s = [1:k] \qquad \text{Eq. 2}$$

where m is the measured electrode and s is the stimulated electrode.

Figure 28:
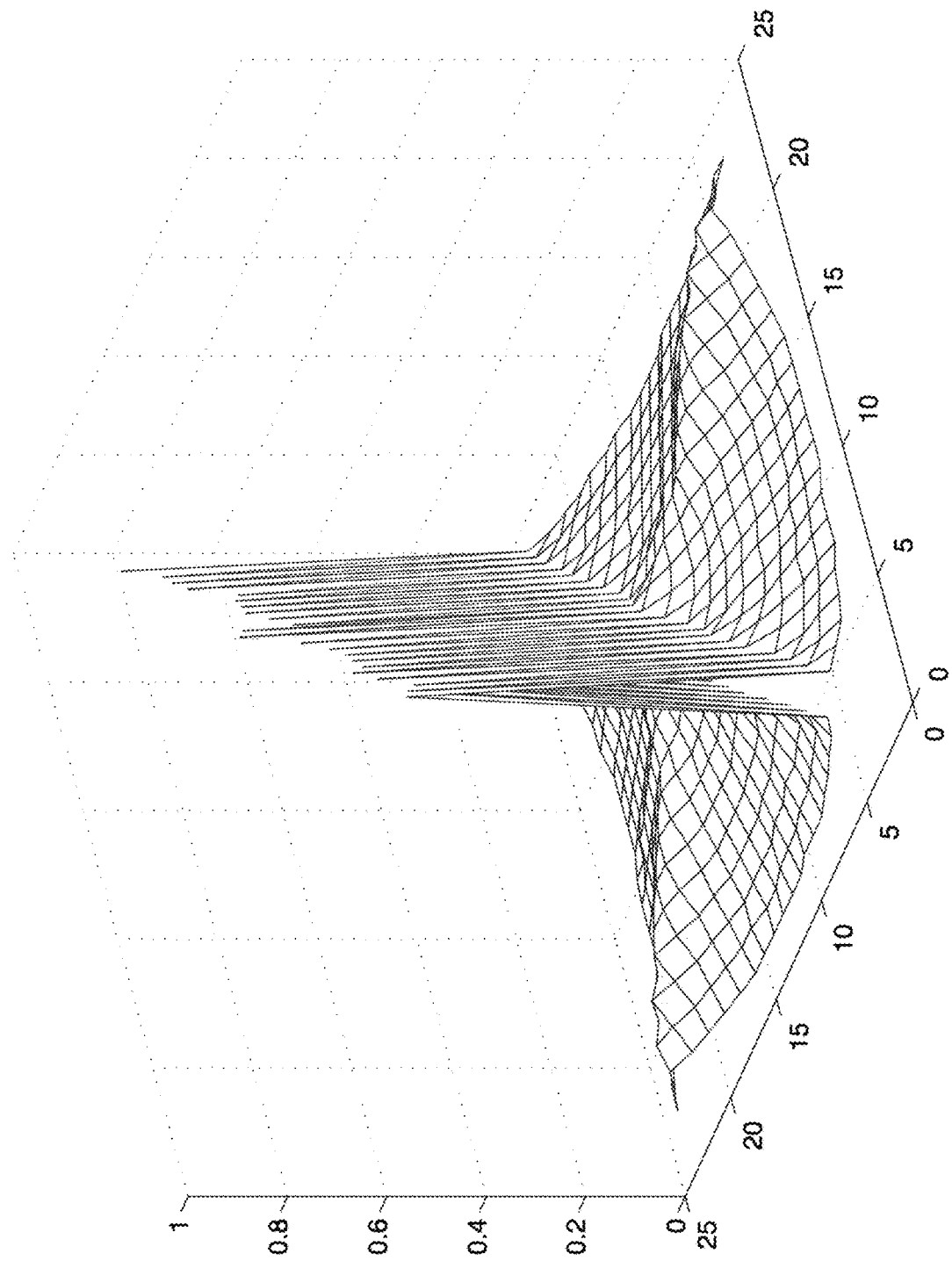

In this embodiment, all the electrodes are sequentially stimulated, and the received potential is recorded in all of the electrodes, including in the stimulated electrode. FIG. 28 depicts the obtained matrix that is exposed (a voltage matrix). When the tip fold over appears, a matrix with a second diagonal besides the principal diagonal can be observed, as seen in FIG. 28. The intersection between the main diagonal and the second matrix indicates the place where the fold over occurs, identifying the pivoting electrode and providing information about how severe the fold over is, as it has been test in previous laboratory tests. The main diagonal is $$Y=X \qquad \text{Eq. 3}$$

And the second diagonal, when the tip folds over case, is $$Y=aX+b \qquad \text{Eq. 4}$$

In at least some embodiments, the electric potential always decays with distance (Eq. 1), so the relative position of the electrodes can be correlated with the measured potential, in order to deduct the relative position between them. In a tip fold over situation (FIG. 30—where the graph depicts the voltage for the given measure electrode), an increase of the received potential is detected, compared with the normal situation (no tip fold over—FIG. 29—where the graph depicts the voltage for the given measure electrode), in a place where the potential should be reducing (FIGS. 29 and 30 depict measured potential with stimulation of the most apical electrode).

Briefly, as noted above, in some exemplary scenarios, an open electrode exists, and this skews the data. FIGS. 8 and 9 are thus comparable to FIGS. 29 and 30 in the general sense. As noted above, embodiments can take into account that an electrode is in Open-Circuit it is disconnected from the current source, so the electrode will not be able to emit the impulse, as the connection have been interrupted. This fact will make the potential received in other electrodes null (0 and also negative values due to ADC) when the affected electrode emits the impulse, and maximum when measured on that electrode, which phenomenon is depicted above in FIGS. 8 and 9, vis-à-vis measured potential while stimulation in an open circuit case.

Also, as noted above, sometimes, part of the electrode array stays outside of the cochlea (lack of space, ossifications, cochlear diameter, etc.). The electrodes affected have, in some embodiments, a similar behavior as the Open Circuit ones. The received potential is maximum when the measured electrode is the stimulated one, however, neighbor electrodes have low potential values, but higher than in the Open Circuit case. This is depicted in FIGS. 12 and 13, as noted above, where the measured potential is measured while stimulation exist, in a no insert electrode scenario.

As noted above, there are other physical phenomenon associated with electrodes that can skew the data set that is utilized to create the matrix. In view of the above, in an exemplary embodiment, there is an automatic detection method that enables the system to be used in a relatively easy manner or otherwise to provide methods that enable the detection of any problem in the electrode array vis-à-vis positioning intraoperatively, as opposed to postoperatively which is defined as that which includes the utilization of radio graphic imaging or the like.

As noted above, some exemplary embodiments of the systems and methods detailed herein include two different stages: first, the electrodes that, for example, cannot be inserted or disconnected from the current source, are discovered. The information is then processed for a second time in order to detect tip or electrode fold over or any other anomalous electrode location scenario to which the teachings detailed herein can be applicable towards detecting, such as dislocation and bowing, for example. The methods detailed above can be implemented to do this, and still further, FIG. 31 presents another exemplary flowchart according to an exemplary method, where at the commencement of the detection method, such as the automatic detection method, the first action that is executed is a determination of the presence and/or absence of an open circuit and/or a no insert electrode. FIG. 31 is a subroutine to be executed in the automatic methods detailed herein. The method represented by FIG. 31 can correspond to method action 1720 detailed above.

Figure 32:
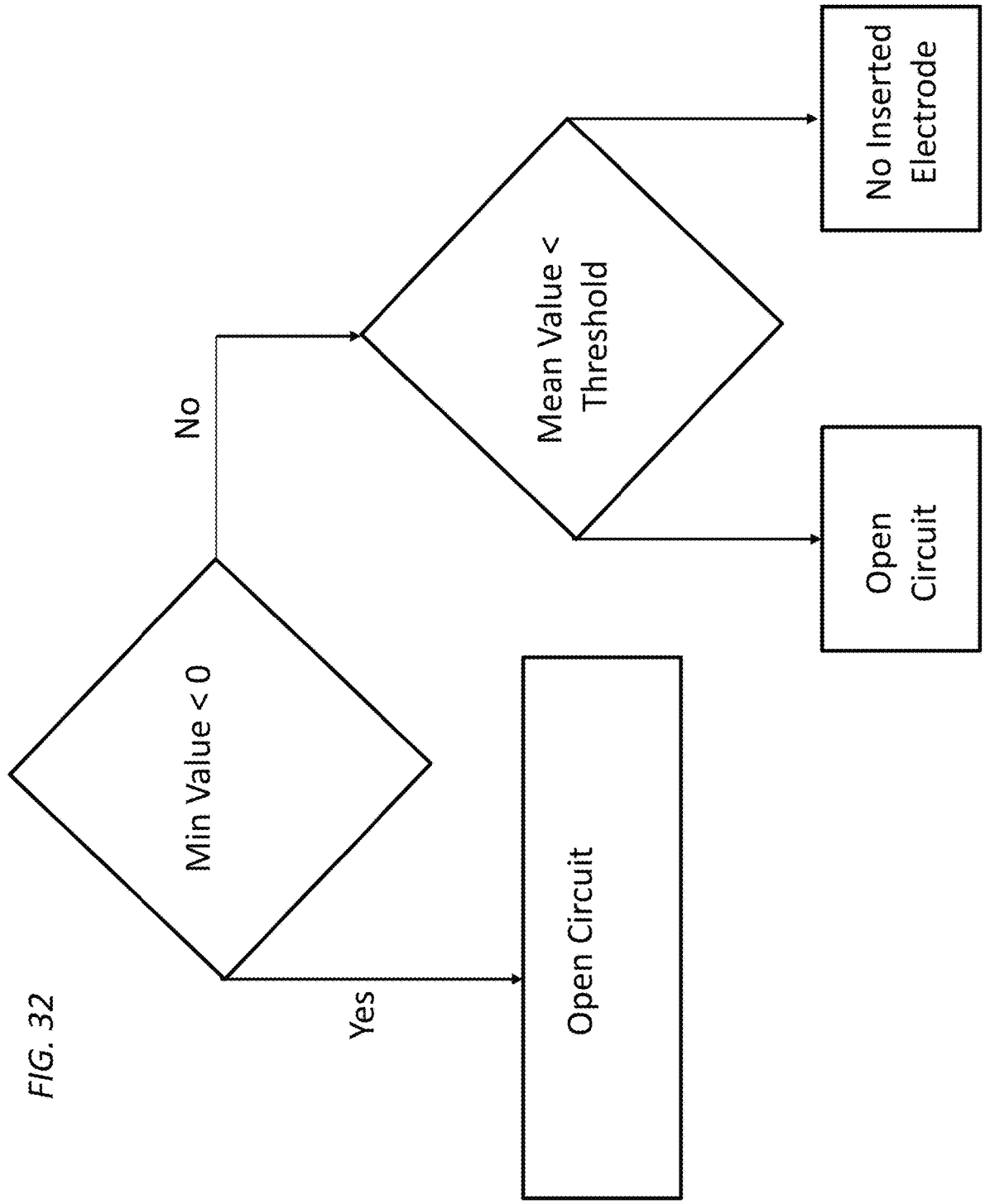

As can be seen, the automatic system can be arranged so as to determine whether or not an Open-Circuit and No-Insert-Electrode scenario exists. In an exemplary embodiment, the procedure identifies the values in the main diagonal in which the received potential value is higher than a usual value and/or an expected value. As referred to before, the main diagonal is compounded by the measurements done when the stimulus is emitted and received in the same electrode. Once the problematic electrodes have been identified, the system classifies the problem, detecting open circuit or no inserted electrode. FIG. 32 presents an exemplary flowchart for an exemplary method of detecting open circuit or no inserted electrodes, which can have utilitarian value or otherwise can be executed within the methods detailed herein such as those detailed above. As with the method of claim 31, the method of claim 32 can correspond to method action 1720 detailed above.

In an exemplary embodiment, once the problematic channel has been localized and identified, the related data can be marked as null in the voltage matrix (which can be an action according to method action 1730, detailed above), making the information relatively easier process in the next step of the procedure: anomalous electrode location position detection.

$$V_{i,[i,k]}=\text{null}$$

$$V_{i[i,k],j}=\text{null} \qquad \text{Eq. 5}$$

In an exemplary embodiment, the anomalous electrode location position detection portion of the system (which can correspond to method action 1740 detailed above) first starts with analyzing for the presence or absence of a possible tip fold over, followed by an analysis for one of the other anomalous location scenarios, such as, for example, dislocation, buckling, bowing, etc. It is noted that in at least some exemplary embodiments, the anomalous electrode location detection procedure could instead start with one of the other scenarios, such as for example, and not by way of limitation, dislocation. It is also noted that in an exemplary embodiment, the analysis can be directed to two or more of these scenarios at the same time. Still, for the purposes of explanation only, the tip fold over will be first detailed.

Figure 33:
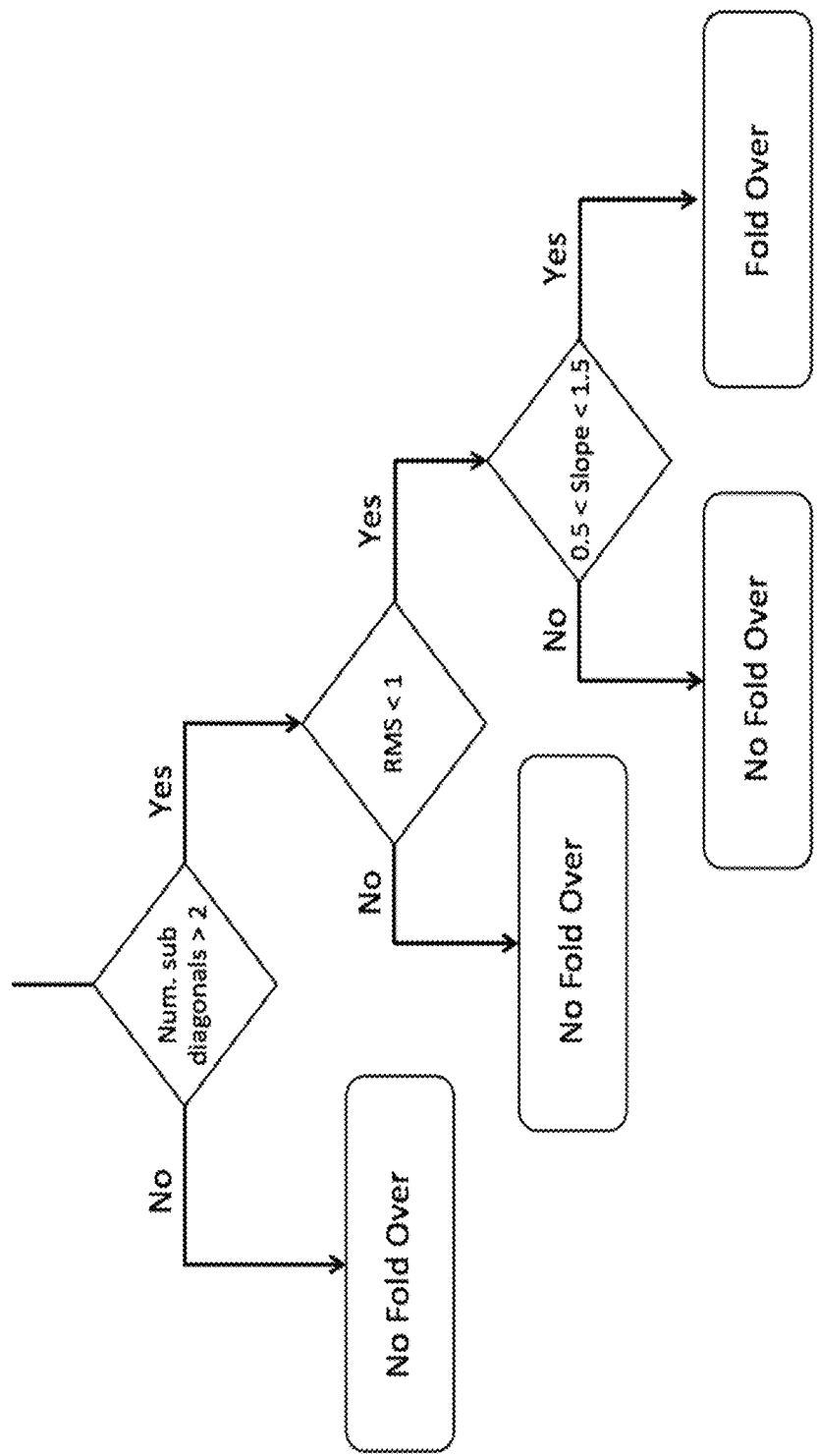

It is noted that in an exemplary embodiment, the fold over detection task should confirm three measurements to classify the voltage matrix as a fold over situation. This is presented by way of example only and not by way of limitation in the flowchart of FIG. 33.

First, in some embodiments, all the values in the matrix are normalized with the maximum and minimum value:

$$V_{ij}^n = \frac{V_{ij} - \min(m_v)}{\max(m_v) - \min(m_v)} \qquad \text{Eq. 6}$$

It is noted that while in this exemplary embodiment, this is presented is the first action of the anomalous electrode location detection portion of the system. It is to be understood that in an alternative embodiment, this could be the last action, or can be an action that is executed in between other actions detailed herein. It is further noted that, consistent with the teachings detailed above, in some executions of the anomalous electrode location detection portion, normalization is not executed, such as, for example, when determining the presence or absence of bowing. In any event, for the purposes of this portion of the disclosure, the first action executed for determining the presence or absence of a tip fold over condition will be normalization, but again, this can be executed at the end or anywhere else where such can have utilitarian value of doing so.

Tip Fold over detection process executes an identification of the main diagonal:

$$V_{ij}^n \Rightarrow i = j \qquad \text{Eq. 7}$$

$$M_V^n = \begin{bmatrix} V_{11}^n & \cdot & \cdot & \cdot \\ \cdot & V_{22}^n & \cdot & \cdot \\ \cdot & \cdot & \cdot & \cdot \\ \cdot & \cdot & \cdot & V_{kk}^n \end{bmatrix} \qquad \text{Eq. 8}$$

Starting from the main diagonal, in some exemplary embodiments, the system will look (automatically, at least with respect to the embodiments that are automated) for one or more or all of the secondary diagonals that are parallels thereto:

$$S_d^+ = V_{u+d,u}^n$$

$$\forall u = [i,k], d = [i,k-i]$$

$$S_d^- = V_{u-d,u}^n \qquad \text{Eq. 9}$$

To validate the results, the system calculates the difference between the minimum and the local maximum value, discarding, in some exemplary scenarios, the results below a prefixed threshold, and calculating the number of points that fits this condition.

$$\max(S_d) - \min(S_d) \geq \text{Threshold} \qquad \text{Eq. 10}$$

If the maximum and minimum values of subdiagonal, $S_i$, commit Eq. 11, the coordinates in the matrix, $M_V^n$, are stored. Then, if the obtained coordinates are at least 3, the best fitting of Eq. 4 is calculated to fit this coordinates. Least-square fitting method can be applied in order to adapt the Eq. 4 to the data. Any regime of manipulating the data that can have utilitarian value and can otherwise enable the teachings detailed herein can be executed in some embodiments Once the fitting is done, the slope of the polynomial fitting and the root mean squared are calculated. The obtained slope of the polynomial should be almost 1 in order provide utilitarian value with respect to warranting its perpendicularity with the main diagonal.

$$m = \frac{\Delta y}{\Delta x} \simeq 1 \qquad \text{Eq. 11}$$
$$1 - \delta \leq m \leq 1 + \delta$$

The Root Mean Square Value (RMS) can be used to measure how good the fitting is to the extracted points:

$$\text{RMS} = \sqrt{\frac{\sum_{i=1}^{n}(\overline{X} - X_i)^2}{n}} \qquad \text{Eq. 12}$$

The pivoting electrode (the electrode where the electrode array bends) can then be identified as the one located at the intersect coordinates of the polynomial fitting and the main diagonal of the voltage matrix. Thus, based on Eq. 3 and Eq. 4 the intersection point and the pivoting electrode is $$P_{FO} = \frac{b}{(1-a)} \qquad \text{Eq. 13}$$

Figure 34:
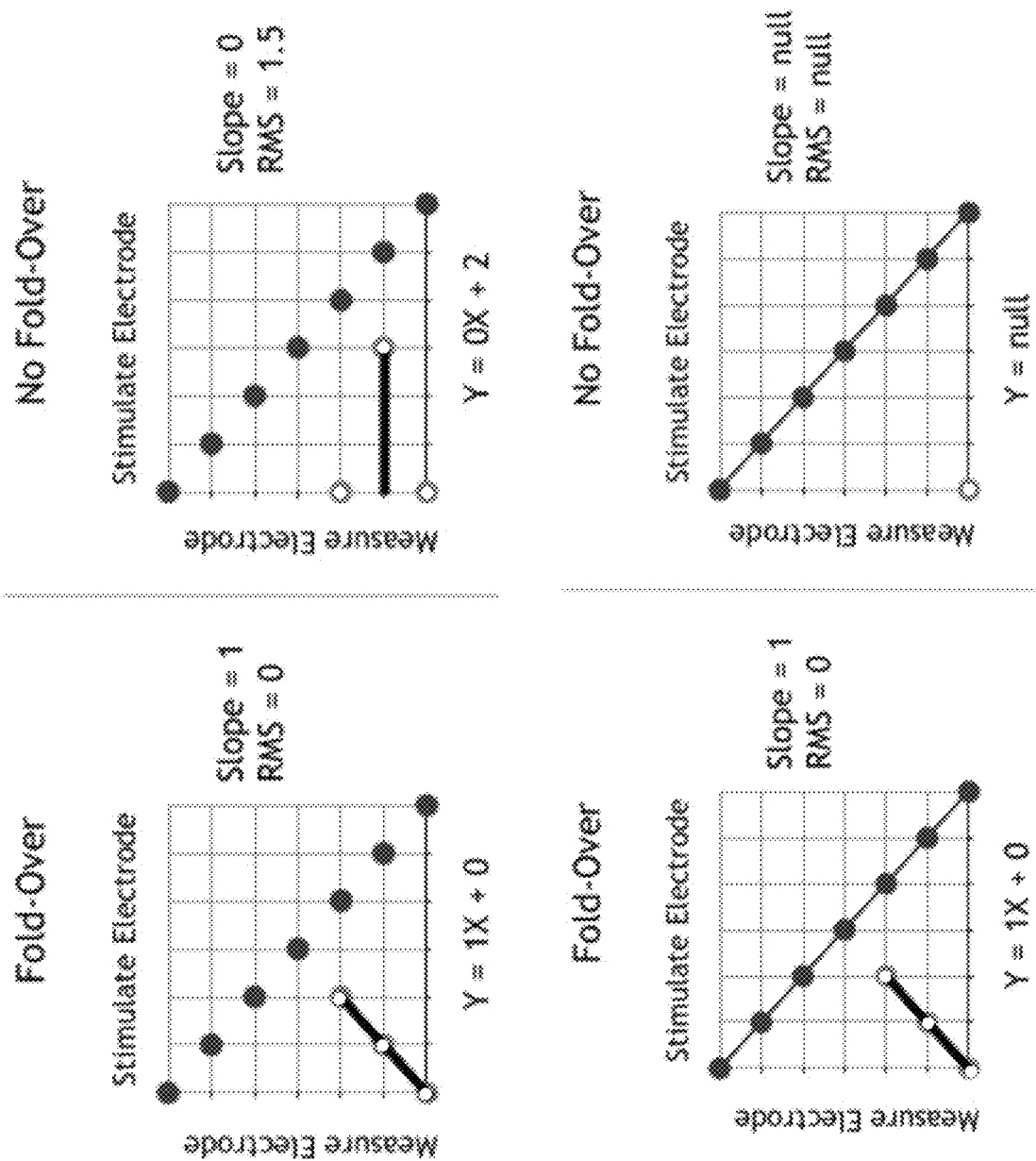
FIGS. 34-37 present some exemplary graphics associated with some exemplary insertion regimes.

FIG. 34 depicts different situations of possible measurements according to an exemplary representation thereof, presented by way of example only and not by way of limitation. The solid dots represent the main diagonal and the hollow dots are the coordinates of the maximum values that have reached the threshold. The line is the polynomial fitting.

Again, while the embodiments detailed above have been directed to fold over, and more specifically, tip fold over, the above embodiments can be modified so as to detect for other types of conditions, such as main body fold over, buckling, bowing, dislocation, etc.

Consistent with the teachings above, in an exemplary embodiment, the method actions detailed herein are directed towards evaluating the array position intraoperatively in an automated manner. To demonstrate the efficacy of the teachings herein, the teachings herein were executed and compared to results from radiological evaluation. In the aforementioned execution, the patients met the following inclusion criteria: adults and children with bilateral sensorineural hearing loss, without medical or psychological conditions that contraindicate undergoing general anesthesia or surgery or ossification, malformation or any other cochlear anomaly. All of the patients (recipients) were implanted with Cochlear Ltd.™ devices (CI512 and CI532). The study was approved by the Ethics Committee of the Complejo Hospitalario Universitario Insular Materno Infantil de Gran Canaria.

The surgical procedure for the cochlear implantation followed the same scheme as in daily routine cochlear implantation: retro auricular incision, mastoidectomy, tympanotomy, cochleostomy or round window opening, electrode insertion, intraoperative measurements and closing. Intraoperative measurements were executed to stage the fold over detection system and a Fluoroscopic imaging (BV Pulsera system Philips). During the surgery, if there was no presence of fold over, the surgery was completed. If there was an indication of fold over, a reinsertion of the electrode array, at least in the case of CI532, was done and the results re-evaluated. Data acquisition for the fold over detection system was done on a Python script developed by using the Nucleus Implant Communicator (NIC)™ library, provided by Cochlear Ltd.™, which enabled the performance of voltage matrix acquisition. In order to validate the results, the University Hospital of Las Palmas de Gran Canaria made use of a prototype of the automatic system which executed some of the teachings detailed herein, which was developed in Visual Studio and Python. The prototype was responsible for representing in a clear and simple way the evaluation of the insertion of the implant in the cochlea from the analysis of the voltage matrix.

Figure 35:
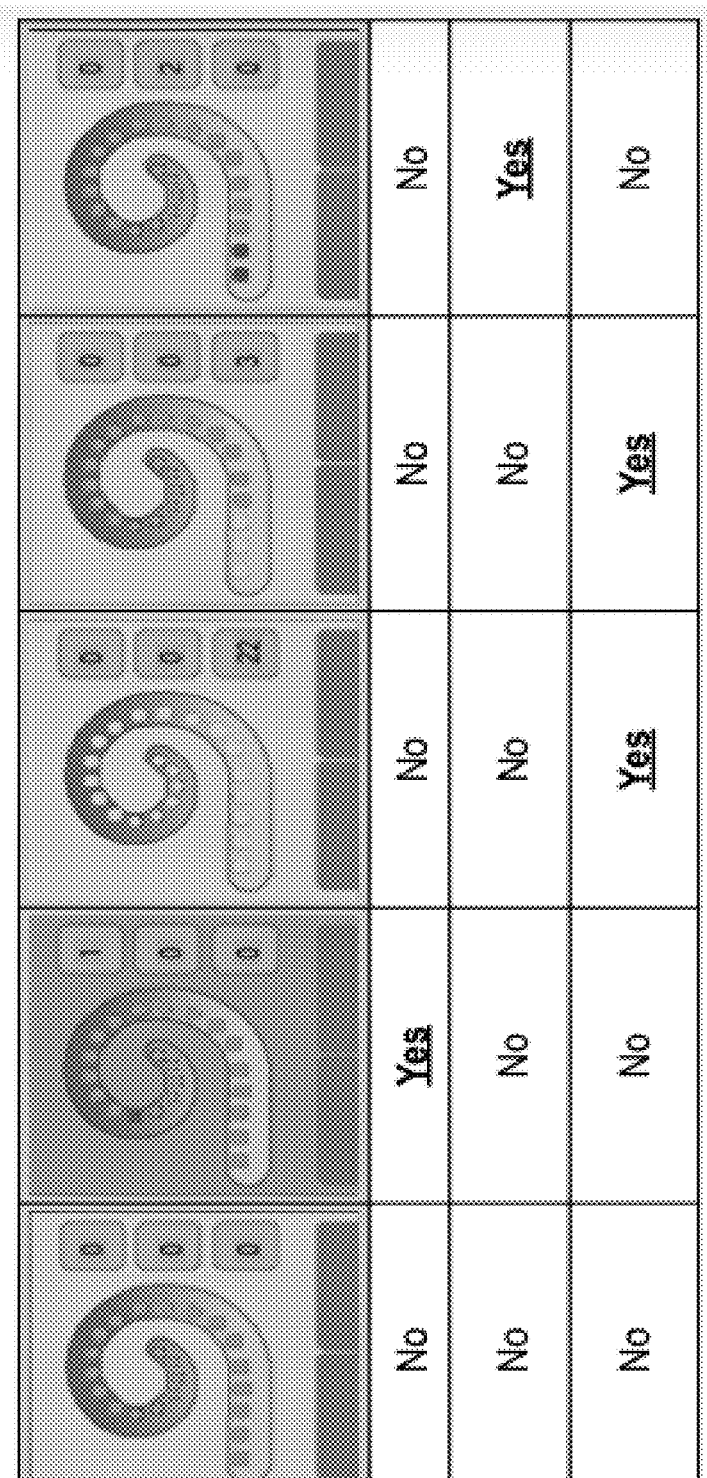

FIG. 35 depicts different outputs of an exemplary embodiment of the automated system, which can be displayed on a computer monitor. In case of fold over detection, the graphical user interface (GUI) indicates the fold with a red background, and the pivoting electrode in blue. In no insert case, the affected electrodes are highlighted in yellow, while the open circuit electrodes are marked in red. Of course, in alternate embodiments, such can be provided in a different manner, such as utilizing different color schemes and the like. In an exemplary embodiment, there can be an anomalous electrode location automatic diagnosis system, which can be executed utilizing a personal computer or the like with the inputs and outputs to/from the cochlear implant as will be described in greater detail below, or otherwise executed utilizing a dedicated medical device diagnostics equipment that receives inputs and outputs to from the cochlear implant, and the system can have a display, such as a computer display, and the GUI thereof can indicate the presence of fold over (red background) and the pivoting point (blue electrode) and/or a N-Insert (highlighted in yellow) and/or an Open-Circuit (highlighted in red) or any other type of physical phenomenon according to the teachings detailed herein and variations thereof.

Also, it is noted that while the embodiment of FIG. 35 presents a relatively sophisticated output, in an alternate embodiment, a less sophisticated output can be provided, such as, for example, the simple elimination of a light or the like to indicate the presence of tip fold over and/or dislocation and/or electrode non-insertion. Alternatively and/or in addition to this, the generation of an audible tone to indicate the presence of tip fold over and/or dislocation and/or electrode non-insertion can be utilized. In an exemplary embodiment, different colored lights or even different lights entirely can be utilized to indicate the various anomalous electrode location scenarios. Such is also the case with respect to the tones that could be generated by a machine. By way of example, a first tone/sound can be generated to indicate electrode dislocation, a second tone or sound of a different type can be generated by machine to indicate tip fold over, a third tone or sound of a different type can be generated by machine to indicate bowing, a fourth tone or sound of a different type can be generated by machine to indicate buckling, etc. Such is also the case with the lights or other visual indicators—different colored lights were different lights entirely can be illuminated. In this regard, by way of example only and not by way of limitation, in an exemplary embodiment, upon the execution of one or more or all of the method actions detailed herein, upon a determination by the system that an anomalous electrode position scenario exists, the methods can be utilized to automatically trigger a machine to output an indication to the surgeon or other healthcare professional that such an anomalous electrode position exists. Indeed, in an exemplary embodiment where the insertion is executed utilizing a robotic and/or a semi-robotic device, such as an insertion guide with an actuator that drives the electrode array into the cochlea, the methods detailed herein can be executed upon a determination that an anomalous electrode position exists, the methods can be utilized to cause the actuator to retract the electrode array at least partially out of the cochlea, and then begin the insertion process again. Still further, in an exemplary embodiment, the methods can be utilized to halt insertion of the electrode by stopping the actuator. Still further the methods could be used to control the speed, angle or rotation of the actuator. Of course, in some embodiments, the teachings detailed herein are directed towards providing an indicator to the surgeon. In an exemplary embodiment, an illumination device or the like can be present on the aforementioned insertion guide. The methods detailed herein can be utilized to execute the elimination of a light or the like on the insertion guide that is clearly visible to the surgeon to provide an indication there to of the anomalous electrode location.

Figure 37:
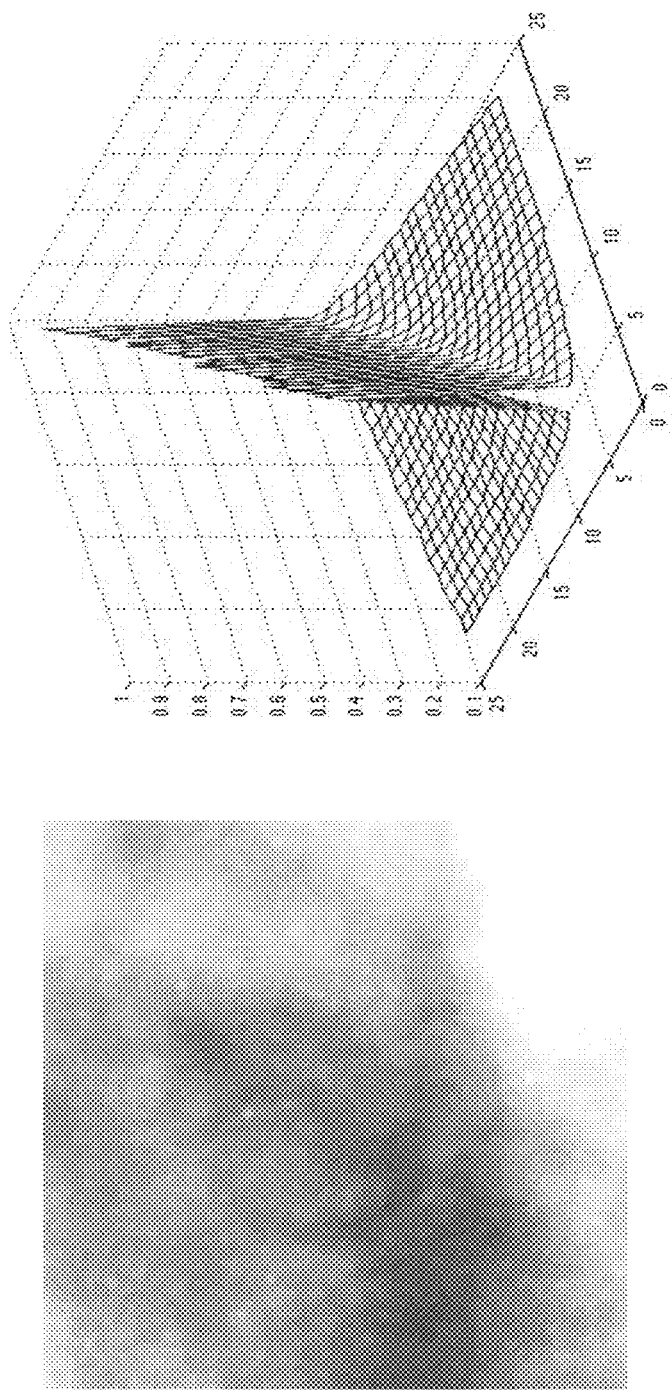

The statistical analysis to evaluate the performance of the implemented algorithm was a confusion matrix (false positive—false negative). The results were also correlated with radiological findings. Each column of the matrix represents the output of the classifier while each row represents the real state of the electrode array. The false positive and negative rate, the accuracy, sensitivity and specificity of the system can be then calculated. In a sample of 80 patients, 100 implanted ears, was collected during a 16 months period, of whom 57% were men and 43% were women. The patients' age range from 1.5 to 77 years old, with an average of 42 years and a standard deviation of 13.12 years. 57.5% of the subjects were adults and 42.5% children. Simultaneous bilateral implantation was performed on the 76.4% of the children. In adults, 6.5% of cases were a re-implantation and 34.78% corresponded to second implanted ears. 18% of the patients were implanted with CI512 (n=18), 71% with CI532 (n=71) and 11% with the CI422/CI522 (n=11). In the operating theatre, the voltage matrix and its automatic diagnosis output was collected and compared with a fluoroscopic image, as seen for example in FIG. 36 and FIG. 37, which were sequentially obtained, where FIG. 36 presents a fold over case with a voltage telemetry matrix of the fold over position, and FIG. 37 presents a correct placement image; with a voltage telemetry matrix of the correct placement.

Then, an expert surgeon evaluated the fluoroscopic images associated to every voltage matrix and indicates the presence or lack of a Tip Fold over in order to compare the results. (Again, in an exemplary embodiment of the teachings herein, there is no expert evaluation.)

A confusion matrix was created to evaluate the automatic Fold over detection system. The false positive and false negative rate was 0, sensitivity 100%, specificity 100%, accuracy 100%

TABLE 1

Confusion matrix.

|  |  | Automatic System | |
|---|---|---|---|
|  |  | Positive | Negative |
| Expert | Positive | 6 | 0 |
|  | Negative | 0 | 94 |

Figure 38:
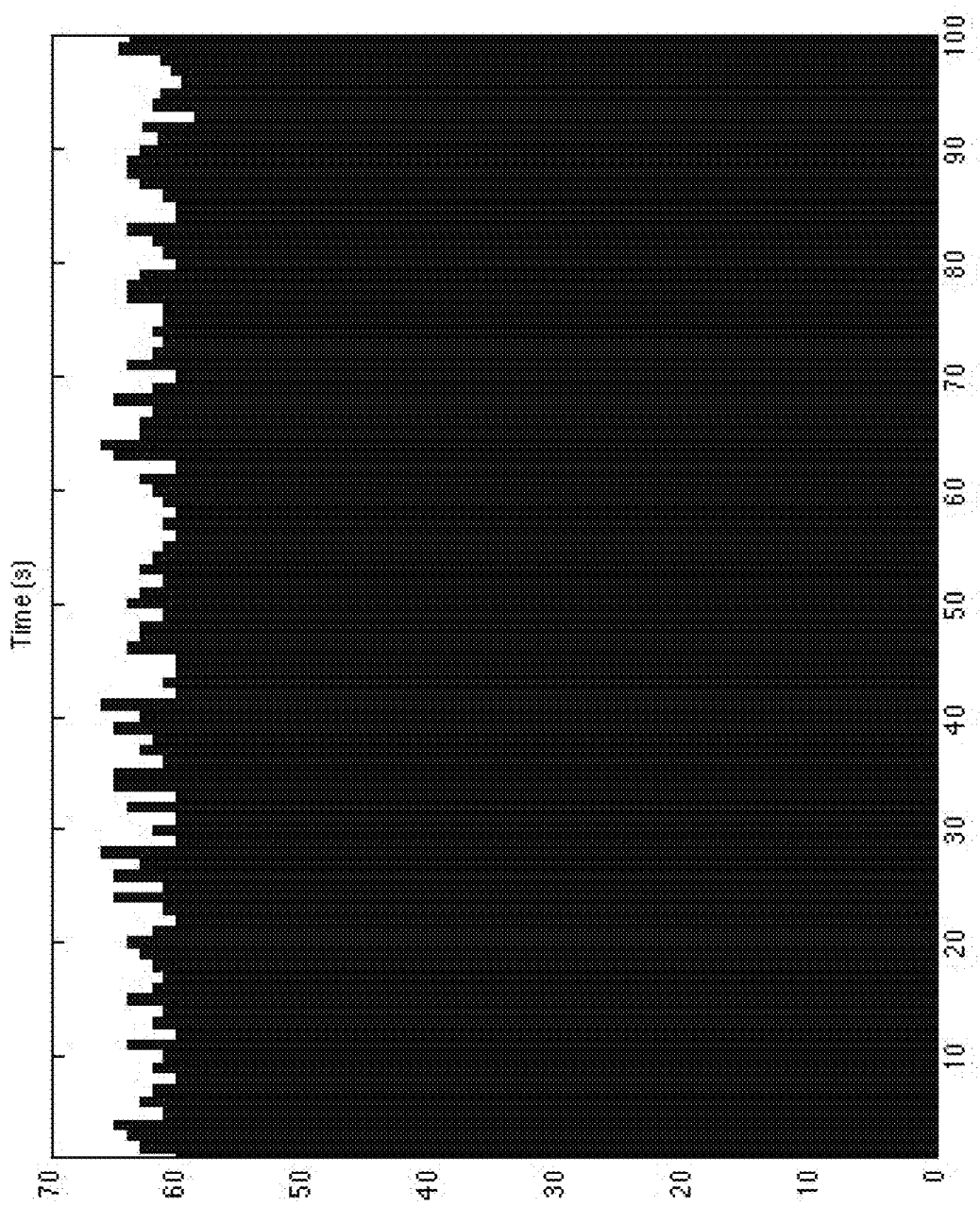
FIG. 38 presents some statistical data.
Figure 39A:
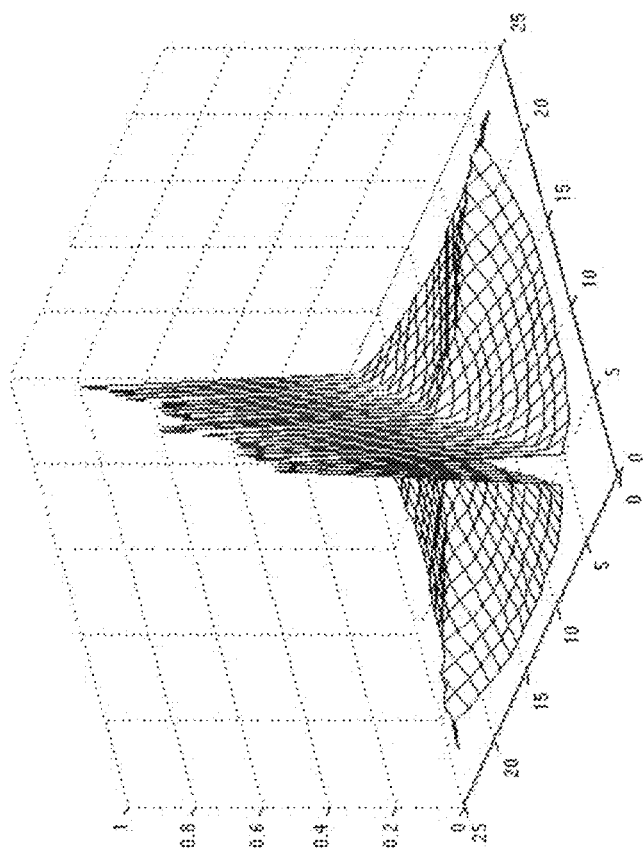
FIGS. 39A-39F present some exemplary graphics associated with some exemplary insertion regimes.
Figure 39B:
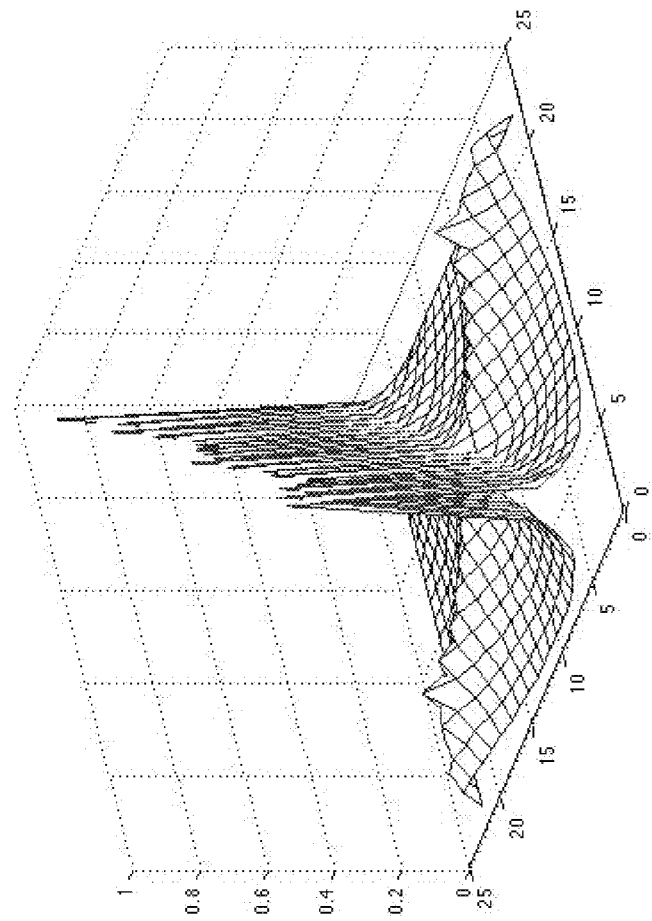
Figure 39C:
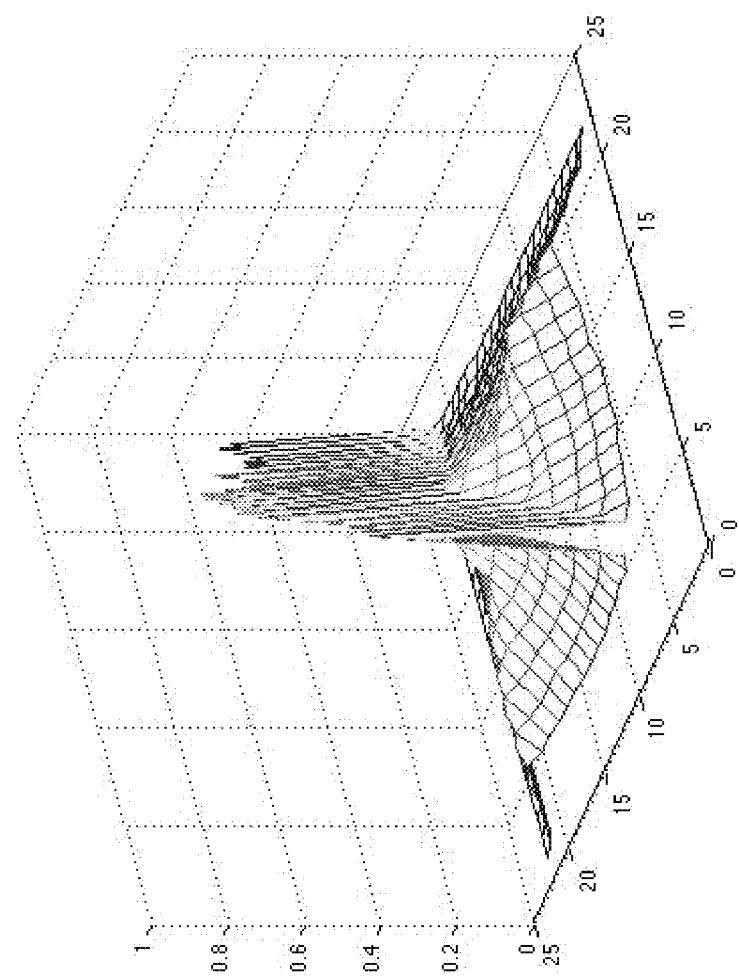
Figure 39D:
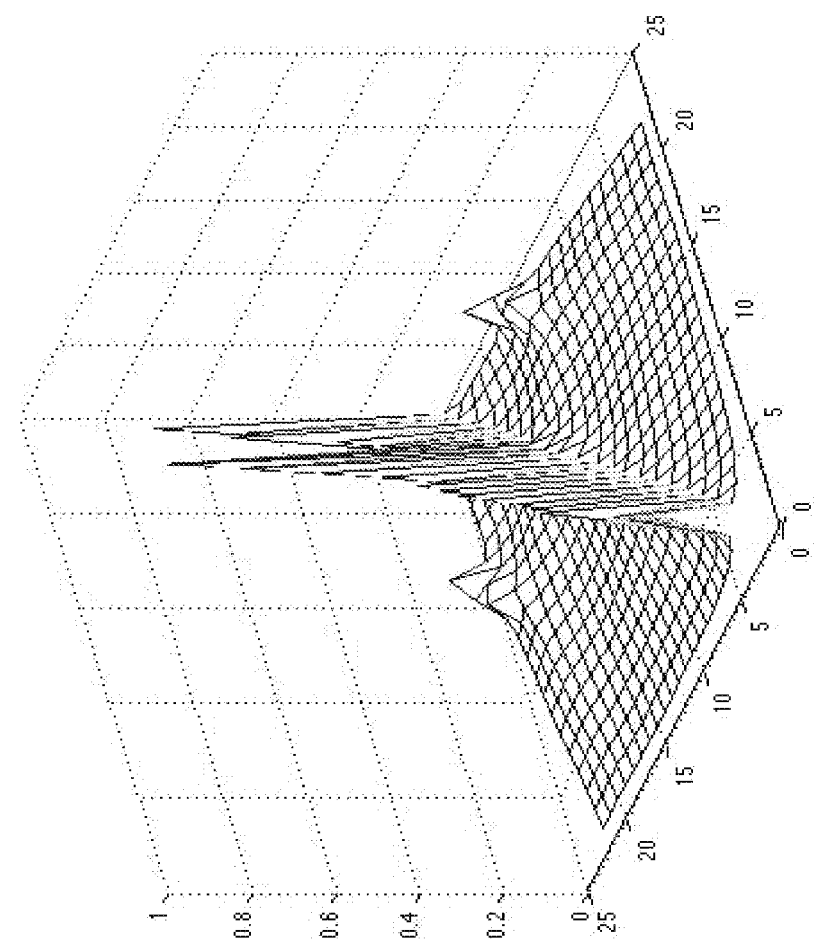
Figure 39E:
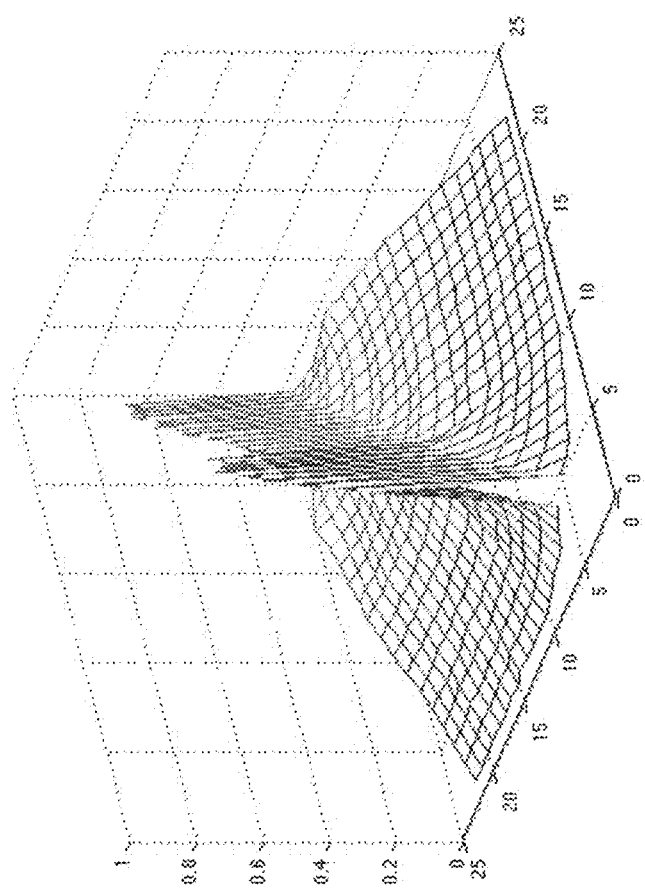
Figure 39F:
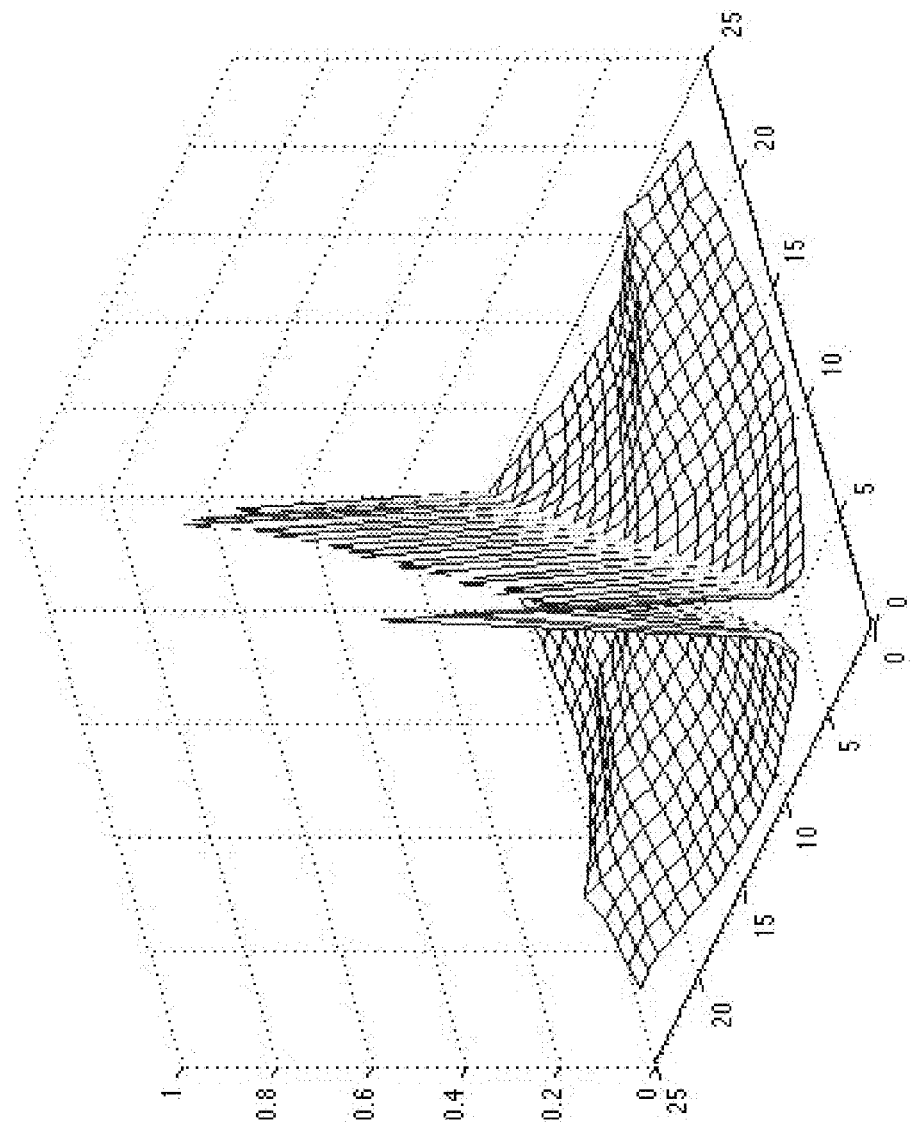

The presence or absence of fold over (100 cases) was correctly detected. The total diagnosis time took an average of 63.78 seconds in all subjects (see FIG. 38, detailing the acquisition time of the voltage telemetry matrix and the automatic diagnosis) instead of 21 minutes of the fluoroscopy imaging. The entire fold over detections were produced on electrode array CI532 ™, as seen in FIGS. 39A-D, and the pivoting electrodes are detailed below:

TABLE 2

Pivoting electrode in Fold over detections

| Case | Pivoting Electrode | Fold over |
|---|---|---|
| 1 | 11 | Electrode fold over |
| 2 | 11 | Electrode fold over |
| 3 | 16 | Tip fold over |
| 4 | 17 | Tip fold over |
| 5 | 19 | Tip fold over |
| 6 | 8 | Electrode fold over |

In some embodiments, the teachings detailed herein and/or the results of the methods are executed without using neural response telemetry, without using Ecog, without using imaging systems, and/or without using standard impedance spectrography. The teachings detailed herein can enable an evaluation of the positional arrangement of the electrode array to determine the presence and/or absence of anomalous electrode locations within few seconds or a few minutes, without any side effects to the patients or surgical team, such as by way of example only and not by way of limitation, radiological testing.

In some embodiments of the teachings detailed herein, the methods are executed with respect to the insertion of a perimodiolar array/curved array, with the goal of having an array that is in contact with the perimodiolar wall upon full implantation of the array.

Teachings detailed herein can enable the division of the fold over between tip or electrode fold over. This differentiation can be based on how aggressive is the fold over. Such cases that the fold over is produced on the tip of the electrode (involve only 3-5 electrodes) are called Tip Fold over. The other situations where we have a complete Fold over, the electrode array folded in half, can, in some instances, provide a more significant impact on the cochlear implant outcome, and in some instances, require re-implantation. Indeed, in an exemplary embodiment, the teachings detailed herein are utilized to determine whether the anomalous electrode position is a tip fold over or an electrode fold over/complete fold over, and an indication is provided to a surgeon, where the surgeon can make a determination as to attempt to re-implant or otherwise reposition the electrode array based on such. In an exemplary embodiment, the surgeon does not attempt to reposition the electrode array, when such an indication is provided that it is a tip fold over, while in some exemplary embodiments, the surgeon does attempt to reposition the electrode array in a scenario where it is a complete fold over. In an exemplary embodiment, the automated system can be configured to analyze the given scenario and provide an automatic indication to the surgeon as to whether or not the surgeon should attempt to reposition the electrode array. In an exemplary embodiment of this exemplary embodiment, a database of previous cases and resulting performance can be utilitarian with respect to comparing the data to determine whether or not the surgeon should attempt to reposition the electrode array. In an exemplary embodiment, the algorithm can determine whether or not it is simply a tip fold over or a complete fold over, and the system can indicate that the electrode array should be repositioned in the case of a determination that it is the latter and not the former. Still further, in an exemplary embodiment, an automated system can automatically execute the re-positioning.

According to at least some exemplary embodiments herein, there is provided an automatic system for intra-operative fold over detection and/or dislocation and/or buckling and/or bowing that has 90, 91, 92, 93, 94, 95, 96, 97, 98, 99 and even in some embodiments 100% accuracy, at least with respect to determining that such exists, without false positive or negative indications. In at least some exemplary embodiments, the teachings detailed herein provide a system that enables surgically, without imaging tests, the detection of the correct insertion of the implant. It allows working in patients without neural responses, eliminating imaging tests, with the utilitarian value that brings the patient to avoid radiation and also decreasing surgical time, especially in simultaneous bilateral implantations.

In view of the above, in an exemplary embodiment, there is a system, comprising, a control unit configured to receive telemetry from an implantable system of a cochlear implant electrode array (described in greater detail below) and determine a feature related to a global position of the electrode array relative to an interior of the cochlea of the recipient (e.g., a tip fold over, bowing, buckling—the overall state of the array relative to the structure inside the cochlea as opposed to merely individual locations/relative locations of individual parts of the array) wherein the telemetry includes data based on electrical phenomenon associated with the electrode array. In an exemplary embodiment, the control unit can be executed utilizing a personal computer or the like or some other device that includes a processor. The control unit can be located remote from the surgeon/surgical room (in some embodiments, in signal communication there with via the Internet or the like), or can be located therewith. The control unit is further configured to automatically analyze the data to determine whether or not portions of the data are acceptable for use in determining the feature, and the control unit is configured to automatically modify the data to at least one of eliminate or replace the portions of the data that are deemed not acceptable for use in determining the feature, and use the modified data to determine the feature related to the global position of the electrode. In an exemplary embodiment, the aforementioned control unit can be configured to execute one or more or all of the method actions detailed herein, and thus can include a program product or otherwise can include a non-transitory computer readable media having recorded thereon, a computer program for executing at least one or more or all of the method actions detailed herein and/or variations thereof, the computer program including code for executing one or more or all of the method actions detailed herein, which code can be a combination code or a code that is specific to each of the individual method actions detailed herein, etc.

In an exemplary embodiment, the control unit is configured to provide output that enables a virtual indication of the feature to a healthcare professional proximate the cochlear implant electrode array while the healthcare professional has direct access to the implantable system (e.g., in the operating room). To be clear, the system need not be configured to actually provide the virtual indication, only that the output be such that the virtual indication is enabled. Again, in an exemplary embodiment, the teachings detailed herein can be utilized with a remote unit that is in signal communication with a hospital the like by the Internet. The hospital can have the component that can provide the indication to the recipient. Indeed, in an exemplary embodiment, the output can be directed over phone lines and be heard over a speakerphone that is in the operating room, in some such exemplary embodiments. Again, in an exemplary embodiment, the methods and actions detailed herein can enable the activation of a machine, in an automated manner, that will output a signal that will cause a machine to provide an indication to the surgeon. Still further, the teachings detailed herein can enable automated insertion and reinsertion and adjustment of the location of the electrode array, such as in an embodiment that utilizes a robotic device, where the control unit is located many miles, and in some instances, on another continent, from where the robotic device is located/the surgery is execute.

In an exemplary embodiment, the feature is a fold over (tip or otherwise) of a tip of the cochlear electrode array, and the control unit is configured to provide an indication of the occurrence of the fold over of a tip of the cochlear electrode array while the healthcare professional has direct access to the implantable system. Also, the control unit can be configured to provide an indication of the location of the fold over of the cochlear electrode array while the healthcare professional has direct access to the implantable system.

Consistent with the teachings above, the system can be configured to provide the aforementioned indication at a rate that is statistically more reliable than a single X-ray of the cochlear of the recipient with the electrode array therein. Also, the control unit can be further configured to automatically analyze the data to determine whether or not portions of the data are indicative of an open circuit, a short circuit, a bubble proximate the electrode array, an electrode not in the cochlea, an electrode conditioning phenomenon or a detrending phenomenon, and deem the data unacceptable for use if the data is indicative thereof, again, consistent with the teachings detailed above. Also, the control unit is configured, in some embodiments, to establish at least a virtual matrix of electrical readings based on the electrical phenomenon, wherein the matrix has rows corresponding to target electrodes and columns corresponding to measurement electrodes, or vice versa and/or adjust and/or provide new components of the matrix for data that is determined to be unacceptable for use in determining the feature; and/or determine the feature by analyzing the matrix. Alternatively or in addition to this, the control unit is configured to normalize the components of the matrix after any adjustment and/or providing of new components.

It is noted that in at least some exemplary embodiments, the control unit is configured to execute one or more or all of the method actions detailed herein and/or variations thereof. In an exemplary embodiment, the control unit includes a non-transitory computer readable media having recorded thereon, a computer program for executing the methods and/or the method actions detailed herein, that computer program including code for doing so.

It is noted that at least some of the teachings detailed herein can be executed in conjunction with one or more or all of the method actions, devices and/or systems disclosed in U.S. Patent Application Publication No. 20120316454 to Paul Carter, filed on 2011 Jun. 10, the contents of which are hereby incorporated by reference in their entirety. Accordingly, in an exemplary embodiment, there is a method that includes executing one or more or all of the method actions disclosed in the '454 patent publication as well as including executing one or more of the method actions disclosed in this application. In this regard, in an exemplary embodiment, the teachings detailed herein can be utilized to condition the data (and obtain the data that is required for the conditioning) that is obtained by executing one or more or all of the method actions in the '454 patent publication followed by subsequent processing as disclosed in the '454 patent publication. It is also noted that at least some of the teachings detailed herein can be executed in conjunction with one or more or all of the method actions, devices and/or systems disclosed in U.S. Patent Application No. 62/476,295 to Nicholas Charles Pawsey, filed on Mar. 27, 2017, in the USPTO, the contents of which are incorporated herein by reference in their entirety. Accordingly, in an exemplary embodiment, there is a method that includes executing one or more or all of the method actions disclosed in the '295 patent application as well as including executing one or more of the method actions disclosed in this application. In this regard, in an exemplary embodiment, the teachings detailed herein can be utilized to condition the data that is obtained by executing one or more or all of the method actions in the '295 patent application followed by subsequent processing as disclosed in the '295 patent application. Moreover, in an exemplary embodiment, the teachings of the '295 that are directed towards determining the distance between the electrode array and the modiolus wall can be utilized to obtain data to identify a bowing condition. By way of example only and not by way of limitation, in an exemplary embodiment, if the distances as a mean, median and/or mode, or as an individual instance, are (is) above a certain value (which could be above zero, in some embodiments), where such distances are determined utilizing the teachings of the '295 patent, a determination can be made that the electrode array is bowing. Also, the data that is utilized to determine the distances can be conditioned according to the teachings detailed herein prior to executing the analysis that provided the distance determination.

Figure 40:
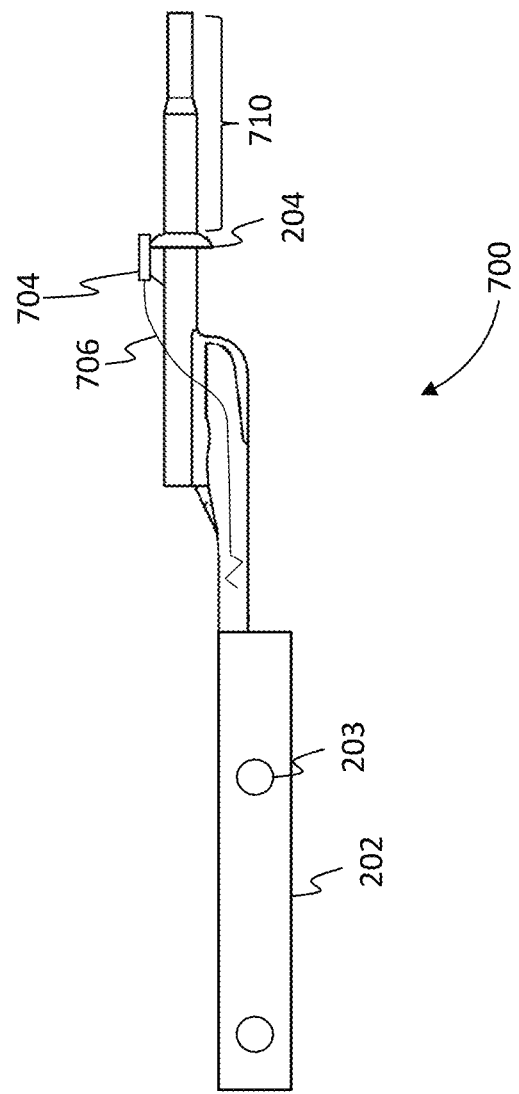
FIGS. 40-77 present some exemplary embodiments of hardware for implementing some of the teachings detailed herein.
Figure 41:
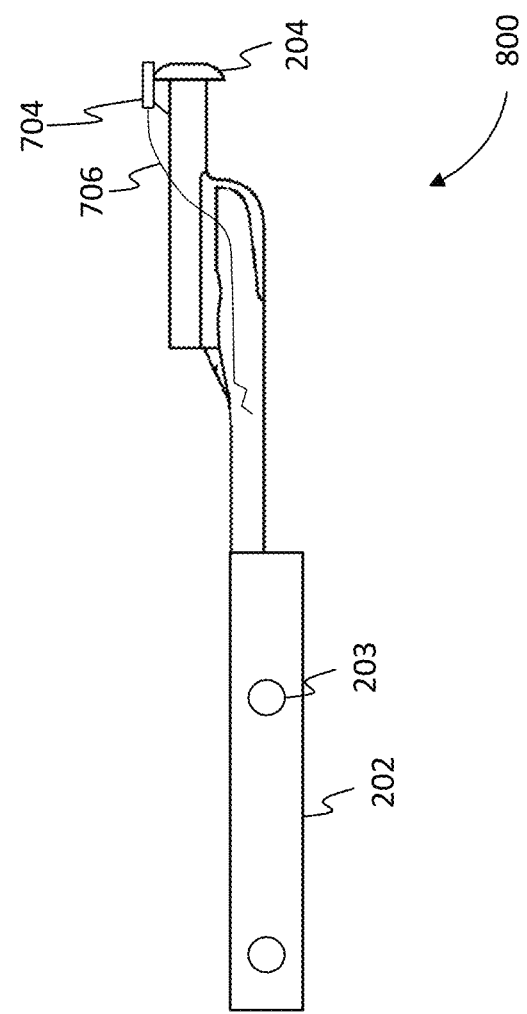

FIG. 40 depicts an exemplary embodiment of a cochlear electrode array insertion guide 700. In an exemplary embodiment, the insertion guide 700 corresponds to that of the insertion guide 200 detailed above, with the exception of the addition of electrode 704, and the modifications to the tool so as to support the electrode and the associated components thereof (e.g., electrical leads 706 (only the "distal" portion of the lead (distal relative to the tool 800) is depicted, the "break' being conceptual), etc.—more on this below). Accordingly, FIG. 40 depicts a cochlear electrode array insertion guide comprising an array guide (e.g., the insertion guide tube (210 of FIG. 2)) and an active functional component (e.g., electrode 704). Some additional details of some exemplary functional components, including some exemplary active functional components, will be described in greater detail below. However, it is briefly noted at this time that not all embodiments of the cochlear electrode array insertion guide include an intracochlear portion. In this regard, FIG. 40 depicts a tool 700 that includes an intracochlear portion 710. This is the portion to the right of stop 204/the portion on the distal side of stop 204 (distal relative to the entire insertion guide). Conversely, FIG. 41 depicts a tool 800 that does not include an intracochlear portion. Instead, stop 204 is configured to be placed against the outside of the cochlea such that the passageway through the tool through which the electrode array is passed is aligned with the pertinent window and/or cochleostomy such that no parts of the tool 800 enters the cochlea.

It is noted that while the teachings detailed herein with respect to extra functionality of the insertion guide are based on the insertion guide detailed above with respect to FIGS. 5A-6D, these teachings can be applicable to other types of insertion guides. Indeed, as will be detailed below, some embodiments of the insertion guides do not have an intracochlear portion at all. Accordingly, the teachings above with respect to FIGS. 5A-6D serve as but one example of an insertion guide that the following teachings can be utilized in conjunction therewith.

With reference back to FIG. 40, the exemplary active functional component can be an electrode (read or energizing, etc.).

Figure 42:
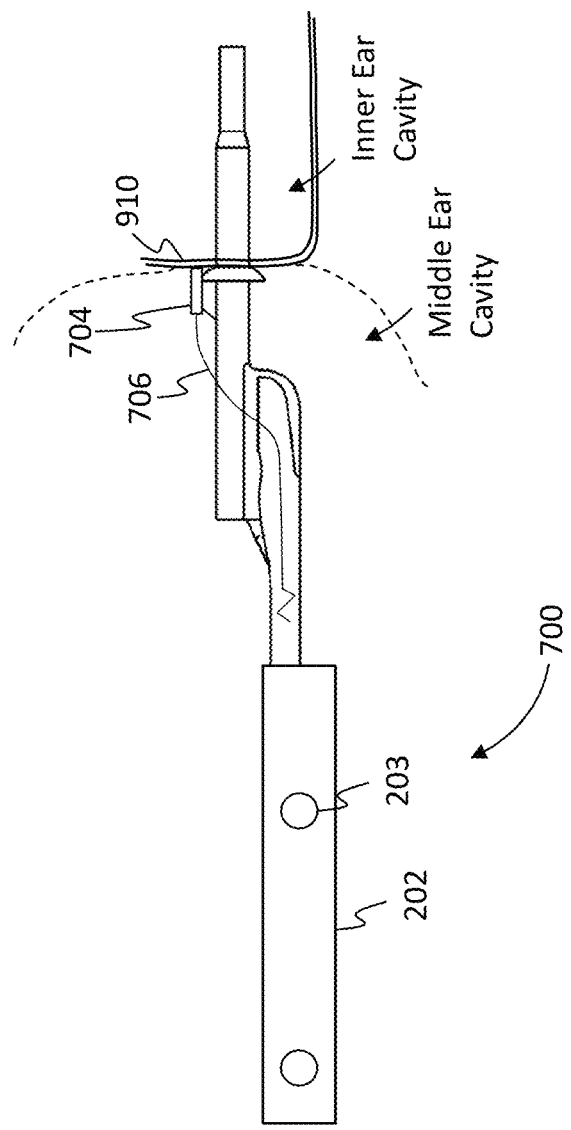

The embodiments of FIGS. 40 and 41 are such that the electrode 704 abuts the outside of the cochlea during use so as to establish physical contact with the outside of the cochlea. FIG. 42 depicts an exemplary scenario of use, where element 910 is the wall of the cochlea that separates the middle ear cavity from the inner cavity. In an exemplary embodiment, electrode 704 abuts the cochlear promontory. In an exemplary embodiment, electrode 704 abuts the round window and/or oval window. With respect to the "and/or" it is noted that while the embodiments depicted herein indicate a single electrode, in alternative embodiments, two or more electrodes can be utilized in an array such that one contacts the oval window and the other contacts the round window.

In any event, it is again noted that the electrode can be located anywhere on the guide that the electrode can have utilitarian value with respect to establishing a read and/or a stimulation electrode according to the teachings herein (or a reference electrode).

Figure 43:
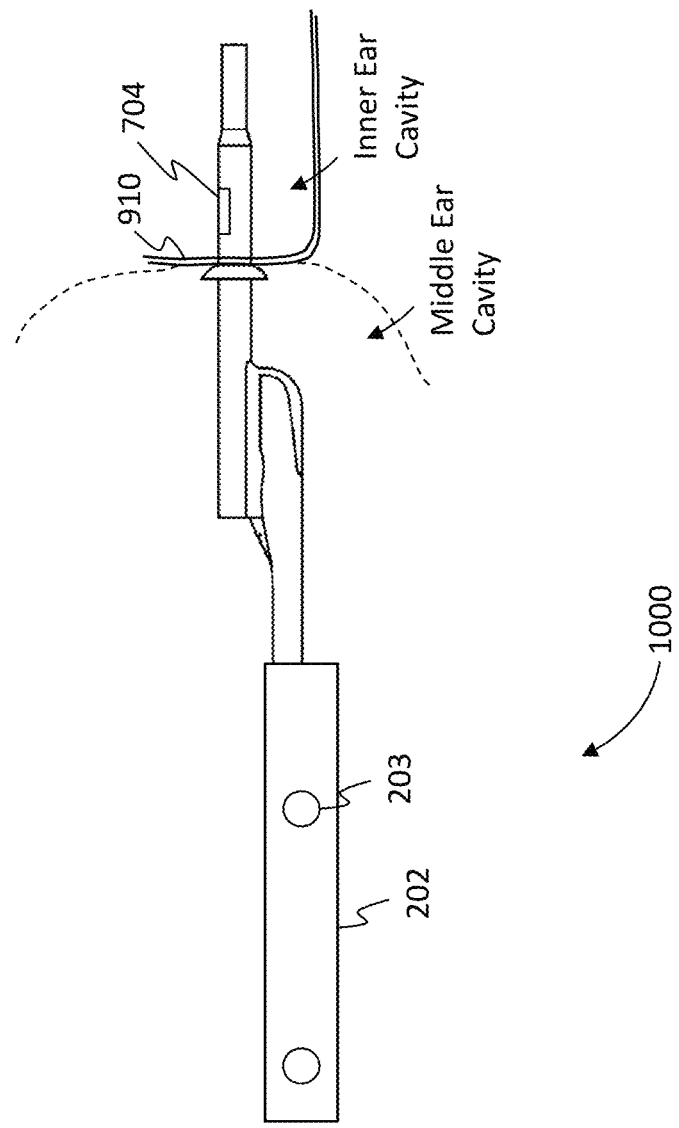
Figure 44:
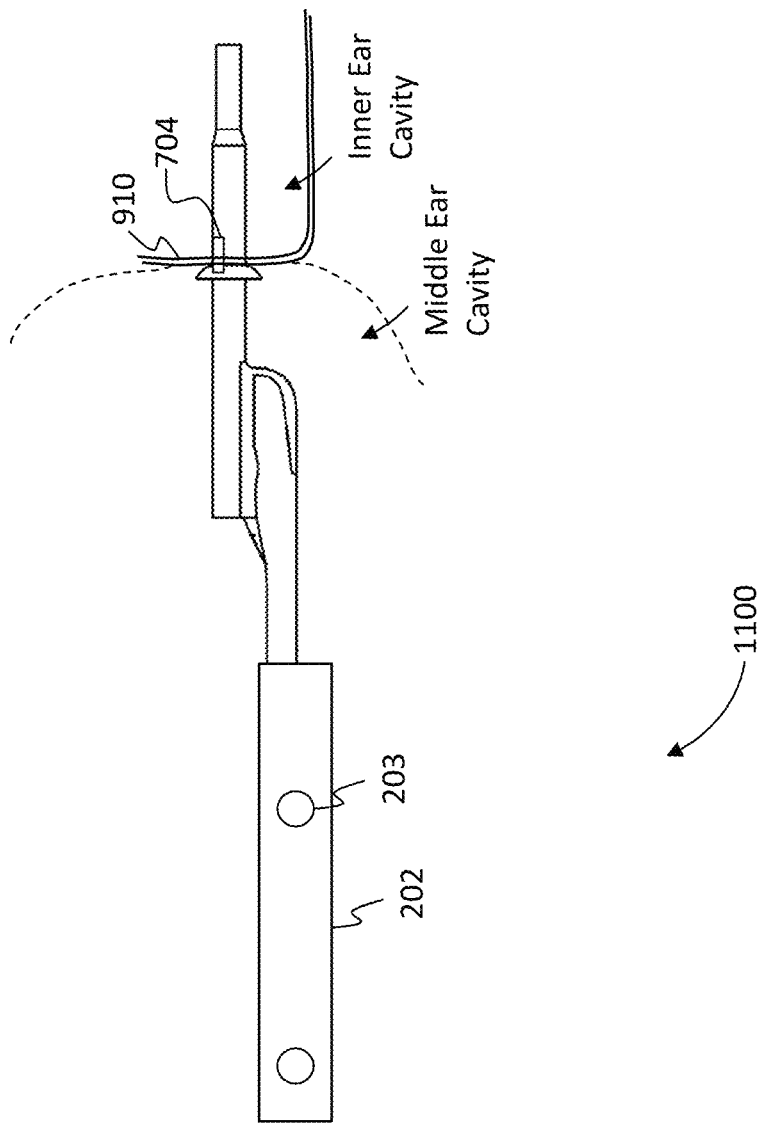

While the embodiments detailed above have focused on the electrode being located entirely outside the cochlea (e.g., entirely inside the middle ear), in an alternative embodiment, the electrode is located inside the cochlea during use. FIG. 43 depicts an exemplary insertion regime utilizing exemplary electrode array insertion guide 1000 where the electrode is located entirely in the inner cavity (in the cochlea) when the insertion guide is fully inserted into the inner ear cavity. Still further, FIG. 44 depicts an exemplary insertion regime utilizing exemplary electrode array insertion guide 1100 where the electrode being is located in the wall that separates the middle ear cavity from the inner ear cavity when the insertion guide is fully inserted into the inner ear cavity. In an exemplary embodiment, a portion of the electrode 704 is located in the middle ear cavity, and another portion of the electrode 704 is located in the wall 910 and/or in the inner cavity when the insertion guide 1100 is fully inserted into the cochlea. In an exemplary embodiment, the guide is such that the entire electrode 704 is located in the wall 910 (i.e., in the hole through the wall) when the insertion electrode 1100 is fully inserted into the inner ear cavity. That is, no part of the electrode is located in the middle ear cavity where the inner ear cavity (where, for the purposes of this paragraph only, the volume corresponding to the hole that is formed in the cochlea so that the array can pass from the middle ear cavity to the inner ear cavity is neither in the middle ear cavity nor in the inner ear cavity). In an exemplary embodiment, the guide is such that a portion of the electrode 704 is located in the wall 910 when the insertion guide 1100 is fully inserted into the inner ear cavity, and a portion of the electrode is located in the inner ear cavity when the insertion guide is fully inserted into the inner ear cavity.

Figure 45:
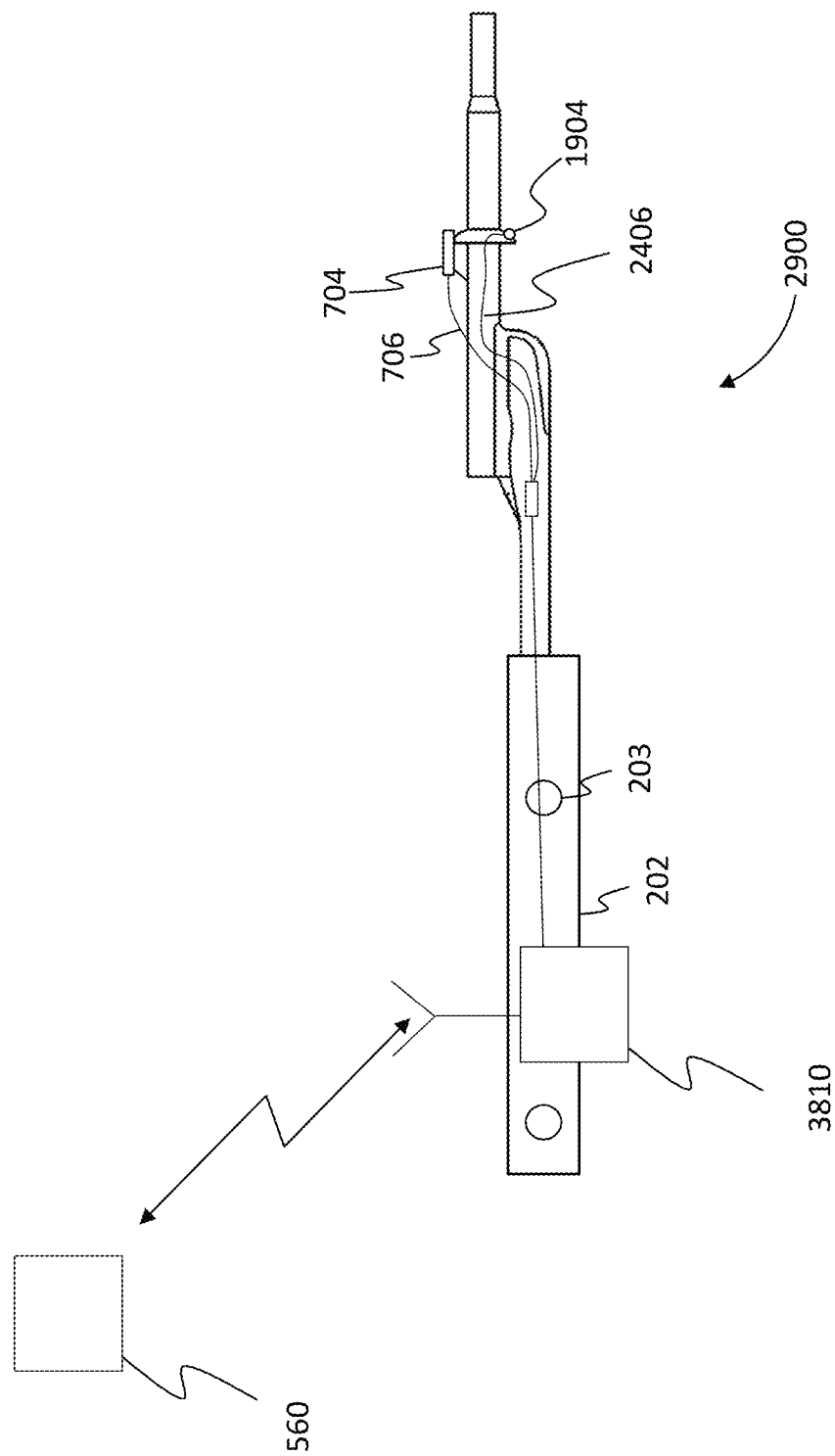

FIG. 45 depicts an insertion guide 2900 that is in wireless communication via element 3810 with a remote component 560, which could be a test unit or a control unit as disclosed further below.

Figure 46:
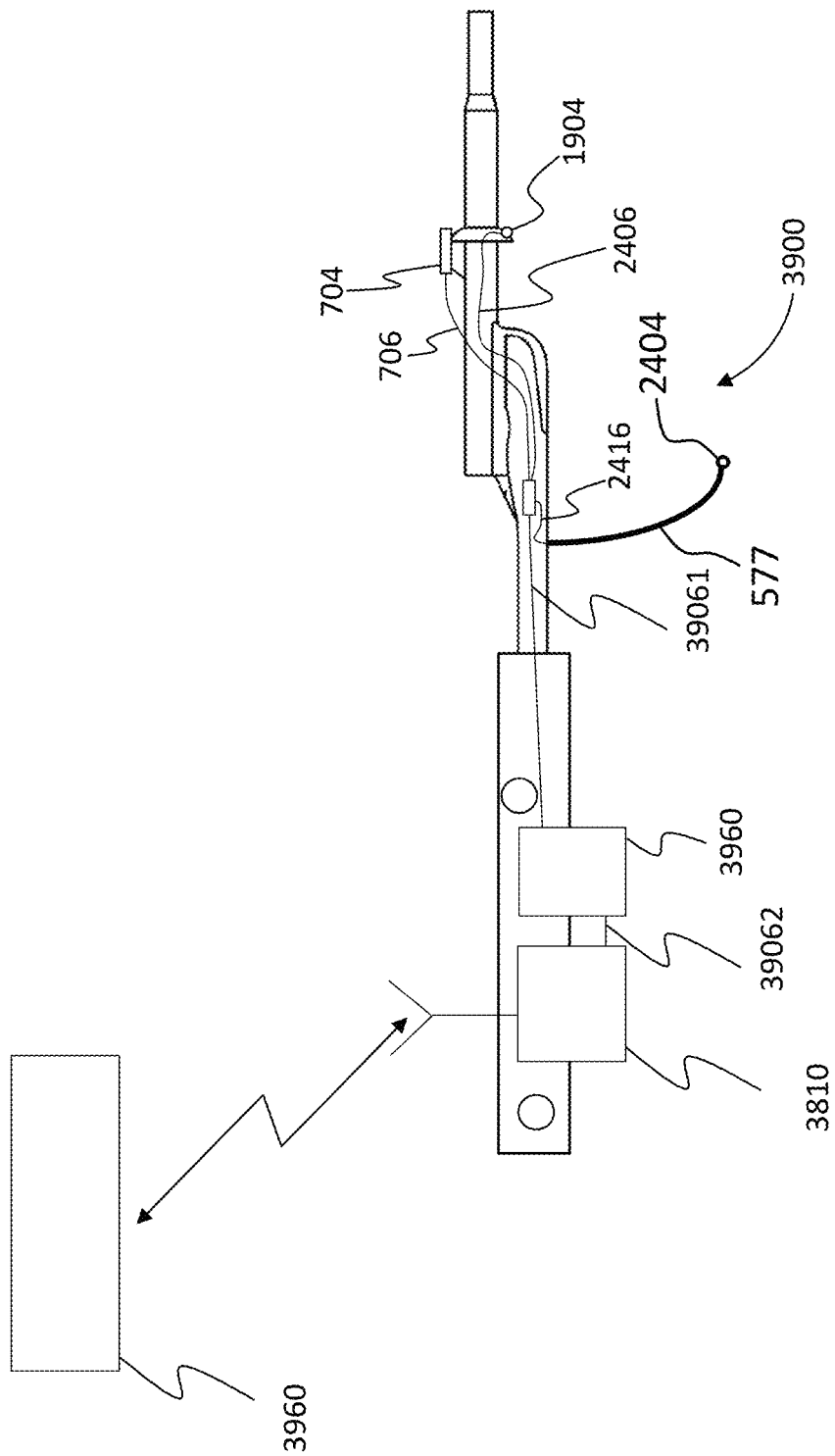

As briefly noted above, in at least some exemplary embodiments, some exemplary insertion guides can include a self-contained measurement system. FIG. 46 depicts such an exemplary embodiment of an insertion guide 3900. Insertion guide 3900 contains a complete measurement system. As can be seen, the insertion guide 3900 further includes a reference electrode 2404, which is in signal communication with the electrical leads of the system via lead 2416. Lead 39061 extends from the connector to test unit 3960, which can correspond to test a test unit configured to executes one or more or all of the test teachings herein, and can be a personal computer programmed to execute such. Test unit 3960 is in signal communication with communication unit 3810 via lead 39062. Communications unit 3810 can be in wireless communications with remote device 3960. In an exemplary embodiment, the remote device 3960 is a data storage device/data recording device that records the data transmitted via the communications unit 3810. For example, 3960 can be a desktop and/or a laptop computer having memory therein to record the data. In an alternate embodiment, device 3960 can be a control unit or the like, again such as a computer, that can control measurement system of the guide 3900. That said, in an exemplary embodiment, the guide 3900 includes an activation switch or the like so that the system can be activated and/or deactivated by the surgeon or other healthcare professional.

It is noted that in an exemplary embodiment, reference electrode 2404 can be configured so as to clamp or otherwise mount onto one or more of the reference electrodes of the receiver stimulator of the cochlear implant. In an exemplary embodiment, instead of reference electrode 2404 at the end of lead 577, there is an alligator clip or the like that clips onto the "can" of the receiver stimulator of the cochlear implant, which has an electrical configuration of a reference electrode/sink of the cochlear implant. That said, in an alternate embodiment, such can be placed into electrical communication with the so-called hardball electrode of the cochlear implant electrode array. That said, in an alternate embodiment, a more sophisticated connection mechanism can be utilized, such as a snap coupling or the like on the can. Also, it is noted that while the electrodes 704 and 1904 are depicted as being on the outside of the cochlea during insertion, in an alternate embodiment, the electrodes (one or more or all) can be located on the inside the cochlea in alternate embodiments where the electrodes are different than that depicted in FIG. 46.

It is also noted that while the embodiment of FIG. 46 utilizes a reference electrode 2404, in an alternate embodiment, the reference electrode can be any of the electrodes of the insertion guide detailed above. In an exemplary embodiment, any of those electrodes can be placed into electrical communication with the can of the cochlear implant and/or the hardball, or any other electrode of the cochlear implant, again by way of, for example, alligator clip or other fastening mechanism that can permit electrical communication from the electrode(s) of the insertion tool to the cochlear implant. Such can have utilitarian value with respect to establishing a reference electrode closer to the source and sink electrodes that are utilized for stimulation.

Figure 47:
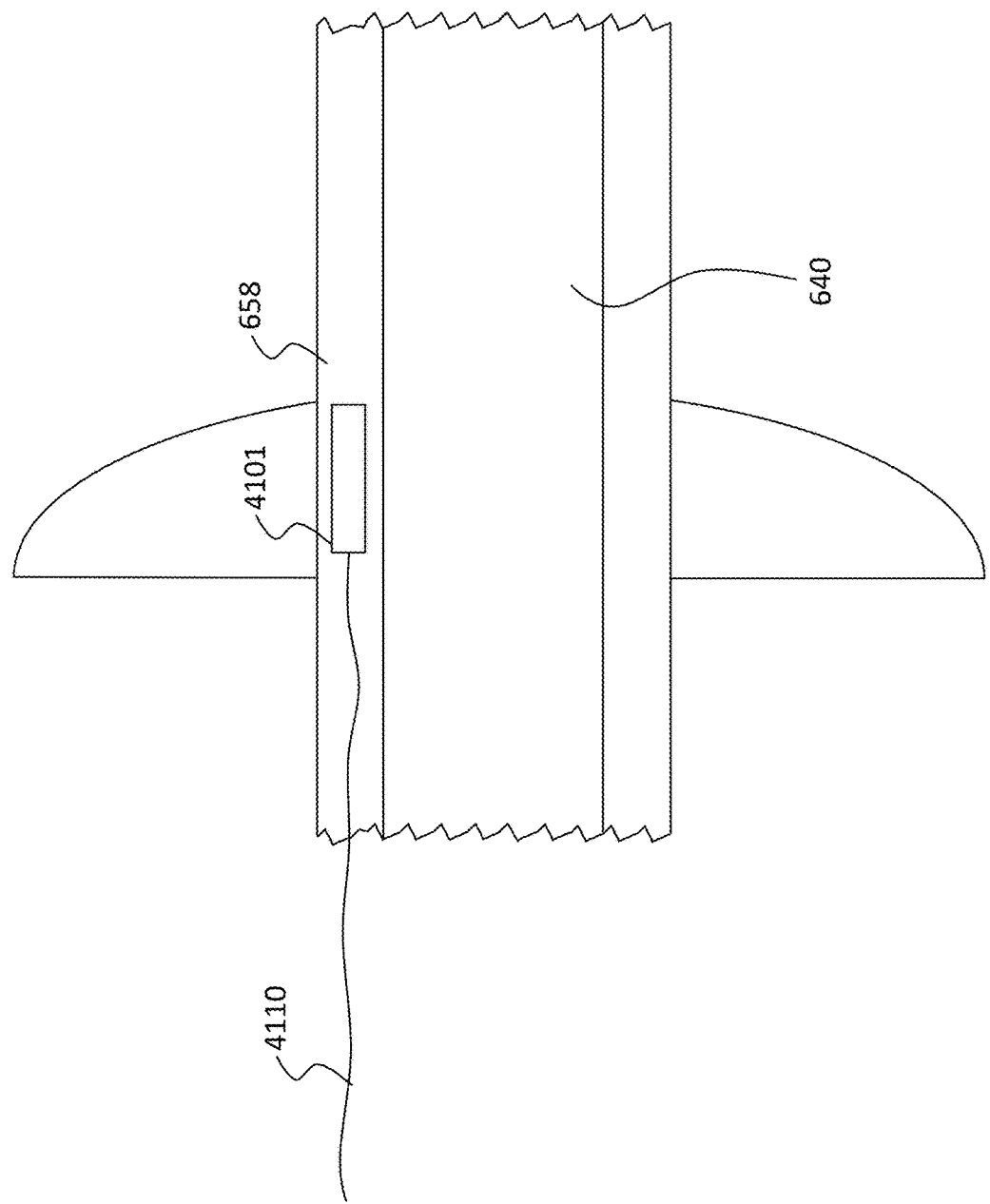

FIG. 47 depicts another exemplary embodiment of an insertion guide that has a functionality beyond that of an electrode array support/an electrode array insertion device. Particularly, the embodiment of FIG. 47 depicts a portion of the insertion guide tube at the stop 204 where a sensor 4101 is located in the wall 658 of the tube, although in other embodiments, the sensor 4101 is located on the inside wall of the tube and in other embodiments, the sensor 4101 is located on the outside wall of the tube. In this exemplary embodiment, the sensor is configured to sense or otherwise detect individual electrodes in the array as they pass by the sensor as the electrode array is inserted through the lumen 640 into the cochlea, and output a signal via lead 1410 indicative of at least one of an electrode passing the sensor 4101 or, in a more sophisticated embodiment, the speed of the electrode/electrode array passing by sensor 4101. In an exemplary embodiment, the sensor 4101 can be a sensor that utilizes capacitive sensing. In an exemplary embodiment, it could be a Hall effect sensor. In some embodiments, the sensor could be a sensor that comes into direct contact with the electrodes of the electrode array. In an exemplary embodiment, there is a system that receives the signal from lead 1410 and outputs data indicative of the insertion speed of the electrode. In an exemplary embodiment, the system can be a personal computer with an algorithm that analyzes the signal 4110, and outputs data to the surgeon. Exemplary output can be output by a speaker or the like indicating the speed of the insertion of the electrode array. Exemplary output can be output by a visual device indicating the speed of insertion of the electrode array. Exemplary output can correspond to the speed of insertion, a go/no go data package (e.g., insertion too fast/insertion speed fine). Such can be done via audio and/or visual devices. For example, a green light can indicate acceptable speed and a red light can indicate an unacceptable speed. Moreover, the system can be binary. The activation of the light will indicate that the speed is too fast/the audio indication (which could be a buzzer or a tone, etc.) activates when the insertion speed is too fast. The alternative could also be the case. The tone and/or light can be activated while the insertion speed is acceptable, and the tone or light is deactivated when the insertion speed is unacceptable. It will be noted that these indicators can also be utilized to indicate other sensed phenomenon or otherwise detected phenomenon as detailed herein.

Figure 48:
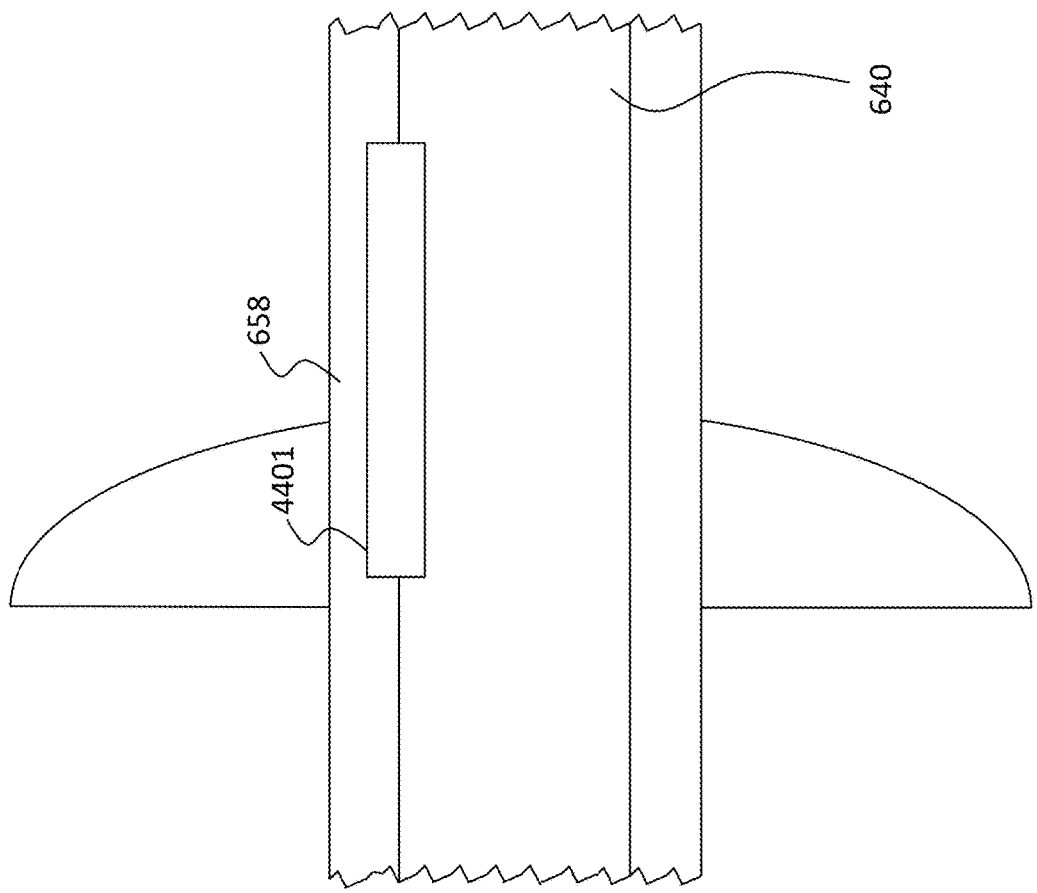
Figure 49:
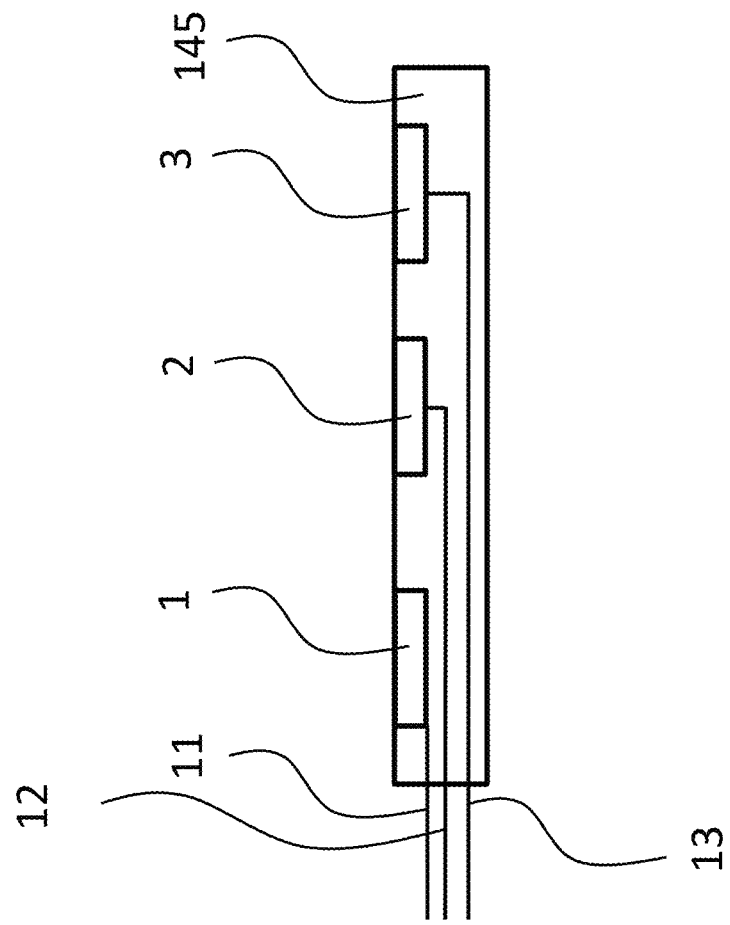

FIG. 48 depicts a portion of an exemplary insertion guide that is configured to enable testing for an open circuit between two or more electrodes of the electrode array as the array passes through the lumen 640. Briefly, component 4401 is made of a conductive material that essentially "shorts" two electrodes of the electrode array as they pass by in contact with the component 4401. As will be detailed below, component 4401 can be a flexible component so as to provide a compressive force on the outside of the electrode array so as to establish sufficient electrical conductivity between an electrode, component 4401, and another electrode. In general terms, FIG. 49 depicts a quasi-functional diagram of a portion of electrode array 145, depicting electrodes 1, 2, and 3, which are respectively connected to leads 11, 12, and 13, which leads extend from the respective electrodes to the proximal end of the electrode array assembly, and then to a receiver/stimulator thereof. While only three electrodes and three leads are depicted in FIG. 49, it is to be understood that in at least some embodiments, more electrodes and more leads are present in electrode array 145. Only three electrodes and only three leads are depicted in FIG. 45 for clarity.

In isolation, without any contact with any outer material other than air, to test for a short, a source of current is applied to any one of the leads 11, 12, or 13. If current is detected (this phenomenon is described generally—in at least some exemplary embodiments, the "detection" corresponds to a given functionality of the receiver/stimulator that can be telemetrically transmitted and analyzed—more on this below) at any one of the other leads 11, 12, and/or 13, a determination can be made that a short exists. This is because the impedance between the electrodes 11, 12, and 13 should be relatively high (the material connecting the electrodes 148 is typically made of silicone). The leads 11, 12, and 13 are insulated from one another and from the electrodes other than the respective electrodes associated with the respective leads.

Conversely, to detect for an open, in the absence of contact with any other material other than air, because of the high impedance between the respective electrodes, and the aforementioned electrical insulation, there is nothing to close the circuit between a source of electrical current applied to one lead, and a detector (again, this is used generally—more on this below) located at any of the other leads.

Accordingly, in an exemplary embodiment, the apparatus 4401 is configured to enable testing for an open circuit between two electrodes by utilizing conductive material that is sufficiently conductive to test for an open circuit when placed into contact with two or more electrodes of the electrode array 144. In use, component 4401 extends a sufficient distance into the lumen 640 and has sufficient length such that it can contact two electrodes as the electrode array passes by component 4401. In an exemplary embodiment, the entire component 4401 is made of a requisite conductive material. In an exemplary embodiment, only a portion thereof is made of the requisite conductive material. By way of example only and not by way of limitation, at least the bottom surface (the surface that faces the electrodes/the surface that comes into contact with the electrodes) can be made of the requisite conductive material, or at least coated with the requisite material or otherwise the requisite material is attached to the interior thereof). In an exemplary embodiment, only a portion of the component 4401 is made of the requisite conductive material. Any arrangement that can enable the testing of an open circuit while electrode array assembly is being passed can be utilized in at least some embodiments.

In an exemplary embodiment, the material of the component 4401 and/or other material forming a portion of the component 4401 and/or any other material that enables testing for an open circuit has a "midrange" impedance, or at least enables the establishment of a midrange impedance between two or more electrodes, such that both testing for an open circuit and testing for a short circuit can be implemented. In other exemplary embodiments, the component 4401 has a relatively high range impedance.

In an exemplary embodiment, the component 4401 is configured to provide a controlled impedance between two or more electrodes that will enable at least testing for an open circuit between two electrodes, if not both testing for an open circuit and testing for a short circuit between two electrodes.

Thus, in an exemplary embodiment, the component 4401 is configured to enable two types of conductivity testing of the electrode array (e.g., testing for an open circuit and testing for a short circuit) in some embodiments.

Figure 50:
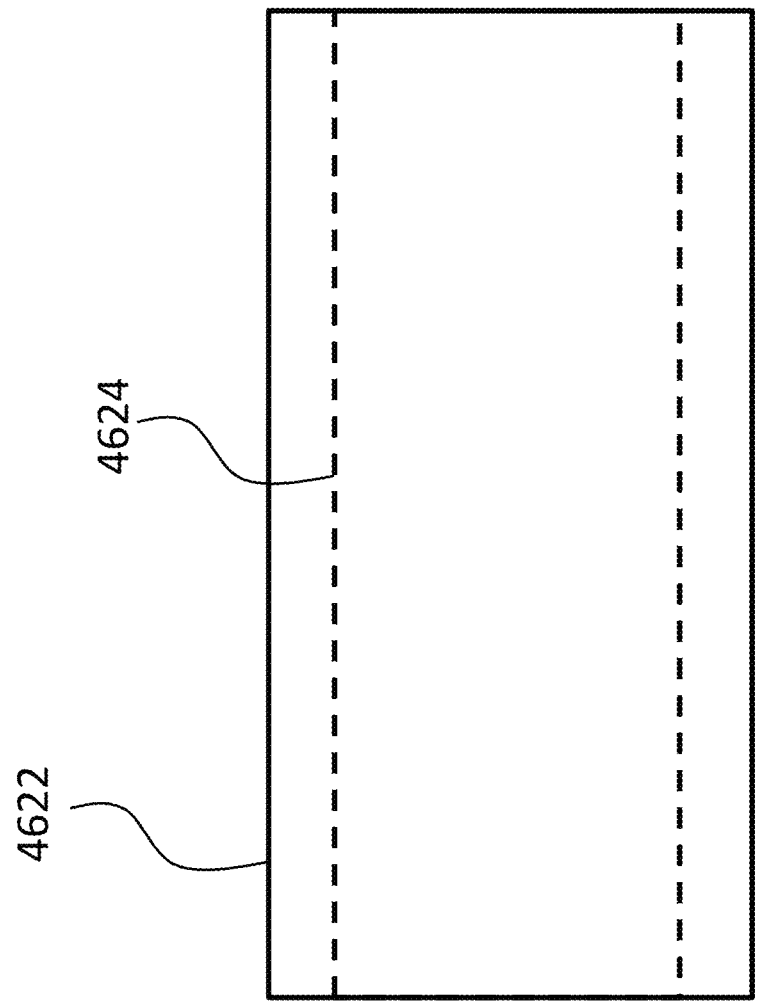

FIG. 50 depicts an exemplary conductive apparatus 4622 in the form of an elongate cylinder having a passage 4624 therethrough, wherein the passage 4624 is sized and dimensioned to receive the electrode array 145 therein such that at least two electrodes of the electrode array 145 contact the interior walls of the passage 4624 to establish electrical conductivity between the electrodes. In an exemplary embodiment, the conductive apparatus 4622 is configured such that an impedance between any two locations on the interior surface of the passage 4624 within a distance corresponding to the distance between two electrodes of the electrode array 145 that will be inserted or otherwise located within passage 4624 is less than about 500 ohms (or any other value that will enable testing for an open circuit between two electrodes—more on this below). In this regard, it is noted that all disclosures of impedance and related phenomenon detailed herein both correspond to the structure being described, and how the structure is arranged or otherwise used. That is, because impedance varies both with respect to distance and with respect to material type (along with some other features) and it is the resulting impedance that imparts utilitarian value on to the teachings detailed herein, as opposed to the specific impedance of a given material or the like, any disclosure herein regarding material properties also corresponds to the functionality of the resulting apparatuses when utilized according to the teachings detailed herein and/or variations thereof.

Figure 53:
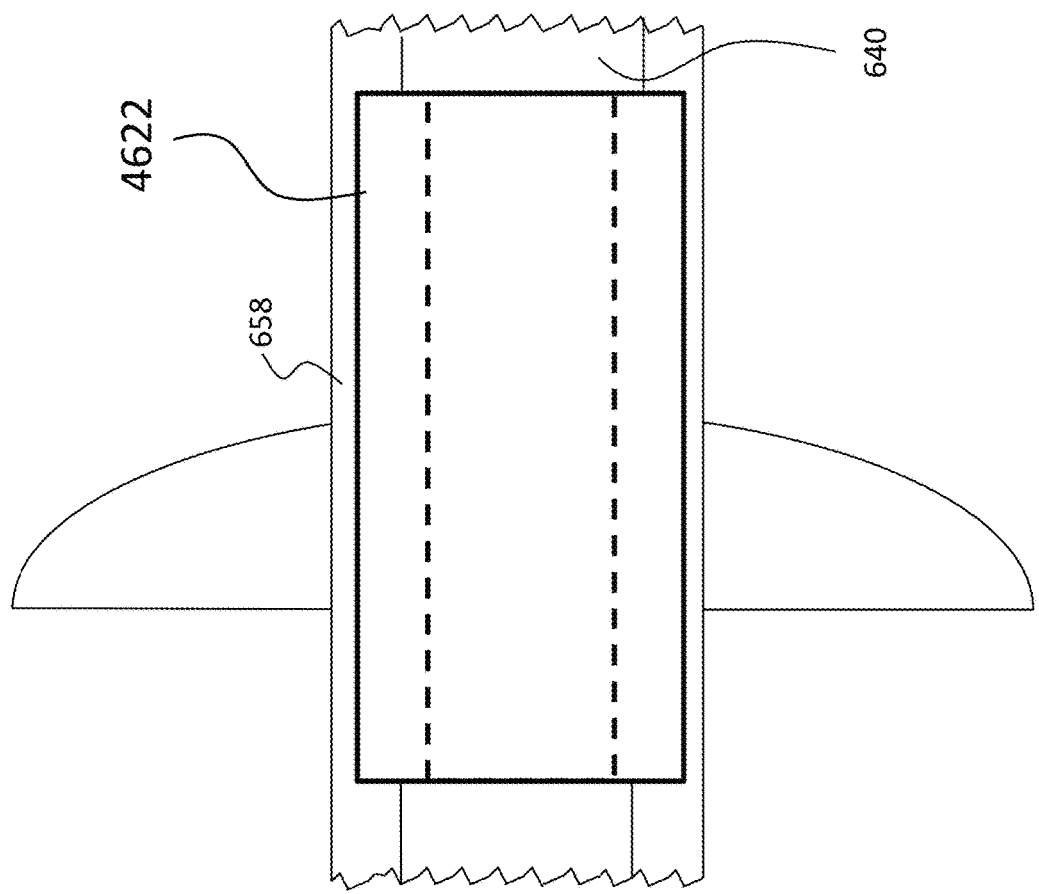

FIG. 53 depicts the conductive apparatus 4622 located in the insertion guide tube 610 of the insertion guide. In an exemplary embodiment, the interior of the conductive apparatus at the ends thereof is rounded so as to provide a smooth interface between the interior wall of the tube wall 658 and the "bump up" that is the interior of conductive apparatus 4622. That is, because the interior of conductive apparatus 4622 is proud of the interior wall of the tube wall 658, ramping can be used so as to avoid binding or otherwise catching the electrode array one the edges of the conductive apparatus 4622.

Briefly, the embodiments utilizing apparatus 4622 and variations thereof to "short" two electrodes rely on, in some embodiments, the ability of the receiver/stimulator of the cochlear implant to provide an electrical signal to one of the electrodes and sense a voltage and/or current at the other of the electrodes. In an exemplary embodiment, a device is in inductance communication (or any other applicable communication format that will enable the teachings detailed herein and/or variations thereof to be practiced) with the receiver/stimulator of the cochlear implant so as to communicate data therefrom indicating whether or not an open circuit is present. Indeed, in an exemplary embodiment, the device that is in inductance communication with the receiver/stimulator is the device that initiates the current to one of the electrodes and the first instance. In an exemplary embodiment, the communication can correspond to the communication that transcutaneously takes place between the external component 142 and the implantable component 144 vis-à-vis the system of FIG. 1. That is, in an exemplary embodiment, the communication from the receiver/stimulator and/or to the receiver/stimulator can be executed utilizing techniques that are the same as, or at least analogous to, the transcutaneous communication that takes place while the cochlear implant 100 is implanted in a recipient fully and completely beneath the skin.

Figure 5I:
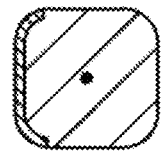
Figure 5H:
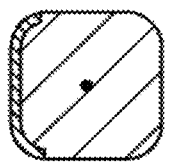
Figure 5G:
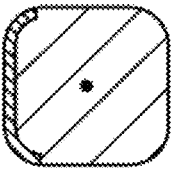
Figure 5F:
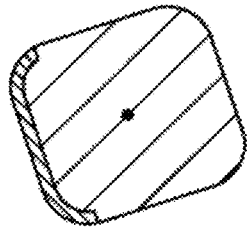
Figure 52:
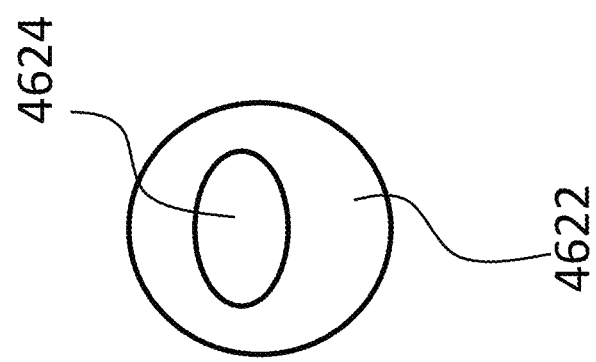

FIG. 52 depicts a view looking down the longitudinal axis of the conductive apparatus 4622. It is noted that the geometric shapes presented in these FIGs. are but exemplary. Any configuration that will enable the teachings detailed herein and/or variations thereof to be practiced can be utilized. FIG. 5I also depicts a view looking down, where, with respect to a cross-section of an array, an electrode can be seen.

It is further noted that while the embodiment depicted in the figures are depicted as a monolithic component (in an exemplary embodiment, the entire body 4622 is made from a conductive material, and thus conductive apparatus 4622 is a tube or cylinder of conductive material), in an alternative embodiment, the conductive apparatus 4622 can be a multilithic component. Indeed, in an exemplary embodiment, the walls of the passageway 4624 can be coated with a conductive material (e.g., gold), and the remainder of the conductive apparatus 4622 is made of a relatively nonconductive material (e.g., rubber, silicone, etc.). In this regard, for embodiments where the conductor used to test for the open circuit is movable in and out of position, the impedance range of the conductor can be very low.

It is noted that in an exemplary embodiment, the entire body 4622 and/or a portion thereof (e.g., the portion making up the walls of the passageway 4624) is a conductive foam or conductive polymer. Typically, this is foam or polymer containing conductive elements (e.g., loaded with silver, gold, carbon, etc.). This can have utilitarian value with respect to deforming around the electrode array as the electrode array passes through body 4622. Accordingly, such can have utilitarian value with respect to contracting as the localized width of the electrode array relative to body 4622 becomes wider as the electrode array is passed therethrough during insertion of the electrode array.

Figure 51:
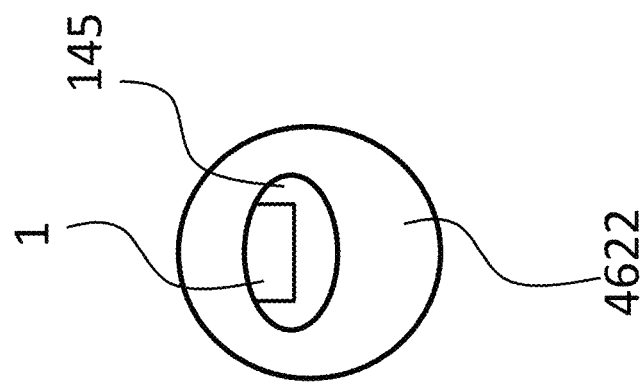
Figure 54:
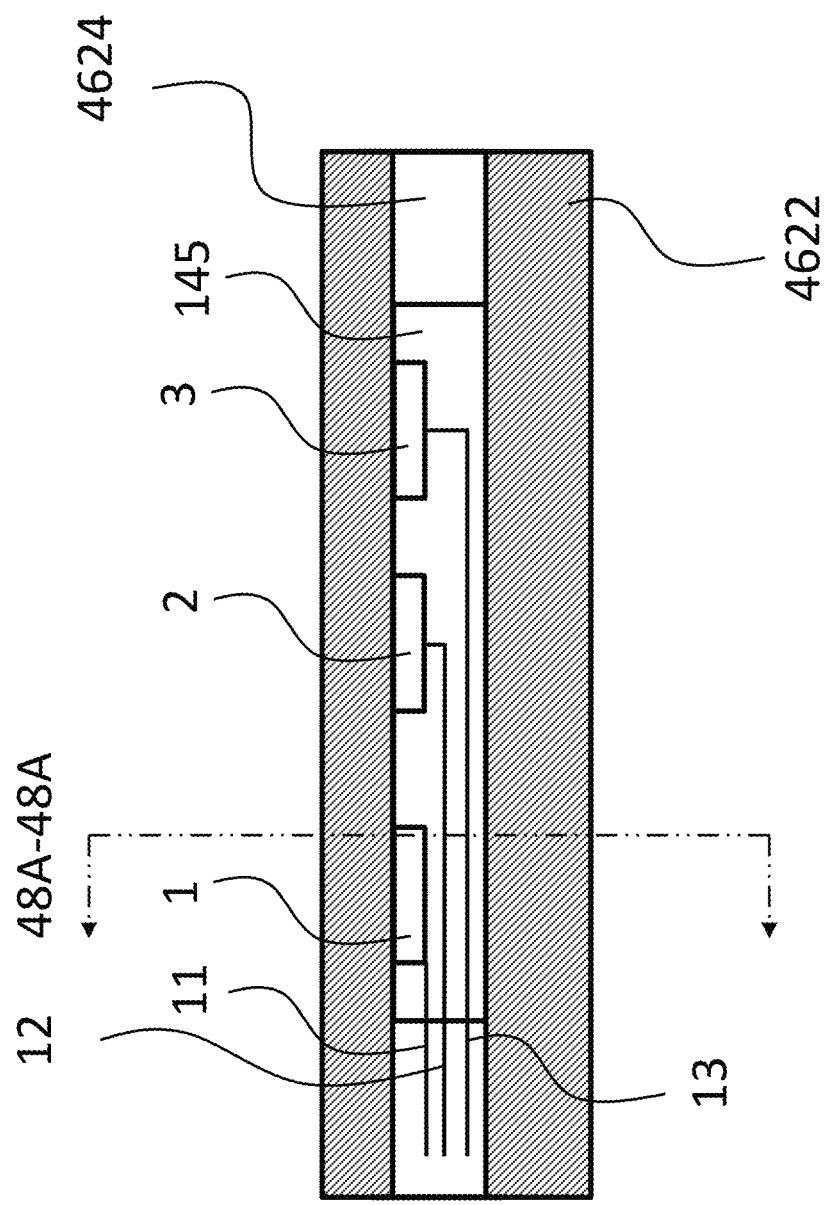

FIG. 5I depicts the view of FIG. 50, with the addition of the electrode array 145 being located in the passage 4624 (the array is shown in cross-section). More particularly, the view of depicts a cross-sectional view of an electrode array 145 taken at a location where electrode 1 is located. FIG. 54 presents FIG. 51 in greater context, which depicts a side view of a cross-section through the conductive apparatus 4622 with the electrode array 145 located therein.

As can be seen, the electrodes are in contact with the inner surface of the passageway 4624. In this embodiment, the contact is sufficient to provide electrical conductivity from electrode 1 to electrode 2 and/or electrode 3 such that testing for an open circuit between one of these electrodes can be implemented. Corollary to this is that the conductive apparatus 4622 is configured to maintain the requisite contact to enable testing for an open circuit between two or more of the electrodes and/or be placed and held in that configuration for such testing to be executed. In an exemplary embodiment, conductive apparatus 4622 is made of a conductive foam material, wherein an interference fit is established between the electrode array 145, and thus the electrodes 148, and the inner surface of the passage 4624. In an exemplary embodiment, the interference fit ensures that sufficient contact will be made between the inner surface of the passage 4624 and the respective surfaces of the electrodes 148. In an exemplary embodiment, the use of foam ensures or otherwise substantially lessens the chance that the array 145 will be damaged due to contact between the array and the conductive apparatus 4622. This will be described in greater detail below.

Figure 55:
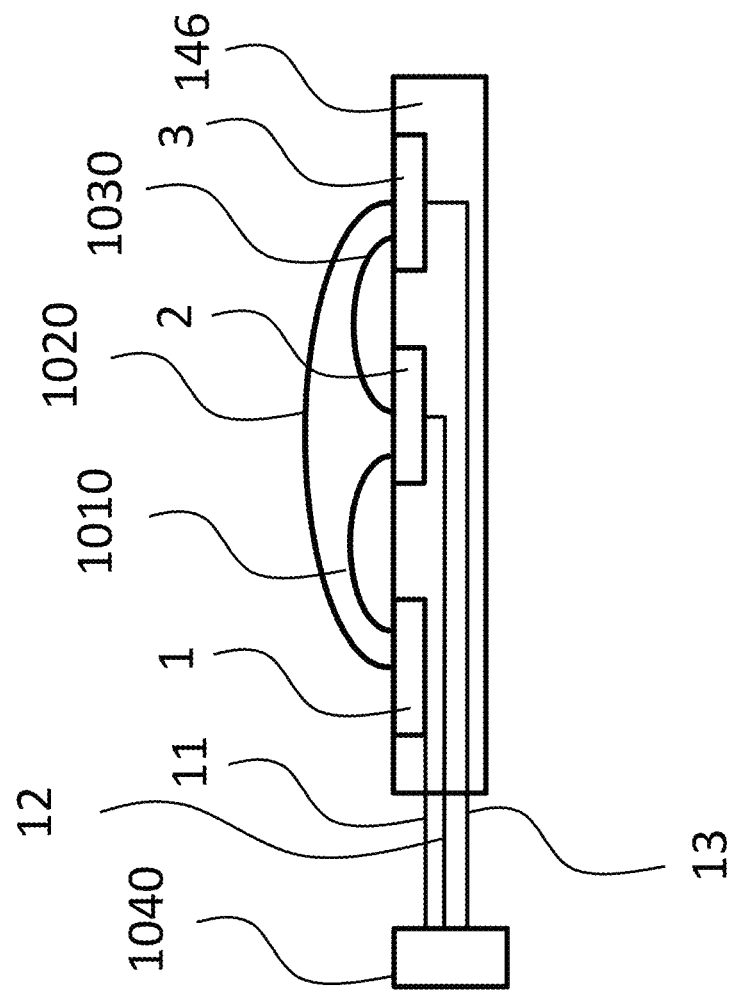

FIG. 55 presents a functional representation of the functionality of the conductive apparatus 622, where hypothetical leads 1010 and 1020 are located between electrodes 1 and 2 and between electrodes 1 and 3, respectively. Also shown is hypothetical lead 1030, which is located between electrodes 2 and 3. These leads place the various electrodes into electrical conductivity with one another so that testing for an open circuit can be executed. Also depicted by way of black box format is a current generator/detector 1040, which is configured to apply current to one or more of the leads 11, 12, 13, and detect a current (if there is no open circuit) at one or more of the other of leads 11, 12, 13. The current generator/detector 1040 is but a functional representation of the operation of the receiver/stimulator 180 and/or a test device. That said, in some alternate embodiments, current generator/detector 1040 can be an ohmmeter and/or a multimeter, albeit one adapted for the types of voltage and current suitable for testing of a cochlear electrode array or other array to which the teachings detailed herein are applicable.

Briefly, in an exemplary embodiment, a current is applied by current generator/detector 1040 to lead 12. Current generator/detector 1040 "looks" for a current at either or both of leads 11 and 13. (In an exemplary embodiment, the insertion guide includes a generator configured to generate current at a programmed amount through lead 12 and return it through one or all of the remaining electrodes. In an exemplary embodiment, the guide provides an output indicative of voltage required to drive this amount of current. In an exemplary embodiment, if the voltage is above a certain threshold, it is deemed an open circuit. Otherwise, it is assumed the current is flowing and thus this circuit is closed.) Because the conductive apparatus 622 has placed electrode 2 into electrical conductivity with electrodes 1 and 3 via hypothetical leads 1010 and 1030, a current should register at one or both of leads 11 and 13 (or only one of the leads if only one of the hypothetical leads 1010 and 1030 or present) thus indicating that there is no open circuit between current generator detector 1040 and electrode 2.

Note that by "looking" for a current at two or more leads, the scenario where an open circuit exists with respect to one of the other leads, which open circuit could give a "false-negative" with respect to the lead under test can be accounted for in an exemplary embodiment. For example, if lead 12 is being tested (or, more precisely, testing for an open circuit is being performed between current generator/detector 1040 and electrode 2), and if only one lead, such as lead 11, was being utilized for the test, failure to detect a current by current generator/detector 1040 at lead 11 would not necessarily indicate a break for an open circuit associated with lead 12. This is because lead 11 could have failed. However, if a current is detected at lead 13 but not lead 11, it can be surmised that lead 12 is in proper working order, and lead 11 has experienced a failure mode. That is, it can be extrapolated or otherwise inferred that lead 11 has failed in some manner (i.e., the open circuit is between current generator/detector 1040 and electrode 1). In this regard, exemplary embodiments include algorithms to more quickly test a plurality of circuits in view of the fact that deductive logic can be utilized when more than two electrodes are placed into electrical conductivity with one another via conductive apparatus 622.

Note further that to test for a short circuit, the hypothetical leads are removed from the electrodes (e.g., the electrode array is moved away from conductive apparatus 4622). A current is applied to one or more of the leads, and current is looked for at one or more of the other leads. No current (or only specific current—more on this below) should be detected because the hypothetical leads have been removed.

Figure 56:
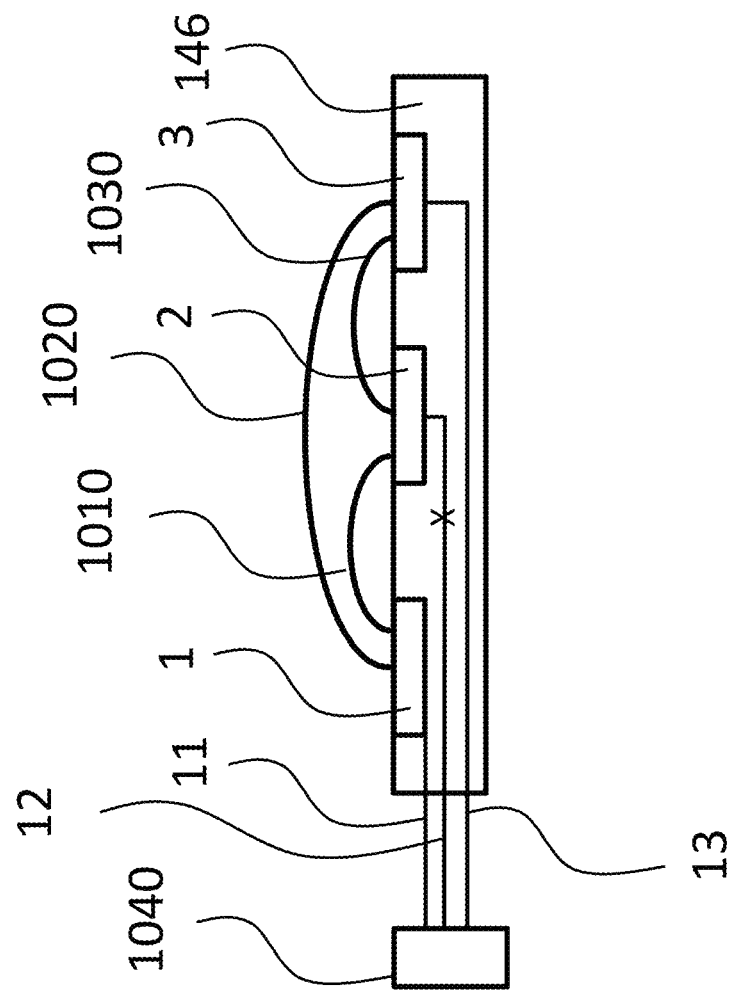

FIG. 56 presents a hypothetical open circuit scenario, where lead 12 has experienced a break at the location indicated by the "X." In an exemplary method, a current is applied by current generator/detector 1040 to lead 12. Current generator/detector 1040 "looks" for a current at either or both of leads 11 and 13. Because the conductive apparatus 4622 has placed electrode 2 into electrical conductivity with electrodes 1 and 3 via hypothetical leads 1010 and 1030, a current will not register at either of leads 11 and 13 (or only one of the leads if only one of the hypothetical leads 1010 and 1030 or present) thus indicating that there is an open circuit, most likely between current generator detector 1040 and electrode 2.

Note that by "looking" for a current at two or more leads, it can be immediately deduced that there is a fault between current generator/detector 1040 and electrode 2 (or a simultaneous fault in electrodes 1 and 3, which can be addressed by running the test by applying current at lead 11 and/or lead 13 and looking at lead 12).

In an exemplary embodiment, a common ground impedance (voltage required to drive a current between a chosen electrode and all the other electrodes shorted together) is measured for each electrode in turn many times a second (1, 2, 3 . . . 22, 1, 2, 3 . . . 22, 1, 2, 3 . . . 22, etc.). In this way, whatever electrodes are in contact with the contacts in the sheath, such will show up as low impedance. As the electrode array advances through the sheath, the low impedance point will travel down the array from electrode 22 to electrode 1. An open circuit will be evident as the electrodes that never go to low impedance.

Note further that in at least some exemplary methods, the methods are not executed to detect which lead or which connection is open or otherwise has experienced a failure mode. A determination that there is some failure anywhere will typically be utilitarian in that a determination can be made in view of the single failure detection that the cochlear implant 100 should not be implanted in the recipient at that time. In an exemplary embodiment, a new cochlear implant 100, such as a cochlear implant 100 located in a new apparatus 400, will be obtained, and a new round of testing for an open circuit will be executed. Such is also the case with respect to detecting which particular electrodes are associated with a short circuit.

Note that by way of example only and not by way of limitation, in an exemplary embodiment, a failure mode can correspond to a break in a lead and/or a disconnect between a lead and an electrode, which failure mode can typically result in an open circuit. In an exemplary embodiment, this can occur during shipping of the apparatus 400.

Figure 57:
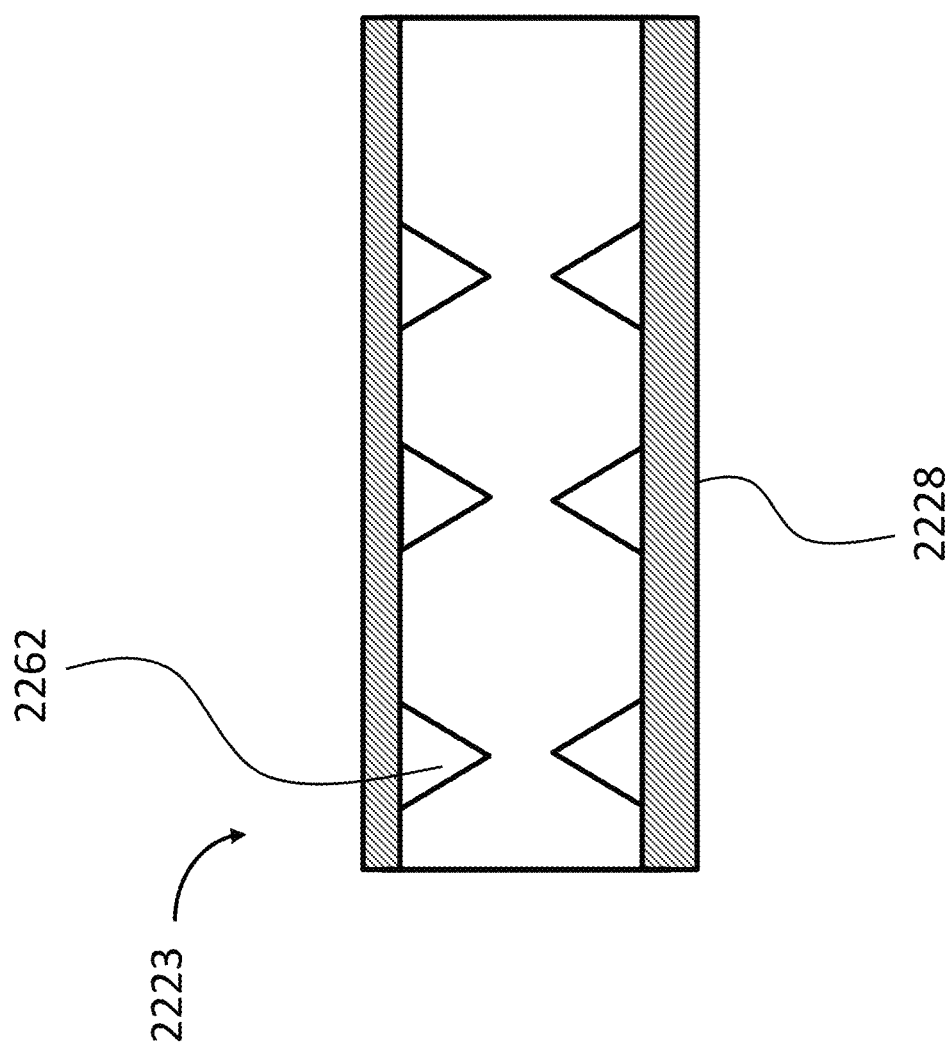
Figure 57B:
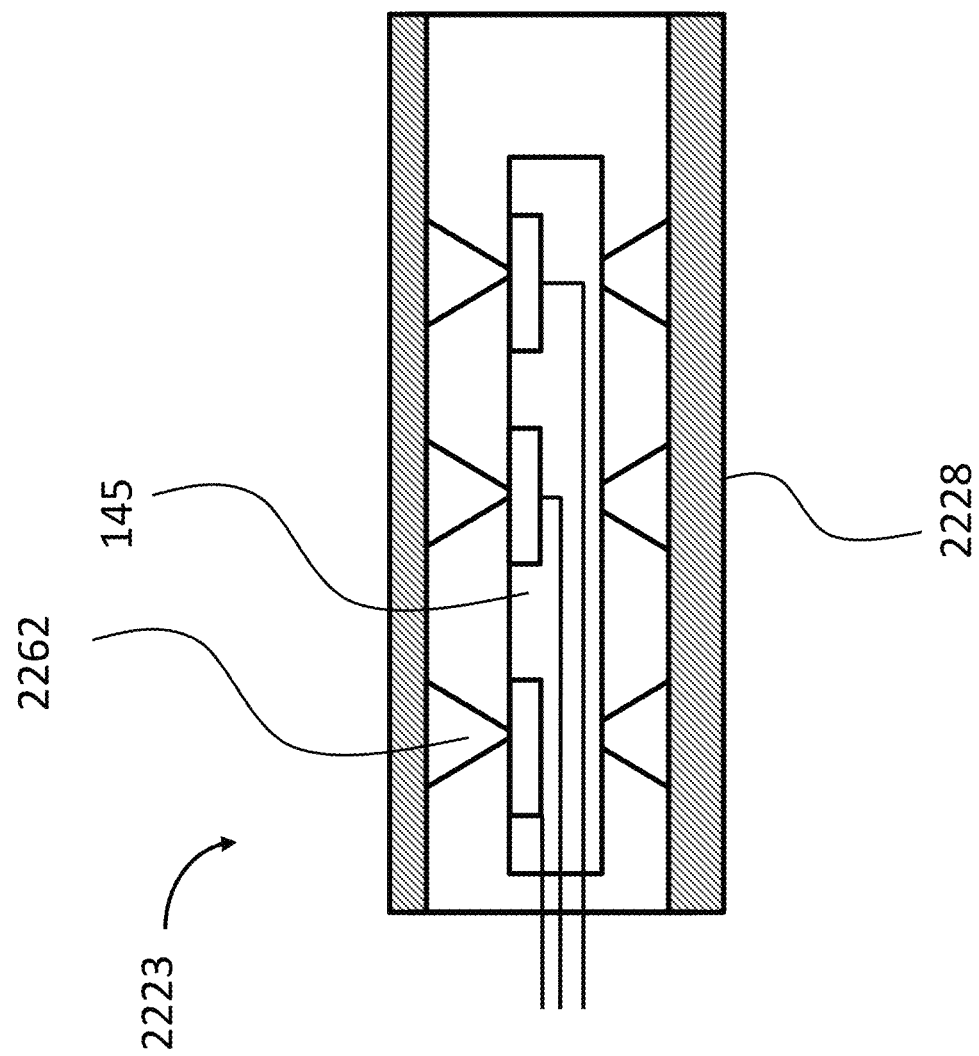
Figure 58:
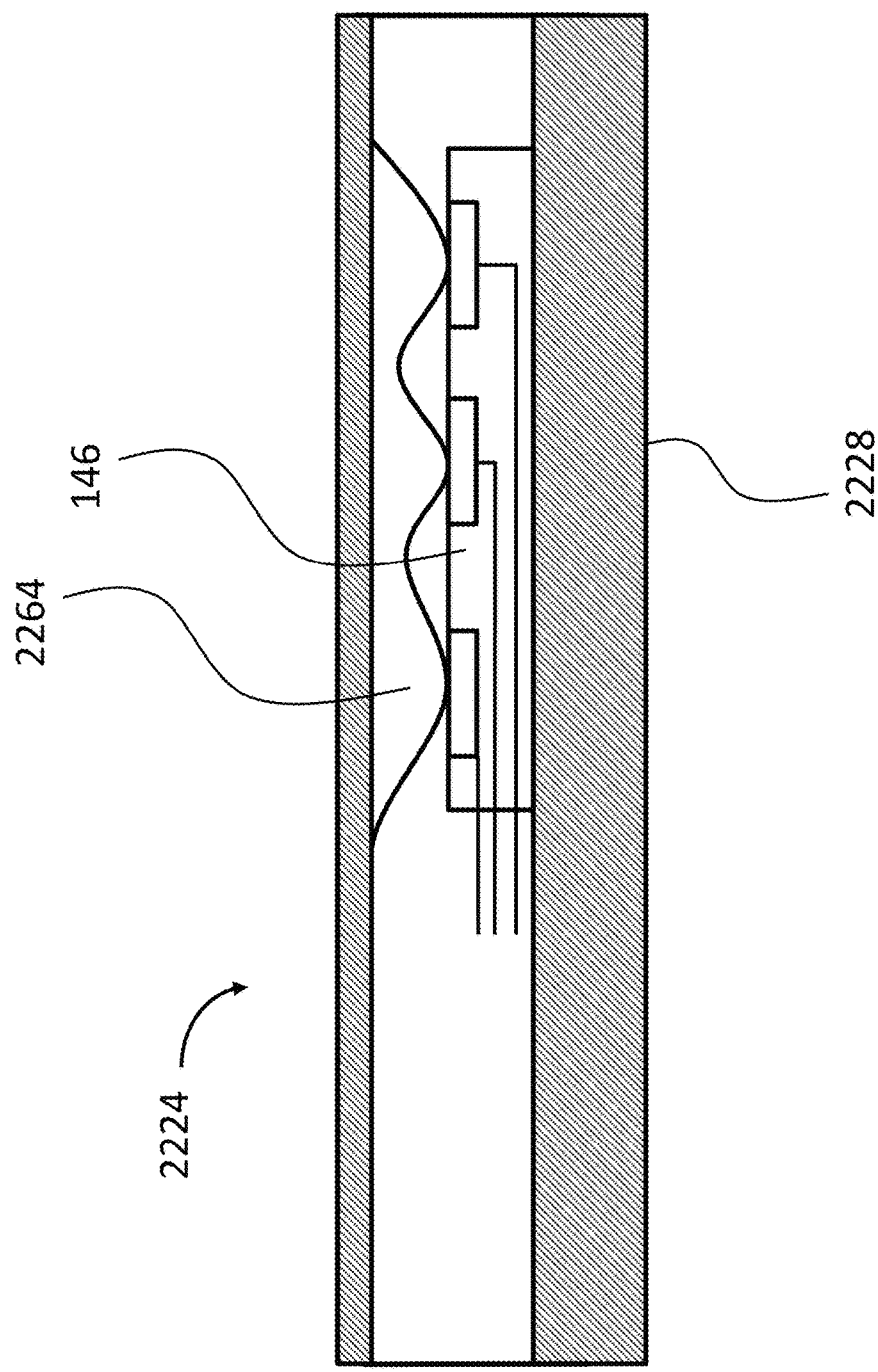

It is further noted that in an exemplary embodiment, instead of a solid or contiguous conductive component that contacts the various electrodes, separate contacts 2262 supported by conductive body that extends between the contacts can be configured to be compressible, at least with respect to the portions on the tip, as can be seen in FIGS. 57A and 57B. In an exemplary embodiment, element 4622 is replaced by conductive apparatus 2223. Alternatively, and/or in addition to this, the contacts 2262 can be supported on a flexible material that flexes to provide space. The contact can also be spring loaded in another exemplary embodiment (more on this below). FIG. 58 depicts another exemplary embodiment of a conductive apparatus 2224 that can be utilized in place of element 4622. Also, in this exemplary embodiment, the conductors 2262 can be located only at the top of the conductive apparatus 2223, instead of all the way around, as is the case with the embodiment of FIG. 58.

It is further noted that variations of the concepts depicted herein can be implemented to enable the teachings detailed herein. Instead of utilizing triangular contacts as seen, square contacts can be utilized. Still further, undulating contact surfaces can be utilized such that the crests of each undulation are in phase with the respective electrodes (e.g., aligned with the centers of the electrodes) of the electrode array. FIG. 58 depicts an exemplary embodiment of a conductive apparatus 2224 utilizing a "wavy" contact surface, where contact apparatus 2264 can be seen to have crests that are in phase with the electrodes of the electrode array 145.

In an exemplary embodiment, any of the teachings of U.S. patent application Ser. No. 15/164,789, filed on May 26, 2016, to Inventor Grahame Walling, for testing for an open circuit can be incorporated into an insertion guide with the requisite modifications to enable open circuit testing.

It is noted that any of the aforementioned opened circuit detection devices and/or the short circuit detection devices can be placed into signal communication with a control unit and/or a testing unit according to the system detailed herein that can receive the data and determine whether or not there exists an open circuit and/or a short circuit, etc., which data can be utilized to implement the system detailed herein vis-à-vis the collecting data for the conditioning methods.

Figure 59:
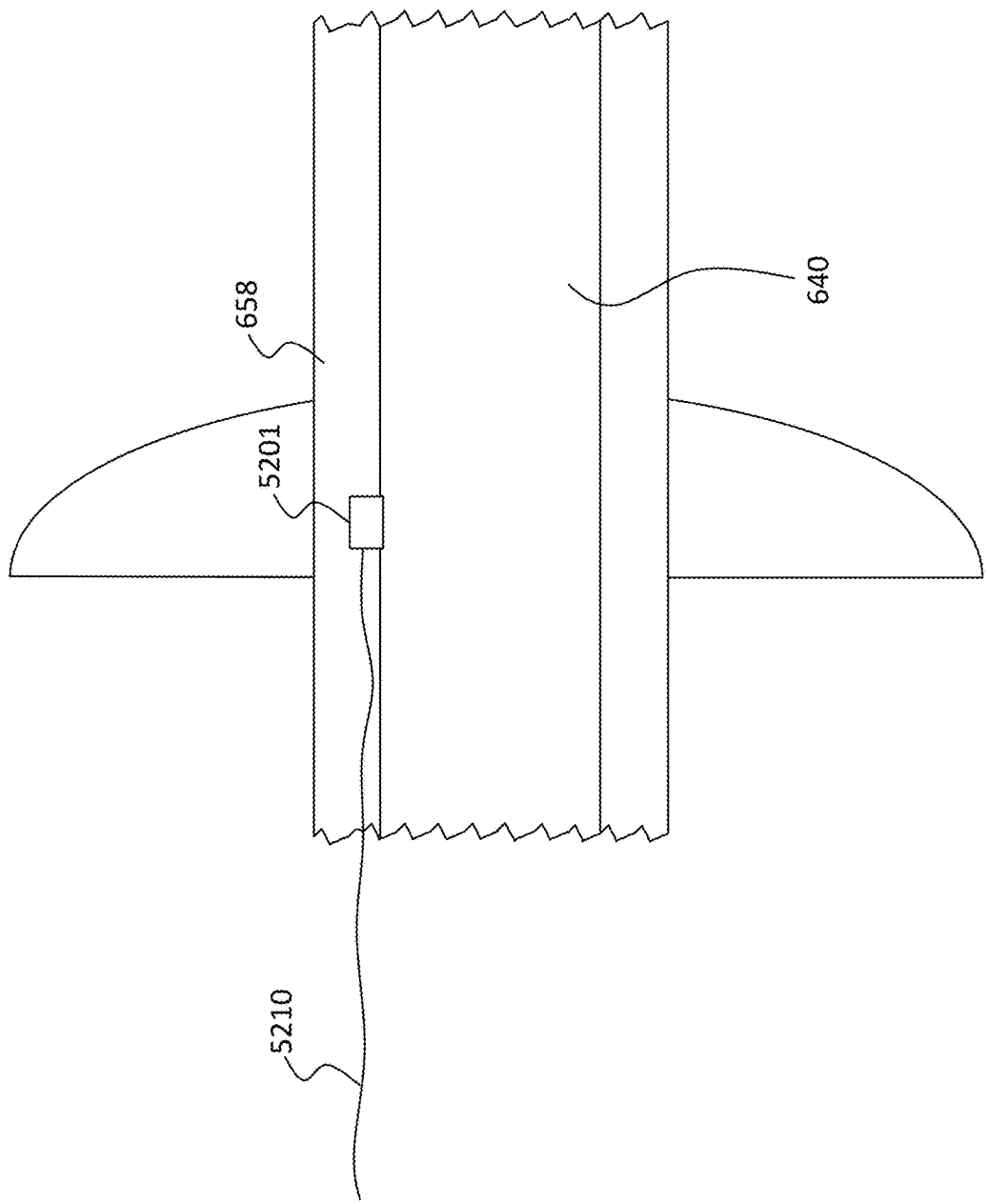

While the embodiments detailed above have been directed towards a device that shorts two electrodes, an alternate embodiment utilizes an electrode in the insertion guide to establish a capacitive coupling with the electrodes of the electrode array as the electrodes of the electrode array pass by the electrode of the insertion guide. FIG. 59 depicts an alternate embodiment of an electrode array insertion tube having another functionality beyond that associated with supporting and/or guiding the electrode array into the cochlea. In this regard, element 5201 is an electrode that is utilized as part of an open circuit testing system. Here, electrode 5201 can establish a capacitive coupling between the electrodes in the array and the insertion guide in general, and the electrode 5201 in particular.

Figure 60:
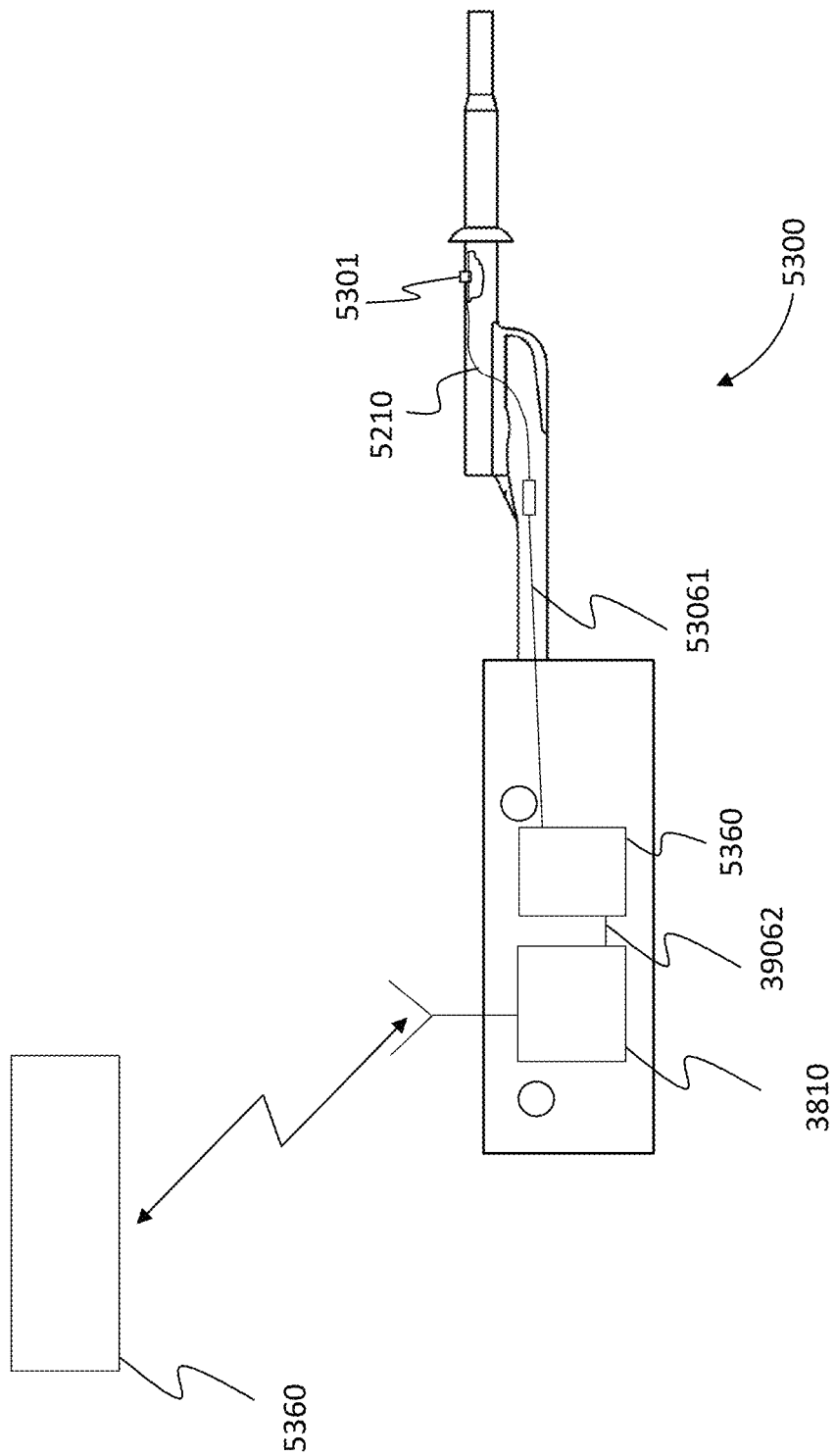

As can be seen, electrode 5201 is connected to a lead 5210. In an exemplary embodiment, this lead energizes the electrode with an electrical current. In an alternate embodiment, this lead provides a return path in a scenario where the electrodes of the electrode array are energized. FIG. 60 depicts an exemplary embodiment of an insertion guide 5300 having the electrode 5301 to establish the capacitive coupling with the electrodes of the electrode array. Here, electrode 5301 is located to the left (proximally) of the stop 204. FIG. 60 depicts a cutout view of the tube of the insertion guide showing electrode 5301 extending into the lumen. Lead 5210 can be seen extending from electrode 5301 to a coupling, to which is connected a lead 53061, which in turn extends to test unit 5360. Test unit 5360 is configured to energize the electrode 5301 in at least some exemplary embodiments. In some alternate embodiments, test unit 5360 is configured to receive current from electrode 5301 in the case where the electrodes of the array are energized.

Figure 61:
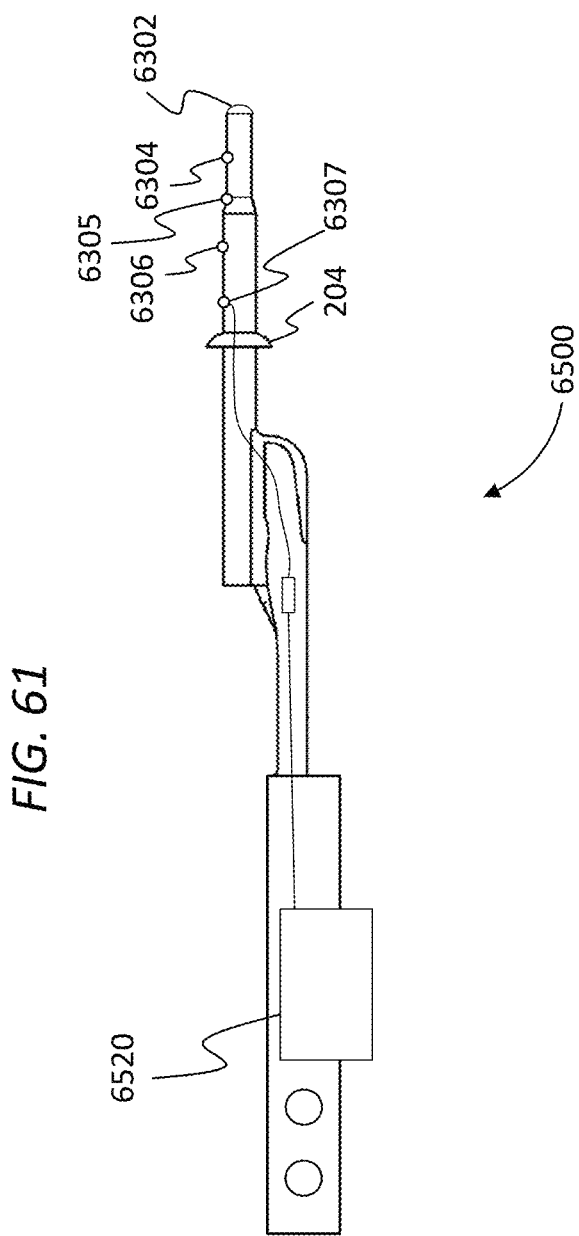

FIG. 61 depicts electrode 6307 in signal communication with a lead that leads to connector 6320. In an exemplary embodiment, connector 6320 is connected to a device that analyzes the output of lead. All of the connectors disclosed herein can be connected to the reference electrode(s) of the cochlear implant.

Figure 62:
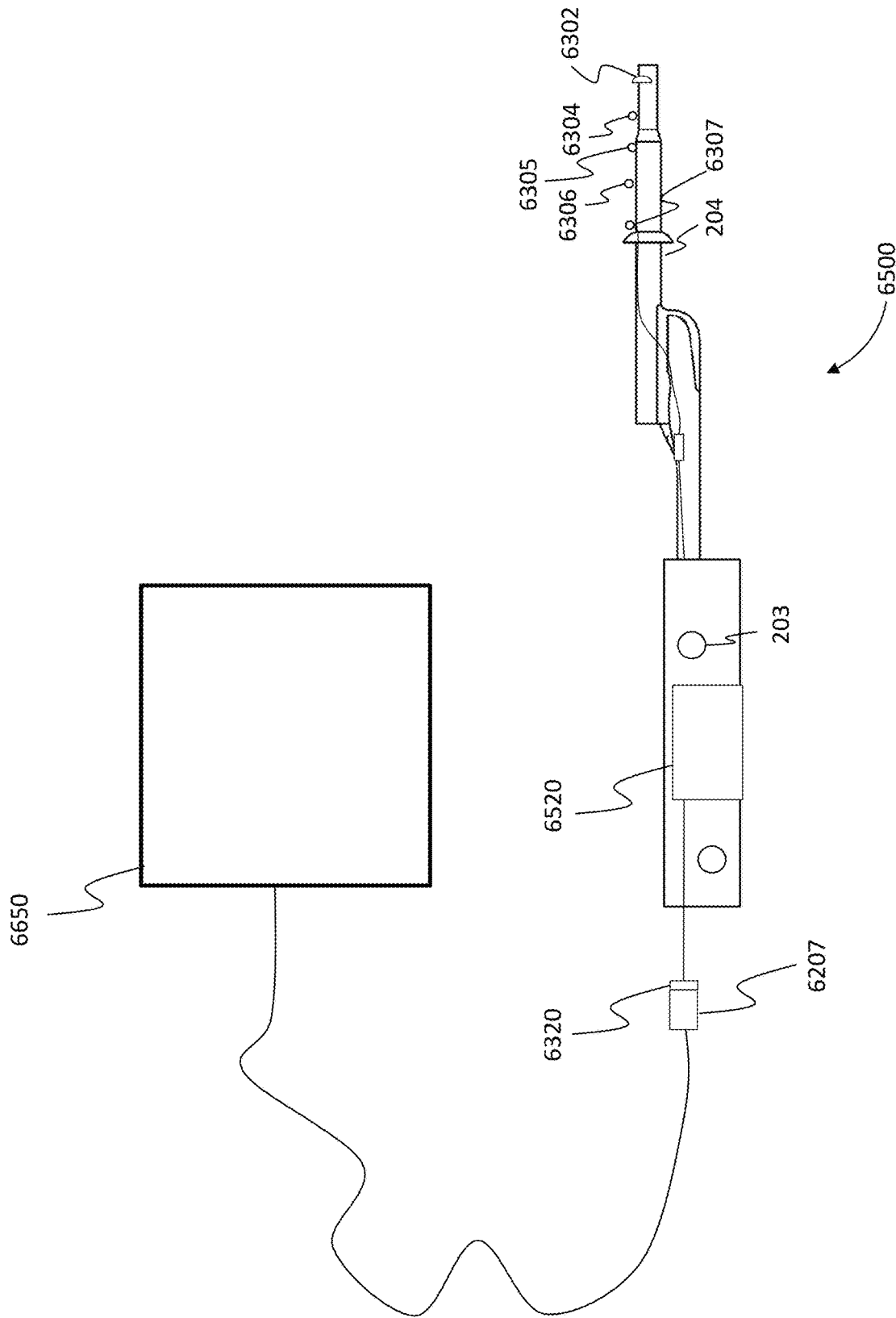

In an exemplary embodiment, the electrode array insertion guide provides source currents from the electrodes thereof. In an exemplary embodiment, the electrode array insertion guide is configured with a current generator that provides a specific current at a specific voltage from the electrode(s) of the guide. In this regard, the electrodes of the electrode array insertion guide can operate as a source with respect to the teachings of U.S. patent application Ser. No. 14/843,255. To this end, FIG. 61 depicts an exemplary insertion guide 6500, that provides a current and voltage generator 6520, which is in communication with electrode 6307 via an electrical lead extending therefrom. In an exemplary embodiment, the generator 6520 can also be in communication with the other electrodes of the electrode array insertion guide. In an exemplary embodiment, the generator 6520 includes relays and/or transistors and/or switching components that enable the generator to alternately switch delivery of current from one electrode to the other electrode. In this regard, in an exemplary embodiment, the generator 6520 can have the functionality and/or the structure of the components of the receiver/stimulator of the cochlear implant of U.S. patent application Ser. No. 14/843, 255 with respect to generating a source current from the electrodes of the electrode array, when implementing the teachings of that patent application. In an exemplary embodiment, the generator 6520 can be a battery that is connected to circuitry that outputs a stable current at a stable voltage. In an exemplary embodiment, the generator 6520 can be adjustable so as to output different currents at different voltages. Consistent with the teachings detailed herein, the guide 6500 can have a switch or the like to allow the surgeon to activate and/or deactivate the current generator 6520. Alternatively, and/or in addition to this, the guide 6500 can be configured so as to allow selective energizement and/or deenergizement of the electrodes of the guide. While some embodiments permit such as part of the handheld guide, in some alternate embodiments, the guide is configured to be placed into communication with a control unit. For example, as seen in FIG. 62, guide 6500 can be equipped with a connector 6320 in signal communication with the voltage/current generator 6520. The connector can be connected to a connector 6207 that is connected to a control unit 6650, which can be a personal computer or the like. In an exemplary embodiment, the control unit 6650 can control the output of the current generator 6520 with respect to the current, the voltage, and which electrodes are operated as the source. Note further that in some exemplary embodiments, the voltage/current generator 6520 is not part of the guide 6500, but instead is part of the control unit 6650. Indeed, in such an exemplary embodiment, there can be separate leads from each electrode that extend to the connector 6320. It is noted that the electrode can be also located on the outside of the cochlea in some other embodiments, consistent with the teachings detailed above.

It is noted that in an exemplary embodiment, the control unit 6650 is the implant itself. In an exemplary embodiment, it is the receiver-stimulator unit of a cochlear implant, alone in some embodiments, or when placed into inductance communication with an external component or a component that replicates the functionality of the external component, etc. It is noted that the electrodes can be used as read electrodes, consistent with the teachings detailed herein, and thus the electrodes can be used as reference electrodes when the lead connects to the implant (e.g., can or hard ball).

By way of example only and not by way of limitation, a lead from the guide, such as the lead leading from connector 6207, could clip onto the existing extra cochlear electrode (sometimes referred to as the hardball) of the implant, allowing the implant to look for open circuits, measure voltages, etc., through the electrode on the guide. In this regard, in an exemplary embodiment, the electrodes of the insertion guide can become an extension of the extra cochlear electrode. Accordingly, an embodiment exists where any functionality of the cochlear implant that relies on the extra cochlear electrode can thus also rely on the electrodes of the insertion guide to achieve such functionality. Corollary to this is that in an exemplary embodiment, any of the functions detailed herein that utilize the electrodes of the insertion guide can be executed by the implants in at least some exemplary embodiments when the implant is in signal communication with the implant, or at least when the insertion guide is connected to the extra cochlear electrode of the electrode array.

Still, in at least some exemplary embodiments, the guide 6500 can be configured so that the surgeon or the like can toggle from one electrode to another. For example, the guide can be provided with a switch or a button that the surgeon depresses to selectively energize a given electrode. The electrodes can be energized in sequence by repeatedly pressing the button. In an exemplary embodiment, an indicator on the guide can be provided so as to convey information to the surgeon as to which electrode is being operated as the source. By way of example only and not by way of limitation, an array of LEDs can be arrayed about the insertion stop 204. As a given electrode is energized, the LEDs can light. The LED at the 9 o'clock position could indicate that the closest electrode to the stop has been energized (e.g., electrode 6307). The LED at the 3 o'clock position (when viewing the stop 204 from the surgeon point of view) could indicate that the furthest electrode to the stop has been energized (e.g., electrode 6302). The electrodes in between can correspond to LEDs in between the 9 o'clock position in the 3 o'clock position. Alternatively, LEDs having different colors can be utilized to indicate to the surgeon which electrode is being utilized as a source. The LEDs can be utilized according the teachings detailed herein to disclose, for example, the indicator of an anomalous electrode position. Such is also the case with respect to LCDs or the like when so utilized.

Figure 63:
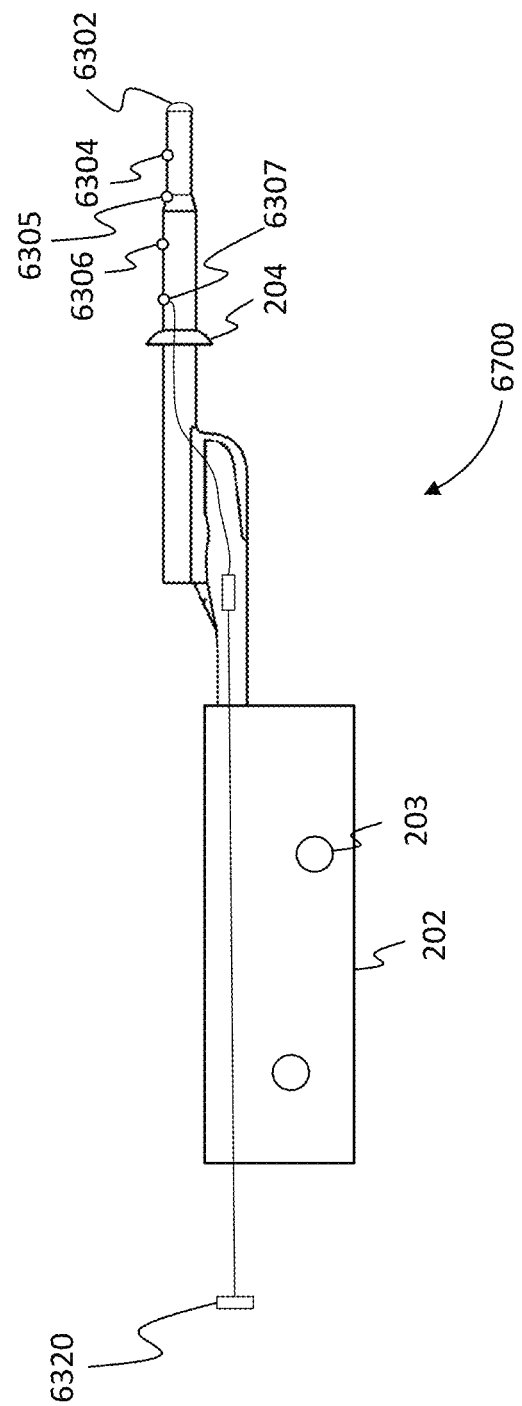

FIG. 63 depicts an alternate embodiment of the electrode array insertion guide, insertion guide 6700, that is utilized as a sink and/or read electrode. Here, a lead extends from electrode 6307 to a connector 6320. Other leads also extend in a similar manner, but are not shown. In an exemplary embodiment, connector 6320 can be hooked up to or otherwise connected to a unit that will receive the signal from the electrodes when used as a sink and/or a read electrode By way of example only and not by way of limitation, in an exemplary embodiment, a test unit can be a personal computer in signal communication with connector 6320. The personal computer can analyze the output from connector 6320 indicative of the current/voltage at electrode 6307 or any other electrode of the electrode array insertion guide. That said, in an exemplary embodiment, the guide 6700 can be placed into signal communication with the receiver/stimulator of the cochlear implant, and the cochlear implant can be configured to utilize the electrodes of the insertion guide as the reference electrodes and/or stimulation electrodes. That is, this is also that this is the case with respect to embodiments where the electrodes of the electrode array insertion guide are utilized as the source. That is, connector 6320 can allow the insertion guide to be placed into signal communication with the receiver/stimulator of the cochlear implant, and the cochlear implant can be configured to utilize the electrodes of the insertion guide as the source electrode.

Note also that in an exemplary embodiment, whether the guide is utilized as a source or a sink for the current, and/or the read electrode(s) the insertion guide 6700 can be configured to be placed into signal communication with any ancillary equipment utilized in the teachings of the '255 application so as to implement the teachings thereof where the electrodes of the insertion guide are the source or the sink.

Any arrangement of the insertion guide that can enable electrodes thereof to operate as a source or a sink instead of utilizing the electrodes of the electrode array as the respective source or a sink when implementing the teachings of the '255 patent application can be utilized in at least some exemplary embodiments. Thus, in an exemplary embodiment, the guide is configured to interface with any of the components detailed in the '255 patent application to enable such.

Figure 64:
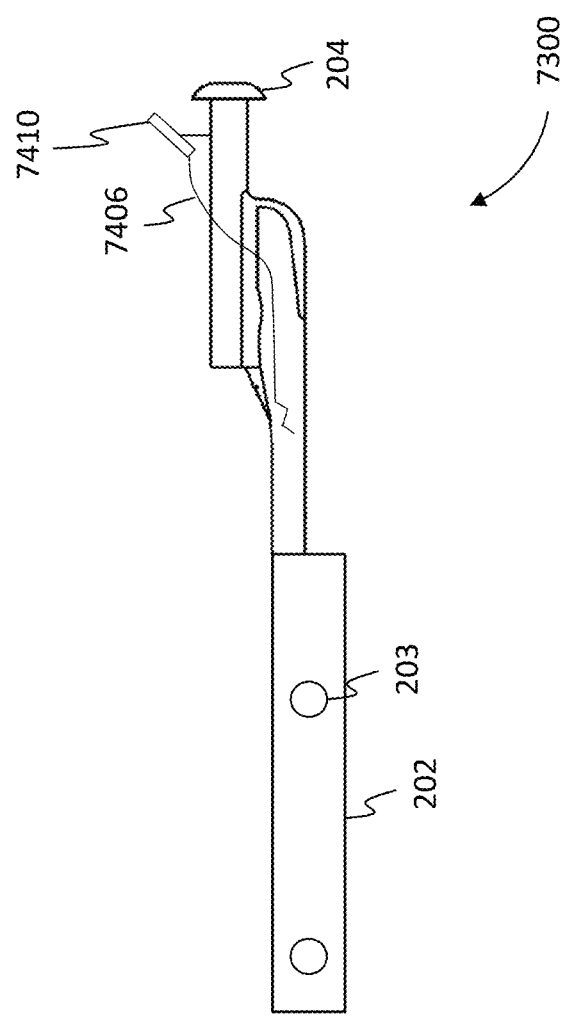

As noted above, the insertion guide can incorporate visual indicators to provide intraoperative feedback to the surgeon. As detailed above, exemplary embodiments have LEDs or the like arrayed about the stop. Still further, in an exemplary embodiment, a liquid crystal display or the like can be incorporated in or on the insertion guide. In this regard, FIG. 64 depicts an exemplary embodiment of an insertion guide 7300 which includes LCD 7410 mounted on the insertion guide tube. LCD 7410 is in electrical communication with other components of the guide and/or other systems remote from the guide via electrical lead 7406. In an exemplary embodiment, the LCD can provide text and/or numerical data to the surgeon during implantation/insertion of the electrode array. The LCD or the other visual indicators can be located anywhere on the guide that will be within the surgeon's immediate field-of-view, but also where the indicator will not obstruct the surgeon's field-of-view of the pertinent portions of the anatomy of the recipient and/or the pertinent portions of the guide 7300 during insertion of the electrode array. In an exemplary embodiment, the indicators provide information pertaining to insertion depth, which can include the absolute depth and/or an indication that the electrode array has reached the intended or programmed stopped depth. Indication can be an insertion speed, which can be absolute speed of insertion or can be an indication that the insertion speed limit has been exceeded. The indication can be an adverse measurement indication. This measurement can be a general indication, such as an indicator that something has gone wrong whatever that is, or specific indication, such as an indication explicitly relating to tip fold over, basilar membrane contact, scala dislocation, etc. Accordingly, in an exemplary embodiment, such indication can correspond to any of the anomalous electrode position indicators detailed herein.

Figure 65:
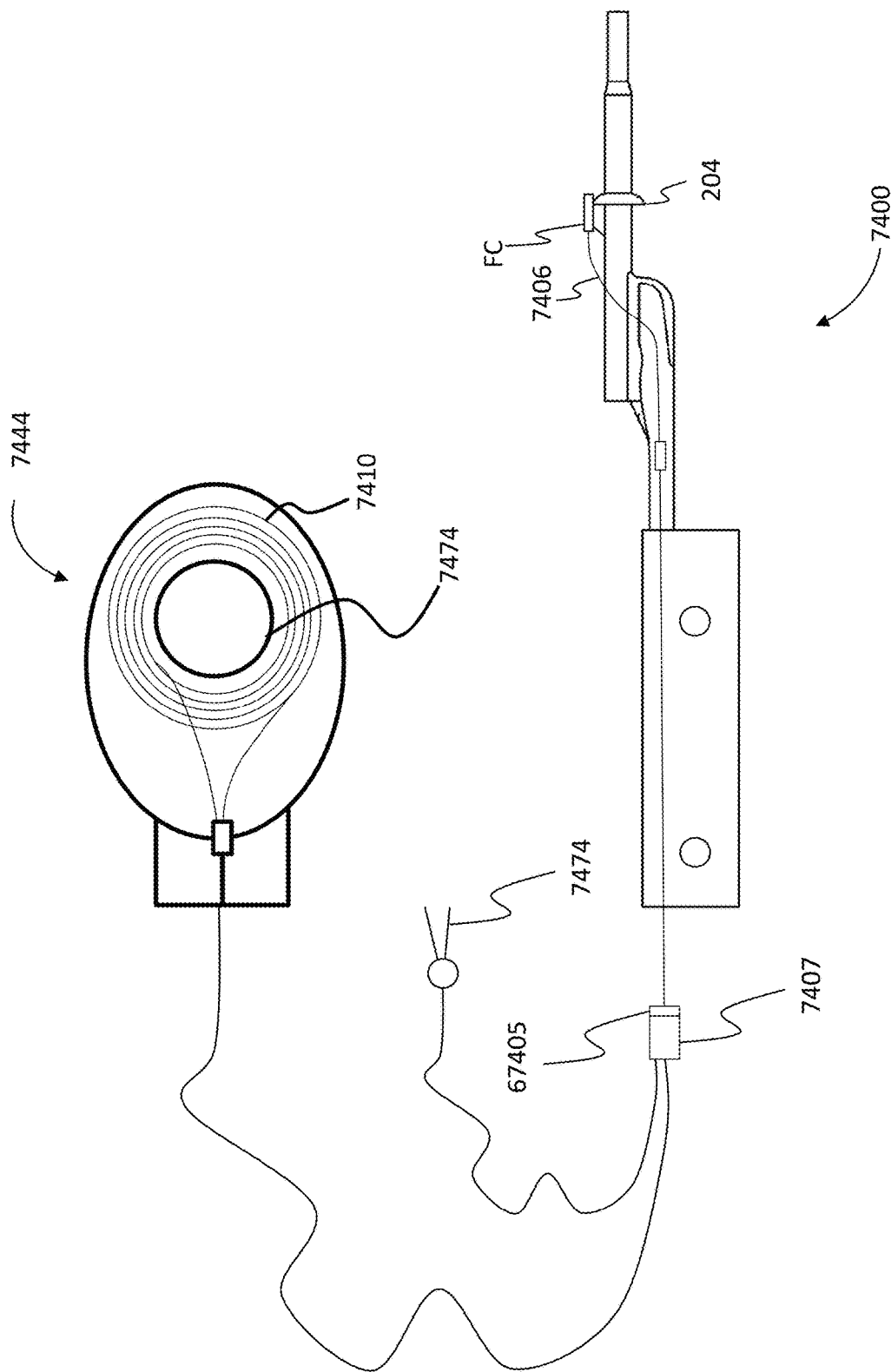

As noted above, embodiments include an insertion guide configured to communicate with a receiver/stimulator of a cochlear implant. In this regard, FIG. 65 depicts an exemplary insertion guide 7400 which is presented by way of concept. Insertion guide 7400 is a functional component FC mounted thereon. This functional component is representative of any of the additional functionalities of the insertion guide detailed herein and/or variations thereof. For example, element FC could be an electrode, it could be the acoustic stimulation generator, or it could be the ultrasonic transducer. FC could also be any of the indicators detailed herein (e.g., the LCD screen). As can be seen, insertion guide 7400 includes connector 64705 in electrical communication with the functional component FC via electrical lead 746. Connector 64705 is connected to connector 7407 of inductance coil 7444. In an exemplary embodiment, inductance coil 7444 includes coil 7410 configured to establish a magnetic inductance field so as to communicate with the corresponding coil of the receiver-stimulator of the cochlear implant. Inductance coil 7444 includes a magnet 7474 so as to hold the inductance coil 7474 against the coil of the receiver/stimulator of the cochlear implant in a manner analogous to how the external component of the cochlear implant is held against the implanted component, and how the coils of those respective components are aligned with one another. While the embodiment depicted in FIG. 65 depicts no other functional component between the functional component FC and the inductance coil 7444, in an alternate embodiment, one or more of the units detailed herein can be located there between. By way of example, generator 6520 with respect to the insertion guide 6500 detailed above can be located therebetween or otherwise be in signal communication with the leads so as to establish communication with that element with the cochlear implant. In an exemplary embodiment, a communications unit or the like is located between or otherwise is in signal communication with the leads so as to establish communication with the cochlear implant receiver-stimulator. In an exemplary embodiment, the insertion guide includes logic or a processor or other type of control unit that enables the insertion guide to work in conjunction with the cochlear implant so as to execute any of the methods detailed herein, such as, for example, where one or more electrodes of the electrode array insertion guide are utilized in a state of one or more electrodes of the electrode array as taught in those applications.

FIG. 65 also shows second lead from connector 7407 extending to alligator clip 7474, which in an exemplary embodiment, configured to clip onto the hard ball and/or the can of the implant, in which clip is in electrical communication with one or more electrodes on the electrode array that would be inside and/or outside of the cochlea during insertion. Indeed, it is also noted that in an exemplary embodiment, the entire portion that is inserted into the cochlea of the insertion guide can be the electrode, and thus be in electrical communication with the alligator clip 7474.

Figure 66:
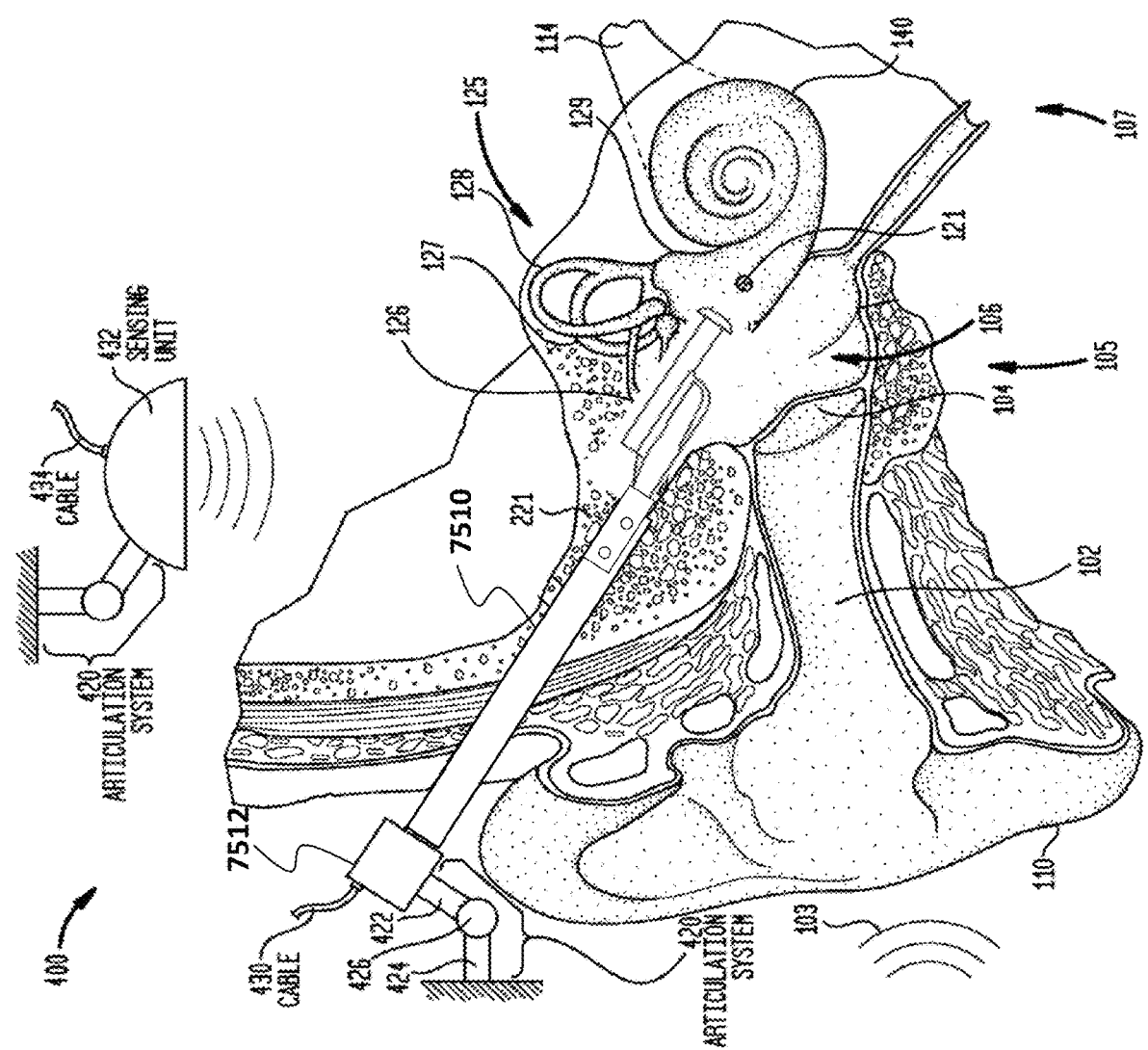

It is noted that at least some exemplary embodiments include utilization of the insertion guides detailed herein and/or variations thereof with a robotic electrode array insertion system. In this regard, FIG. 66 is a perspective view of an exemplary embodiment of an insertion system 400. It is noted that the embodiment depicted in FIG. 66 is presented for conceptual purposes only. Features are provided typically in the singular show as to demonstrate the concept associated therewith. However, it is noted that in some exemplary embodiments, some of these features are duplicated, triplicated, quadplicated, etc. so as to enable the teachings detailed herein and/or variations thereof. Briefly, it is noted that any teaching detailed herein can be combined with a robotic apparatus and/or a robotic system according to the teachings detailed herein and/or variations thereof. In this regard, any method action detailed herein corresponds to a disclosure of a method action executed by a robotic apparatus and/or utilizing a robot to execute that action and/or executing that method action is part of a method where other actions are executed by robot and/or a robotic system etc. Still further, it is noted that any apparatus detailed herein can be utilized in conjunction with a robotic apparatus and/or a robot and/or a system utilizing such. Accordingly, any disclosure herein of an apparatus corresponds to a disclosure of an apparatus that is part of a robotic apparatus and or a robotic system etc. and or a system that includes a robotic apparatus etc.

System 400 includes a robotic insertion apparatus including arm 7510 to which insertion guide 200 or any other insertion guide according to the teachings detailed herein and/or variations thereof is attached (e.g., bolted to arm 7510). In this exemplary embodiment, arm 7510 is depicted as a single structure extending from the insertion guide to mount 7512. However, in an alternate embodiment, arm 7510 can be a multifaceted component which is configured to articulate at various locations thereabout.

In an exemplary embodiment, arm 7510 is releasably connected by way of a releasable connection to mount 7512, which is supported by a support and movement system 420, comprising support arm 422 which is connected to joint 426 which in turn is connected to support arm 424. Support arm 424 is rigidly mounted to a wall, a floor, or some other relatively stationary surface. That said, in an alternative embodiment, support arm 424 is mounted to a frame that is attached to the head of the recipient or otherwise connected to the head of the recipient such that global movement of the head will result in no relative movement of the system 400 in general, and the insertion guide in particular, relative to the cochlea. Joint 426 permits arm 2510, and thus the insertion guide, to be moved in one, two, three, four, five, or six degrees of freedom. (It is noted again that FIG. 66 is but a conceptual FIG.—there can be joints located along the length of arm 7510, so as to enable arm 75102 articulate in the one or more aforementioned degrees of freedom at those locations. In an exemplary embodiment, joint 426 includes actuators that move mount 7512, and thus the insertion guide, in an automated manner, as will be described below. In an exemplary embodiment, the system is configured to be remotely controlled via communication with a remote control unit via communication lines of cable 430. In an exemplary embodiment, the system is configured to be automatically controlled via a control unit that is part of the system 400. Additional details of this will be described below.

The system 400 further includes by way of example only and not by way of limitation, sensor/sensing unit 432. That said, in some embodiments, sensor 432 is not part of system 400. In some embodiments, it is a separate system. Still further, in some embodiments, it is not utilized at all with system 400. While sensor 432 is depicted as being co-located simultaneously with the insertion guide, etc., as detailed below, sensor 432 may be used relatively much prior to use of the insertion guide. Sensing unit 432 is configured to scan the head of a recipient and obtain data indicative of spatial locations of internal organs (e.g., mastoid bone 221, middle ear cavity 423 and/or ossicles 106, etc.) In an exemplary embodiment, sensing unit 432 is a unit that is also configured to obtain data indicative of spatial locations of at least some components of the insertion guide and/or other components of the robotic apparatus attached thereto. The obtained data may be communicated to remote control unit 440 via communication lines of cable 434. As may be seen, sensor 432 is mounted to a support and movement system 420 that may be similar to or the same as that used by the robotic apparatus supporting the insertion guide.

Figure 67:
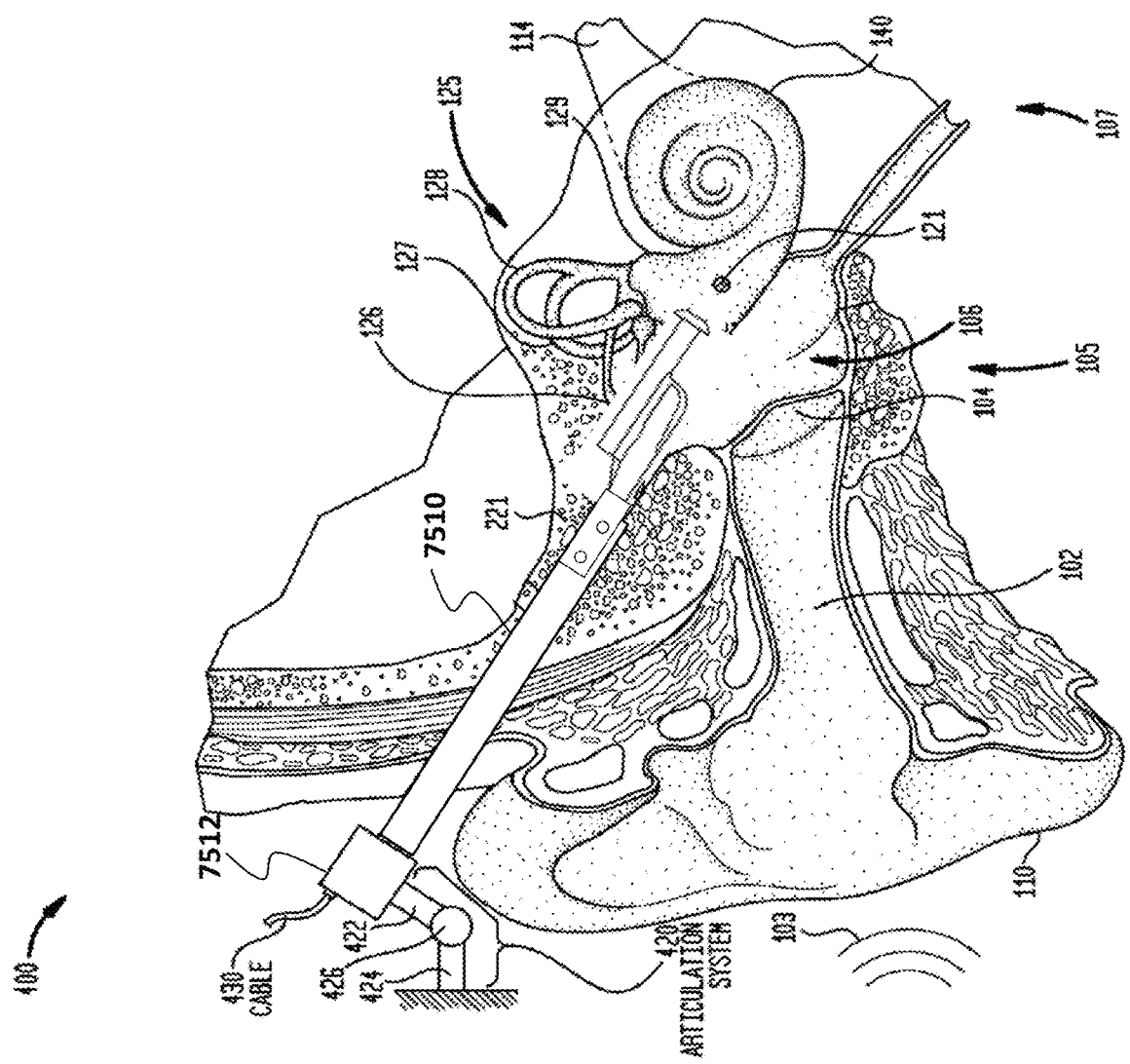

In an exemplary embodiment, sensing unit 432 is an MRI system, an X-Ray system, an ultrasound system, a CAT scan system, or any other system which will permit the data indicative of the spatial locations to be determined as detailed herein and/or variations thereof. As will be described below, this data may be obtained prior to surgery and/or during surgery. It is noted that in some embodiments, at least some portions of the insertion guide are configured to be better imaged or otherwise detected by sensing unit 432. In an exemplary embodiment, the tip of the insertion guide includes radio-opaque contrast material. The stop of the insertion guide can also include such radio-opaque contrast material. In an exemplary embodiment, at least some portions of insertion guide in general, and the robotic system in particular, or at least the arm 7510, mount 7512, arm 422, etc., are made of non-ferromagnetic material or other materials that are more compatible with an MRI system or another sensing unit utilized with the embodiment of FIG. 66 than ferromagnetic material or the like. As will be described in greater detail below, the data obtained by sensing unit 432 is used to construct a 3D or 4D model of the recipient's head and/or specific organs of the recipient's head (e.g., temporal bone) and/or portions of the robotic apparatus of which the insertion guide is a part. That said, to be clear, in some embodiments, sensing unit 432 is not present, as seen in FIG. 67.

It is also noted that in some exemplary embodiments of system 400, there are actuators or the like that drive the electrode array through the insertion guide into the cochlea. These actuators can be in signal communication with the control unit. In an exemplary embodiment, the control unit can control the actuators to push the electrode array into and/or out of the cochlea as will be described in greater detail below. Concomitant with the robotic assembly supporting the insertion guide, in an exemplary embodiment, the control unit is configured to automatically control these actuators.

Figure 68:
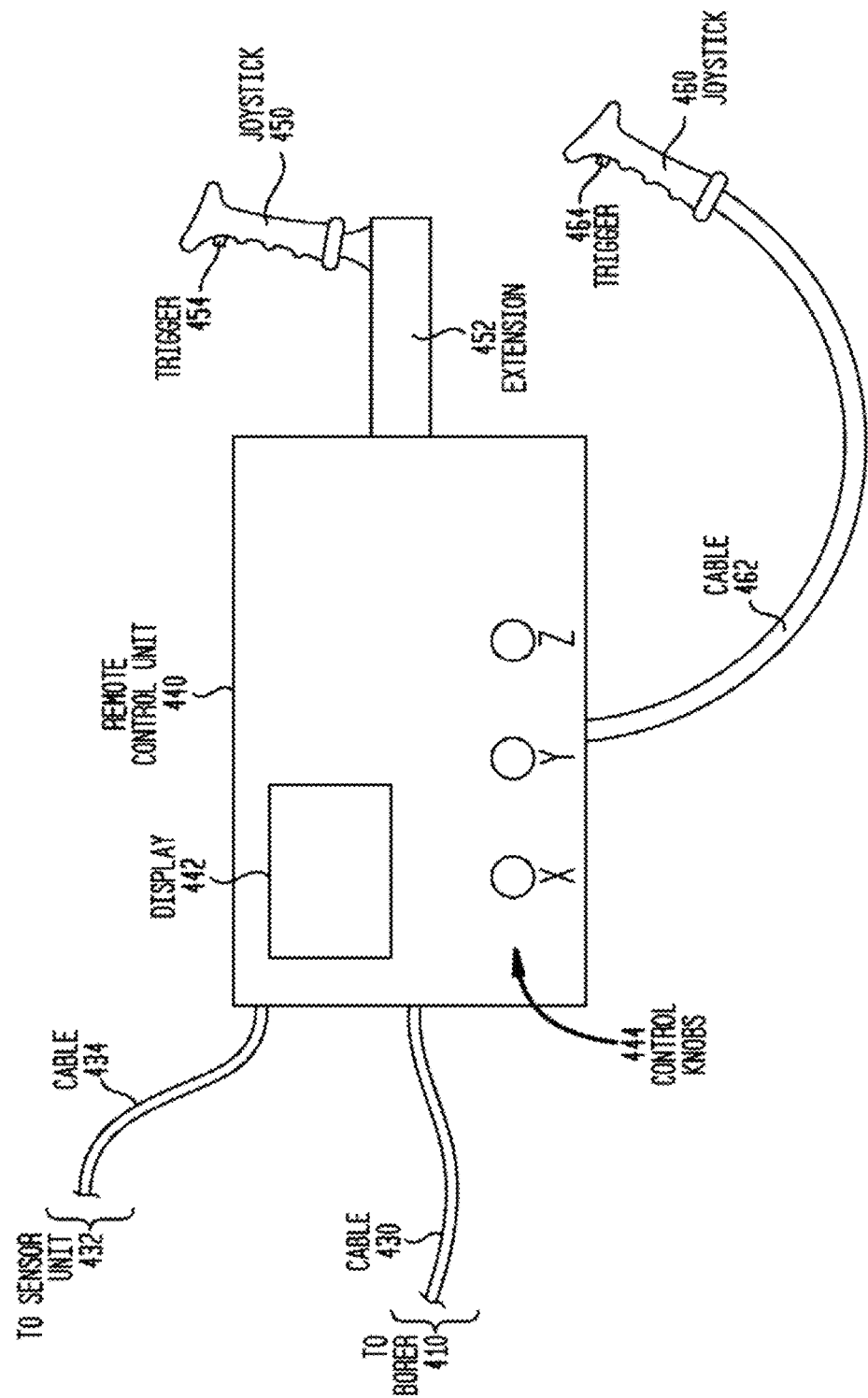

FIG. 68 is a simplified block diagram of an exemplary embodiment of a remote control unit 440 for controlling the robotic apparatus supporting the insertion guide and sensing unit 432 via communication lines 430 and 434, respectively. Again, it is noted that in some alternate embodiments, the remote control unit 440 is an entirely automated unit. That said, in some alternate embodiments, the remote control unit can be operated automatically as well as manually, which details will be described below.

Remote control unit 440 includes a display 442 that displays a virtual image of the mastoid bone obtained from sensor 432 and may superimpose a virtual image of the insertion apparatus onto the virtual image indicative of a current position of the drill bit relative to the ear anatomy. An operator (e.g., surgeon, certified healthcare provider, etc) utilizes remote control unit 440 to control some or all aspects of the robotic apparatus and/or sensing unit 432. Exemplary control may include depth of insertion guide insertion, angle of guide insertion, speed of advancement and/or retraction of electrode array, etc. Such control may be exercised via joystick 450 mounted on extension 452 which fixedly mounts joystick 450 to a control unit housing. Such control may be further exercised via joystick 460 which is not rigidly connected to housing of remote control unit 440. Instead, it is freely movable relative thereto and is in communication with the remote control unit via communication lines of cable 462. Joystick 462 may be part of a virtual system in which the remote control unit 440 extrapolates control commands based on how the joystick 462 is moved in space, or joystick may be a device that permits the operator more limited control over the cavity borer 410. Such control may include, for example an emergency stop upon release of trigger 464 and/or directing the robot to drive the insertion guide further into the cochlea by squeezing the trigger 464 (which, in some embodiments, may control a speed at which the insertion guide is advanced by squeezing harder and/or more on the trigger). In the same vein, trigger 454 of joystick 450 may have similar and/or the same functionality.

Control of the robot assembly supporting the insertion guide may also be exercised via knobs 440 which may be used to adjust an angle of the insertion guide in the X, Y and Z axis, respectively. Other controls components may be included in remote control 440.

FIG. 68 depicts an exemplary insertion guide which can correspond to any of the insertion guide detailed herein and/or variations thereof, or any other insertion guide for that matter, further including an electrode array insertion actuator 7720. In an exemplary embodiment, actuator assembly 7720 includes a passageway therethrough through which the electrode array extends. The actuator assembly drives the electrode array in a manner replicating that by which the surgeon pushes the electrode array forward along the insertion guide and into the insertion tube and thus into the cochlea.

Figure 69:
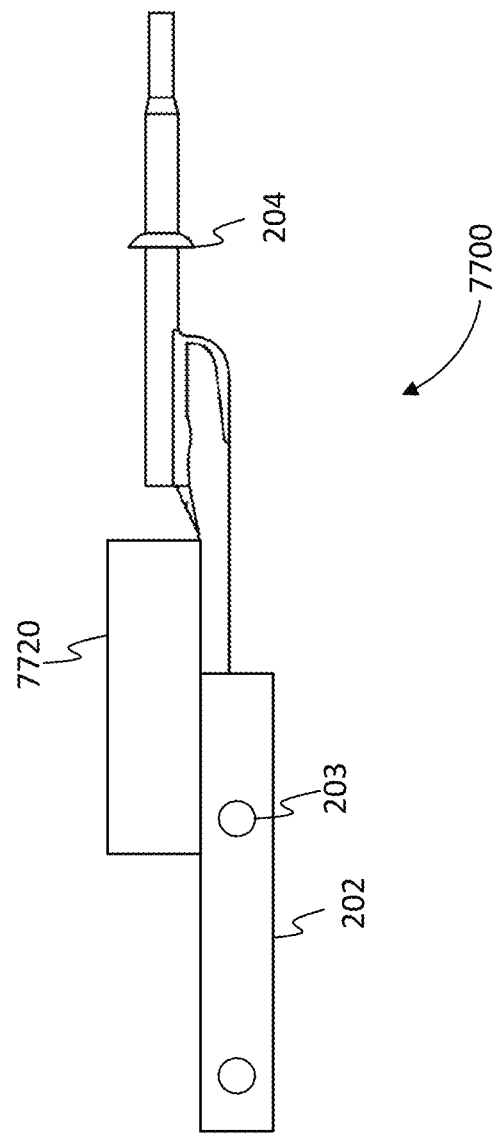
Figure 70:
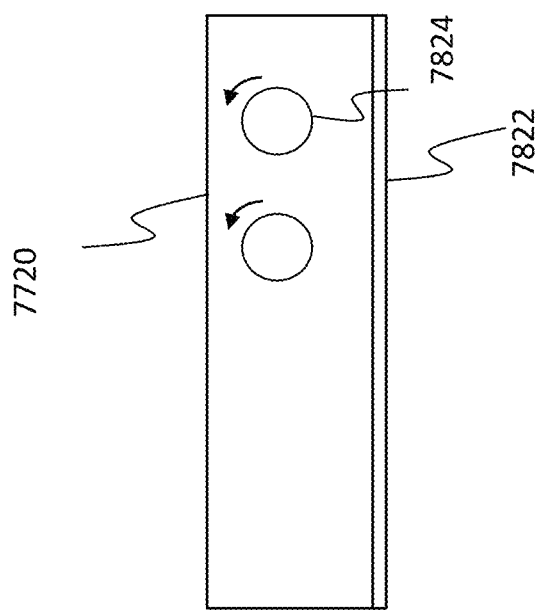

FIG. 69 depicts an exemplary embodiment of the actuator assembly 7720. As can be seen, actuator assembly includes two actuators 7824 in the form of wheels mounted to electric motors that rotate the wheels in a counterclockwise direction so as to advance the electrode array, and in a clockwise direction so as to retract the electrode array. Actuator assembly 7720 further includes a floor 7822. The floor 7822 works in combination with the actuators 7824 so as to "trap" the electrode array there between with a sufficiently compressive force so that the friction forces between the actuators 7824 and the electrode array enable the actuators 7824 to drive the electrode array forward and/or backwards, but not enough so as to damage the electrode array. FIG. 70 depicts an exemplary movement of the wheels 7824.

Figure 71:
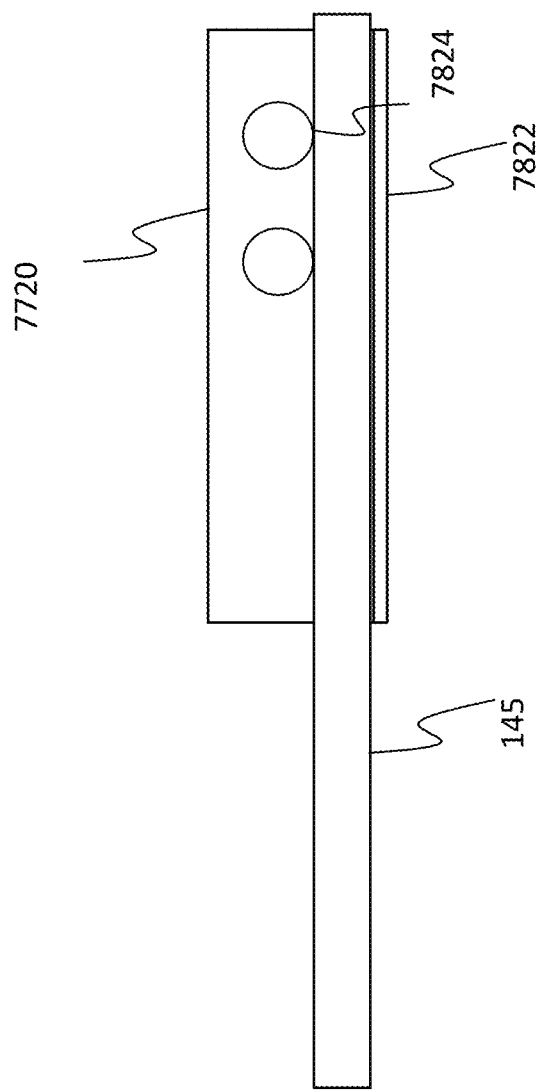
Figure 72:
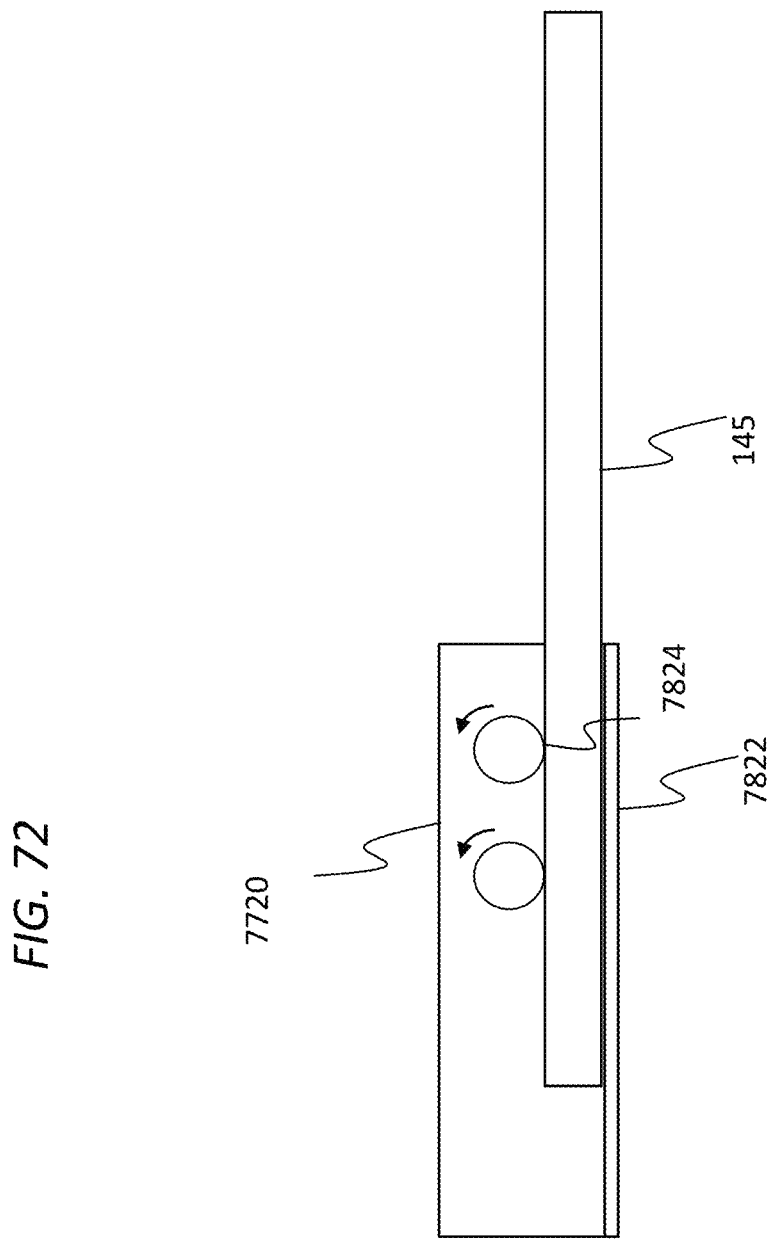
Figure 73:
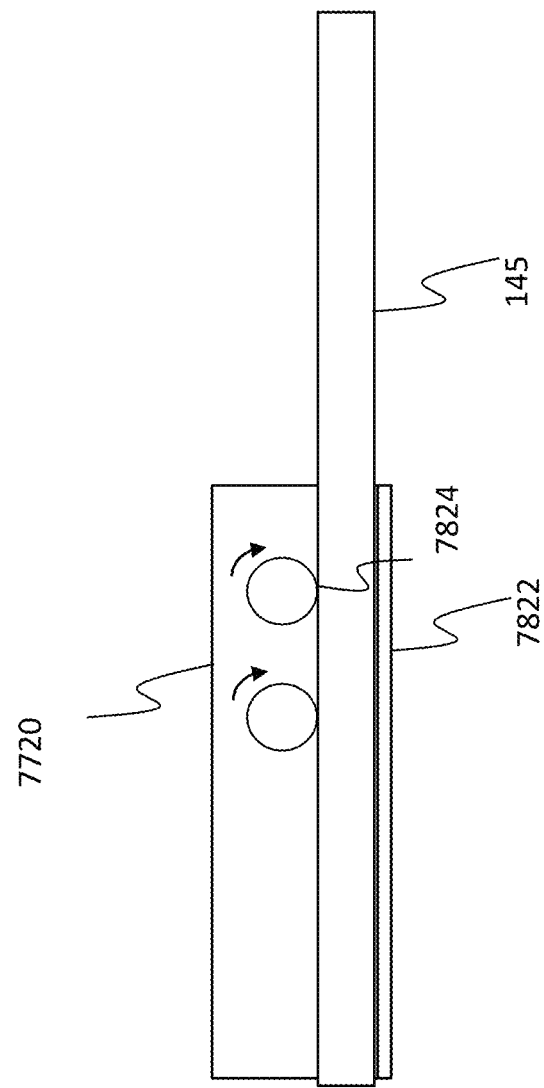

FIG. 71 functionally depicts an electrode array 145 "loaded" in actuator assembly 7720 prior to driving the electrode array into the insertion sheath. FIG. 72 functionally depicts the electrode array being driven forward (FIG. 72 is depicted in a functional manner—in reality, the electrode array 145 would extend up the ramp and then into the insertion sheath), and FIG. 73 functionally depicts the electrode array being retracted from the position seen in FIG. 72.

While the embodiment of the actuator assembly depicted in FIG. 71 includes two top actuators, in an alternate embodiment, only one top actuator is utilized and/or in another embodiment, three or four or five or six or more actuators are utilized. Also, in an exemplary embodiment, one or more bottom actuators can also be utilized. Note also that instead of the actuators being located on the top and the floor 7822 being on the bottom, the actuators can be located on the bottom and the floor can be located on the top.

It is noted that while the embodiment of FIG. 71 is depicted utilizing actuators having round wheels, in an alternate embodiment, other types of working and of the actuators can be utilized To be clear, the embodiment of FIG. 68 depicted above can also include the actuator assembly's detailed herein and/or variations thereof. That is, insertion guide 7700 can be attached to the arm 7510 of the system 400. Moreover, the actuators of the actuator assembly can be placed into signal communication with the control unit 440 or any other control unit of the system 400 to enable the control unit to advance and/or retract the electrode array. Note also that in some alternate embodiments, the system 400 is such that the only non-manually actuating component is the actuator assembly. That is, in an exemplary embodiment, system 400 can be such that the frame of the like is placed around the recipient's head and secured thereto, and the arm 7510 supporting the insertion guide attached thereto can be moved manually by the surgeon, such that the surgeon can align or otherwise place the insertion guide into the cochlea. In this regard, by way of example only and not by way of limitation, the insertion guide can be configured so as to attached to the arm 7510 on a trolley or the like. In an exemplary embodiment, the surgeon moves arm 7510 into position so that the insertion guide is aligned with the cochlea, at the desired angle, etc., and then be surgeon manually pushes the insertion guide forward into the cochlea (in the case of an intra-cochlear insertion guide) or against the cochlea in the case of a non-intra-cochlea insertion guide). After that, the actuator assembly can be utilized in a remote-controlled and/or automated manner.

That said, in an alternate embodiment, the general positions of the system 400 can be established utilizing manual methods, and then the positions can be refined utilizing automated/remote controlled methods (e.g., the actuators on the arm 7510 and/or the actuator at joint 426 can be actuated so as to finally position the insertion guide.

Figure 74:
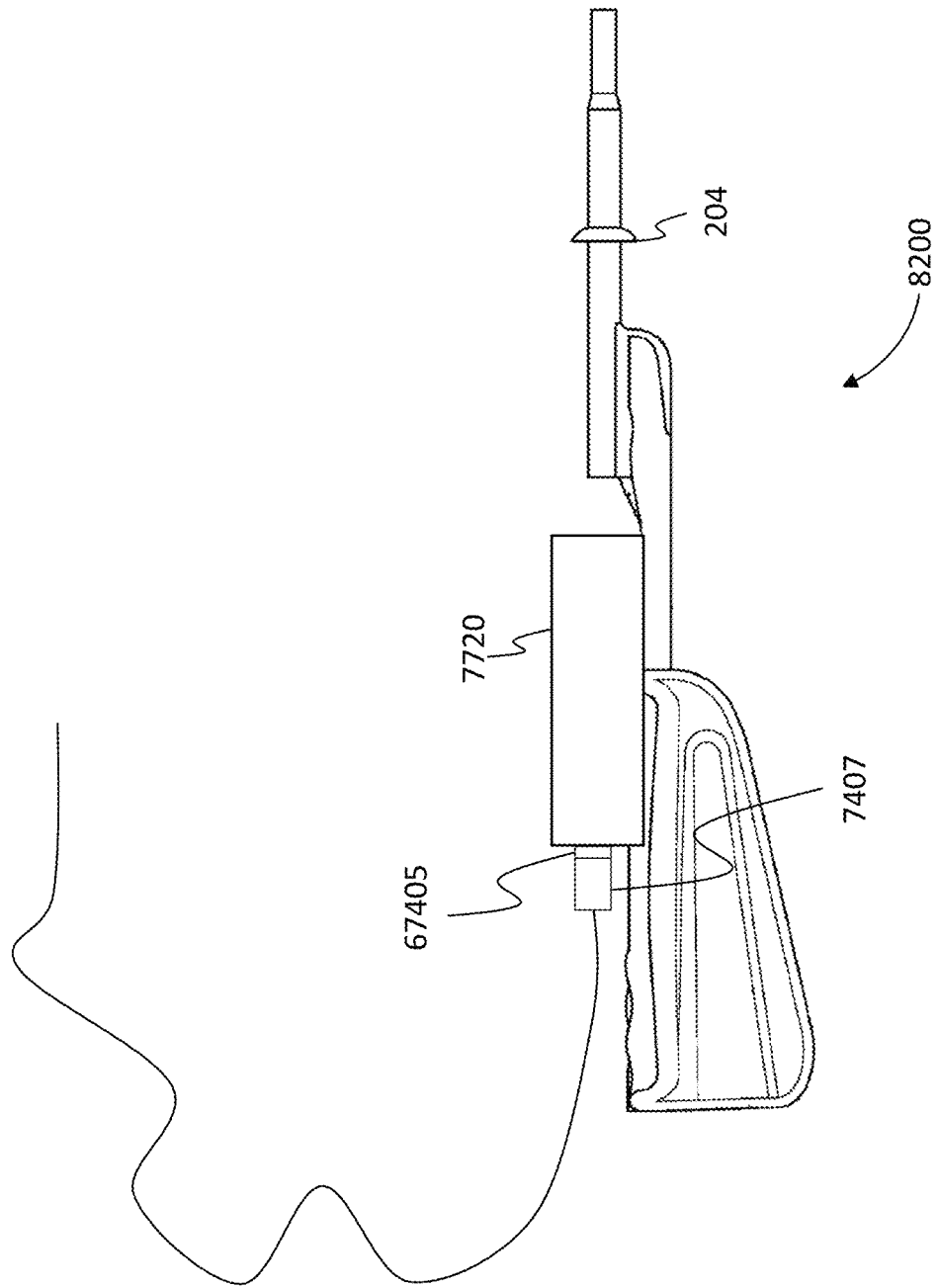

Note also that in some exemplary embodiments, the actuator assembly's detailed herein and/or variations thereof that are utilized to advance and/or retract the electrode array are configured to be utilized with an insertion tool that is handheld instead of being attached to arm 750 system 400. To this end, FIG. 74 depicts an exemplary insertion tool 8200 that includes actuator apparatus 7720 as seen. Hereinafter, the reference will often be made to actuator apparatus 7720 as utilized in conjunction with other components detailed herein. Any disclosure herein of the utilization of actuator apparatus 7720 in conjunction with other teachings detailed herein corresponds to a disclosure of the utilization of the actuator apparatus 8123 or any of the other actuator apparatuses detailed herein or variations thereof utilized to grip and support and/or insert the electrode array into the cochlea. FIG. 74 depicts a connector 67405 in signal communication with an actuator apparatus 7720, which connector is connected to connector 7407, which in turn is connected to a lead which extends to the control unit. In an exemplary embodiment, the surgeon holds the tool 8200 in the traditional manner of use, but the control unit controls the actuation of the actuator 7720 to advance and/or retract the electrode array. In an exemplary embodiment, the surgeon or other healthcare professional can exercise override control over the insertion of the electrode array and/or the retraction of the electrode array. For example, switching components of the like or other types of input devices can be located on the tool 8200 so that the surgeon or the like can provide input into the system of which the tool 8200 is a part. In an alternate embodiment, the tool 8200 can include an input device that interacts with the surgeon, where the surgeon provides the direction to the system advance and/or retract the electrode array, but the control unit evaluates the inputs from the surgeon and controls the actuation accordingly. By way of example only and not by way of limitation, such a system can be analogous to a fly by wire system on an aircraft, where the pilot moves the controls in a manner correlated to the direction that the pilot wants the aircraft to move, and the flight control system controls everything else to achieve the desired outcome. Note also that any the other actuators detailed herein and/or variations thereof can be part of a system that is operated in a similar manner. By way of example only and not by way of limitation, the system 400 can be configured such that the surgeon pushes on the arm 7510 to move the insertion guide is desired, but the system 400 moves the arm 7510 using actuators. That is, the system 400 is configured to sense or otherwise detect the force is applied on to the structure thereof by the surgeon, and then determine what actuator action should be executed so as to position the insertion guide at the desired location in a manner analogous to fly by wire.

It is noted that the electrical lead assembly and the connectors thereof depicted in FIG. 74 can be applicable to any of the insertion guides detailed herein and/or variations thereof so as to place the insertion guide in general, and the actuator assembly thereof in particular, into signal communication with the control unit or other controllers of the system. Note also that in an exemplary embodiment, the lead apparatus depicted in FIG. 74 can be utilized to also convey the other signals detailed herein and/or variations thereof with respect to the other functionalities associated with the insertion guides. Alternatively, and/or in addition to this, the other lead apparatuses detailed herein and variations thereof can be utilized to convey the signals from the actuator apparatus 7720 to the control unit or the like when the insertion guides detailed above are utilized in conjunction with the actuator assembly so as to provide a machine drive to advance and/or retract the electrode array. Any device, system and/or method of communication between any functional component of any of the insertion guides detailed herein and/or variations thereof with a control unit and/or vice versa and/or the implantable component of the electrode array, etc., can be utilized in at least some exemplary embodiments It is also noted that while the embodiments detailed herein have been directed towards an electrode array guide, it is also noted that in some alternate embodiments, an electrode array support is instead utilized, which support may not necessarily guide the electrode array, but otherwise might simply support the electrode array proximate to the cochlea. Note that in an electrode array support can also be an electrode array guide, and vice versa.

In view of the above, it can be understood that in an exemplary embodiment, there is an apparatus, such as any of the insertion guides detailed herein and/or variations thereof, that includes an electrode array support, and an actuator. In at least some of these exemplary embodiments, the apparatus is configured to inserts an electrode array into cochlea by a controlled actuation of the actuator. In an exemplary embodiment of such an exemplary embodiment, the controlled actuation is at least partially based on electrical phenomenon of the recipient. Some additional details of such will now be described.

Figure 75:
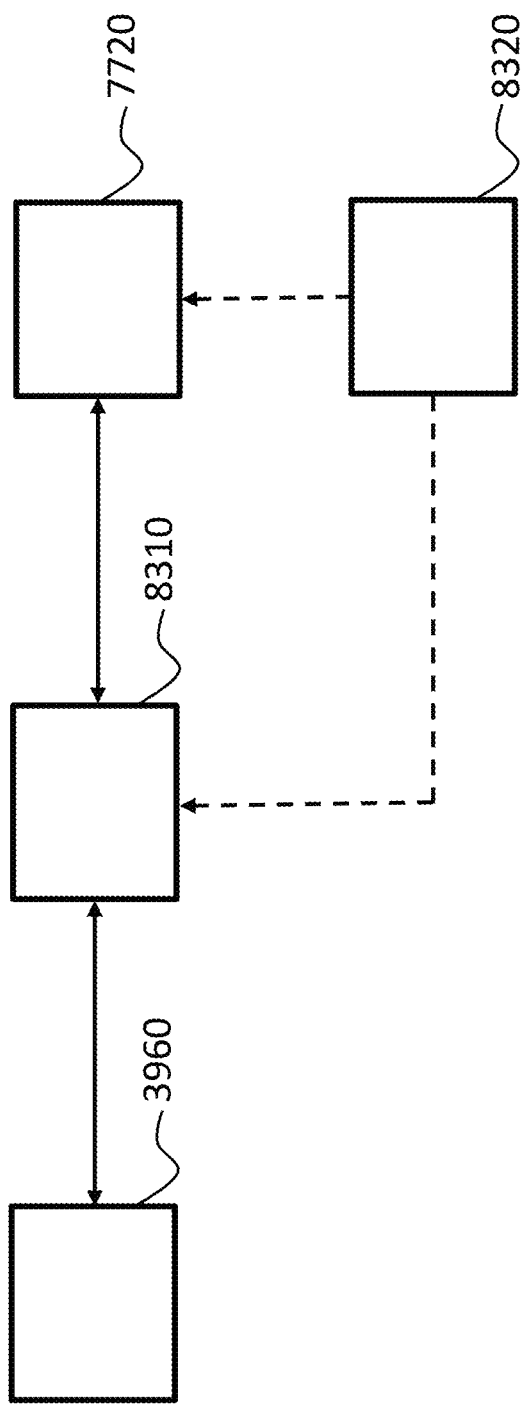

FIG. 75 depicts an exemplary functional schematic of an exemplary system that includes the test unit 3960 detailed above in signal communication with a control unit 8310 which is in turn in signal communication with the actuator assembly 7720. The test unit and the control unit can be one and the same in some embodiments.

It is also noted that in some embodiments, the there is no control unit and/or there is no actuator assembly. That is, the system can be a purely test system, which conveys information to the surgeon or other healthcare professional to instruct (e.g., the output of the control unit and/or the test unit can be instead an instruction as opposed to a control signal) or otherwise provide an indication of the phenomenon to the surgeon or other healthcare professional.

Also functionally depicted in FIG. 75 is the optional embodiment where an input device 8320 is included in the system (e.g., which could be on an embodiment where the actuator assembly 7720 is part of a hand tool or where actuator assembly 7720 is part of an insertion guide, where the input device 8320 is located remote from the insertion guide, which could be part of a remote unit 440). In an exemplary embodiment, the input device 8320 could be the trigger for 54 and/or 464 of the remote control unit 440. In an exemplary embodiment, the input device 8320 could be a trigger on the tool 8200. Again, in an exemplary embodiment, the input device 8320 can be utilized to enable advancement and/or withdrawal of the electrode array, and the system 400 could control the advancement and/or withdrawal based on an automated protocol or some other flyby wire type system. In the embodiment of FIG. 75, the input device 8320 can be in signal communication directly to the actuator assembly 7720, and/or in signal communication with the control unit 8310.

In an exemplary embodiment, control unit 8310 can correspond to the remote unit 440. That said, in an alternate embodiment, remote unit 440 can be a device that is in signal communication with control unit 8310. Indeed, in an exemplary embodiment, input device 8320 can correspond to remote control unit 440.

More particularly, control unit 8310 can be a signal processor or the like or a personal computer or the like or a mainframe computer or the like etc., that is configured to receive signals from the test unit 3960 and analyze those signals to evaluate an insertion status of the electrode array. More particularly, the control unit 8310 can be configured with software the like to analyze the signals from test unit 3960 in real time and/or in near real time as the electrode array is being advanced into the cochlea by actuator assembly 7720. The control unit 8310 analyzes the input from test unit 3960 as the electrode array advanced by the actuator assembly 7720 and evaluates the input to determine if there exists an undesirable insertion status of the electrode array and/or evaluates the input to determine if the input indicates that a scenario could occur or otherwise there exists data in the input that indicates that a scenario is more likely to occur relative to other instances where the insertion status of the electrode array will become undesirable if the electrode array is continued to be advanced into the cochlea, all other things remaining the same (e.g., insertion angle/trajectory, etc., which can be automatically changed as well via—more on this below). In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). In at least some exemplary embodiments, control unit 8310 can be configured to override the input from input unit 8320 input by the surgeon or the user or the like of the systems herein.

In an exemplary embodiment, the outputs of test unit 3960 corresponds to the outputs indicated herein. Alternatively and/or in addition to this, input into control unit 8310 can flow from other sources. Any input relating to the measurement of voltage associated executing the teachings herein into control unit 8310 can be utilized in at least some exemplary embodiments.

In an exemplary embodiment, control unit 8310 can be configured to determine, based on the input from test unit 3960, whether the electrode array has come into contact with the basilar membrane of the cochlea and/or that one or more of the anomalous electrode positions has occurred and/or whether there exists an increased likelihood that such will occur, and automatically control the actuator assembly 7720 accordingly. In an exemplary embodiment, control unit 8310 does not necessarily determine that such an insertion status exists or is more likely to exist, but instead is programmed or otherwise configured so as to control the actuator assembly 7720 according to a predetermined regime based on the input from the test unit 3960. That is, the control unit 8310 need not necessarily "understand" otherwise "know" the actual insertion status or the forecasted insertion status of the electrode array, but instead need only be able to control the actuator assembly 7720 based on the input.

In an exemplary embodiment, control unit 8310 can be configured to determine, based on the input from test unit 3960, the insertion depth of the electrode array and/or a forecasted insertion depth of the electrode array, and automatically control the actuator assembly 7720 accordingly. In an exemplary embodiment, control unit 8310 does not necessarily determine the insertion depth or forecasted insertion depth, but instead is programmed or otherwise configured so as to control the actuator assembly 7720 according to a predetermined regime based on the input from the test unit 3960. That is, the control unit 8310 need not necessarily "understand" otherwise "know" the actual insertion depth or the forecasted insertion depth of the electrode array, but instead need only be able to control the actuator assembly 7720 based on the input.

In an exemplary embodiment, control unit 8310 can be configured to determine, based on the input from test unit 3960, executing, for example, the methods/techniques disclosed herein, whether the electrode array has buckled and/or bent and/or any other anomalous electrode location as disclosed herein or otherwise may be the case and/or whether there exists an increased likelihood that such will occur, and automatically control the actuator assembly 7720 accordingly. In an exemplary embodiment, control unit 8310 does not necessarily determine that such buckling and/or bending exists or is more likely to exist, but instead is programmed or otherwise configured so as to control the actuator assembly 7720 according to a predetermined regime based on the input from the test unit 3960. That is, the control unit 8310 need not necessarily "understand" otherwise "know" that the electrode array has actually buckled or will buckle in the future, but instead need only be able to control the actuator assembly 7720 based on the input.

Thus, it can be understood that there is an apparatus that is configured to receive input indicative of the electrical phenomenon/phenomena inside the recipient, and develop data indicative of a position of the electrode array within the cochlea based on the input. (It is briefly noted that unless otherwise specified, the singular term phenomenon also includes a disclosure of the plural thereof, and vis-a-versa, as is also the case with the disclosure of data). Still further, such an exemplary embodiment can be configured to adjust the control of the actuation of the actuator based on the develop data indicative of the position of the electrode array.

Figure 76:
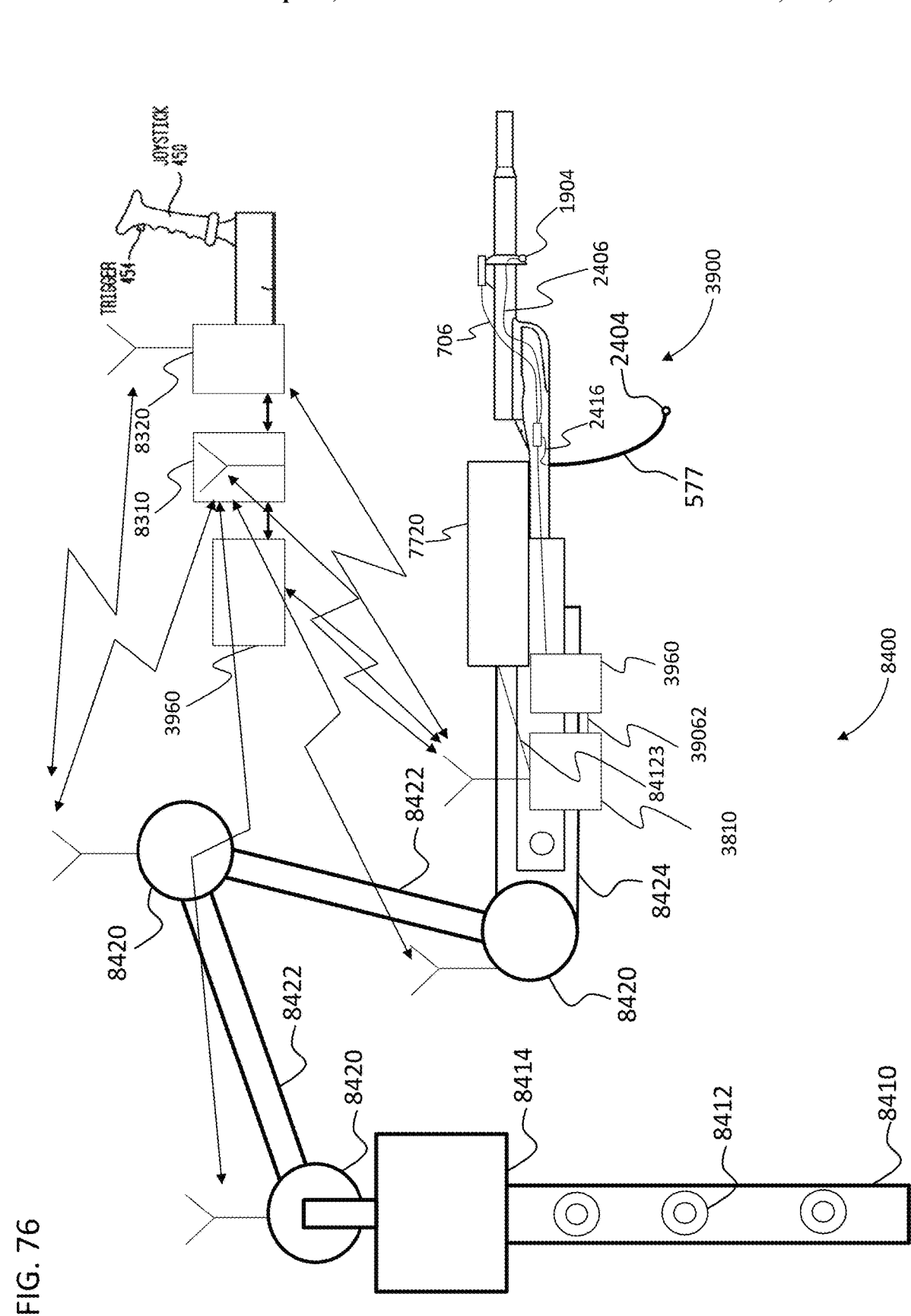

To be clear, while the embodiment detailed above is focused on controlling the actuator assembly 7720 based on data from the system so as to control the advancement and/or retraction of the electrode array based on the data disclosed herein and, in an alternate embodiment, the system 400 controls one or more other actuators of the robot apparatus of system 400. These one or more other actuators can be exclusive from the actuator assembly 7720, or can include the actuator assembly 7720. In this regard, FIG. 76 depicts an exemplary robot apparatus 8400, that includes the insertion guide 3900 detailed above with respect to the integration of a system ad disclosed herein therewith mounted on arm 8424 utilizing bolts in a manner concomitant with that detailed above. In an exemplary embodiment, robot apparatus 8400 has the functionality or otherwise corresponds to that of the embodiment of FIG. 68. In this regard, any functionality associated or otherwise described with respect to the embodiment of FIG. 68 corresponds to that of the embodiment of FIG. 76, and vice versa. In this exemplary embodiment, the actuator apparatus 7720 is in signal communication with unit 3810 via electrical lead 84123. In this regard, signals to and/or from the actuator assembly 7720 can be transmitted to/from the antenna of unit 8310 (in FIG. 84, the "Y" shaped elements are antennas) and thus communicated via lead 84123. It is briefly noted that while the embodiment depicted in FIG. 76 utilizes radiofrequency communication, in alternate embodiments, the communications can be wired. In an exemplary embodiment both can be utilized.

The robot apparatus 8400 includes a recipient interface 8410 which entails an arch or halo like structure made out of metal or the like that extends about the recipient's cranium or other parts of the body. The interface 8410 is bolted to the recipient's head via bolts 8412. That said, in alternate embodiments, other regimes of attachment can be utilized, such as by way of example only and not by way of limitation, strapping the robot to the recipient's head. In this regard, the body and interface 8410 can be a flexible strapping can be tightened about the recipient's head.

Housing 8414 is located on top of the interface 8410, as can be seen. In an exemplary embodiment, housing 8414 includes a battery or the like or otherwise provides an interface to a commercial/utility power supply so as to power the robot apparatus. Still further, in an exemplary embodiment, housing 8414 can include hydraulic components/connectors to the extent that the actuators herein utilize hydraulics as opposed to and/or in addition to electrical motors. Mounted on housing 8414 is the first actuator 8420, to which arm 8422 is connected in an exemplary embodiment, actuator 8420 enables the components "downstream" (i.e., the arm connected to the actuator, and the other components to the insertion guide) to articulate in one, two, three, four, five or six degrees of freedom. A second actuator 8420 is attached to the opposite end of the arm 8422, to which is attached a second arm 8422, to which is attached a third actuator 8420, to which is attached to the insertion guide attachment structure 8424. Elements 8422 and 8424 can be metal beams, such as I beams or C beams or box beams, etc. actuators 8420 can be electrical actuators and/or hydraulic actuators.

As can be seen, each actuator 8420 is provided with an antenna, which antenna is in signal communication with the control unit 8310. In an exemplary embodiment, control unit 8310 can control the actuation of those actuators 8420 so as to position the insertion guide 3900 at the desired position relative to the recipient. That said, in an alternate embodiment, a single antenna can be utilized, such as one mounted on housing 8414, which in turn is connected to a decoding device that outputs a control signal, such as a driver signal based on the decoded RF signal, to the actuators 8420 (as opposed to each actuator having such a device), which control signals can be provided via a wired system/electrical leads extending from housing 8414 to the actuators. Note also that in some alternate embodiments, control unit 8310 is in wired communication with the actuators, either directly or indirectly, and/or is in wired communication with the decoding device located in the housing 8414. Any arrangement that can enable control of the robot apparatus in general, and the actuators thereof in particular, via control unit 8310 can be utilized in at least some exemplary embodiments.

Note also that while the embodiment depicted in FIG. 76 is such that the actuators 8420 must actuate so as to extend the intracochlear portion of the insertion guide into the cochlea, in an alternate embodiment, as noted above, the insertion guide can be mounted on a rail system or the like, wherein a cylindrical actuator or the like pushes the insertion guide in a linear manner into the cochlea and withdrawals the insertion guide in the linear manner from the cochlea. In an exemplary embodiment, this actuator apparatus can enable one degree of freedom movements of the insertion guide, while in other embodiments, this actuator apparatus can enable two or three or four or five or six degrees of freedom. Indeed, in an exemplary embodiment, this actuator apparatus can enable movement only in a linear direction, but can enable rotation of the insertion guide about the longitudinal axis thereof. Any arrangement of actuator assemblies that will enable the insertion guide to be positioned relative to the cochlea and/or inserted into the cochlea via robotic positioning thereof can be utilized in at least some exemplary embodiments.

Any control unit and/or test unit or the like disclosed herein can be a personal computer programs was to execute one or more or all of the functionalities associated therewith are the other functionalities disclosed herein. In an exemplary embodiment, any control unit and/or test unit or the like can be a dedicated circuit assembly configured so as to execute one or more or all of the functionalities associated there with or the other functionalities disclosed therein. In an exemplary embodiment, and the control unit and/or test unit or the like disclosed herein can be a processor or the like or otherwise can be a programmed processor.

Figure 77:
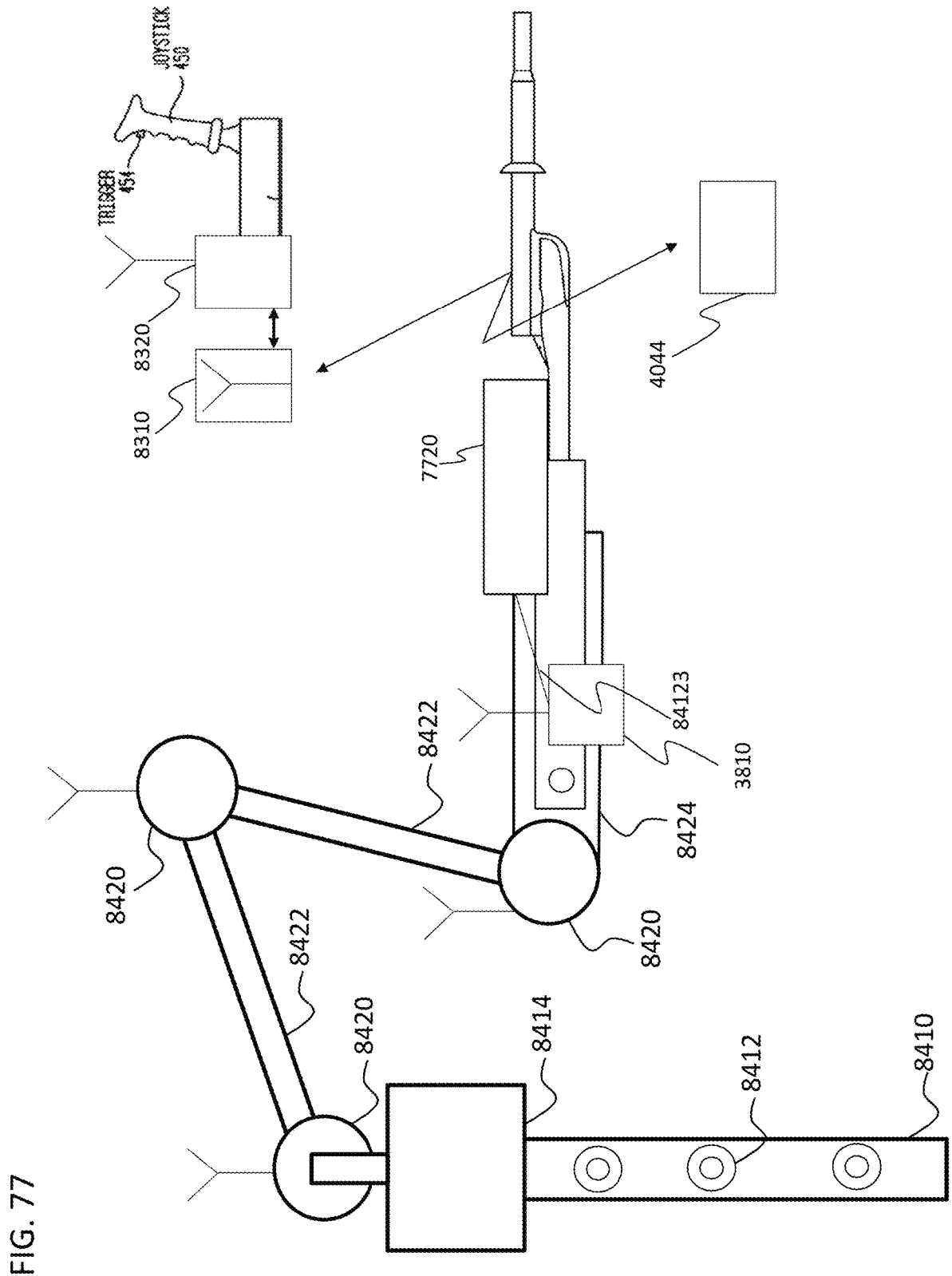

FIG. 77 depicts another exemplary embodiment, as seen. FIG. 77 presents such an exemplary embodiment, with the links between the antennas removed for clarity. Testing system 4044 detailed shown in signal communication with control unit 8310. In this exemplary embodiment, system 4044 corresponds to that detailed above vis-à-vis determining anomalous electrode location with the exception that it is entirely divorced from the insertion guide, save for the communication between system 4044 and the control unit 8310, to the extent such is relevant for the purposes of discussion, where control unit 8310 is in signal communication with one or more of the assemblies of the robot apparatus, such as the actuator assembly 7720. Here, during insertion, and/or prior to insertion and/or after insertion, the system 4044 monitors or otherwise measures electrical phenomenon detailed herein and communicates those measurements and/or the analysis thereof to control unit 8310, which analyzes those signals and develops a control regime for electrode array insertion and/or electrode array positioning based on those signals. Note also that in some exemplary embodiments, the system 4044 can have multiple measurement electrodes and/or signal generators/sources of acoustic signal generation, some of which are part of the robot apparatus, and some of which are separate from the robot apparatus, all of which are part of system 4044. Alternatively, these various components of the system 4044 can communicate with test unit 3960. Such can have utilitarian value with respect to a scenario where measurements are first taken prior to placing the electrode array near the cochlea and after inserting the electrode array into the cochlea, where it is undesirable to have the insertion guide and/or electrode array support proximate the cochlea. Any device, system, and/or method that will enable controlled movement of the electrode array relative to the cochlea based on electrical phenomenon associated with the recipient/based on electrical characteristics associated with the recipient can be utilized in at least some exemplary embodiments.

Again, the test unit and the system 4044 can be one and the same in some embodiments, and in some embodiments, functionality can be bifurcated between the two as separate units. Indeed, 4044 in FIG. 77 can be a proxy for the control unit and/or the test units detailed above.

In view of the above, it can be seen that some embodiments provide for the automatic detection of a fold over array, a dislocation, bowing or buckling, or other phenomenon, in patients with cochlear implants in an objective manner, and such can provide an automated method for identifying the affected area. Again, the teachings herein can be executed without or in addition to medical imaging tests (e.g. CT scan, X-ray, etc.), or otherwise requiring the recipient/patient to be exposed to radiation during the process of obtaining medical images, and/or subsequent analysis by an expert to assess the correct insertion of the electrode holder and/or measuring neuronal activation after stimulation. In some embodiments, the teachings herein can be executed with methods to attempt to detect neural activation, and can still provide the above reliability in a scenario where there is no neuronal response due to several causes not related to the orientation of the array.

In view of the above, it can be seen that in an exemplary embodiment, there is a methodology for detecting one or more fold-overs of a patient's electrode holder, which can include a method and device for obtaining the values of the electric potential produced by the activation of one evaluation electrode with respect to all others, obtaining an activation level (in some implementations defined in coulombs) of the electrode of the electrode holder under evaluation, in some embodiments, the other electrodes on the electrode holder store the electrical potential value of each electrode while the electrode holder under evaluation is stimulated. In an exemplary method, the potentials obtained are organised in a data array structure, where the rows represent the stimulated electrode and the columns represent the potential perceived at each electrode, or vice versa. The existence of one or more secondary diagonals of the array can be detected and verified. In some implementations, the secondary diagonal can be detected by:

Standard deviation;
Search for positive slopes in potential;
Search for a change of slope in potential;
Peak location;
Search for positive slopes in potential;
Search for a change of slope in potential;

In the event of having a secondary diagonal, the occurrence of a fold-over can be verified and the crossing between the primary diagonal (where in some embodiments the primary diagonal is that where the electrode that is stimulated and the one that perceives the potential are the same) and the secondary one is defined as the point or points of fold-over.

In an exemplary embodiment of this method, it is possible to determine after the insertion of the electrode holder (array) whether or not there is a fold-over and if it exists, on which electrode or electrodes the fold-over has occurred. Basically, obtaining the measurements of the potential using the electrodes of the electrode holder and the processing of these potential measurements allows to obtain as a result the existence or non-existence of the Fold-Over and in which electrode or electrodes it occurs.

In some examples, the method may further comprise the action of conditioning the potential measurements, this conditioning step being configured to reduce the noise of these measurements, detection of defective electrodes and scaling and normalised measurements at the interval [0,1] prior to the process stage. To this end, this conditioning step may comprise one or more filtering elements of the electrical potential measurements. Where any of the implementations of these filters could be:

Median filter;
Mean filter;
Adaptive filter;

According to some examples, the electrical stimulus entails a monopolar two-phase pulse and the potential measurement is obtained at the end of the first phase of the stimulus. In this way, the potential obtained can be a maximum.

In some examples, the matrix data structure may degenerate into a vector when a single electrode is evaluated with regard to the rest of the electrodes. Thus the value of the electrical potential in all electrodes is not necessarily recorded when one of them is under evaluation.

The above-mentioned computer programme may be stored in physical storage media, such as recording media, computer memory, or read-only memory, or may be carried by a carrier wave, such as electrical or optical.

As seen above, a computer system is described which may comprise a memory and a processor, instructions are stored in the memory which can be executed by the processor and these instructions comprise functionalities to execute a procedure to detect if a fold-over has occurred and on which Electrode it has occurred, as described above.

An exemplary embodiment includes an array organized as follows:

Evaluated electrodes are found in the columns of the array.
The rows of the array are made up of the electrodes that have recorded the potential.
In each of the array cells the potential value is recorded.

Therefore, for example, field [10,3] of the array stores the value of the potential recorded by electrode number 10 while electrode number 3 was being activated. At this point it is noted that the potentials array may comprise different numbers of electrodes depending on the electrode holder guide used.

In an exemplary embodiment, there is a method that include the action of obtaining potentials array, the action of conditioning the potential measurements obtained. Filtering actions can be executed by utilizing any of the following:

Median filter;
Mean filter;
Adaptive filter;

Another action includes, the detection in the electrode holder such as short circuits, open circuit, bubbles or other problems not related to the Fold-Over, and the action of, where the presence of a second diagonal is detected, where any of the implementations could be:

Standard deviation;
Search for positive slopes in potential;
Search for a change of slope in potential;
Peak location;
Search for positive slopes in potential;
Search for a change of slope in potential;

Another action includes calculating the electrode on which the fold-over pivots is calculated in the event a fold-over has been detected in the previous action.

At this point it is noted that a method for detecting fold-overs may comprise different configurations at the stage level. Thus, as described above, in these examples the configuration is based on the use of an array data structure.

In an exemplary embodiment, there is a method for detecting a fold-over in cochlear implant electrode holders characterised by an action for obtaining the values of the electric potential produced by the activation of an evaluation electrode with respect to all others, to which potentials are organised in an array data structure, where the stimulated electrode is represented in the rows, and the perceived potential at each electrode is represented in the columns, or vice versa, an action for detecting and verifying the existence of one or more secondary diagonals of the array. In the event of having a secondary array, the occurrence of a fold-over is verified and the crossing between the primary and secondary diagonal is defined as the point or points of fold-over.

In view of the above, there is a device for executing one or more of the method detailed above, including the ability to define an activation value of an evaluation electrode at a level of activation (in some implementations defined in Coulombs) defined by the user to record the potential generated by the electrode, inside the cochlea. In view of the above, there is a device for executing one or more of the method detailed above, including the ability to obtain electrical potential values in one or more electrodes housed in the electrode holder which may include the evaluation electrode itself. In view of the above, there is a device for executing one or more of the method detailed above, including the ability to average potential measurements at each measuring electrode.

In an exemplary embodiment of the methods detailed above, the values of the potentials are organised into an array data structure which can degenerate into a vector data structure. In an exemplary embodiment, there is the action of applying a filtering step to improve the quality of the data comprising a filter, such as:

Median filter;
Mean filter;
Adaptive filter;

In an exemplary embodiment of the methods detailed above, there is the ability to exclude electrodes with other types of errors such as air bubbles, short circuits and open circuits when searching for fold-overs. In an exemplary embodiment of the methods detailed above, wherein the existence of one or more secondary diagonals of the value of the obtained potential is identified. In an exemplary embodiment of the methods detailed above, there is one or more executions of a search for a secondary diagonal, using the following schemes:

Standard deviation;
Search for positive slopes in potential;
Search for change of slope in potential;

In an exemplary embodiment of the methods detailed above, wherein the existence of one or more secondary diagonal is executed, when the structure containing the potential values has degenerated to a vector, as for example:

Peak location;
Search for positive slopes in potential;
Search for a change of slope in potential;

In an exemplary embodiment of the methods detailed above, there is a search for the intersection between the primary diagonal and any of the secondary ones indicating the electrode on which the fold-over occurs. Also, there is a computer program comprising computer instructions to cause a computer system to execute a method according to any of the teachings herein to detect an anomalous condition. There can also be a computer system comprising a memory and a processor, with instructions stored on its memory which can be executed by the processor and such instructions comprising functionalities for executing a method according to any of that disclosed herein, in full or in part, for detecting a fold-over or a dislocation or any other anomalous electrode location of a cochlear implant.

In some embodiments, there are a plurality of electrodes that include at least one electrode configured to record the voltage produced by the electrode under evaluation.

In an exemplary embodiment, there is a method, comprising:

obtaining information indicative of a phenomenon sensed at, at least one read electrode relative to at least one reference of a cochlear implant electrode array and/or at a read electrode remote from the electrode array relative to a reference where at least one of the electrodes of the cochlear implant electrode array was energized;

executing a first analysis of the information to identify one or more first meanings from among a first group of meanings of the sensed phenomenon;

conditioning the obtained information based on the identified one or more first meanings; and executing a second analysis of the conditioned information to identify one or more second meanings from among a second group of meanings of the sensed phenomenon.

In an exemplary embodiment, there is a method as described above and/or below, wherein the one or more first meanings corresponds to an electrical phenomenon that at least one of will not change or will change with time without further movement of the electrode array in the cochlea, all other things being equal.

In an exemplary embodiment, there is a method as described above and/or below, further comprising:

providing a virtual indication to a healthcare professional that a fold over of the electrode array has occurred and the location thereof based on the second analysis.

In an exemplary embodiment, there is a method, comprising:

commencing insertion of a cochlear electrode array into a cochlea of a person;

establishing a source and sink of electrical current in the recipient, wherein the source is one of an energized stimulation electrode of the electrode array that is located inside the cochlea or an energized electrode remote from the electrode array;

reading at least one read electrode, relative to at least one reference, that received an electrical signal from the energized stimulation electrode; and determining, based on the reading, that a physical characteristic associated with the electrode array that is strictly local to the electrode array existed and/or exists.

In an exemplary embodiment, there is a method as described above and/or below, wherein the physical characteristic is a temporally dynamic characteristic related to the physical condition of the electrode array.

In an exemplary embodiment, there is a method as described above and/or below, wherein:

after the determining action, adjusting a location of the electrode array in the cochlea and executing a second reading of the read electrode/s or of at least one other read electrode of the electrode array; and determining, based on the second reading, that the physical characteristic is a first characteristic as opposed to a second characteristic because the second reading, after the movement, is effectively different than the reading.

In an exemplary embodiment, there is a method as described above and/or below, further comprising:

after the determining action, adjusting a location of the electrode array in the cochlea and executing a second reading of the read electrode/s relative to a reference or of at least one other read electrode of the electrode array relative to a reference; and determining, based on the second reading, that the physical characteristic is a second characteristic as opposed to a first characteristic because the second reading, after the movement, is effectively the same as the reading.

In an exemplary embodiment, there is a method as described above and/or below, further comprising:

after the determining action, adjusting a location of the electrode array in the cochlea and executing a second reading of the read electrode/s relative to a reference or of another read electrode of the electrode array, relative to a reference; and determining, based on the second reading, that the physical characteristic associated with the electrode array no longer exists.

In an exemplary embodiment, there is a method as described above and/or below, wherein, further comprising:

after the determining action, adjusting a location of the electrode array in the cochlea and executing a second reading of the read electrode/s relative to a reference or of another read electrode of the electrode array, relative to a reference; and determining, based on the second reading, that the physical characteristic associated with the electrode array no longer exists.

In an exemplary embodiment, there is a method as described above and/or below, wherein
the physical characteristic is a temporally static characteristic related to the physical condition of the electrode array, and wherein the method further comprising:
second energizing at least one stimulation electrode of the electrode array that is located inside the cochlea or an electrode remote from the electrode array;
second reading at least one read electrode relative to at least one reference that received an electrical signal from the energized stimulation electrode, wherein the read electrode/s is part of the electrode array if the energized stimulation electrode is an electrode remote from the electrode array; and
confirming the prior determination, based on the second reading, that the physical characteristic associated with the electrode array that is strictly local to the electrode array existed and/or exists.

In an exemplary embodiment, there is a method, comprising:
(i) obtaining information indicative of a phenomenon sensed at, at least one read electrode relative to at least one reference of a cochlear implant electrode array; and
(ii) using that information to determine whether or not a deleterious cochlear electrode array position exists inside the cochlea of a recipient, wherein
the actions used to make the determination correspond to a statistical based accuracy rating of at least 90 out of 100 vis-à-vis determinations that a deleterious cochlear electrode array position exists.

In an exemplary embodiment, there is a method as described above and/or below, wherein:
action "ii" includes first conditioning the obtained information and then analyzing the conditioned information to make the determination.

In an exemplary embodiment, there is a method as described above and/or below, further comprising:
after conditioning the information or prior to conditioning the information, and prior to analyzing, normalizing the information and then analyzing the normalized conditioned information or the conditioned normalized information to make the determination.

In an exemplary embodiment, there is a method as described above and/or below, further comprising:
reanalyzing the information without the normalizing or analyzing the information before normalizing to make a second determination as to whether or not another type of deleterious cochlear electrode array position exists inside the cochlea of the recipient.

In an exemplary embodiment, there is a method as described above and/or below, further comprising:
executing a normalizing action on the information conditioned according to the second type prior to analyzing such; and
not executing a normalizing action on the information conditioned according to the first type prior to analyzing such.

In an exemplary embodiment, there is a method as described above and/or below, further comprising:
after action "i," determining whether or not to execute a conditioning action on the obtained information and/or what type of conditioning action is to be executed on the obtained information; and
normalizing the information before or after executing the conditioning action, if executed, and analyzing the normalized information to make the determination.

In an exemplary embodiment, there is a method as described above and/or below, wherein:
the result of the action of determining what type of conditioning action is a determination to execute a type of conditioning action that is conducive to determining whether or not dislocation has occurred; and
the method further includes determining not to normalize the information.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted.

Any disclosure herein of a method of making a device herein corresponds to a disclosure of the resulting device. Any disclosure herein of a device corresponds to a disclosure of making such a device.

Any one or more elements or features disclosed herein can be specifically excluded from use with one or more or all of the other features disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:
1. A method, comprising:
obtaining information indicative of a phenomenon sensed at, at least one read electrode relative to at least one reference of a cochlear implant electrode array and/or at a read electrode remote from the electrode array relative to a reference where at least one of the electrodes of the cochlear implant electrode array was energized;
executing a first analysis of the information to identify one or more first meanings from among a first group of meanings of the sensed phenomenon;
conditioning the obtained information based on the identified one or more first meanings;
executing a second analysis of the conditioned information to identify one or more second meanings from among a second group of meanings of the sensed phenomenon; and
analyzing the information to determine whether or not portions of the information are acceptable for use in identifying the one or more second meanings, wherein
the action of conditioning includes modifying the information to at least one of eliminate or replace the portions of the information that are deemed not acceptable for use in identifying the one or more second meanings and using the modified information to identify the one or more second meanings, and
the first group of meanings includes at least one of an open circuit, a short circuit, a shunt circuit, a bubble proximate the electrode array, an electrode not in the cochlea, an electrode conditioning phenomenon or a phenomenon associated with a geometric property of a cochlea.

2. The method of claim 1, wherein:
the one or more second meanings relates to a feature that impacts the conduction of electricity globally relative to the electrode array.

3. The method of claim 1, further comprising:
providing a virtual indication to a healthcare professional that a dislocation or a fold over of the electrode array has occurred and the location thereof based on the second analysis.

4. The method of claim 1, wherein:
the one or more second meanings relates to a feature that is identifiable only if a specific electrode is known of a plurality of potential intracochlear sources of current corresponding to respective electrodes of the cochlear array supplies current to the one or more read electrodes.

5. The method of claim 1, wherein:
the one or more second meanings corresponds to an electrical phenomenon that will only change with further movement of the electrode array in the cochlea, all other things being equal.

6. The method of claim 1, wherein:
the second group of meanings includes at least one of fold over, dislocation, bowing or electrode array misplacement.

7. The method of claim 1, wherein:
the phenomenon sensed at the one or more read electrodes was sensed at least one of while the electrode array was being inserted into the cochlea or before the electrode array was inserted into the cochlea.

8. The method of claim 1, wherein:
the actions of obtaining information, executing the first analysis, conditioning and executing the second analysis are executed after the electrode array is fully inserted into a cochlea such that at least sixteen (16) stimulating electrodes, used to evoke a hearing percept in operation, of the electrode array, are located in the cochlea.

9. The method of claim 1, wherein:
the one or more first meanings corresponds to an electrical phenomenon that at least one of will not change or will change with time without further movement of the electrode array in the cochlea, all other things being equal.

10. The method of claim 1, wherein:
the actions of obtaining information, executing the first analysis, conditioning and executing the second analysis are executed when at least sixteen (16) stimulating electrodes, used to evoke a hearing percept in operation, of the electrode array, are located in the cochlea.

11. The method of claim 1, wherein:
the action of obtaining information is executed via wired communication between the electrode array and a computing device outside a recipient of the electrode array.

12. The method of claim 1, wherein:
the first group of meanings includes at least an electrode conditioning phenomenon; and
second group of meanings includes at least one of fold over, dislocation, bowing or electrode array misplacement.

13. The method of claim 1, wherein:
the actions of obtaining information, executing the first analysis, conditioning and executing the second analysis are executed as part of a method where an imaging technique has not been used within 120 minutes after the electrode array is fully inserted into the cochlea.

14. The method of claim 1, wherein:
the identified one or more second meanings is an array fold over of the cochlear electrode array;
wherein the method further comprises repeating the actions of obtaining, executing the first analysis, conditioning, executing the second analysis, wherein the identified one or more second meanings identified in the second analysis, is an array fold over of the cochlear electrode array, at least 5 times, and the action of identifying the array fold over of the cochlear electrode array is executed at a rate that is statistically more reliable than a single X-ray of the cochlear of the recipient with the electrode array therein.

15. The method of claim 1, wherein:
the identified one or more second meanings is that a physical characteristic associated with the electrode array that is strictly local to the electrode array existed and/or exists.

16. The method of claim 1, wherein:
the identified one or more second meanings is that a physical characteristic associated with the electrode array that is strictly local to the electrode array existed and/or exists, wherein the physical characteristic is a temporally static characteristic related to the physical condition of the electrode array.

17. The method of claim 1, wherein:
the identified one or more second meanings is that a physical characteristic associated with the electrode array that is strictly local to the electrode array existed and/or exists; and
the method further comprises, subsequent to the execution of the second analysis:
obtaining second information indicative of a phenomenon sensed at at least one read electrode relative to at least one reference of the cochlear implant electrode array and/or at a read electrode remote from the electrode array relative to a reference where at least one of the electrodes of the cochlear implant electrode array was energized; and
determining, based on the second information, that the physical characteristic associated with the electrode array that is strictly local to the electrode array no longer exists.

18. The method of claim 1, wherein:
the one or more second meanings is that a deleterious cochlear electrode array position exists inside the cochlea of a recipient, wherein
the actions used to make the identification that a deleterious cochlear electrode array position exists correspond to a statistical based accuracy rating of at least 90 out of 100 vis-à-vis determinations that a deleterious cochlear electrode array position exists.

19. The method of claim 1, wherein:
after conditioning the obtained information or prior to conditioning the information, and prior to executing the second analysis, normalizing the information and then executing the second analysis with the normalized conditioned information or the conditioned normalized information.

20. The method of claim 1, further comprising:
in addition to conditioning the obtained information, placing the obtained information into a matrix.

* * * * *